US010981934B2

United States Patent
Kawakita et al.

(10) Patent No.: US 10,981,934 B2
(45) Date of Patent: *Apr. 20, 2021

(54) FUSED HETEROCYCLIC COMPOUND

(71) Applicant: TAKEDA PHARMACEUTICAL COMPANY LIMITED, Osaka (JP)

(72) Inventors: Youichi Kawakita, Tokyo (JP); Takuto Kojima, Fujisawa (JP); Noriyuki Nii, Fujisawa (JP); Yoshiteru Ito, Fujisawa (JP); Nobuki Sakauchi, Fujisawa (JP); Hiroshi Banno, Fujisawa (JP); Xin Liu, Shanghai (CN); Koji Ono, Fujisawa (JP); Keisuke Imamura, Fujisawa (JP); Shinichi Imamura, Fujisawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/663,601

(22) Filed: Oct. 25, 2019

(65) Prior Publication Data

US 2020/0140462 A1 May 7, 2020

Related U.S. Application Data

(63) Continuation of application No. 16/094,030, filed as application No. PCT/JP2017/016717 on Apr. 27, 2017, now Pat. No. 10,577,382.

(30) Foreign Application Priority Data

Apr. 28, 2016 (JP) ................... 2016-091717

(51) Int. Cl.
| A61K 31/53 | (2006.01) |
| C07D 519/00 | (2006.01) |
| A61K 31/444 | (2006.01) |
| A61K 31/5025 | (2006.01) |
| A61K 31/519 | (2006.01) |
| A61K 31/4985 | (2006.01) |
| A61P 35/00 | (2006.01) |

(52) U.S. Cl.
CPC .......... *C07D 519/00* (2013.01); *A61K 31/444* (2013.01); *A61K 31/4985* (2013.01); *A61K 31/5025* (2013.01); *A61K 31/519* (2013.01); *A61K 31/53* (2013.01); *A61P 35/00* (2018.01)

(58) Field of Classification Search
CPC ................. A61K 31/53; A61P 35/00
USPC .................................. 514/243, 258
See application file for complete search history.

(56) References Cited

U.S. PATENT DOCUMENTS

| 8,436,012 B2 | 5/2013 | Ohtsuka et al. |
| 10,577,382 B2 * | 3/2020 | Kawakita ............... A61P 35/00 |
| 2004/0063707 A1 | 4/2004 | Bhide et al. |
| 2005/0124621 A1 | 6/2005 | Bhide et al. |
| 2006/0004007 A1 | 1/2006 | Hunt et al. |
| 2013/0165426 A1 | 6/2013 | Ruel et al. |
| 2014/0256719 A1 | 9/2014 | Finlay et al. |

FOREIGN PATENT DOCUMENTS

| JP | 2005-538989 | 12/2005 |
| WO | 00/71129 | 11/2000 |
| WO | 2004/009784 | 1/2004 |
| WO | 2012/003576 | 1/2012 |
| WO | 2014/143610 | 9/2014 |

OTHER PUBLICATIONS

International Search Report dated Jul. 4, 2017 in International (PCT) Application No. PCT/JP2017/016717.
International Preliminary Report on Patentability dated Oct. 30, 2018 in International (PCT) Application No. PCT/JP2017/016717.

* cited by examiner

*Primary Examiner* — Charanjit Aulakh
(74) *Attorney, Agent, or Firm* — Wenderoth, Lind & Ponack, L.L.P.

(57) ABSTRACT

Provided is a compound represented by the following formula, or a salt thereof:

[Chemical Formula]

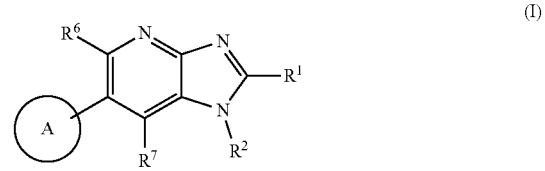

(I)

[wherein each symbol is as defined herein.].

5 Claims, No Drawings
Specification includes a Sequence Listing.

FUSED HETEROCYCLIC COMPOUND

TECHNICAL FIELD

The present invention relates to a novel compound having an inhibitory action against cdc2-like kinase (cdc2-like kinase; hereinafter sometimes abbreviated as CLK), or a salt thereof. The present invention also relates to a medicament which contains the compound or salt thereof and which is used for preventing or treating a CLK-related disease such as cancer.

BACKGROUND ART

Abnormal control of an alternative splicing mechanism has been reported in various diseases such as neurodegenerative disease, amyotrophic lateral sclerosis and cancer. Particularly in cancer, cancer-specific splicing variants produced by abnormal alternative splicing have been shown to play an important role in cancer survival and invasion. In recent years, it has been shown that spliceosome constituent factors such as SF3B1, SRSF2 and U2AF1 are mutated with high frequency in the myelodysplastic syndrome. These findings indicate that control of an alternative splicing mechanism plays an important role in cancer.

CLK family kinase is a type of bispecific protein kinase retaining both serine/threonine kinase activity and tyrosine kinase activity, and include four types of kinase: CLK1 to CLK4. CLK phosphorylates SR proteins such as SRSF1 to control localization of the proteins, so that a splicing regulation mechanism by SR proteins is controlled. It has been shown that by regulating alternative splicing by inhibition of CLK kinase activity, signals essential for survival of cancer can be hindered to inhibit growth of cancer cells. In addition, CLK2 has been shown to act as an oncogene in breast cancer. Therefore, inhibition of kinase activity of CLK may be a promising treatment for cancer.

Patent Literatures 1 and 2 disclose a fused heterocyclic compound as a compound having a tyrosine kinase inhibitory action. Patent Literatures 3 and 4 disclose a fused heterocyclic compound having other pharmacological activities.

CITATION LIST

Patent Literature

PATENT LITERATURE 1: WO 00/71129
PATENT LITERATURE 2: WO 2004/009784
PATENT LITERATURE 3: WO 2014/143610
PATENT LITERATURE 4: WO 2012/003576

SUMMARY OF INVENTION

Technical Problem

An object of the present invention is to provide a compound which has an excellent CLK inhibitory action, and is satisfactory as a pharmaceutical product.

Solution to Problem

The present inventors have found that a compound represented by the following formula or a salt thereof has excellent CLK inhibitory activity, and is useful for prevention and treatment of cancer and the like. On the basis of this finding, the present inventors have conducted intensive studies, leading to completion of the present invention. That is, the present invention is as follows.

[1] A compound represented by formula (I), or a salt thereof (herein sometimes abbreviated as "compound (I)"):

[Chemical Formula 1]

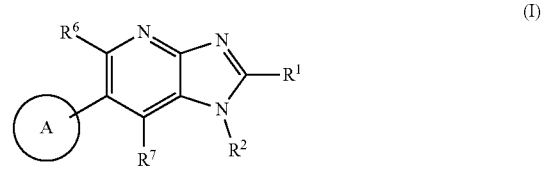

[wherein $R^1$ represents a substituent or a hydrogen atom;

$R^2$ represents an optionally substituted hydrocarbon group or an optionally substituted heterocyclic group;

$R^6$ and $R^7$ each independently represent a hydrogen atom, a halogen atom or an optionally substituted hydrocarbon group; and ring A represents a bicyclic aromatic heterocyclic ring selected from the following formulas (1), (2), (3), (4) and (5):

[Chemical formula 2]

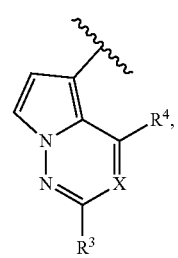

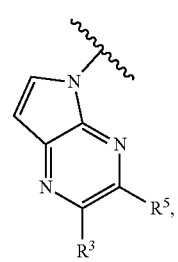

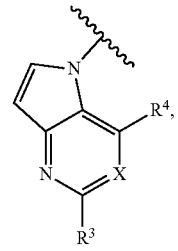

-continued

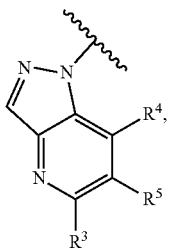
(4)

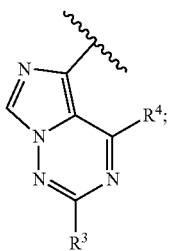
(5)

wherein Xs each independently represent N or C(R$^5$); and R$^3$, R$^4$ and R$^5$ each independently represent a hydrogen atom or a substituent.].

[2] The compound or salt thereof according to [1], wherein
R$^2$ is
(I) a C$_{1-6}$ alkyl group optionally having 1 to 3 five- or six-membered monocyclic aromatic heterocyclic groups optionally having 1 to 3 optionally halogenated C$_{1-6}$ alkyl groups; or
(II) an optionally halogenated C$_{7-16}$ aralkyl group.

[3] The compound or salt thereof according to [1], wherein ring A is a bicyclic aromatic heterocyclic ring represented by the following formula (1).

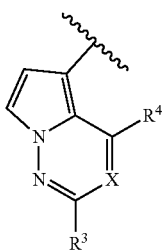
(1)

[4] The compound or salt thereof according to [1], wherein R$^3$ is a hydrogen atom;
R$^4$ is (a) an amino group optionally monosubstituted or disubstituted with a C$_{1-6}$ alkyl group, or
(b) a C$_{1-6}$ alkoxy group; and
R$^5$ is (a) a C$_{1-6}$ alkoxy group, or
(b) a C$_{1-6}$ alkyl group optionally having 1 to 3 hydroxy groups.

[5] The compound or salt thereof according to [1], wherein R$^1$ is
(I) a C$_{1-6}$ alkyl group optionally having 1 to 5 substituents each selected from
(a) a halogen atom,
(b) a hydroxy group,
(c) a cyano group,
(d) a C$_{1-6}$ alkoxy group optionally having 1 to 3 substituents each selected from
(i) a halogen atom, and
(ii) a hydroxy group, and
(e) a three- to eight-membered nonaromatic heterocyclic group having 1 to 3 halogen atoms;
(II) a three- to eight-membered nonaromatic heterocyclic group optionally having 1 to 5 substituents each selected from
(a) a C$_{1-6}$ alkoxy group,
(b) a halogen atom, and
(c) a hydroxy group;
(III) a five- to fourteen-membered aromatic heterocyclic group optionally having 1 to 3 optionally halogenated C$_{1-6}$ alkyl groups;
(IV) a C$_{1-6}$ alkoxy group optionally having 1 to 5 substituents each selected from
(a) a hydroxy group,
(b) a three- to eight-membered nonaromatic heterocyclic group, and
(c) a five- or six-membered monocyclic aromatic heterocyclic group optionally having 1 to 3 optionally halogenated C$_{1-6}$ alkyl groups;
(V) an optionally halogenated C$_{3-10}$ cycloalkyl group; or
(VI) an amino group optionally monosubstituted or disubstituted with a C$_{1-6}$ alkyl group optionally having 1 to 5 substituents each selected from
(a) (i) halogen atom,
(ii) a hydroxy group, and
(iii) C$_{1-6}$ alkoxy group;
R$^2$ is
(I) a C$_{1-6}$ alkyl group optionally having 1 to 3 five- to fourteen-membered aromatic heterocyclic groups optionally having 1 to 3 substituents each selected from
(a) a halogen atom,
(b) a C$_{1-6}$ alkyl group optionally having 1 to 7 substituents each selected from
(i) a halogen atom,
(ii) a hydroxy group, and
(iii) a C$_{1-6}$ alkoxy group,
(c) an optionally halogenated C$_{3-10}$ cycloalkyl group,
(d) a C$_{1-6}$ alkoxy group,
(e) a C$_{1-6}$ alkyl group-C$_{3-10}$ cycloalkyl group,
(f) a C$_{1-6}$ alkyl group-three- to eight-membered monocyclic nonaromatic heterocyclic group, and
(g) an oxo group; or
(II) a C$_{7-16}$ aralkyl group optionally having 1 to 3 substituents each selected from
(a) a C$_{1-6}$ alkyl group optionally having 1 to 3 substituents each selected from
(i) a halogen atom, and
(ii) a hydroxyl group,
(b) a C$_{1-6}$ alkoxy-carbonyl group,
(c) a halogen atom,
(d) a C$_{1-6}$ alkoxy group optionally having 1 to 3 substituents each selected from
(i) a halogen atom, and
(ii) a hydroxyl group
(e) a mono- or di-C$_{1-6}$ alkyl-carbamoyl group,
(f) a cyano group,
(g) an amino group optionally monosubstituted or disubstituted with a substituent selected from
(i) a C$_{1-6}$ alkyl group, and
(ii) a C$_{1-6}$ alkoxy-carbonyl group,
(h) a nitro group, and
(i) a carboxy group;
each of R$^6$ and R$^7$ is a hydrogen atom;
ring A is a bicyclic aromatic heterocyclic ring selected from the formulas (1), (2), (3) and (4);

Xs each independently represents $C(R^5)$ or N;
$R^3$ is a hydrogen atom;
$R^4$ is
(I) a hydrogen atom,
(II) a halogen atom,
(III) an optionally halogenated $C_{1-6}$ alkoxy group, or
(IV) an amino group optionally monosubstituted or disubstituted with a $C_{1-6}$ alkyl group; and
$R^5$ is
(I) a hydrogen atom,
(II) a halogen atom,
(III) a cyano group,
(IV) a $C_{1-6}$ alkyl group optionally having 1 to 5 substituents each selected from
  (a) a halogen atom,
  (b) a $C_{1-6}$ alkoxy group,
  (c) a $C_{1-6}$ alkoxy-$C_{1-6}$ alkoxy group,
  (d) a hydroxy group, and
  (e) a $C_{1-6}$ alkyl-carbonyloxy group,
(V) a $C_{1-6}$ alkoxy group,
(VI) a $C_{2-6}$ alkenyl group optionally having 1 to 3 $C_{1-6}$ alkoxy groups,
(VII) a $C_{2-6}$ alkynyl group,
(VIII) a cyano-$C_{6-14}$ aryl group,
(IX) a five- to fourteen-membered aromatic heterocyclic group optionally having 1 or 2 $C_{1-6}$ alkyl groups optionally having 1 to 3 substituents each selected from
  (a) a halogen atom,
  (b) a five- or six-membered monocyclic aromatic heterocyclic group, and
  (c) a three- to eight-membered monocyclic nonaromatic heterocyclic group,
(X) a $C_{1-6}$ alkyl-carbonyl group,
(XI) a hydroxy group,
(XII) a $C_{1-6}$ alkyl-five- to fourteen-membered aromatic heterocyclic oxy group,
(XIII) a three- to eight-membered monocyclic nonaromatic heterocyclic group optionally having 1 to 3 substituents each selected from
  (a) a halogen atom,
  (b) a $C_{1-6}$ alkoxy group, and
  (c) an oxo group, or
(XIV) an amino group optionally monosubstituted or disubstituted with an optionally halogenated $C_{1-6}$ alkyl.

[6] 6-(4-methoxypyrrolo[2,1-f][1,2,4]triazin-5-yl)-2-methyl-1-((3-methyl-1,2,4-thiadiazol-5-yl)methyl)-1H-imidazo[4,5-b]pyridine, or a salt thereof.

[7] 1-((5-(difluoromethyl)-1,3,4-oxadiazol-2-yl)methyl)-6-(4-methoxypyrrolo[2,1-f][1,2,4]triazin-5-yl)-2-methyl-1H-imidazo[4,5-b]pyridine, or a salt thereof.

[8] 1-((5-(1,1-difluoroethyl)-1,3,4-oxadiazol-2-yl)methyl)-6-(4-methoxypyrrolo[2,1-f][1,2,4]triazin-5-yl)-2-methyl-1H-imidazo[4,5-b]pyridine, or a salt thereof.

[9] 1-((5-((1R)-1-fluoroethyl)-1,3,4-oxadiazol-2-yl)methyl)-6-(4-methoxypyrrolo[2,1-f][1,2,4]triazin-5-yl)-2-methyl-1H-imidazo[4,5-b]pyridine, or a salt thereof.

[10] A medicament including the compound or salt thereof according to [1].

[11] The medicament according to [10] which is a CLK inhibitor.

[12] The medicament according to [10] which is a prophylactic or therapeutic agent for cancer.

[13] A method for inhibiting CLK in a mammal, including administering to the mammal an effective amount of the compound or salt thereof according to [1].

[14] A method for preventing or treating cancer in a mammal, including administering to the mammal an effective amount of the compound or salt thereof according to [1].

[15] The compound or salt thereof according to [1] for use in prevention and treatment of cancer.

[16] Use of the compound or salt thereof according to [1] for producing a prophylactic or therapeutic agent for cancer.

Advantageous Effects of Invention

The compound (I) has an excellent CLK inhibitory action, and is useful for prevention and treatment of cancer and the like.

DESCRIPTION OF EMBODIMENTS

Hereinafter, compounds of the present invention, methods for production thereof, and uses of thereof will be described in detail.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl. In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[substituent group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),

(18) an optionally halogenated $C_{1-6}$ alkylsulfonyloxy group (e.g., methylsulfonyloxy, trifluoromethyl sulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl)($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonyl amino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methyl sulfonylamino, ethyl sulfonylamino),
(56) a $C_{6-14}$ arylsulfonylamino group optionally substituted by a $C_{1-6}$ alkyl group (e.g., phenyl sulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonyl amino), a $C_{6-14}$ arylsulfonylamino group (e.g., phenylsulfonylamino), a ($C_{1-6}$ alkyl) ($C_{1-6}$ alkyl-carbonyl)amino group (e.g., N-acetyl-N-methylamino) and a ($C_{1-6}$ alkyl)($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_6$-14 aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-6}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "$C_{1-6}$ alkylene group" include —$CH_2$—, —$(CH_2)_2$—, —$(CH_2)_3$—, —$(CH_2)_4$—, —$(CH_2)_5$—, —$(CH_2)_6$—, —CH($CH_3$)—, —C($CH_3$)$_2$—, —CH($C_2H_5$)—, —CH($C_3H_7$)—, —CH(CH($CH_3$)$_2$)—, —(CH($CH_3$))$_2$—, —$CH_2$—CH($CH_3$)—, —CH($CH_3$)—$CH_2$—, —$CH_2$—$CH_2$—C($CH_3$)$_2$—, —C($CH_3$)$_2$—$CH_2$—$CH_2$—, —$CH_2$—$CH_2$—$CH_2$—C($CH_3$)$_2$— and —C($CH_3$)$_2$—$CH_2$—$CH_2$—$CH_2$—.

In the present specification, examples of the "$C_{2-6}$ alkenylene group" include —CH=CH—, —$CH_2$—CH=CH—, —CH=CH—$CH_2$—, —C($CH_3$)$_2$—CH=CH—, —CH=CH—C($CH_3$)$_2$—, —$CH_2$—CH=CH—$CH_2$—, —$CH_2$—$CH_2$—CH=CH—, —CH=CH—$CH_2$—$CH_2$—, —CH=CH—CH=CH—, —CH=CH—$CH_2$—$CH_2$—$CH_2$— and —$CH_2$—$CH_2$—$CH_2$—CH=CH—.

In the present specification, examples of the "$C_{2-6}$ alkynylene group" include —C≡C—, —$CH_2$—C≡C—, —C≡C—$CH_2$—, —C($CH_3$)$_2$—C≡C—, —C≡C—C($CH_3$)$_2$—, —$CH_2$—C≡C—$CH_2$—, —$CH_2$—$CH_2$—C≡C—, —C≡C—$CH_2$—$CH_2$—, —C≡C—C≡C—, —C≡C—$CH_2$—$CH_2$—$CH_2$— and —$CH_2$—$CH_2$—$CH_2$—C≡C—.

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepanine, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

In the present specification, "a group via a carbon atom" means a group having an atomic bonding on the carbon atom; examples include a cyano group, a hydrocarbon group optionally having substituent(s), an acyl group, an optionally esterified carboxyl group, an imidoyl group optionally having substituent(s), an amidino group optionally having substituent(s), a carbamoyl group optionally having substituent(s), a thiocarbamoyl group optionally having substituent(s), a heterocyclic group via a carbon atom, optionally having substituent(s), etc.

Examples of "a heterocyclic group via a carbon atom" in the "a heterocyclic group via a carbon atom, optionally having substituent(s)" include a heterocyclic group having an atomic bonding on the carbon atom in the "heterocyclic group".

Examples of "an acyl group via a carbon atom" include an acyl group having an atomic bonding on the carbon atom in the "acyl group"; examples include a formyl group, a carboxyl group, a carbamoyl group, a thiocarbamoyl group, etc, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

In the present specification, "a group via a nitrogen atom" means a group having an atomic bonding on the nitrogen atom; examples include heterocyclic groups via a nitrogen atom (1) a nitro group, (2) an amino group optionally having 1 or 2 of the above described "a group via a carbon atom", (3) an amino group optionally having 1 or 2 "a group via a nitrogen atom", (4) a heterocyclic group via a nitrogen atom, optionally having a substituent.

In the present specification, "a group via an oxygen atom" means a group having an atomic bonding on the oxygen atom; examples include a hydroxy group optionally having one "group via a carbon atom" described above.

In the present specification, "a group via a sulfur atom" means a group having an atomic bonding on the sulfur atom; examples include a sulfanyl group optionally having one "group via a carbon atom" or "group via a nitrogen atom" described above, optionally being oxidized.

Hereinafter, the definition of each symbol in the formula (I) will be described in detail.

$R^1$ is preferably a substituent selected from (I) a $C_{1-6}$ alkyl group (particularly methyl or ethyl) optionally having 1 to 5 substituents each selected from
   (a) a halogen atom (particularly fluorine atom),
   (b) a hydroxy group,
   (c) a cyano group,
   (d) a $C_{1-6}$ alkoxy group (particularly methoxy or ethoxy) optionally having 1 to 3 substituents each selected from
     (i) a halogen atom (particularly fluorine atom), and
     (ii) a hydroxy group, and
   (e) a three- to eight-membered nonaromatic heterocyclic group (particularly azetidinyl) having 1 to 3 halogen atoms (particularly fluorine atoms);

(II) a three- to eight-membered nonaromatic heterocyclic group (particularly azetidinyl or pyrrolidinyl) optionally having 1 to 5 (particularly 1 or 2) substituents each selected from
   (a) a $C_{1-6}$ alkoxy group (particularly methoxy)
   (b) a halogen atom (particularly fluorine), and
   (c) a hydroxy group;

(III) a five- to fourteen-membered aromatic heterocyclic group (particularly five- or six-membered monocyclic aromatic heterocyclic group (preferably pyrazolyl or oxazolyl)) optionally having 1 to 3 (particularly 1) optionally halogenated $C_{1-6}$ alkyl groups (particularly methyl or difluoromethyl);

(IV) a $C_{1-6}$ alkoxy group (particularly methoxy or ethoxy) optionally having 1 to 5 (particularly 1) substituents each selected from
   (a) a hydroxy group,
   (b) a three- to eight-membered nonaromatic heterocyclic group (particularly tetrahydrofuranyl), and
   (c) a five- or six-membered monocyclic aromatic heterocyclic group optionally having 1 to 3 (particularly 1) optionally halogenated $C_{1-6}$ alkyl groups (particularly methyl or difluoromethyl);

(V) an optionally halogenated $C_{3-10}$ cycloalkyl group (particularly cyclopropyl or difluorocyclobutyl); and (VI) an amino group optionally monosubstituted or disubstituted with a $C_{1-6}$ alkyl group (particularly methyl, ethyl or isobutyl) optionally having 1 to 5 (particularly 1 to 3) substituents each selected from (a) (i) a halogen atom (particularly fluorine atom),
   (ii) a hydroxy group, and
   (iii) a $C_{1-6}$ alkoxy group (particularly methoxy).

$R^1$ is more preferably a substituent selected from (I) a $C_{1-6}$ alkyl group (particularly methyl) optionally having 1 to 3 substituents each selected from
   (a) a $C_{1-6}$ alkoxy group (particularly methoxy) and
   (b) a hydroxy group;

(II) a three- to fourteen-membered nonaromatic heterocyclic group (particularly azetidinyl);

(III) a $C_{1-6}$ alkoxy group (particularly methoxy or ethoxy); and (IV) an amino group.

$R^1$ is a $C_{1-6}$ alkyl group (particularly methyl) optionally having 1 to 3 (preferably 1) hydroxy groups.

$R^2$ is preferably (I) a $C_{1-6}$ alkyl group (particularly methyl) optionally having 1 to 3 (particularly 1) five- to fourteen-membered aromatic heterocyclic groups (particularly five- or six-membered monocyclic aromatic heterocyclic groups (preferably oxadiazolyl (preferably 1,2,4-oxadiazolyl or 1,3,4-oxadiazolyl), thiadiazolyl (preferably 1,2,4-thiadiazolyl, 1,3,4-thiadiazolyl or 1,2,3-thiadiazolyl), isoxazolyl, isothiazolyl, thiazolyl, triazolyl (preferably 1,2,3-triazolyl or 1,2,4-triazolyl), pyrazinyl, pyrazolyl, pyridyl, pyrimidinyl, oxazolyl or furyl)) optionally having 1 to 3 (particularly 1 or 2) substituents each selected from
   (a) a halogen atom (particularly fluorine or chlorine),
   (b) a $C_{1-6}$ alkyl group (particularly methyl, ethyl, isobutyl, isopropyl or propyl) optionally having 1 to 7 (particularly 1 to 5) substituents each selected from
     (i) a halogen atom (particularly fluorine atom),
     (ii) a hydroxy group, and
     (iii) a $C_{1-6}$ alkoxy group (particularly methoxy),
   (c) an optionally halogenated $C_{3-10}$ cycloalkyl group (particularly, 2,2-difluorocyclopropyl, cyclobutyl, cyclopropyl or difluorocyclobutyl (particularly 3,3-difluorocyclobutyl), fluorocyclobutyl (particularly 1-fluorocyclobutyl), fluorocyclopropyl),
   (d) a $C_{1-6}$ alkoxy group (particularly methoxy),
   (e) a $C_{1-6}$ alkyl group-$C_{3-10}$ cycloalkyl group (particularly methyl-cyclopropyl),
   (f) a $C_{1-6}$ alkyl group-three- to eight-membered monocyclic nonaromatic heterocyclic group (particularly methyl-oxetanyl), and
   (g) oxo group; or (II) a $C_{7-16}$ aralkyl group (particularly benzyl) optionally having 1 to 3 substituents each selected from
   (a) a $C_{1-6}$ alkyl group (methyl or isopropyl) optionally having 1 to 3 substituents each selected from
     (i) a halogen atom (particularly fluorine atom), and
     (ii) a hydroxyl group,
   (b) a $C_{1-6}$ alkoxy-carbonyl group (particularly methoxy-carbonyl),
   (c) a halogen atom (fluorine or chlorine)
   (d) a $C_{1-6}$ alkoxy group (particularly methoxy or ethoxy) optionally having 1 to 3 substituents each selected from
     (i) a halogen atom (particularly fluorine atom), and
     (ii) a hydroxyl group
   (e) a mono- or di-$C_{1-6}$ alkyl-carbamoyl group (particularly methylcarbamoyl),
   (f) a cyano group,
   (g) an amino group optionally monosubstituted or disubstituted (particularly monosubstituted) with a substituent selected from (i) a $C_{1-6}$ alkyl group, and (ii) a $C_{1-6}$ alkoxy-carbonyl group (particularly tert-butoxy-carbonyl), (h) a nitro group, and (i) a carboxy group.

$R^2$ is more preferably (I) a $C_{1-6}$ alkyl group (particularly methyl) optionally having 1 to 3 (preferably 1) five- or six-membered monocyclic aromatic heterocyclic groups (particularly oxadiazolyl (preferably 1,2,4-oxadiazolyl or 1,3,4-oxadiazolyl), thiadiazolyl (preferably 1,2,4-thiadiazolyl, 1,3,4-thiadiazolyl or 1,2,3-thiadiazolyl), isoxazolyl, thiazolyl, triazolyl (preferably 1,2,3-triazolyl or 1,2,4-triazolyl), pyrazinyl, pyrazolyl, pyridyl, pyrimidinyl or oxazolyl) optionally having 1 to 3 (preferably 1) substituents each selected from (a) a halogen atom (particularly fluorine), (b) an optionally halogenated $C_{1-6}$ alkyl group (particularly methyl, difluoromethyl, trifluoromethyl, ethyl, difluoroethyl (particularly 1,1-difluoroethyl), 2,2,2-trifluoroethyl, isopropyl, 1-fluoroisopropyl or 1-fluoroethyl), and (c) an optionally halogenated $C_{3-10}$ cycloalkyl group (particularly, 2,2-difluorocyclopropyl, cyclobutyl, cyclopropyl or difluorocyclobutyl (particularly 3,3-difluorocyclobutyl), fluorocyclobutyl (particularly 1-fluorocyclobutyl), fluorocyclopropyl); or (II) a $C_{7-16}$ aralkyl group (particularly benzyl) optionally having 1 to 3 (preferably 1 or 2) substituents each selected from (a) a halogen atom (particularly fluorine or chlorine)

(b) an optionally halogenated $C_{1-6}$ alkyl group (particularly trifluoromethyl), and (c) an optionally halogenated $C_{1-6}$ alkoxy group (particularly difluoromethoxy or trifluoromethoxy).

$R^2$ is still more preferably (I) a $C_{1-6}$ alkyl group (particularly methyl) optionally having 1 to 3 (preferably 1) five- or six-membered monocyclic aromatic heterocyclic groups (particularly oxadiazolyl (preferably 1,2,4-oxadiazolyl or 1,3,4-oxadiazolyl), thiadiazolyl (preferably 1,2,4-thiadiazolyl), isoxazolyl) optionally having 1 to 3 (preferably 1) optionally halogenated $C_{1-6}$ alkyl groups (particularly methyl, difluoromethyl, difluoroethyl, fluoroisopropyl or fluoroethyl); or (II) an optionally halogenated $C_{7-16}$ aralkyl (particularly difluorobenzyl (preferably 3,5-difluorobenzyl)).

$R^2$ is even more preferably a $C_{1-6}$ alkyl group (particularly methyl) having 1 to 3 (preferably 1) five- or six-membered monocyclic aromatic heterocyclic groups (particularly oxadiazolyl (preferably 1,2,4-oxadiazolyl or 1,3,4-oxadiazolyl), thiadiazolyl (preferably 1,2,4-thiadiazolyl), isoxazolyl) having 1 to 3 (preferably 1) halogenated $C_{1-6}$ alkyl groups (particularly methyl, difluoromethyl, difluoroethyl, fluoroisopropyl or fluoroethyl).

$R^6$ is preferably a hydrogen atom.

$R^7$ is preferably a hydrogen atom.

$R^6$ and $R^7$ are preferably each a hydrogen atom.

Ring A is preferably a bicyclic aromatic heterocyclic ring selected from the formulas (1), (2), (3) and (4).

Ring A is more preferably a bicyclic aromatic heterocyclic ring represented by the formula (1).

As preferable examples of $R^3$, $R^4$ and $R^5$, in particular, $R^3$ is a hydrogen atom;

$R^4$ is (I) a hydrogen atom, (II) a halogen atom (particularly chlorine atom), (III) an optionally halogenated $C_{1-6}$ alkoxy group (particularly methoxy, fluoromethoxy, difluoromethoxy or ethoxy), or (IV) an amino group optionally monosubstituted or disubstituted with a $C_{1-6}$ alkyl group (particularly methyl);

$R^5$ is (I) a hydrogen atom, (II) a halogen atom (particularly chlorine), (III) a cyano group, (IV) a $C_{1-6}$ alkyl group (particularly methyl, ethyl or isopropyl) optionally having 1 to 5 (particularly 1 or 2) substituents each selected from (a) a halogen atom (particularly fluorine), (b) a $C_{1-6}$ alkoxy group (particularly methoxy), (c) a $C_{1-6}$ alkoxy-$C_{1-6}$ alkoxy group, and (e) a $C_{1-6}$ alkyl-carbonyloxy group (particularly, 2,2-dimethylpropanoyloxy), (V) a $C_{1-6}$ alkoxy group (particularly methoxy), (VI) a $C_{2-6}$ alkenyl group (particular 1-propenyl or ethenyl) optionally having 1 to 3 (particularly 1) $C_{1-6}$ alkoxy groups (particularly methoxy), (VII) a $C_{2-6}$ alkynyl group (particularly ethynyl), (VIII) a cyano-$C_{6-14}$ aryl group (particularly cyano-phenyl), (IX) a five- to fourteen-membered aromatic heterocyclic group (particularly five- or six-membered monocyclic aromatic heterocyclic group (preferably pyrazolyl, isoxazolyl or pyridyl)) optionally having 1 or 2 $C_{1-6}$ alkyl groups (particularly methyl or ethyl) optionally having 1 to 3 substituents each selected from (a) a halogen atom (particularly fluorine atom), (b) a five- to six-membered monocyclic aromatic heterocyclic group (particularly pyridyl), and (c) a three- to eight-membered monocyclic nonaromatic heterocyclic group (particularly morpholinyl), (X) a $C_{1-6}$ alkyl-carbonyl group (particularly acetyl), (XI) a hydroxy group, (XII) a $C_{1-6}$ alkyl-five- to fourteen-membered aromatic heterocyclic oxy group (particularly methylpyrazolyloxy), (XIII) a three- to eight-membered monocyclic nonaromatic heterocyclic group (particularly pyrrolidinyl, dihydropyranyl (preferably 3,6-dihydropyranyl), azetidinyl, oxetanyl or tetrahydropyranyl) optionally having 1 to 3 substituents each selected from (a) a halogen atom (particularly fluorine), (b) a $C_{1-6}$ alkoxy group (particularly methoxy), and (c) an oxo group, or (XIV) an amino group (particularly 2,2-difluoroethylamino) optionally monosubstituted or disubstituted with an optionally halogenated $C_{1-6}$ alkyl.

As preferable examples of $R^3$, $R^4$ and $R^5$, 1) ring A is a bicyclic aromatic heterocyclic ring of the formula (1), $R^3$ is a hydrogen atom, $R^4$ is a hydrogen atom or a $C_{1-6}$ alkoxy group (particularly methoxy or ethoxy), and $R^5$ is a hydrogen atom; or 2) ring A is a bicyclic aromatic heterocyclic ring of the formula (2), $R^3$ is a hydrogen atom, and $R^5$ is (I) a hydrogen atom, (II) a halogen atom (particularly chlorine), (III) a cyano group, (IV) a $C_{1-6}$ alkyl group (particularly methyl, ethyl or isopropyl) optionally having 1 to 5 (particularly 1 or 2) substituents each selected from (a) a halogen atom (particularly fluorine), (b) a $C_{1-6}$ alkoxy group (particularly methoxy), (c) a $C_{1-6}$ alkoxy-$C_{1-6}$ alkoxy group (particularly methoxy-ethoxy), (d) a hydroxy group, and
(e) a $C_{1-6}$ alkyl-carbonyloxy group (particularly, 2,2-dimethylpropanoyloxy),
(V) a $C_{1-6}$ alkoxy group (particularly methoxy),
(VI) a $C_{2-6}$ alkenyl group (particular 1-propenyl or ethenyl) optionally having 1 to 3 (particularly 1) $C_{1-6}$ alkoxy groups (particularly methoxy),
(VII) a $C_{2-6}$ alkynyl group (particularly ethynyl),
(VIII) a cyano-$C_{6-14}$ aryl group (particularly cyano-phenyl),
(IX) a five- to fourteen-membered aromatic heterocyclic group (particularly five- or six-membered monocyclic aromatic heterocyclic group (preferably pyrazolyl, isoxazolyl or pyridyl)) optionally having 1 or 2 $C_{1-6}$ alkyl groups (particularly methyl or ethyl) optionally having 1 to 3 substituents each selected from
(a) a halogen atom (particularly fluorine atom),
(b) a five- to six-membered monocyclic aromatic heterocyclic group (particularly pyridyl), and
(c) a three- to eight-membered monocyclic nonaromatic heterocyclic group (particularly morpholinyl),
(X) a $C_{1-6}$ alkyl-carbonyl group (particularly acetyl),
(XI) a hydroxy group,
(XII) a $C_{1-6}$ alkyl-five- to fourteen-membered aromatic heterocyclic oxy group (particularly methylpyrazolyloxy),
(XIII) a three- to eight-membered monocyclic nonaromatic heterocyclic group (particularly pyrrolidinyl, dihydropyranyl (preferably 3,6-dihydropyranyl), azetidinyl, oxetanyl or tetrahydropyranyl) optionally having 1 to 3 substituents each selected from
(a) a halogen atom (particularly fluorine),
(b) a $C_{1-6}$ alkoxy group (particularly methoxy), and
(c) an oxo group, or
(XIV) an amino group (particularly 2,2-difluoroethylamino) optionally monosubstituted or disubstituted with an optionally halogenated $C_{1-6}$ alkyl; or
3) ring A is a bicyclic aromatic heterocyclic ring of the formula (3),
$R^3$ is a hydrogen atom,
$R^4$ is
(I) a hydrogen atom,
(II) a halogen atom (particularly chlorine atom),
(III) an optionally halogenated $C_{1-6}$ alkoxy group (particularly methoxy, fluoromethoxy or difluoromethoxy), or
(IV) an amino group optionally monosubstituted or disubstituted with a $C_{1-6}$ alkyl group (particularly methyl); and
$R^5$ is a hydrogen atom; or
4) ring A is a bicyclic aromatic heterocyclic ring of the formula (4),
$R^3$ is a hydrogen atom,
$R^4$ is a hydrogen atom or a $C_{1-6}$ alkoxy group (particularly methoxy), and
$R^5$ is a hydrogen atom.
As more preferable examples of $R^3$, $R^4$ and $R^5$, in particular,
$R^3$ is a hydrogen atom;
$R^4$ is (a) an amino group optionally monosubstituted or disubstituted with a $C_{1-6}$ alkyl group (particularly methyl), or
(b) a $C_{1-6}$ alkoxy group (particularly methoxy); and
$R^5$ is (a) a $C_{1-6}$ alkoxy group (particularly methoxy), or
(b) a $C_{1-6}$ alkyl group (particularly ethyl) optionally having 1 to 3 hydroxy groups.
As more preferable examples of $R^3$, $R^4$ and $R^5$,
1) ring A is a bicyclic aromatic heterocyclic ring of the formula (1),
$R^3$ is a hydrogen atom,
$R^4$ is a $C_{1-6}$ alkoxy group (particularly methoxy), and
$R^5$ is a hydrogen atom; or
2) ring A is a bicyclic aromatic heterocyclic ring of the formula (2),
$R^3$ is a hydrogen atom, and
$R^5$ is (a) a $C_{1-6}$ alkoxy group (particularly methoxy), or
(b) a $C_{1-6}$ alkyl group (particularly ethyl) optionally having 1 to 3 (preferably 1) hydroxy groups; or
3) ring A is a bicyclic aromatic heterocyclic ring of the formula (3),
$R^3$ is a hydrogen atom,
$R^4$ is (a) an amino group optionally monosubstituted or disubstituted with a $C_{1-6}$ alkyl group (preferably methyl), or
(b) a $C_{1-6}$ alkoxy group (particularly methoxy), and
$R^5$ is a hydrogen atom; or
4) ring A is a bicyclic aromatic heterocyclic ring of the formula (4),
$R^3$ is a hydrogen atom,
$R^4$ is a hydrogen atom or a $C_{1-6}$ alkoxy group (particularly methoxy), and
$R^5$ is a hydrogen atom.
More preferably, ring A is a bicyclic aromatic heterocyclic ring represented by the following formula (1)

[Chemical formula 3]

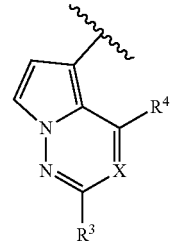

(1)

X is N,
$R^1$ is a hydrogen atom, and
$R^4$ is a $C_{1-6}$ alkoxy group (particularly methoxy).
Preferred specific examples of the compound (I) include the following.
Compound (A) which is a compound of the formula (I) or a salt thereof, wherein
$R^1$ is
(I) a $C_{1-6}$ alkyl group (particularly methyl or ethyl) optionally having 1 to 5 substituents each selected from
(a) a halogen atom (particularly fluorine atom),
(b) a hydroxy group,
(c) a cyano group,
(d) a $C_{1-6}$ alkoxy group (particularly methoxy or ethoxy) optionally having 1 to 3 substituents each selected from
(i) a halogen atom (particularly fluorine atom), and
(ii) a hydroxy group, and
(e) a three- to eight-membered nonaromatic heterocyclic group (particularly azetidinyl) having 1 to 3 halogen atoms (particularly fluorine atoms);
(II) a three- to eight-membered nonaromatic heterocyclic group (particularly azetidinyl or pyrrolidinyl) optionally having 1 to 5 (particularly 1 or 2) substituents each selected from
(a) a $C_{1-6}$ alkoxy group (particularly methoxy)
(b) a halogen atom (particularly fluorine), and
(c) a hydroxy group;
(III) a five- to fourteen-membered aromatic heterocyclic group (particularly five- or six-membered monocyclic aromatic heterocyclic group (preferably pyrazolyl or oxazolyl)) optionally having 1 to 3 (particularly 1) optionally halogenated $C_{1-6}$ alkyl groups (particularly methyl or difluoromethyl);

(IV) a $C_{1-6}$ alkoxy group (particularly methoxy or ethoxy) optionally having 1 to 5 (particularly 1) substituents each selected from
    (a) a hydroxy group,
    (b) a three- to eight-membered nonaromatic heterocyclic group (particularly tetrahydrofuranyl), and
    (c) a five- or six-membered monocyclic aromatic heterocyclic group optionally having 1 to 3 (particularly 1) optionally halogenated $C_{1-6}$ alkyl groups (particularly methyl or difluoromethyl);

(V) an optionally halogenated $C_{3-10}$ cycloalkyl group (particularly cyclopropyl or difluorocyclobutyl); or (VI) an amino group optionally monosubstituted or disubstituted with a $C_{1-6}$ alkyl group (particularly methyl, ethyl or isobutyl) optionally having 1 to 5 (particularly 1 to 3) substituents each selected from
    (a) (i) a halogen atom (particularly fluorine atom),
    (ii) a hydroxy group, and
    (iii) a $C_{1-6}$ alkoxy group (particularly methoxy);
$R^2$ is
    (I) a $C_{1-6}$ alkyl group (particularly methyl) optionally having 1 to 3 (particularly 1) five- to fourteen-membered aromatic heterocyclic groups (particularly five- or six-membered monocyclic aromatic heterocyclic groups (preferably oxadiazolyl (preferably 1,2,4-oxadiazolyl or 1,3,4-oxadiazolyl), thiadiazolyl (preferably 1,2,4-thiadiazolyl, 1,3,4-thiadiazolyl or 1,2,3-thiadiazolyl), isoxazolyl, isothiazolyl, thiazolyl, triazolyl (preferably 1,2,3-triazolyl or 1,2,4-triazolyl), pyrazinyl, pyrazolyl, pyridyl, pyrimidinyl, oxazolyl or furyl)) optionally having 1 to 3 (particularly 1 or 2) substituents each selected from
    (a) a halogen atom (particularly fluorine or chlorine),
    (b) a $C_{1-6}$ alkyl group (particularly methyl, ethyl, isobutyl, isopropyl or propyl) optionally having 1 to 7 (particularly 1 to 5) substituents each selected from
        (i) a halogen atom (particularly fluorine atom),
        (ii) a hydroxy group, and
        (iii) a $C_{1-6}$ alkoxy group (particularly methoxy),
    (c) an optionally halogenated $C_{3-10}$ cycloalkyl group (particularly, 2,2-difluorocyclopropyl, cyclobutyl, cyclopropyl or difluorocyclobutyl (particularly 3,3-difluorocyclobutyl), fluorocyclobutyl (particularly 1-fluorocyclobutyl), fluorocyclopropyl),
    (d) a $C_{1-6}$ alkoxy group (particularly methoxy),
    (e) a $C_{1-6}$ alkyl group-$C_{3-10}$ cycloalkyl group (particularly methyl-cyclopropyl),
    (f) a $C_{1-6}$ alkyl group-three- to eight-membered monocyclic nonaromatic heterocyclic group (particularly methyl-oxetanyl), and
    (g) oxo group; or (II) a $C_{7-16}$ aralkyl group (particularly benzyl) optionally having 1 to 3 substituents each selected from
    (a) a $C_{1-6}$ alkyl group (methyl or isopropyl) optionally having 1 to 3 substituents each selected from
        (i) a halogen atom (particularly fluorine atom), and
        (ii) a hydroxyl group,
    (b) a $C_{1-6}$ alkoxy-carbonyl group (particularly methoxy-carbonyl),
    (c) a halogen atom (fluorine or chlorine)
    (d) a $C_{1-6}$ alkoxy group (particularly methoxy or ethoxy) optionally having 1 to 3 substituents each selected from
        (i) a halogen atom (particularly fluorine atom), and
        (ii) a hydroxyl group (e) a mono- or di-$C_{1-6}$ alkyl-carbamoyl group (particularly methylcarbamoyl),
    (f) a cyano group,
    (g) an amino group optionally monosubstituted or disubstituted (particularly monosubstituted) with a substituent selected from
        (i) a $C_{1-6}$ alkyl group (particularly methyl), and
        (ii) a $C_{1-6}$ alkoxy-carbonyl group (particularly tert-butoxy-carbonyl),
    (h) a nitro group, and
    (i) a carboxy group;
each of $R^6$ and $R^7$ is a hydrogen atom;
ring A is a bicyclic aromatic heterocyclic ring selected from the formulas (1), (2), (3) and (4);
Xs each independently represents N or $C(R^5)$;
$R^3$ is a hydrogen atom;
$R^4$ is (I) a hydrogen atom,
    (II) a halogen atom (particularly chlorine atom),
    (III) an optionally halogenated $C_{1-6}$ alkoxy group (particularly methoxy, fluoromethoxy, difluoromethoxy or ethoxy), or
    (IV) an amino group optionally monosubstituted or disubstituted with a $C_{1-6}$ alkyl group (particularly methyl);
$R^5$ is (I) a hydrogen atom,
    (II) a halogen atom (particularly chlorine),
    (III) a cyano group,
    (IV) a $C_{1-6}$ alkyl group (particularly methyl, ethyl or isopropyl) optionally having 1 to 5 (particularly 1 or 2) substituents each selected from
        (a) a halogen atom (particularly fluorine),
        (b) a $C_{1-6}$ alkoxy group (particularly methoxy),
        (c) a $C_{1-6}$ alkoxy-$C_{1-6}$ alkoxy group (particularly methoxy-ethoxy),
        (d) a hydroxy group, and
        (e) a $C_{1-6}$ alkyl-carbonyloxy group (particularly, 2,2-dimethylpropanoyloxy),
    (V) a $C_{1-6}$ alkoxy group (particularly methoxy),
    (VI) a $C_{2-6}$ alkenyl group (particular 1-propenyl or ethynyl) optionally having 1 to 3 (particularly 1) $C_{1-6}$ alkoxy groups (particularly methoxy),
    (VII) a $C_{2-6}$ alkynyl group (particularly ethynyl),
    (VIII) a cyano-$C_{6-14}$ aryl group (particularly cyano-phenyl),
    (IX) a five- to fourteen-membered aromatic heterocyclic group (particularly five- or six-membered monocyclic aromatic heterocyclic group (preferably pyrazolyl, isoxazolyl or pyridyl)) optionally having 1 or 2 $C_{1-6}$ alkyl groups (particularly methyl or ethyl) optionally having 1 to 3 substituents each selected from
        (a) a halogen atom (particularly fluorine atom),
        (b) a five- to six-membered monocyclic aromatic heterocyclic group (particularly pyridyl), and
        (c) a three- to eight-membered monocyclic nonaromatic heterocyclic group (particularly morpholinyl),
    (X) a $C_{1-6}$ alkyl-carbonyl group (particularly acetyl),
    (XI) a hydroxy group,
    (XII) a $C_{1-6}$ alkyl-five- to fourteen-membered aromatic heterocyclic oxy group (particularly methylpyrazolyloxy),
    (XIII) a three- to eight-membered monocyclic nonaromatic heterocyclic group (particularly pyrrolidinyl, dihydropyranyl (preferably 3,6-dihydropyranyl), azetidinyl, oxetanyl or tetrahydropyranyl) optionally having 1 to 3 substituents each selected from
        (a) a halogen atom (particularly fluorine),
        (b) a $C_{1-6}$ alkoxy group (particularly methoxy), and
        (c) an oxo group, or (XIV) an amino group (particularly 2,2-difluoroethyl-amino) optionally monosubstituted or disubstituted with an optionally halogenated $C_{1-6}$ alkyl.

Compound (A') which is the compound (A), wherein
1) ring A is a bicyclic aromatic heterocyclic ring of the formula (1),
$R^3$ is a hydrogen atom,
$R^4$ is a hydrogen atom or a $C_{1-6}$ alkoxy group (particularly methoxy or ethoxy),
$R^5$ is a hydrogen atom; or
2) ring A is a bicyclic aromatic heterocyclic ring of the formula (2),
$R^3$ is a hydrogen atom,
$R^5$ is
(I) a hydrogen atom,
(II) a halogen atom (particularly chlorine),
(III) a cyano group,
(IV) a $C_{1-6}$ alkyl group (particularly methyl, ethyl or isopropyl) optionally having 1 to 5 (particularly 1 or 2) substituents each selected from
(a) a halogen atom (particularly fluorine)
(b) a $C_{1-6}$ alkoxy group (particularly methoxy)
(c) a $C_{1-6}$ alkoxy-$C_{1-6}$ alkoxy group (particularly methoxy-ethoxy)
(d) a hydroxy group, and
(e) a $C_{1-6}$ alkyl-carbonyloxy group (particularly, 2,2-dimethylpropanoyloxy),
(V) a $C_{1-6}$ alkoxy group (particularly methoxy),
(VI) a $C_{2-6}$ alkenyl group (particular 1-propenyl or ethynyl) optionally having 1 to 3 (particularly 1) $C_{1-6}$ alkoxy groups (particularly methoxy),
(VII) a $C_{2-6}$ alkynyl group (particularly ethynyl),
(VIII) a cyano-$C_{6-14}$ aryl group (particularly cyano-phenyl),
(IX) a five- to fourteen-membered aromatic heterocyclic group (particularly five- or six-membered monocyclic aromatic heterocyclic group (preferably pyrazolyl, isoxazolyl or pyridyl)) optionally having 1 or 2 $C_{1-6}$ alkyl groups (particularly methyl or ethyl) optionally having 1 to 3 substituents each selected from
(a) a halogen atom (particularly fluorine atom),
(b) a five- to six-membered monocyclic aromatic heterocyclic group (particularly pyridyl), and
(c) a three- to eight-membered monocyclic nonaromatic heterocyclic group (particularly morpholinyl),
(X) a $C_{1-6}$ alkyl-carbonyl group (particularly acetyl),
(XI) a hydroxy group,
(XII) a $C_{1-6}$ alkyl-five- to fourteen-membered aromatic heterocyclic oxy group (particularly methyl pyrazolyloxy),
(XIII) a three- to eight-membered monocyclic nonaromatic heterocyclic group (particularly pyrrolidinyl, dihydropyranyl (preferably 3,6-dihydropyranyl), azetidinyl, oxetanyl or tetrahydropyranyl) optionally having 1 to 3 substituents each selected from
(a) a halogen atom (particularly fluorine),
(b) a $C_{1-6}$ alkoxy group (particularly methoxy), and
(c) an oxo group, or
(XIV) an amino group (particularly 2,2-difluoroethyl-amino) optionally monosubstituted or disubstituted with an optionally halogenated $C_{1-6}$ alkyl; or
3) ring A is a bicyclic aromatic heterocyclic ring of the formula (3),
$R^1$ is a hydrogen atom,
$R^4$ is
(I) a hydrogen atom,
(II) a halogen atom (particularly chlorine atom),
(III) an optionally halogenated $C_{1-6}$ alkoxy group (particularly methoxy, fluoromethoxy or difluoromethoxy), or
(IV) an amino group optionally monosubstituted or disubstituted with a $C_{1-6}$ alkyl group (particularly methyl); and
$R^5$ is a hydrogen atom; or
4) ring A is a bicyclic aromatic heterocyclic ring of the formula (4),
$R^3$ is a hydrogen atom,
$R^4$ is a hydrogen atom or a $C_{1-6}$ alkoxy group (particularly methoxy), and
$R^5$ is a hydrogen atom.

Compound (B) which is the compound (A), wherein
$R^1$ is
(I) a $C_{1-6}$ alkyl group (particularly methyl) optionally having 1 to 3 substituents each selected from
(a) a $C_{1-6}$ alkoxy group (particularly methoxy), and
(b) a hydroxy group;
(II) a three- to fourteen-membered nonaromatic heterocyclic group (particularly azetidinyl);
(III) a $C_{1-6}$ alkoxy group (particularly methoxy or ethoxy); or
(IV) an amino group;
$R^2$ is
(I) a $C_{1-6}$ alkyl group (particularly methyl) optionally having 1 to 3 (preferably 1) five- or six-membered monocyclic aromatic heterocyclic groups (particularly oxadiazolyl (preferably 1,2,4-oxadiazolyl or 1,3,4-oxadiazolyl), thiadiazolyl (preferably 1,2,4-thiadiazolyl, 1,3,4-thiadiazolyl or 1,2,3-thiadiazolyl), isoxazolyl, thiazolyl, triazolyl (preferably 1,2,3-triazolyl or 1,2,4-triazolyl), pyrazinyl, pyrazolyl, pyridyl, pyrimidinyl or oxazolyl) optionally having 1 to 3 (preferably 1) substituents each selected from
(a) a halogen atom (particularly fluorine),
(b) an optionally halogenated $C_{1-6}$ alkyl group (particularly methyl, difluoromethyl, trifluoromethyl, ethyl, difluoroethyl (particularly 1,1-difluoroethyl), 2,2,2-trifluoroethyl, isopropyl, 1-fluoroisopropyl or 1-fluoroethyl), and
(c) an optionally halogenated $C_{3-10}$ cycloalkyl group (particularly, 2,2-difluorocyclopropyl, cyclobutyl, cyclopropyl or difluorocyclobutyl (particularly 3,3-difluorocyclobutyl), fluorocyclobutyl (particularly 1-fluorocyclobutyl), fluorocyclopropyl); or
(II) a $C_{7-16}$ aralkyl group (particularly benzyl) optionally having 1 to 3 (preferably 1 or 2) substituents each selected from
(a) a halogen atom (particularly fluorine or chlorine)
(b) an optionally halogenated $C_{1-6}$ alkyl group (particularly trifluoromethyl), and
(c) an optionally halogenated $C_{1-6}$ alkoxy group (particularly difluoromethoxy or trifluoromethoxy);
$R^3$ is a hydrogen atom;
$R^4$ is (a) an amino group optionally monosubstituted or disubstituted with a $C_{1-6}$ alkyl group (particularly methyl), or
(b) a $C_{1-6}$ alkoxy group (particularly methoxy); and
$R^5$ is (a) a $C_{1-6}$ alkoxy group (particularly methoxy), or
(b) a $C_{1-6}$ alkyl group (particularly ethyl) optionally having 1 to 3 hydroxy groups.

Compound (B') which is the compound (B), wherein
1) ring A is a bicyclic aromatic heterocyclic ring of the formula (1),
$R^3$ is a hydrogen atom,
$R^4$ is a $C_{1-6}$ alkoxy group (particularly methoxy), and
$R^5$ is a hydrogen atom; or
2) ring A is a bicyclic aromatic heterocyclic ring of the formula (2), $R^3$ is a hydrogen atom, and
$R^5$ is (a) a $C_{1-6}$ alkoxy group (particularly methoxy), or
(b) a $C_{1-6}$ alkyl group (particularly ethyl) optionally having 1 to 3 (preferably 1) hydroxy groups; or
3) ring A is a bicyclic aromatic heterocyclic ring of the formula (3),
$R^3$ is a hydrogen atom,
$R^4$ is (a) an amino group optionally monosubstituted or disubstituted with a $C_{1-6}$ alkyl group (preferably methyl), or
(b) a $C_{1-6}$ alkoxy group (particularly methoxy), and
$R^5$ is a hydrogen atom; or
4) ring A is a bicyclic aromatic heterocyclic ring of the formula (4), $R^3$ is a hydrogen atom, $R^4$ is a hydrogen atom or a $C_{1-6}$ alkoxy group (particularly methoxy), and $R^5$ is a hydrogen atom.

Compound (C) which is the compound (B), wherein
$R^1$ is a $C_{1-6}$ alkyl group (particularly methyl) optionally having 1 to 3 (preferably 1) hydroxy groups;
$R^2$ is
(1) a $C_{1-6}$ alkyl group (particularly methyl) optionally having 1 to 3 (preferably 1) five- or six-membered monocyclic aromatic heterocyclic groups (particularly oxadiazolyl (preferably 1,2,4-oxadiazolyl or 1,3,4-oxadiazolyl), thiadiazolyl (preferably 1,2,4-thiadiazolyl), isoxazolyl) optionally having 1 to 3 (preferably 1) optionally halogenated $C_{1-6}$ alkyl groups (particularly methyl, difluoromethyl, difluoroethyl, fluoroisopropyl or fluoroethyl); or
(II) an optionally halogenated $C_{7-16}$ aralkyl group (particularly difluorobenzyl (preferably 3,5-difluorobenzyl));
ring A is a bicyclic aromatic heterocyclic ring represented by the following formula (1)

[Chemical formula 4]

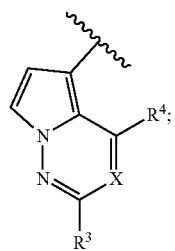

(1)

X is N;
$R^1$ is a hydrogen atom;
$R^4$ is a $C_{1-6}$ alkoxy group (particularly methoxy).

In the compound (C), it is more preferable that $R^2$ is a $C_{1-6}$ alkyl group (particularly methyl) having 1 to 3 (preferably 1) five- or six-membered monocyclic aromatic heterocyclic groups (particularly oxadiazolyl (preferably 1,2,4-oxadiazolyl or 1,3,4-oxadiazolyl), thiadiazolyl (preferably 1,2,4-thiadiazolyl), isoxazolyl) having 1 to 3 (preferably 1) halogenated $C_{1-6}$ alkyl groups (particularly methyl, difluoromethyl, difluoroethyl, fluoroisopropyl or fluoroethyl).

The salt of the compound (I) is preferably a pharmacologically acceptable salt. Examples thereof include a salt with an inorganic base, a salt with an organic base, a salt with an inorganic acid, a salt with an organic acid and a salt with a basic or acidic amino acid.

Preferable examples of the salt with an inorganic base include: an alkali metal salt such as sodium salt, potassium salt and the like; an alkaline earth metal salt such as calcium salt, magnesium salt and the like; and an aluminum salt and an ammonium salt.

Preferable examples of the salt with an organic base include a salt with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine or N,N-dibenzylethylenediamine.

Preferable examples of the salt with an inorganic acid include a salt with hydrochloric acid, hydrobromic acid, nitric acid, sulfuric acid or phosphoric acid.

Preferable examples of the salt with an organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid or p-toluenesulfonic acid.

Preferable examples of the salt with a basic amino acid include a salt with arginine, lysine or ornithine.

Preferable examples of the salt with an acidic amino acid include a salt with aspartic acid or glutamic acid.

The method for producing the compound of the present invention will be described below.

A starting material or a reagent used in each step in the production method given below and the obtained compound may each form a salt. Examples of such a salt include the same as the aforementioned salt of the compound of the present invention, and the like.

When the compound obtained in each step is a free compound, this compound can be converted to a salt of interest by a method known per se in the art. On the contrary, when the compound obtained in each step is a salt, this salt can be converted to a free form or another type of salt of interest by a method known per se in the art.

The compound obtained in each step may be used in the next reaction in the form of its reaction solution or after being obtained as a crude product. Alternatively, the compound obtained in each step can be isolated and/or purified from the reaction mixture by a separation approach such as concentration, crystallization, recrystallization, distillation, solvent extraction, fractionation, chromatography or the like according to a routine method.

If a starting material or a reagent compound for each step is commercially available, the commercially available product can be used directly.

In the reaction of each step, the reaction time may differ depending on the reagent or the solvent used and is usually 1 minute to 48 hours, preferably 10 minutes to 8 hours, unless otherwise specified.

In the reaction of each step, the reaction temperature may differ depending on the reagent or the solvent used and is usually −78° C. to 300° C., preferably −78° C. to 150° C., unless otherwise specified.

In the reaction of each step, the pressure may differ depending on the reagent or the solvent used and is usually 1 atm to 20 atm, preferably 1 atm to 3 atm, unless otherwise specified.

In the reaction of each step, a microwave synthesis apparatus, for example, Initiator manufactured by Biotage Japan Ltd., may be used. The reaction temperature may differ depending on the reagent or the solvent used and is usually room temperature to 300° C., preferably 50° C. to 250° C., unless otherwise specified. The reaction time may differ depending on the reagent or the solvent used and is usually 1 minute to 48 hours, preferably 1 minute to 8 hours, unless otherwise specified.

In the reaction of each step, the reagent is used at 0.5 equivalents to 20 equivalents, preferably 0.8 equivalents to 5 equivalents, with respect to the substrate, unless otherwise specified. In the case of using the reagent as a catalyst, the reagent is used at 0.001 equivalents to 1 equivalent, preferably 0.01 equivalents to 0.2 equivalents, with respect to the substrate. When the reagent also serves as a reaction solvent, the reagent is used in the amount of the solvent.

In the reaction of each step, this reaction is carried out without a solvent or by dissolution or suspension in an appropriate solvent, unless otherwise specified. Specific examples of the solvent include a solvent described in Examples and the following:
alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
acid anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like; and
water.

Two or more of these solvents may be used as a mixture at an appropriate ratio.

In the case of using a base in the reaction of each step, for example, the following base or a base described in Examples is used:
inorganic bases: sodium hydroxide, magnesium hydroxide, sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like; alkali metal hydrides: sodium hydride and the like;
metal amides: sodium amide, lithium diisopropylamide, lithium hexamethyldisilazide and the like; and
organic lithiums: n-butyllithium and the like.

In the case of using an acid or an acidic catalyst in the reaction of each step, for example, the following acid or acidic catalyst or an acid or an acidic catalyst described in Examples is used:
inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like; and
Lewis acids: boron trifluoride-diethyl ether complex, zinc iodide, anhydrous aluminum chloride, anhydrous zinc chloride, anhydrous iron chloride and the like.

The reaction of each step is carried out according to a method known per se in the art, for example, a method described in The Fifth Series of Experimental Chemistry, Vol. 13 to Vol. 19 (edited by The Chemical Society of Japan); Shin Jikken Kagaku Koza (New Experimental Chemistry in English), Vol. 14 to Vol. 15 (edited by The Chemical Society of Japan); Syntheses in the Organic Chemistry Laboratory, Revised, 2nd Ed. (L. F. Tietze, Th. Eicher, Nankodo Co., Ltd.); Organic Name Reactions; The Reaction Mechanism and Essence, Revised (Hideo Tougo, Kodansha Ltd.); Organic Syntheses Collective Volume I to VII (John Wiley & Sons, Inc.); Modern Organic Synthesis in the Laboratory: A Collection of Standard Experimental Procedures (Jie Jack Li, Oxford University Press); Comprehensive Heterocyclic Chemistry III, Vol. 1 to Vol. 14 (Elsevier Japan KK); Strategic Applications of Named Reactions in Organic Synthesis (translated by Kiyoshi Tomioka, published by Kagaku-Dojin Publishing Company, Inc.); Comprehensive Organic Transformations (VCH Publishers, Inc.) (1989), etc., or a method described in Examples, unless otherwise specified.

In each step, the protection or deprotection reaction of a functional group is carried out according to a method known per se in the art, for example, a method described in "Protective Groups in Organic Synthesis, 4th Ed." (Theodora W. Greene, Peter G. M. Wuts), Wiley-Interscience (2007); "Protecting Groups, 3rd Ed." (P. J. Kocienski) Thieme Medical Publishers (2004), etc., or a method described in Examples.

Examples of a protective group for a hydroxy group in an alcohol or a phenolic hydroxy group or the like include: an ether-type protective group such as methoxymethyl ether, benzyl ether, tert-butyldimethylsilyl ether, tetrahydropyranyl ether and the like; a carboxylic acid ester-type protective group such as acetic acid ester and the like; a sulfonic acid ester-type protective group such as methanesulfonic acid ester and the like; a carbonic acid ester-type protective group such as tert-butyl carbonate and the like; and the like.

Examples of a protective group for a carbonyl group in an aldehyde include: an acetal-type protective group such as dimethylacetal and the like; a cyclic acetal-type protective group such as 1,3-dioxane and the like; and the like.

Examples of a protective group for a carbonyl group in a ketone include: a ketal-type protective group such as dimethylketal and the like; a cyclic ketal-type protective group such as 1,3-dioxane and the like; an oxime-type protective group such as O-methyloxime and the like; a hydrazone-type protective group such as N,N-dimethylhydrazone and the like; and the like.

Examples of a protective group for a carboxyl group include: an ester-type protective group such as methyl ester and the like; an amide-type protective group such as N,N-dimethylamide and the like; and the like Examples of a protective group for a thiol include: an ether-type protective group such as benzyl thioether and the like; an ester-type protective group such as thioacetic acid ester, thiocarbonate, thiocarbamate and the like; and the like.

Examples of a protective group for an amino group or an aromatic heterocycle such as imidazole, pyrrole, indole or the like include: a carbamate-type protective group such as benzyl carbamate and the like; an amide-type protective group such as acetamide and the like; an alkylamine-type protective group such as N-triphenylmethylamine and the like; a sulfonamide-type protective group such as methanesulfonamide and the like; and the like.

These protective groups can be removed by use of a method known per se in the art, for example, a method using an acid, a base, ultraviolet light, hydrazine, phenylhydrazine, sodium N-methyldithiocarbamate, tetrabutylammonium fluoride, palladium acetate or trialkylsilyl halide (e.g., trimethylsilyl iodide, trimethylsilyl bromide) or a reduction method.

In the case of carrying out reduction reaction in each step, examples of the reducing agent used include: metal hydrides such as lithium aluminum hydride, sodium triacetoxyborohydride, sodium cyanoborohydride, diisobutyl aluminum hydride (DIBAL-H), sodium borohydride, tetramethylammonium triacetoxyborohydride and the like; boranes such as a borane-tetrahydrofuran complex and the like; Raney nickel; Raney cobalt; hydrogen; formic acid; triethylsilane and the like. In the case of reducing a carbon-carbon double bond or triple bond, a method using a catalyst such as palladium-carbon, a Lindlar's catalyst or the like can be used.

In the case of carrying out oxidation reaction in each step, examples of the oxidizing agent used include: peracids such as m-chloroperbenzoic acid (mCPBA), hydrogen peroxide, tert-butyl hydroperoxide and the like; perchlorates such as tetrabutylammonium perchlorate and the like; chlorates such as sodium chlorate and the like; chlorites such as sodium chlorite and the like; periodates such as sodium periodate and the like; a high-valent iodine reagent such as iodosylbenzene and the like; a reagent having manganese, such as manganese dioxide, potassium permanganate and the like; leads such as lead tetraacetate and the like; a reagent having chromium, such as pyridinium chlorochromate (PCC), pyridinium dichromate (PDC), Jones reagents and the like; halogen compounds such as N-bromosuccinimide (NBS) and the like; oxygen; ozone; a sulfur trioxide-pyridine complex; osmium tetroxide; selenium dioxide; 2,3-dichloro-5,6-dicyano-1,4-benzoquinone (DDQ); and the like.

In the case of carrying out radical cyclization reaction in each step, examples of the radical initiator used include: an azo compound such as azobisisobutyronitrile (AIBN) and the like; a water-soluble radical initiator such as 4-4'-azobis-4-cyanopentanoic acid (ACPA) and the like; triethylboron in the presence of air or oxygen; benzoyl peroxide; and the like. Examples of the radical reaction agent used include tributylstannane, tris(trimethylsilyl)silane, 1,1,2,2-tetraphenyldisilane, diphenylsilane, samarium iodide and the like.

In the case of carrying out Wittig reaction in each step, examples of the Wittig reagent used include alkylidenephosphoranes and the like. The alkylidenephosphoranes can be prepared by a method known per se in the art, for example, the reaction between a phosphonium salt and a strong base.

In the case of carrying out Horner-Emmons reaction in each step, examples of the reagent used include: phosphonoacetic acid esters such as methyl dimethylphosphonoacetate, ethyl diethylphosphonoacetate and the like; and a base such as alkali metal hydrides, organic lithiums and the like.

In the case of carrying out Friedel-Crafts reaction in each step, examples of the reagent used include a combination of a Lewis acid and an acid chloride and a combination of a Lewis acid and an alkylating agent (e.g., alkyl halides, alcohols, olefins, etc.). Alternatively, an organic acid or an inorganic acid may be used instead of the Lewis acid, and an acid anhydride such as acetic anhydride or the like may be used instead of the acid chloride.

In the case of carrying out aromatic nucleophilic substitution reaction in each step, a nucleophile (e.g., amines, imidazole, etc.) and a base (e.g., organic bases, etc.) are used as reagents.

In the case of carrying out nucleophilic addition reaction using a carbanion, nucleophilic 1,4-addition reaction (Michael addition reaction) using a carbanion or nucleophilic substitution reaction using a carbanion in each step, examples of the base used for generating the carbanion include organic lithiums, metal alkoxides, inorganic bases, organic bases and the like.

In the case of carrying out Grignard reaction in each step, examples of the Grignard reagent include: aryl magnesium halides such as phenyl magnesium bromide and the like; and alkyl magnesium halides such as methyl magnesium bromide and the like. The Grignard reagent can be prepared by a method known per se in the art, for example, the reaction between alkyl halide or aryl halide and metal magnesium with ether or tetrahydrofuran as a solvent.

In the case of carrying out Knoevenagel condensation reaction in each step, an active methylene compound sandwiched by two electron-attracting groups (e.g., malonic acid, diethyl malonate, malononitrile, etc.) and a base (e.g., organic bases, metal alkoxides, inorganic bases) are used as reagents.

In the case of carrying out Vilsmeier-Haack reaction in each step, phosphoryl chloride and an amide derivative (e.g., N,N-dimethylformamide, etc.) are used as reagents.

In the case of carrying out azidation reaction of alcohols, alkyl halides or sulfonic acid esters in each step, examples of the azidating agent used include diphenylphosphorylazide (DPPA), trimethylsilylazide, sodium azide and the like. In the case of azidating, for example, alcohols, a method using diphenylphosphorylazide and 1,8-diazabicyclo[5.4.0]undec-7-ene (DBU), a method using trimethylsilylazide and a Lewis acid, or the like can be used.

In the case of carrying out reductive amination reaction in each step, examples of the reducing agent used include sodium triacetoxyborohydride, sodium cyanoborohydride, hydrogen, formic acid and the like. When the substrate is an amine compound, examples of the carbonyl compound used include paraformaldehyde as well as aldehydes such as acetaldehyde and the like, and ketones such as cyclohexanone and the like. When the substrate is a carbonyl compound, examples of the amines used include: ammonia; primary amine such as methylamine and the like; secondary amine such as dimethylamine and the like; and the like.

In the case of carrying out Mitsunobu reaction in each step, azodicarboxylic acid esters (e.g., diethyl azodicarboxylate (DEAD), diisopropyl azodicarboxylate (DIAD), etc.) and triphenylphosphine are used as reagents.

In the case of carrying out esterification reaction, amidation reaction or ureation reaction in each step, examples of the reagent used include: an acyl halide form such as acid chloride, acid bromide and the like; and activated carboxylic acids such as an acid anhydride, an active ester form, a sulfuric acid ester form and the like. Examples of the activating reagent for carboxylic acid include: a carbodiimide condensing agent such as 1-ethyl-3-(3-dimethylaminopropyl)carbodiimide hydrochloride (WSCD) and the like; a triazine condensing agent such as 4-(4,6-dimethoxy-1,3,5-triazin-2-yl)-4-methylmorpholinium chloride-n-hydrate (DMT-MM) and the like; a carbonic acid ester condensing agent such as 1,1-carbonyldiimidazole (CDI) and the like; diphenylphosphorylazide (DPPA); benzotriazol-1-yloxytrisdimethyl aminophosphonium salt (BOP reagent); 2-chloro-1-methyl-pyridinium iodide (Mukaiyama reagent); thionyl chloride; lower alkyl haloformate such as ethyl chloroformate and the like; O-(7-azabenzotriazol-1-yl)-N,N,N',N'-tetramethyluronium hexafluorophosphate (HATU); sulfuric acid; and combinations thereof; and the like. In the case of using a carbodiimide condensing agent, an additive such as 1-hydroxybenzotriazole (HOBt), N-hydroxysuccinimide (HOSu), dimethylaminopyridine (DMAP) or the like may be further added for the reaction.

In the case of carrying out coupling reaction in each step, examples of the metal catalyst used include: a palladium compound such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride, palladium(II) acetate and the like; a nickel compound such as tetrakis(triphenylphosphine)nickel(0) and the like; a rhodium compound such as tris(triphenylphosphine)rhodium (III) chloride and the like; a cobalt compound; a copper compound such as copper oxide, copper(I) iodide and the like; a platinum compound; and the like. A base may be further added for the reaction. Examples of such a base include inorganic base and the like.

In the case of carrying out thiocarbonylation reaction in each step, diphosphorus pentasulfide is typically used as a thiocarbonylating agent. A reagent having a 1,3,2,4-dithiadiphosphetane-2,4-di sulfide structure such as 2,4-bis(4-methoxyphenyl-1,3,2,4-dithiadiphosphetane-2,4-disulfide (Lawesson's reagent) or the like may be used instead of diphosphorus pentasulfide.

In the case of carrying out Wohl-Ziegler reaction in each step, examples of the halogenating agent used include N-iodosuccinimide, N-bromosuccinimide (NBS), N-chlorosuccinimide (NCS), bromine, sulfuryl chloride and the like. The reaction can be accelerated by the further addition of a radical initiator such as heat, light, benzoyl peroxide, azobisisobutyronitrile or the like for the reaction.

In the case of carrying out halogenation reaction of a hydroxy group in each step, examples of the halogenating agent used include a hydrohalic acid and an acid halide of an inorganic acid, specifically, hydrochloric acid, thionyl chloride, phosphorus oxychloride and the like for chlorination, and 48% hydrobromic acid and the like for bromination. Also, a method for obtaining an alkyl halide form from an alcohol by the action of triphenylphosphine and carbon tetrachloride or carbon tetrabromide or the like may be used. Alternatively, a method for synthesizing an alkyl halide form through 2-step reactions like involving the conversion of an alcohol to sulfonic acid ester and the subsequent reaction with lithium bromide, lithium chloride or sodium iodide may be used.

In the case of carrying out Arbuzov reaction in each step, examples of the reagent used include: alkyl halides such as ethyl bromoacetate and the like; and phosphites such as triethyl phosphite, tri(isopropyl)phosphite and the like.

In the case of carrying out sulfonic acid esterification reaction in each step, examples of the sulfonylating agent used include methanesulfonyl chloride, p-toluenesulfonyl chloride, methanesulfonic anhydride, p-toluenesulfonic anhydride and the like.

In the case of carrying out hydrolysis reaction in each step, an acid or a base is used as a reagent. In the case of carrying out acid hydrolysis reaction of tert-butyl ester, formic acid, triethylsilane or the like may be added for reductively trapping a by-product tert-butyl cation.

In the case of carrying out dehydration reaction in each step, examples of the dehydrating agent used include sulfuric acid, diphosphorus pentoxide, phosphorus oxychloride, N,N'-dicyclohexylcarbodiimide, alumina, polyphosphoric acid and the like.

In the case of carrying out alkylation reaction in each step, examples of the alkylating agent include optionally substituted alkyl halide (e.g., iodomethane), optionally substituted alkyl having an optionally substituted $C_{1-6}$ alkylsulfonyloxy group as a leaving group, optionally substituted alkyl having a $C_{6-14}$ arylsulfonyloxy group optionally substituted by a $C_{1-6}$ alkyl group. Examples of the base used include organic lithiums, metal alkoxides, inorganic bases, organic bases and the like. In order to activate the reaction, an additive such as sodium iodide or a quarternary ammonium salt like tetrabutylammonium iodide (TBAI) may further be added in the reaction.

Examples of the reagent to be used when an acylation reaction is carried out in each step include activated carboxylic acids such as acyl halides such as acid chloride and acid bromide, active esters, esters and sulfuric acid esters. Examples of the carboxylic acid activating agent include carbodiimide-based condensing agents such as acid anhydrides (e.g. acetic anhydride) and 1-ethyl-3-(3-dimethylaminopropyl) carbodiimide hydrochloride (WSCD); triazine-based condensing agents such as 4-(4,6-dimethoxy-1,3,5-triazin-2-yl)-4-methylmorpholinium chloride-n-hydrate (DMT-MM); carbonic acid ester-based condensing agents such as 1,1-carbonyldiimidazole (CDI); diphenylphosphoryl azide (DPPA); benzotriazol-1-yloxy-trisdimethylaminophosphonium salts (BOP reagents); 2-chloro-1-methyl-pyridinium iodide (Mukaiyama Reagent); thionyl chloride; haloformic acid lower alkyls such as ethyl chloroformate; O-(7-azabenzotriazol-1-yl)-N,N,N',N'-tetramethyluronium hexafluorophosphate (HATU); sulfuric acid; and combinations thereof. When a carbodiimide-based condensing agent is used, additives such as 1-hydroxybenzotriazole (HOBt), N-hydroxysuccinimide (HOSu), dimethylaminopyridine (DMAP) and the like may be further added to the reaction.

Examples of the halogenating agent to be used when an aromatic compound halogenation reaction is carried out in each step include N-bromosuccinimide (NB S), N-iodosuccinimide (NIS), N-chlorosuccinimide (NCS), 1,3-diiodo-5, 5'-dimethylhydantoin (DIH), dibromoisocyanuric acid (DBI), N-bromophthalimide, N-iodophthalimide, N-chlorophthalimide, N-bromosaccharin, N-iodosaccharin, trimethylphenylammonium tribromide, bromine, iodine and chlorine. Further, by adding a radical initiator such as heat, light, benzoyl peroxide or azobisisobutyronitrile to the reaction, the reaction can be accelerated.

As a reducing agent to be used when a nitro group reduction reaction is carried out in each step, a metal powder of reduced iron, zinc, tin or the like is used in the Bechamp reduction method, and a catalyst such as palladium-carbon or platinum-carbon nickel is used in the catalytic reduction method.

A ligand may be added in a reaction system when a coupling reaction is carried out in each step, and examples of the ligand include phosphine ligands [e.g. triphenylphosphine, 2,2'-bis(diphenylphosphino)-1,1'-binaphthyl, 2-dicyclohexylphosphino-2',6'-diisopropoxy-1,1'-biphenyl, 2-(dicyclohexylphosphino)-3,6-dimethoxy-2',4',6'-triisopropyl-1,1'-biphenyl, 2-di-tert-butylphosphino-3,4,5,6-tetramethyl-2',4',6'-triisopropyl-1,1'-biphenyl, 2-(di-tert-butylphosphino)biphenyl, 2-(dicyclohexylphosphino) biphenyl, 2-dicyclohexylphosphino-2',6'-dimethoxy-1,1'-biphenyl, 2-dicyclohexylphosphino-2',4',6'-triisopropyl-1,1'-biphenyl, 2-(dicyclohexylphosphino)-2'-(N,N-dimethylamino)biphenyl, 1,1'-bis(diphenylphosphino) ferrocene, tri-tert-butylphosphine, tricyclohexylphosphine, 4,5-bis(diphenylphosphino)-9,9-dimethylxanthene], amine ligands (N,N'-dimethylethylenediamine, trans-1,2-diaminocyclohexane, trans-N,N'-dimethyl-1,2-cyclohexanediamine, 1,10-phenanthroline, 4,7-dimethoxy-1,10-phenanthroline, 3,4,7,8-tetramethyl-1,10-phenanthroline and the like), diketone ligands (2-acetylcyclohexanone, 2-isobutyrylhexanone, 2,2,6,6-tetramethyl-3,5-heptanedione and the like), salicylaldoxime, and proline.

Examples of the reagent to be used when an imidazole ring formation reaction is carried out in each step include activated carboxylic acids such as orthocarboxylic acid esters (e.g. trimethyl orthoacetate), N,N-dimethylcarboxylic acid amide dialkyl acetals (e.g. N,N-dimethylacetamide dimethyl acetal), imidate esters (e.g. methyl acetoimidate), acyl halides such as acid chloride and acid bromide, active esters, esters and sulfuric acid esters. Examples of the activating agent when a carboxylic acid is used include carbodiimide-based condensing agents such as propylphosphonic anhydride (cyclic trimer), acid anhydrides (e.g. acetic anhydride) and 1-ethyl-3-(3-dimethyl aminopropyl) carbodiimide hydrochloride (WSCD); triazine-based condensing agents such as 4-(4,6-dimethoxy-1,3,5-triazin-2-yl)-4-methylmorpholinium chloride-n-hydrate (DMT-MM); carbonic acid ester-based condensing agents such as 1,1-carbonyldiimidazole (CDI); diphenylphosphoryl azide (DPPA); benzotriazol-1-yloxy-trisdimethylaminophosphonium salts (BOP reagents); 2-chloro-1-methyl-pyridinium iodide (Mukaiyama Reagent); thionyl chloride; haloformic acid lower alkyls such as ethyl chloroformate; O-(7-azabenzotriazol-1-yl)-N,N,N',N'-tetramethyluronium hexafluorophosphate (HATU); sulfuric acid; and combinations thereof. Additives such as 1-hydroxybenzotriazole (HOBt), N-hydroxysuccinimide (HOSu), dimethylaminopyridine (DMAP), an acid and a base may be further added to the reaction. Alternatively, when an activated carboxylic acid or a carboxylic acid is used, a method may be used in which an imidazole is synthesized through a two-step reaction such that a reaction with an acid or base is carried out after isolation with a carboxylic acid amide.

Examples of the reagent to be used when an alkyne synthesis reaction is carried out in each step include α-diazophosphonate compounds (Seyferth-Gilbert Reagent and Ohira-Bestmann Reagent (e.g. dimethyl (1-diazo-2-oxopropyl)phosphonate acid)), and examples of the base to be used include organic lithiums, metal alkoxides, inorganic bases and organic bases.

Examples of the halogenating agent to be used when a carbonyl group halogenation reaction is carried out in each step include thionyl chloride, phosphorus oxychloride and phosphorus oxybromide. N,N-dimethylformamide may be added to the reaction for the purpose of activating the reaction.

When an aromatic nucleophilic substitution reaction is carried out in each step, alcohols, thiols and salts thereof can be used as nucleophilic agents.

Hereinafter, a method for producing the compound (I), including the reaction formulas, will be described in more detail.

Each symbol in the following reaction schemes has the same meaning as described above unless otherwise specified.

In addition, unless otherwise specified, raw material compounds to be used in the following various production methods can be produced by a method known per se.

The compound (I) has the same meaning as that of the compound represented by the following formula (Id) or a salt thereof.

[Chemical Formula 5]

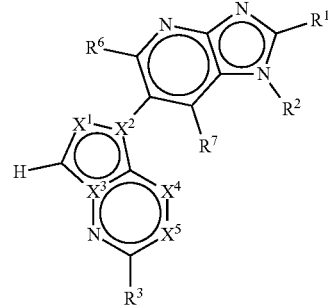

(Id)

[wherein $X^1$, $X^2$, $X^3$, $X^4$ and $X^5$ represent one of the following combinations:

$(X^1, X^2, X^3, X^4, X^5)$=(CH, N, C, $CR^4$, N) (a compound represented by this combination is sometimes referred to as compound A1), (CH, N, C, N, $CR^5$) (a compound represented by this combination is sometimes referred to as compound A2), (CH, N, C, $CR^4$, $CR^5$) (a compound represented by this combination is sometimes referred to as compound A3), (N, N, C, $CR^4$, $CR^5$) (a compound represented by this combination is sometimes referred to as compound A4), (CH, C, N, $CR^4$, N) (a compound represented by this combination is sometimes referred to as compound A5), (N, C, N, $CR^4$, N) (a compound represented by this combination is sometimes referred to as compound A6), and (CH, C, N, $CR^4$, $CR^5$) (a compound represented by this combination is sometimes referred to as compound A7); and each symbol has the same meaning as described above.]

Hereinafter, a method for producing a compound represented by the formula (Id) or a salt thereof will be described.

[Production Method A-1i]

A compound represented by each of the formulae A5 to A7 (compound represented by Ia in the following formula) or a salt thereof, and a compound represented by each of formulae A1 to A4 (compound represented by Ib in the following formula) can be produced from the compound (IIa) by the following method.

[Chemical Formula 6]

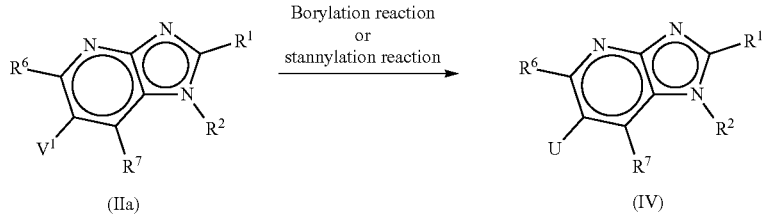

(IIa)            (IV)

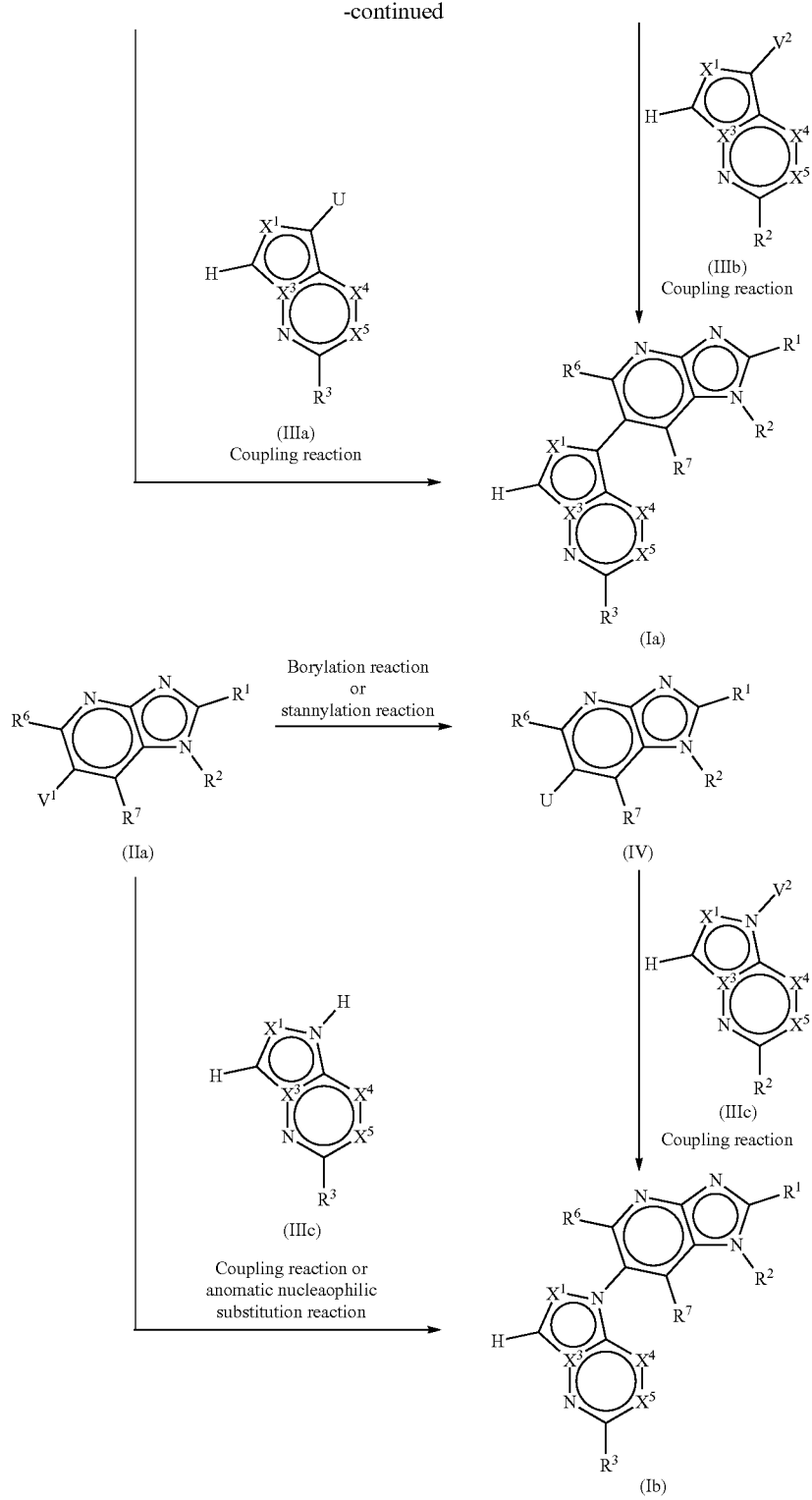

[wherein V¹ and V² are the same or different, and each represent a leaving group (e.g. hydrogen, an alkali metal (e.g. lithium or sodium sodium), a halogen atom (e.g. fluorine, chlorine, bromine or iodine), a $C_{1-6}$ alkoxy group (e.g. methoxy), a $C_{6-14}$ aryloxy group (e.g. phenoxy), an optionally substituted acyl-oxy group (e.g. acetyloxy or benzoyloxy), an optionally substituted C1-6 alkoxysulfonyloxy group (e.g. methoxysulfonyloxy), an optionally halogenated $C_{1-6}$ alkylsulfonyl-oxy group (e.g. methanesulfonyloxy, ethanesulfonyloxy, trichloromethanesulfonyloxy, trifluoromethanesulfonyloxy (triflate)), or an optionally substituted $C_{6-14}$ arylsulfonyl-oxy group (e.g. a $C_{6-14}$ arylsulfonyloxy group (e.g. benzenesulfonyloxy, m-nitrobenzenesulfonyloxy, p-toluenesulfonyloxy or naphthylsulfonyloxy)

optionally having 1 to 3 substituents each selected from a $C_{1-6}$ alkyl group (e.g. methyl, ethyl, propyl, isopropyl, butyl, isobutyl, sec-butyl, tert-butyl, pentyl or hexyl), a $C_{1-6}$ alkoxy group (e.g. methoxy, ethoxy, propoxy, isopropoxy, butoxy, isobutoxy, sec-butoxy, pentyloxy or hexyloxy) and a nitro group;

U represents a boryl group (e.g.

[Chemical Formula 7]

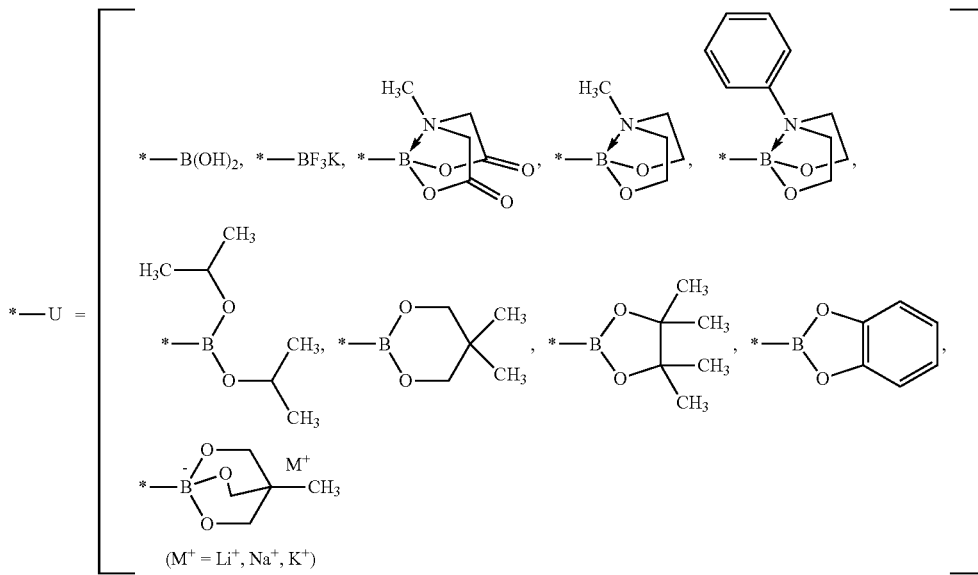

etc.), an optionally substituted $C_{1-6}$ alkylstannyl group (e.g. tributylstannyl or the like), an optionally substituted $C_{2-6}$ alkenylstannyl group, or an optionally substituted $C_{1-6}$ alkynylstannyl group; and each of other symbols has the same meaning as described above.]

The compound (IV) in which U is a boryl group can be produced by a borylation reaction of the compound (IIa). The borylation reaction includes a method using a Miyaura-Ishiyama-Hartwig borylation reaction and a transmetalation reaction as described below, and by using each reaction, a compound (IV) in which U is a boryl group can be produced.

i) Method Using Miyaura-Ishiyama-Hartwig Borylation Reaction

The compound (IV) in which U is a boryl group can be produced by reacting the compound (IIa) and a borylating agent under a metal catalyst and a base (specifically Miyaura-Ishiyama-Hartwig borylation reaction). Preferably, this reaction is carried out under an inert gas atmosphere. This reaction may be carried out in the presence of a ligand and even under microwave irradiation.

Specific examples of the borylating agent include bis(pinacolato)diboron and pinacol borane. Specific examples of the metal catalyst include palladium compounds such as palladium (II) acetate, tetrakis(triphenylphosphine)palladium (0), dichlorobis(triphenylphosphine)palladium (II), dichlorobis(triethylphosphine)palladium (II), tris(dibenzylideneacetone)dipalladium (0), 1,1'-bis(diphenylphosphino)ferrocenepalladium (II) chloride and palladium (II) acetate; nickel compounds such as tetrakis(triphenylphosphine)nickel (0); rhodium compounds such as tris(triphenylphosphine)rhodium (III) chloride; cobalt compounds; copper compounds such as copper oxide and copper (I) iodide; platinum compounds; and iridium compounds. Specific examples of the ligand include phosphine ligands [e.g. triphenylphosphine, 2,2'-bis(diphenylphosphino)-1,1'-binaphthyl, 2-dicyclohexylphosphino-2',6'-diisopropoxy-1,1'-biphenyl, 2-(dicyclohexylphosphino)-3,6-dimethoxy-2',4',6'-triisopropyl-1,1'-biphenyl, 2-di-tert-butylphosphino-3,4,5,6-tetramethyl-2',4',6'-triisopropyl-1,1'-biphenyl, 2-(di-tert-butylphosphino)biphenyl, 2-(dicyclohexylphosphino)biphenyl, 2-dicyclohexylphosphino-2',6'-dimethoxy-1,1'-biphenyl, 2-dicyclohexylphosphino-2',4',6'-triisopropyl-1,1'-biphenyl, 2-(dicyclohexylphosphino)-2'-(N,N-dimethylamino)biphenyl, 1,1'-bis(diphenylphosphino)ferrocene, tri-tert-butylphosphine, tricyclohexylphosphine, 4,5-bis(diphenylphosphino)-9,9-dimethylxanthene], amine ligands (N,N'-dimethylethylenediamine, trans-1,2-diaminocyclohexane, trans-N,N'-dimethyl-1,2-cyclohexanediamine, 1,10-phenanthroline, 4,7-dimethoxy-1,10-phenanthroline, 3,4,7,8-tetramethyl-1,10-phenanthroline and the like), diketone ligands (2-acetylcyclohexanone, 2-isobutyrylhexanone, 2,2,6,6-tetramethyl-3,5-heptanedione and the like), salicylaldoxime, and proline.

ii) Method Using Transmetalation Reaction

The compound (IV) in which U is a boryl group can be produced by reacting the compound (IIa) with a borylating agent in the presence of an organometallic reagent (e.g. organolithium, metal alkoxide, alkali metal hydride, metal amide or isopropyl magnesium chloride) (specifically transmetalation reaction). Specific examples of the borylating agent include trialkoxyboranes (e.g. trimethoxyborane, triethoxyborane and triisopropoxyborane).

The compound (IV) in which U is an optionally substituted $C_{1-6}$ alkylstannyl group (e.g. tributylstannyl or the like), an optionally substituted $C_{2-6}$ alkenylstannyl group, or an optionally substituted $C_{1-6}$ alkynylstannyl group can be produced by a stannylation reaction of the compound (IIa). This reaction is carried out by reacting the compound (IIa) with a stannylating agent in the presence of an organometallic reagent (e.g. organolithium, metal alkoxide, alkali metal hydride or metal amide). Specific examples of the stannylating agent include trimethyl tin chloride, triphenyl tin chloride, trimethyl tin acetate, dimethyl tin dichloride, dibutyl tin dichloride, dimethyl tin diacetate and dibutyl tin diacetate.

[Production Method A-2]

The compound (Id) can also be produced from a compound (Ic) contained in the compound (Id) by the following method.

[Chemical Formula 8]

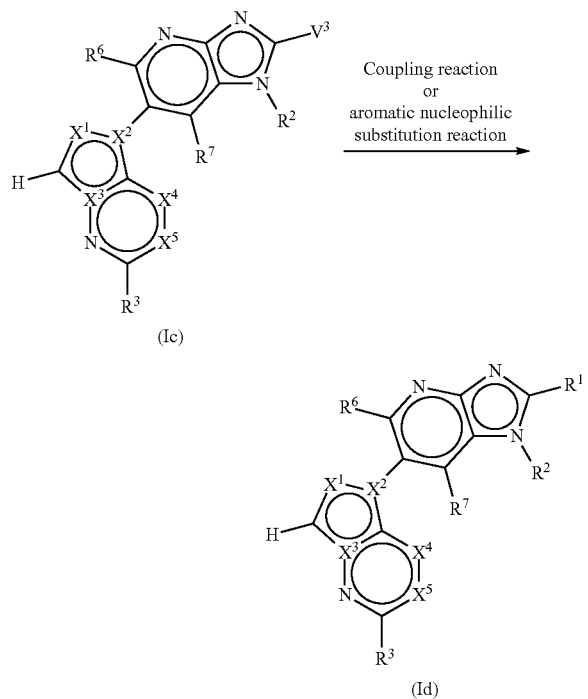

[wherein $V^3$ represents a halogen atom (e.g. fluorine, chlorine, bromine or iodine); and each of other symbols has the same meaning as described above.]

[Production Method A-3]

The compound (Id) can also be produced from a compound (Ie) contained in the compound (Id) by the following method.

[Chemical Formula 9]

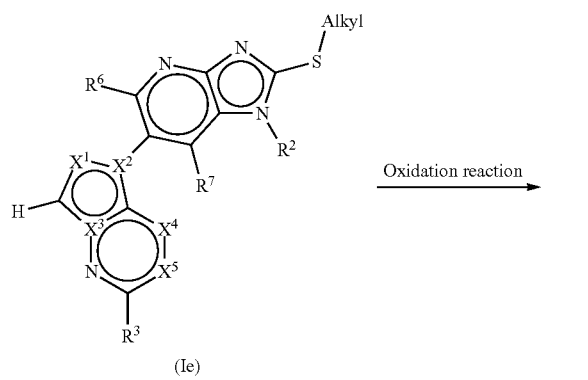

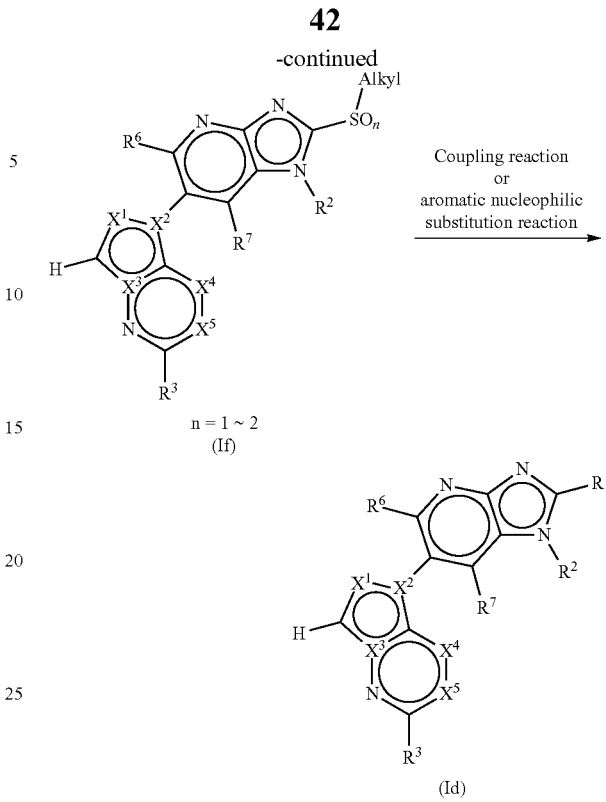

[Production Method A-4]

The compound represented by the formula A1 or each of the formulae A3 to A7 (compound represented by Ii in the following formula) or a salt thereof can be produced from a compound (Ig) contained in the compound (Ii) by the following method.

[Chemical Formula 10]

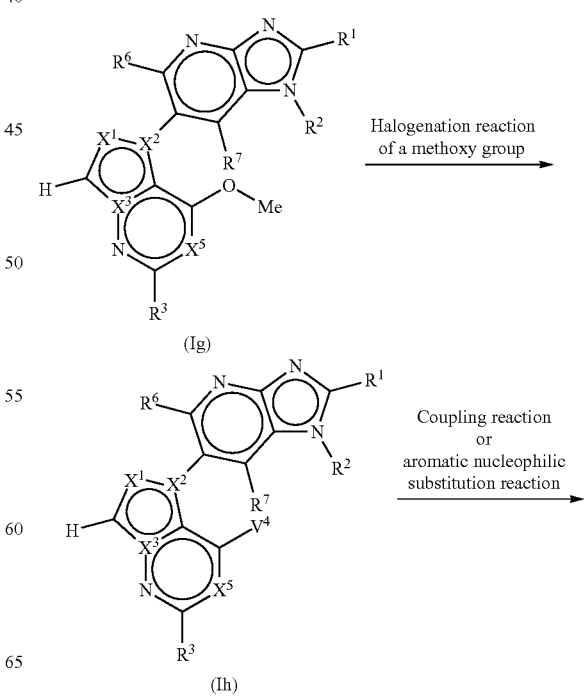

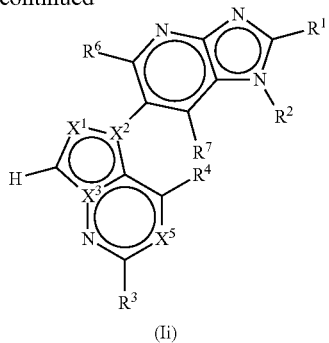

(Ii)

[wherein V⁴ represents a halogen atom (e.g. flourine, chlorine, bromine or iodine); and each of other symbols has the same meaning as described above.]

A compound (Ih) can be produced by a halogenation reaction of a methoxy group of the compound (Ig). This reaction can be carried out similarly to the halogenation reaction of a carbonyl group.

[Production Method A-5]

The compound represented by each of the formulae A2 to A4 or formula A7 (compound represented by Id' in the following formula) or a salt thereof can be produced from a compound (Ij) contained in the compound (Id') by the following method.

[Chemical Formula 11]

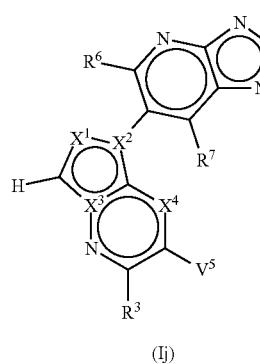

(Ij)

Coupling reaction or aromatic nucleophilic substitution reaction →

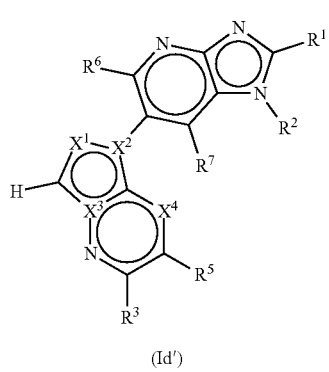

(Id')

[wherein V⁵ represents a halogen atom (e.g. fluorine, chlorine, bromine or iodine); and each of other symbols has the same meaning as described above.]

[Production Method A-6]

A compound (Il) contained in the compound (Id') can be produced from a compound (Ik) contained in the compound (Id') by the following method.

[Chemical Formula 12]

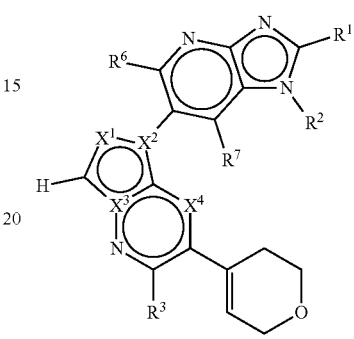

(Ik)

Reduction reaction →

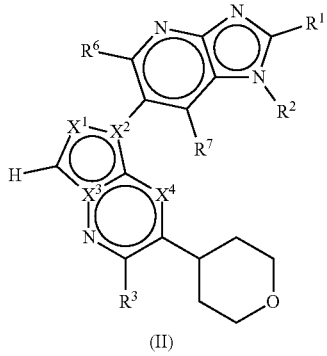

(Il)

[wherein each symbol has the same meaning as described above.]

[Production Method A-7]

Compounds (Io), (Iq) and (Ir) contained in the compound (Id') can be produced from a compound (Im) contained in the compound (Id') by the following method.

[Chemical Formula 13]

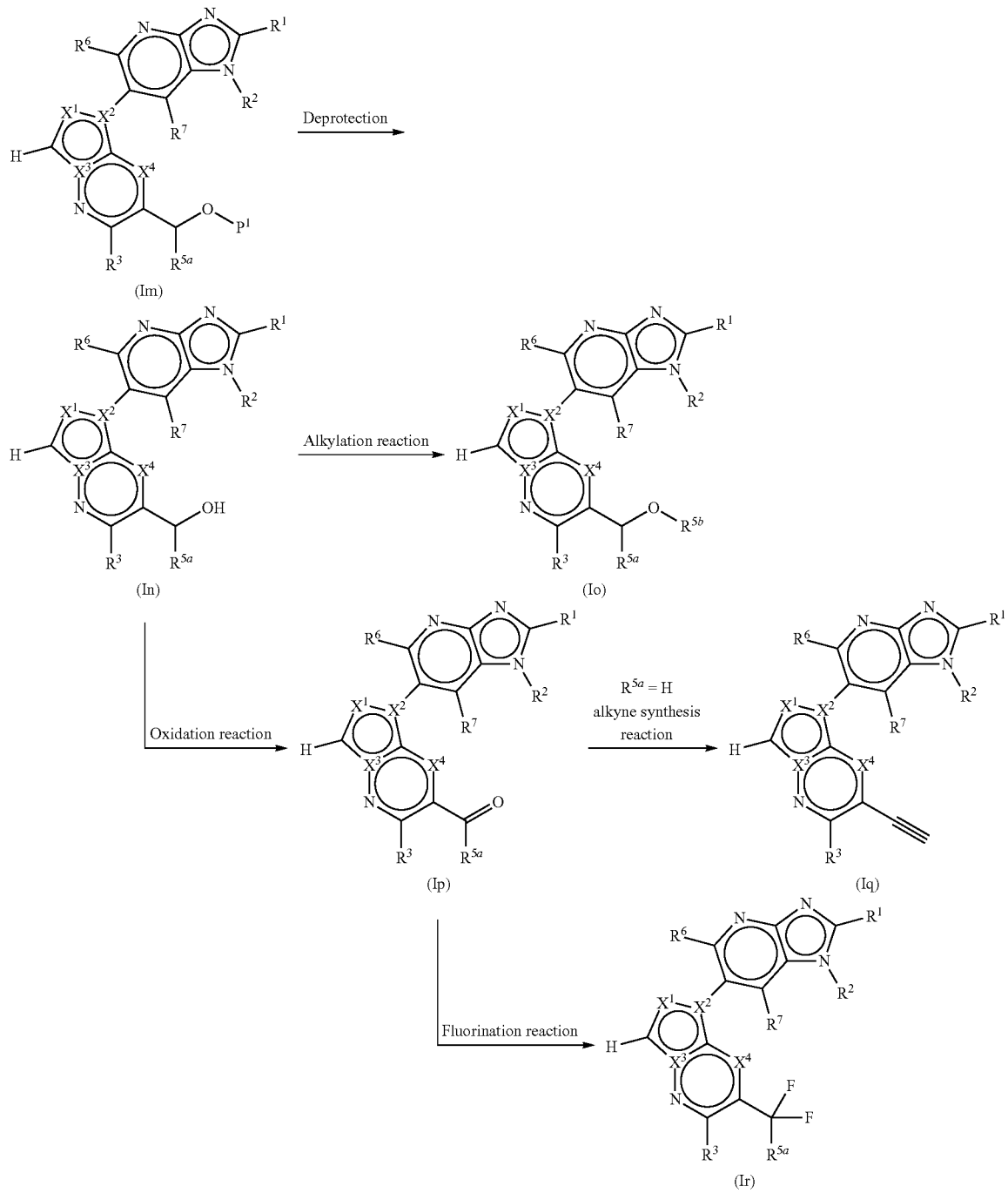

[wherein P¹ represents a protecting group for a hydroxyl group;

$R^{5a}$ represents a hydrogen atom, a group bonded via a carbon atom, a group bonded via a nitrogen atom or a group bonded via an oxygen atom;

$R^{5b}$ represents a group bonded via a carbon atom; and each of other symbols has the same meaning as described above.]

Compound (Ir) can be produced by a fluorination reaction of a compound (Ip). This reaction can be carried out in accordance with a method known per se [e.g. Journal of Medicinal Chemistry, 33(1), 142-6 (1990), Journal of Medicinal Chemistry, 55(21), 9346-9361 (2012), Journal of Medicinal Chemistry, 50(15), 3427-3430 (2007), Bioorganic & Medicinal Chemistry Letters, 20 (16), 4753-4756 (2010), Journal of Medicinal Chemistry, 50(20), 5024-5033 (2007), Tetrahedron, 65(33), 6611-6625 (2009), Synlett, (14), 2111-2114 (2008), Organic Process Research & Development, 14(2), 393-404 (2010), and Bioorganic & Medicinal Chemistry, 23(2), 297-313 (2015)], or a similar method.

[Production Method B-1]

The compound (IIa) to be used in [Production method A-1] can be produced by the following method.

[Chemical Formula 14]

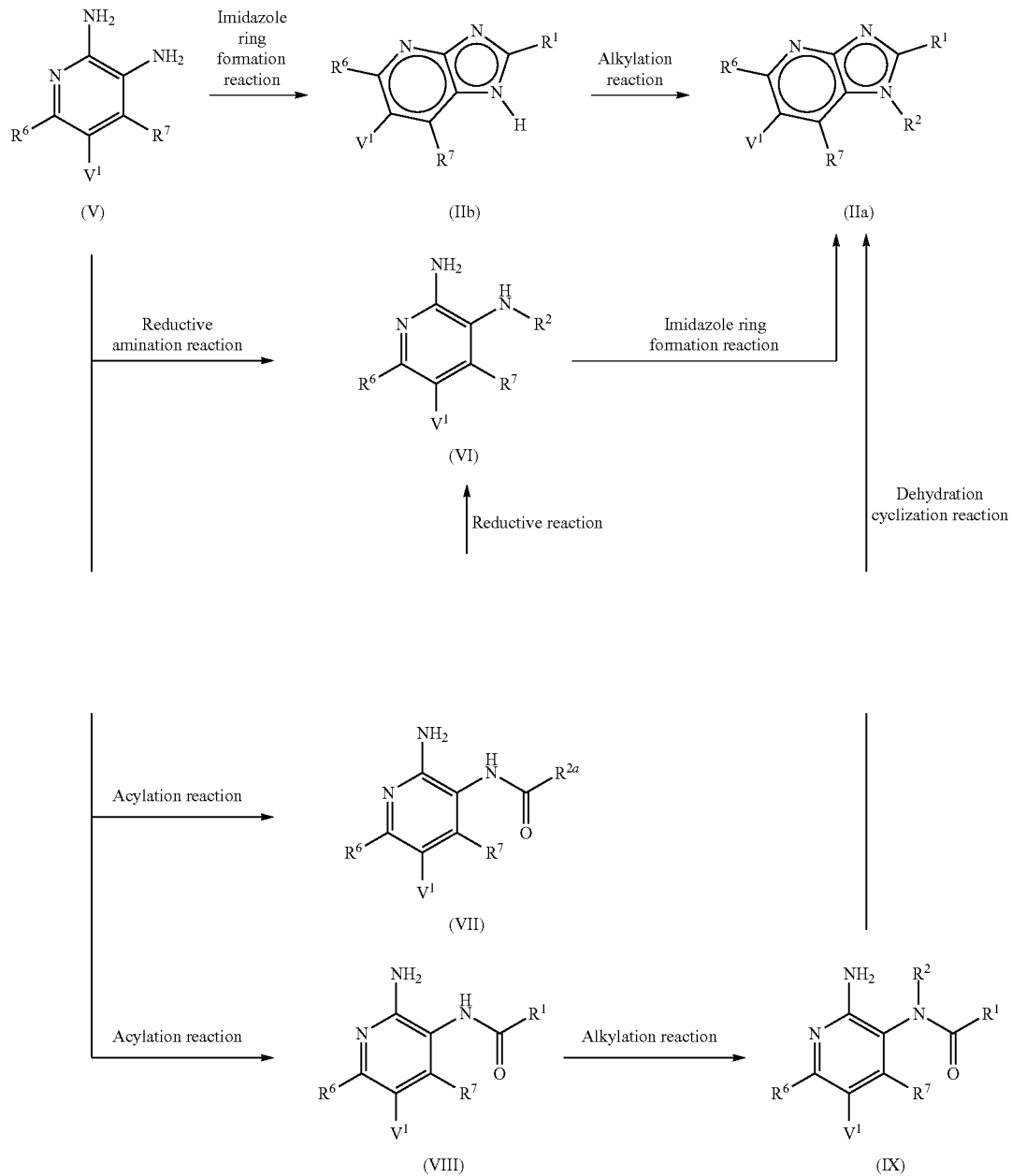

[wherein $R^{2a}$ represents an optionally substituted aromatic ring, an optionally substituted aromatic heterocyclic ring, or an optionally substituted nonaromatic heterocyclic ring; and each of other symbols has the same meaning as described above.]

The compound (IIa) can be produced by a dehydration cyclization reaction of a compound (IX). This reaction can also be carried out by heating. Further, this reaction can also be carried out by heating in the presence of an acid (e.g. inorganic acid, organic acid, Lewis acid or the like) or a base (e.g. organolithium, metal alkoxide, inorganic base, organic base or the like).

A compound (V) is available as a commercially available product, or is produced by a method known per se.

[Production Method B-2]

The compound (IIa) to be used in [Production method A-1] can be produced from a compound (VI) by the following method.

[Chemical Formula 15]

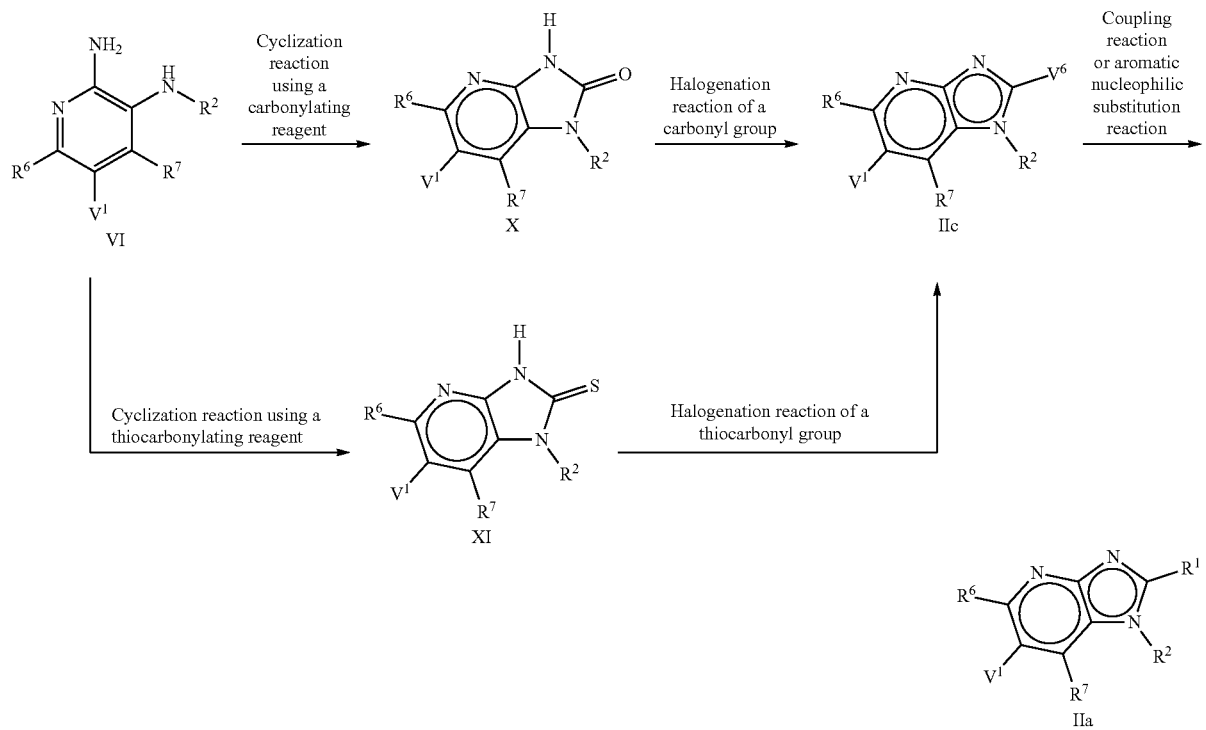

[wherein $V^6$ represents a halogen atom (e.g. fluorine, chlorine, bromine or iodine); and each of other symbols has the same meaning as described above.]

A compound (X) can be produced by a cyclization reaction of the compound (VI) using a carbonylating reagent. Examples of the carbonylating reagent include 1,1'-carbonylbis-1H-imidazole, diphosgene, triphosgene and phenyl chloroformate. The reaction can also be carried out in the presence of a base. Examples of the base include organic bases, inorganic bases and basic salts.

The compound (XI) can be produced by a cyclization reaction of the compound (VI) using a thiocarbonylating reagent. Examples of the thiocarbonylating reagent include carbon disulfide, thiourea, ethyl xanthate, thiophosgene and 1,1'-thiocarbonyldiimidazole. This reaction can also be carried out in the presence of a base. Examples of the base include organic bases, inorganic bases and basic salts.

A compound (IIc) can be produced by a halogenation reaction of a thiocarbonyl group of the compound (XI). This reaction can be carried out similarly to the halogenation reaction of a carbonyl group.

[Production Method B-3]

A compound (IIe), a compound (IIh), a compound (IIk) and a compound (III) contained in the compound (IIa) to be used in [Production Method A-1] can be produced by the following method.

[Chemical Formula 16]

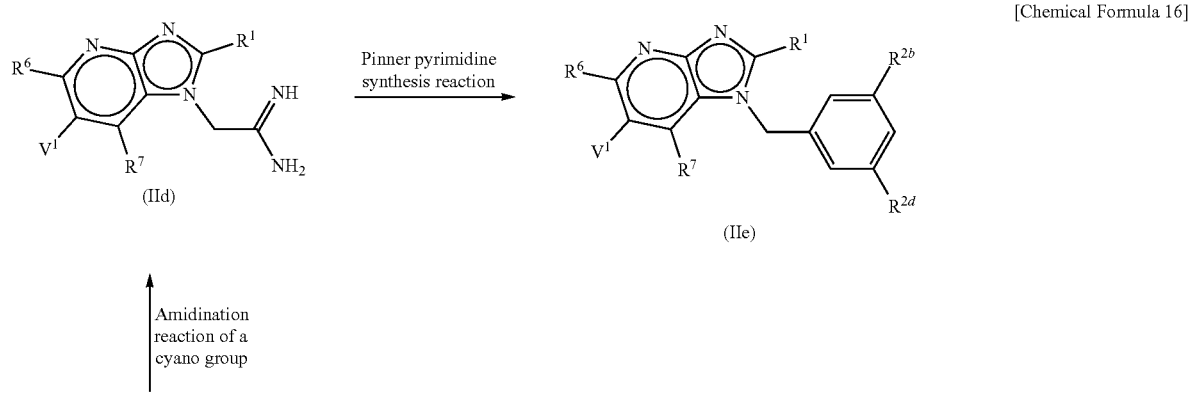

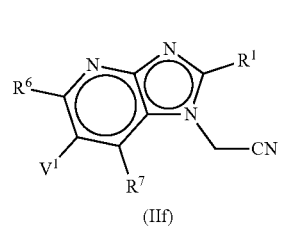 (IIf)

Thioamidination reaction of a cyano group →

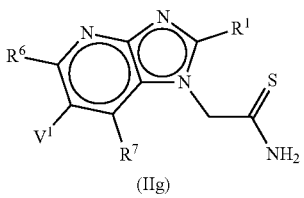 (IIg)

-continued

Thioamidination reaction of a cyano group →

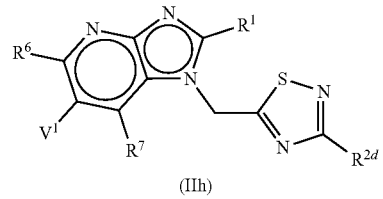 (IIh)

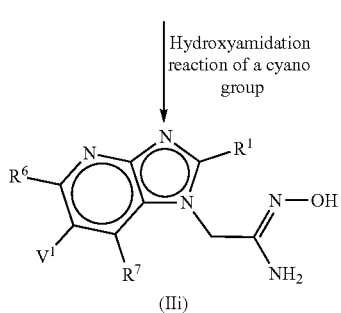 (IIi)

Hydroxyamidation reaction of a cyano group

Cyclization reaction using a carbonyl reagent →

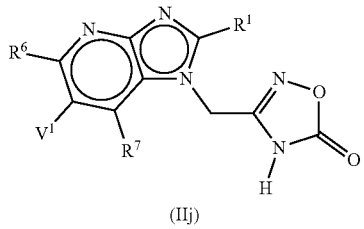 (IIj)

Alkylation reaction →

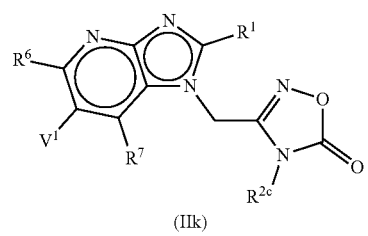 (IIk)

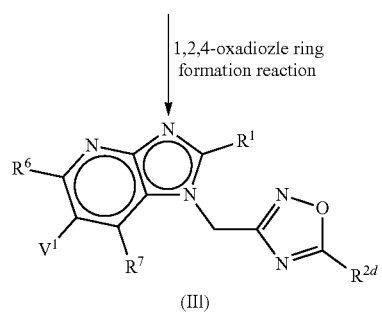 (III)

1,2,4-oxadiozle ring formation reaction

[wherein $R^{2b}$ and $R^{2d}$ each independently represent a hydrogen atom, a group bonded via a halogen atom or a carbon atom, a group bonded via a nitrogen atom, a group bonded via an oxygen atom, or a group bonded via a sulfur atom;

$R^{2c}$ represents a group bonded via a carbon atom; and each of other symbols has the same meaning as described above.]

A compound (IId) can be produced by an amidination reaction of a cyano group of a compound (IIf). This reaction can be carried out in accordance with a method known per se [e.g. Bioorganic & Medicinal Chemistry Letters, 20(19), 5735-5738 (2010), Tetrahedron, 45(20), 6511-18 (1989), Journal of Organic Chemistry, 53(5), 1085-7 (1988), European Journal of Medicinal Chemistry, 16(2), 175-9 (1981), Journal of Medicinal Chemistry, 33(4), 1230-41 (1990), European Journal of Medicinal Chemistry, 60, 395-409 (2013), Journal of Organic Chemistry, 69(20), 6572-6589 (2004), Journal of Labelled Compounds and Radiopharmaceuticals, 56(14), 722-725 (2013), European Journal of Medicinal Chemistry, 103, 29-43 (2015), European Journal of Organic Chemistry, 2014(17), 3614-3621 (2014), and Journal of the American Chemical Society, 107(9), 2743-8 (1985)], or a similar method.

A compound (IIi) can be produced by subjecting a cyano group of the compound (IIf) to a hydroxyamidation reaction in the presence of a hydroxyamidinating reagent. Examples of the hydroxyamidinating reagent include hydroxyamine or a salt thereof. This reaction can be carried out in the presence of an acid or a base. Examples of the acid include inorganic acids, organic acids and Lewis acids. Examples of the base include organic lithiums, metal alkoxides, inorganic bases and organic bases.

A compound (IIg) can be produced by subjecting a cyano group of the compound (IIf) to a thioamidation reaction in the presence of a thioamidating reagent. Examples of the thioamidating reagent include phosphorus pentasulfide, hydrogen sulfide, 2,4-bis(4-methoxyphenyl-1,3,2,4-dithiadiphosphetane-2,4-disulfide (Lowesson reagent), dialkyl dithiophosphates (e.g. O,O'-diethyl dithiophosphate).

The compound (IIe) can be produced by subjecting the compound (IId) to a pinner pyrimidine synthesis reaction in the presence of a reagent. Examples of the reagent include a 1,3-dicarbonyl compounds and α,β-unsaturated carbonyl compounds. This reaction can be carried out in the presence of a base. Examples of the base include organic lithiums, metal alkoxides, inorganic bases and organic bases.

The compound (IIh) can be produced by subjecting the compound (IIg) to a 1,2,4-thiadiazole ring formation reaction in the presence of a reagent. Examples of the reagent include N,N-dialkylcarboxylic acid amide dialkyl acetals (e.g. N,N-dimethylacetamide dimethyl acetal) and hydroxyamine derivatives (e.g. hydroxylamine-O-sulfonic acid). This reaction can be carried out through a two-step reaction such that by the a N,N-dialkylcarboxylic acid amide dialkyl acetal is reacted with the compound (IIg) to isolate a N-(dialkylaminomethylene)thiocarbonyl, and the isolated N-(dialkylaminomethylene)thiocarbonyl is reacted with a hydroxyamine derivative.

The compound (Ill) can be produced by subjecting the compound (IIi) to a 1,2,4-oxadiazole ring formation reaction in the presence of a reagent. Examples of the reagent include activated carboxylic acids such as acyl halides such as acid chloride and acid bromide, active esters, esters and sulfuric acid esters. Examples of the activating agent in preparation of the activated carboxylic acid include carbodiimide-based condensing agents such as propylphosphonic anhydride (cyclic trimer), acid anhydrides (e.g. acetic anhydride) and 1-ethyl-3-(3-dimethylaminopropyl) carbodiimide hydrochloride (WSCD); triazine-based condensing agents such as 4-(4,6-dimethoxy-1,3,5-triazin-2-yl)-4-methylmorpholinium chloride-n-hydrate (DMT-MM); carbonic acid ester-based condensing agents such as 1,1-carbonyldiimidazole (CDI); diphenylphosphoryl azide (DPPA); benzotriazol-1-yloxy-trisdimethyl aminophosphonium salts (BOP reagents); 2-chloro-1-methyl-pyridinium iodide (Mukaiyama Reagent); thionyl chloride; haloformic acid lower alkyls such as ethyl chloroformate; O-(7-azabenzotriazol-1-yl)-N,N,N',N'-tetramethyluronium hexafluorophosphate (HATU); sulfuric acid; and combinations thereof. When the reaction is carried out, additives such as 1-hydroxybenzotriazole (HOBt), N-hydroxysuccinimide (HOSu), dimethylaminopyridine (DMAP), an acid and a base can be added to the activating agent.

[Production Method B-4]

A compound (IIo) and a compound (IIq) contained in the compound (IIa) to be used in [Production Method A-1] can be produced from a compound (IIm) contained in the compound (IIa) by the following method.

[Chemical Formula 17]

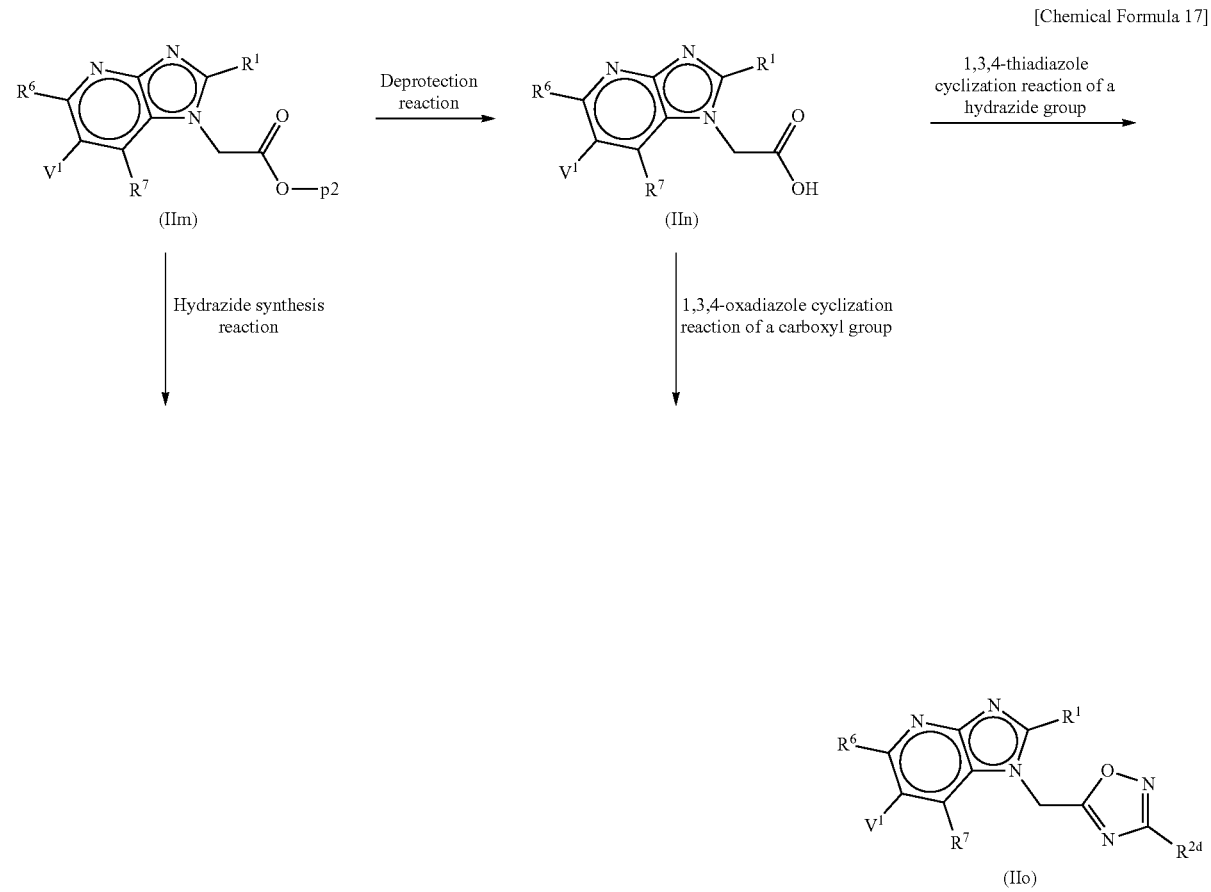

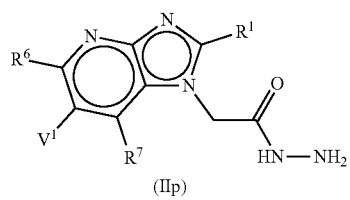
(IIp)

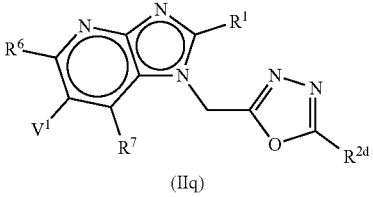
(IIq)

1,3,4-oxadiazole cyclization reaction of a hydrazide group 1,3,4-oxathiazole cyclization reaction of a hydrazide group

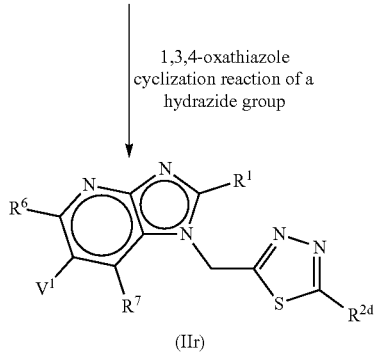
(IIr)

[wherein $P^2$ represents a protecting group for a carboxyl group, and
each of other symbols has the same meaning as described above.]

The compound (IIo) can be produced by subjecting a carboxyl group of the compound (IIn) to a 1,2,4-oxadiazole cyclization reaction in the presence of a reagent. Examples of the reagent include hydroxyamidines (e.g. N-hydroxyacetamidine). Examples of the carboxylic acid activating agent to be used in the reaction include carbodiimide-based condensing agents such as propylphosphonic anhydride (cyclic trimer), acid anhydrides (e.g. acetic anhydride) and 1-ethyl-3-(3-dimethylaminopropyl) carbodiimide hydrochloride (WSCD); triazine-based condensing agents such as 4-(4,6-dimethoxy-1,3,5-triazin-2-yl)-4-methylmorpholinium chloride-n-hydrate (DMT-MM); carbonic acid ester-based condensing agents such as 1,1-carbonyldiimidazole (CDI); diphenylphosphoryl azide (DPPA); benzotriazol-1-yloxy-trisdimethyl aminophosphonium salts (BOP reagents); 2-chloro-1-methyl-pyridinium iodide (Mukaiyama Reagent); thionyl chloride; haloformic acid lower alkyls such as ethyl chloroformate; O-(7-azabenzotriazol-1-yl)-N,N,N',N'-tetramethyluronium hexafluorophosphate (HATU); sulfuric acid; and combinations thereof. When the reaction is carried out, additives such as 1-hydroxybenzotriazole (HOBt), N-hydroxysuccinimide (HOSu), dimethylaminopyridine (DMAP), an acid and a base can be added to the activating agent.

The compound (IIq) can be produced by subjecting a carboxyl group of the compound (IIn) to a 1,3,4-oxadiazole cyclization reaction in the presence of a reagent. Examples of the reagent include hydrazides (e.g. acetohydrazide). Examples of the carboxylic acid activating agent to be used in the reaction include carbodiimide-based condensing agents such as thionyl chloride, phosphorus oxychloride, phosphorus oxybromide, propylphosphonic anhydride (cyclic trimer), acid anhydrides (e.g. acetic anhydride) and 1-ethyl-3-(3-dimethylaminopropyl) carbodiimide hydrochloride (WSCD); triazine-based condensing agents such as 4-(4,6-dimethoxy-1,3,5-triazin-2-yl)-4-methylmorpholinium chloride-n-hydrate (DMT-MM); carbonic acid ester-based condensing agents such as 1,1-carbonyldiimidazole (CDI); diphenylphosphoryl azide (DPPA); benzotriazol-1-yloxy-trisdimethylaminophosphonium salts (BOP reagents); 2-chloro-1-methyl-pyridinium iodide (Mukaiyama Reagent); thionyl chloride; haloformic acid lower alkyls such as ethyl chloroformate; O-(7-azabenzotriazol-1-yl)-N,N,N',N'-tetramethyluronium hexafluorophosphate (HATU); sulfuric acid; and combinations thereof. When the reaction is carried out, additives such as 1-hydroxybenzotriazole (HOBt), N-hydroxysuccinimide (HOSu), dimethylaminopyridine (DMAP), an acid and a base can be added to the activating agent.

This reaction can be carried out through a two-step reaction such that N,N'-diacylhydrazine is isolated, and the isolated N,N'-diacylhydrazine is subjected to a dehydration reaction in the presence of a sulfonating agent (e.g. methanesulfonyl chloride, p-toluenesulfonyl chloride, methanesulfonic anhydride or p-toluenesulfonic anhydride) or a dehydrating agent (e.g. sulfuric acid, diphosphorus pentoxide, phosphorus oxychloride, N,N'-dicyclohexylcarbodiimide, alumina or polyphosphoric acid).

The compound (IIq) can be produced by subjecting a hydrazide group of a compound (IIp) to a 1,3,4-oxadiazole cyclization reaction in the presence of a reagent. Examples of the reagent include activated carboxylic acids such as acyl halides such as acid chloride and acid bromide, active esters, esters and sulfuric acid esters. Examples of the carboxylic acid activating agent when a carboxylic acid is used include carbodiimide-based condensing agents such as thionyl chloride, phosphorus oxychloride, phosphorus oxybromide, propylphosphonic anhydride (cyclic trimer), acid anhydrides (e.g. acetic anhydride) and 1-ethyl-3-(3-dimethylaminopropyl) carbodiimide hydrochloride (WSCD); triazine-based condensing agents such as 4-(4,6-dimethoxy-1,3,5-triazin-2-yl)-4-methylmorpholinium chloride-n-hydrate (DMT-MM); carbonic acid ester-based condensing agents such as 1,1-carbonyldiimidazole (CDI); diphenylphosphoryl azide (DPPA); benzotriazol-1-yloxy-trisdimethylaminophosphonium salts (BOP reagents); 2-chloro-1-methyl-pyridinium iodide (Mukaiyama Reagent); thionyl chloride; haloformic acid lower alkyls such as ethyl chloroformate; O-(7-azabenzotriazol-1-yl)-N,N,N',N'-tetramethyluronium hexafluorophosphate (HATU); sulfuric acid; and combinations thereof.

When the reaction is carried out, additives such as 1-hydroxybenzotriazole (HOBt), N-hydroxysuccinimide (HOSu), dimethylaminopyridine (DMAP), an acid and a base can be further added to the activating agent.

This reaction can be carried out through a two-step reaction such that N,N'-diacylhydrazine is isolated, and the isolated N,N'-diacylhydrazine is subjected to a dehydration reaction in the presence of a sulfonating agent (e.g. methanesulfonyl chloride, p-toluenesulfonyl chloride, methanesulfonic anhydride or p-toluenesulfonic anhydride) or a dehydrating agent (e.g. sulfuric acid, diphosphorus pentoxide, phosphorus oxychloride, N,N'-dicyclohexylcarbodiimide, alumina or polyphosphoric acid).

A compound (IIr) can be produced by subjecting a hydrazide group of a compound (IIp) to a 1,3,4-thiadiazole cyclization reaction in the presence of a reagent. Examples of the reagent include thiocarbonylating reagents (e.g. diphosphorus pentasulfide, 2,4-bis(4-methoxyphenyl-1,3,2,4-dithiadiphosphetane-2,4-disulfide (Lowesson reagent), and activated carboxylic acids such as acyl halides such as acid chloride and acid bromide, active esters, esters and sulfuric acid esters. Examples of the activating agent when a carboxylic acid is used include activating agents similar to those mentioned as carboxylic acid activating agents usable in production of the compound (IIq) from the compound (IIp).

[Production Method C-1]

A compound (IIIa) to be used in [Production Method A-1] can be produced by the following method.

[Chemical Formula 18]

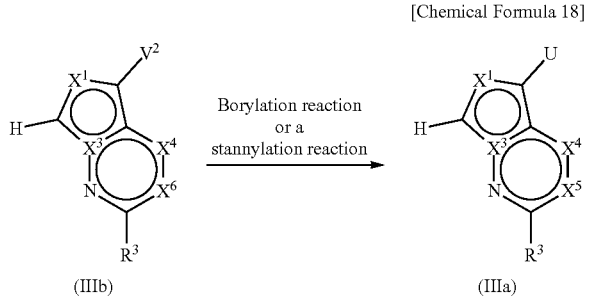

(IIIb)            (IIIa)

[wherein each symbol has the same meaning as described above.]

The compound (IIIa) can be produced by a borylation reaction or a stannylation reaction of the compound (IIIb). The method for the reaction is similar to the method described in [Production Method A-1].

A compound (IIIb) is available as a commercially available product, or is produced by a method known per se.

When a substituent of the compound (I) thus obtained is converted by applying means known per se (i.e. introduction of a substituent or conversion of a functional group), another compound included in the compound (I), or a salt thereof can be produced.

As a method for introduction of a substituent or conversion of a functional group, a general known method is used, and examples thereof include conversion of a halogen atom (e.g. fluorine, chlorine, bromine or iodine) or an optionally halogenated $C_{1-6}$ alkylsulfonyl-oxy group [e.g. methanesulfonyloxy, ethanesulfonyloxy, trichloromethanesulfonyloxy or trifluoromethanesulfonyloxy (triflate)] into a methyl group, a cyclopropyl group, a vinyl group, a cyano group, a formyl group, a carbonyl group, a carboxyl group, a hydroxyl group, an amino group, a boryl group or the like; conversion of a formyl group into an ethynyl group by Seyferth-Gilbert homologation; conversion of an ester into a carboxy group by hydrolysis; conversion of a carboxy group into a carbamoyl group by amidation; conversion of a carboxy group into a hydroxymethyl group by reduction; conversion of a carbonyl group into an alcohol by reduction or alkylation; reductive amination of a carbonyl group; oximation of a carbonyl group; acylation of an amino group; urea formation of an amino group; sulfonylation of an amino group; alkylation of an amino group; substitution or amination of an active halogen by an amine; alkylation of a hydroxy group; and substitution or amination of a hydroxy group.

When a reactive part in which an unintended reaction takes place in the introduction of a substituent or conversion of a functional group is present, a compound falling within the scope of the present invention can be produced by introducing a protecting group into the reactive part beforehand by means known per se as necessary, carrying out an intended reaction, and then removing the protecting group by means known per se.

For example, when a raw material compound or an intermediate has an amino group, a carboxyl group or a hydroxyl group as a substituent, the group may be protected with a protecting group that is generally used peptide chemistry etc. In this case, a target compound can be obtained by removing the protective group as necessary after the reaction.

When a substituent of the compound (I) thus obtained is converted by applying means known per se (i.e. introduction of a substituent or conversion of a functional group), another compound included in the compound (I), or a salt thereof can be produced.

As a method for introduction of a substituent or conversion of a functional group, a general known method is used, and examples thereof include conversion of a halogen atom (e.g. fluorine, chlorine, bromine or iodine) or an optionally halogenated $C_{1-6}$ alkylsulfonyl-oxy group [e.g. methanesulfonyloxy, ethanesulfonyloxy, trichloromethanesulfonyloxy or trifluoromethanesulfonyloxy (triflate)] into a methyl group, a cyclopropyl group, a vinyl group, a cyano group, a formyl group, a carbonyl group, a carboxyl group, a hydroxyl group, an amino group, a boryl group or the like; conversion of a formyl group into an ethynyl group by Seyferth-Gilbert homologation; conversion of an ester into a carboxy group by hydrolysis; conversion of a carboxy group into a carbamoyl group by amidation; conversion of a carboxy group into a hydroxymethyl group by reduction; conversion of a carbonyl group into an alcohol by reduction or alkylation; reductive amination of a carbonyl group; oximation of a carbonyl group; acylation of an amino group; urea formation of an amino group; sulfonylation of an amino group; alkylation of an amino group; substitution or amination of an active halogen by an amine; alkylation of a hydroxy group; and substitution or amination of a hydroxy group.

When a reactive part in which an unintended reaction takes place in the introduction of a substituent or conversion of a functional group is present, a compound falling within the scope of the present invention can be produced by introducing a protecting group into the reactive part beforehand by means known per se as necessary, carrying out an intended reaction, and then removing the protecting group by means known per se.

For example, when a raw material compound or an intermediate has an amino group, a carboxyl group or a hydroxyl group as a substituent, the group may be protected with a protecting group that is generally used peptide chemistry etc. In this case, a target compound can be obtained by removing the protective group as necessary after the reaction.

When the compound (I) has isomers such as optical isomers, stereoisomers, regioisomers and rotational isomers, the compound (I) encompasses any one of the isomers and mixtures of the isomers. For example, when the compound (I) has optical isomers, the compound (I) also encompasses optical isomers divided from racemates. Each of these isomers can be obtained as a single product by a synthesis method or separation method known per se (e.g. concentration, solvent extraction, column chromatography or recrystallization).

The compound (I) may be in the form of a crystal, and the compound (I) encompasses either a single crystal form or a crystal form mixture. The crystal can be produced by performing crystallization using a crystallization method known per se.

In addition, the compound (I) may be in the form of a pharmaceutically acceptable cocrystal or cocrystal salt. Here, the cocrystal or cocrystal salt means a crystalline substance composed of two or more unique solids at room temperature, which have different physical properties (e.g. structure, melting point, heat of fusion, hygroscopic property and stability). The cocrystals or cocrystal salt can be produced in accordance with a cocrystallization method known per se.

The compound (I) may be any of a hydrate, a non-hydrate, a solvate and a non-solvate, all of which are encompassed in the compound (I).

The compound (I) also encompasses compounds each labeled with an isotope (e.g. $^{2}H$, $^{3}H$, $^{11}C$, $^{14}C$, $^{18}F$, $^{35}S$ or $^{125}I$) or the like. The compound (I) labeled or substituted with an isotope can be used as, for example, a tracer (PET tracer) that is used in positron emission tomography (PET), and may be useful in the field of medical diagnosis etc.

The compound (I) may be a prodrug.

The prodrug of the compound (I) is a compound that is converted into the compound (I) by a reaction with an enzyme, gastric acid or the like under physiological conditions in a living body, i.e. a compound that is enzymatically oxidized, reduced or hydrolyzed to change into the compound (I), or a compound that is hydrolyzed by gastric acid etc. to change into the compound (I).

Examples of the prodrug of the compound (I) include:

(1) compounds in which the amino of the compound (I) is acylated, alkylated or phosphorylated (e.g. compounds in which the amino of the compound (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, tert-butylated, ethoxycarbonylated, tert-butoxycarbonylated, acetylated or cyclopropylcarbonylated);

(2) compounds in which the hydroxy of the compound (I) is acylated, alkylated, phosphorylated or borated (e.g. compounds in which the hydroxy of the compound (I) is acetylated, palmitoylated, propanoylated, pivaloylated, succinylated, fumarylated, alanylated or dimethylaminomethylcarbonylated); and (3) compounds in which the carboxy of the compound (1) is esterified or amidated (e.g. carboxy of the compound (I) is ethyl-esterified, phenyl-esterified, carboxymethyl-esterified, dimethylaminomethyl-esterified, pivalolyloxymethyl-esterified, ethoxycarbonyloxyethyl-esterified, phthalidyl-esterified, (5-methyl-2-oxo-1,3-dioxolen-4-yl)methyl-esterified, cyclohexyloxycarbonylethyl-esterified or methylamidated). These compounds can be produced from the compound (I) by a method known per se.

In addition, the prodrug of the compound (I) is a compound which is changed into the compound (I) under physiological conditions as described in "Development of Pharmaceuticals" published by Hirokawa Shoten Co., 1990, Vol. 7, Molecular Design, pages 163 to 198.

In this specification, the prodrug may form a salt, and examples of the salt include salts exemplified as the salt of the compound represented by the formula (I).

The compound (I) or prodrug thereof (herein sometimes abbreviated as a "present invention compound" collectively) has CLK inhibitory activity, and may be useful as a prophylactic or therapeutic agent for cancer, a cancer growth inhibitor, or cancer metastasis inhibitor.

The present invention compound may be useful as a medicament because the present invention compound exhibits selective inhibitory activity against CLK, and is excellent in development of pharmacological effects, pharmacokinetics (e.g. absorbability, distribution, metabolism and excretion), solubility (e.g. water solubility), interaction with other pharmaceutical products (e.g. drug metabolizing enzyme inhibitory action), safety (in terms of, for example, acute toxicity, chronic toxicity, genotoxicity, reproductive toxicity, cardiotoxicity, carcinogenicity and central toxicity) and stability (e.g. chemical stability and stability against enzymes).

Since the present invention compound has low inhibitory activity against SCD family subtypes other than SCD1, the present invention compound may be useful as a prophylactic/therapeutic agent for cancer, which has reduced toxicity to normal cells.

Therefore, the compound of the present invention can be used for inhibiting excess (abnormal) CLK action on mammals (e.g. mouse, rat, hamster, rabbit, cat, dog, bovine, ovine, monkey and human).

The present invention compound can be used as a medicament such as a prophylactic or therapeutic agent for diseases which may be influenced by CLK (herein, sometimes abbreviated as "CLK related diseases"), for example cancers [e.g. colorectal cancer (e.g. colon cancer, rectal cancer, anal cancer, familial colorectal cancer, hereditary nonpolyposis colorectal cancer and gastrointestinal stromal tumor), lung cancer (e.g. non-small-cell lung cancer, small cell lung cancer and malignant mesothelioma), mesothelioma, pancreatic cancer (e.g. pancreatic ductal carcinoma and pancreatic endocrine tumor), pharyngeal cancer, laryngeal cancer, esophageal cancer, stomach cancer (e.g. papillary adenocarcinoma, mucous adenocarcinoma and adenosquamous carcinoma), duodenal carcinoma, small intestinal cancer, breast cancer (e.g. infiltrating duct carcinoma, noninfiltrating intraductal carcinoma and inflammatory breast cancer), ovarian cancer (e.g. epithelial ovarian cancer, extragonadal germ cell tumor, ovarian germ cell tumor and ovarian low malignant potential tumor), testicular tumor, prostatic cancer (e.g. hormone-dependent prostatic cancer, hormone-independent prostatic cancer and castration-resistant prostatic cancer), liver cancer (e.g. hepatic cell carcinoma, primary hepatic cancer and cancer of extrahepatic bile duct), thyroid cancer (e.g. thyroid medullary carcinoma), kidney cancer (e.g. renal cell carcinoma (e.g. clear cell type renal cell carcinoma) and transitional cell carcinoma of renal pelvis and ureter), uterine cancer (e.g. cervical cancer, corpus uteri cancer and uterine sarcoma), gestational choriocarcinoma, brain tumor (e.g. medulloblastoma, glioma, pineal astrocytoma, pilocytic astrocytoma, diffuse astrocytoma, anaplastic astrocytoma and pituitary adenoma), retinoblastoma, skin cancer (e.g. basal cell carcinoma and malignant melanoma), sarcoma (e.g. rhabdomyosarcoma, leiomyosarcoma, soft tissue sarcoma and spindle cell sarcoma), malignant bone tumor, bladder cancer, blood cancer (e.g. multiple myeloma, leukemia (e.g. acute myeloid leukemia), malignant lymphoma, Hodgkin's disease and chronic myeloproliferative disease), and cancer of unknown primary], a cancer growth inhibitor, a cancer metastasis inhibitor, an apoptosis promoting agent, or a therapeutic agent for precancerous lesion (e.g. myelodysplastic syndrome).

In particular, the present invention compound can be used as a medicament for myelodysplastic syndrome, acute myeloid leukemia, multiple myeloma or breast cancer.

From a different point of view, the present invention compound may be useful as a prophylactic or therapeutic agent, a growth inhibitor or a metastasis inhibitor for (i) cancer in which splicing is abnormal (e.g. myelodysplastic syndrome, acute myeloid leukemia, lymphoma, lung cancer, pancreatic cancer, breast cancer, melanoma, bladder cancer and head and neck cancer)

(ii) cancer in which Myc (specifically c-Myc, N-Myc or L-Myc) is activated (e.g. lymphoma, multiple myeloma, neuroblastoma, breast cancer and lung cancer), and (iii) high-CLK expressing cancer (e.g. breast cancer and multiple myeloma).

The compound of the present invention can be orally or parenterally administered as a medicament containing the compound of the present invention alone or as a mixture with a pharmacologically acceptable carrier to a mammal (preferably a human).

Hereinafter, the medicament comprising the compound of the present invention (also referred to as the "medicament of the present invention") will be described in detail. Examples of the dosage form of the medicament of the present invention include an oral preparation such as tablets (e.g., sugar-coated tablets, film-coated tablets, sublingual tablets, buccal tablets and rapidly orally disintegrating tablets), pills, granules, powders, capsules (e.g., soft capsules and microcapsules), syrups, emulsions, suspensions, films (e.g., orally disintegrating films and patch films for application to the oral mucosa) and the like. Other examples of the dosage form of the medicament of the present invention include a parenteral preparation such as injections, transfusions, transdermal preparations (e.g., iontophoresis dermal preparations), suppositories, ointments, transnasal preparations, transpulmonary preparations, eye drops and the like. Alternatively, the medicament of the present invention may be a controlled-release preparation such as a rapid-release preparation, a sustained-release preparation (e.g., a sustained-release microcapsule) or the like.

The medicament of the present invention can be produced by a production method known in the art (e.g., a method described in Japanese Pharmacopoeia) generally used in the field of pharmaceutical technology. If necessary, the medicament of the present invention can appropriately contain an appropriate amount of an additive usually used in the pharmaceutical field, such as an excipient, a binder, a disintegrant, a lubricant, a sweetener, a surfactant, a suspending agent, an emulsifier, a colorant, a preservative, a fragrance, a corrigent, a stabilizer, a viscosity modifier and the like.

Examples of the pharmacologically acceptable carrier described above include these additives.

For example, the tablets can be produced using an excipient, a binder, a disintegrant, a lubricant and the like. The pills and the granules can be produced using an excipient, a binder and a disintegrant. The powders and the capsules can be produced using an excipient and the like. The syrups can be produced using a sweetener and the like. The emulsions or the suspensions can be produced using a suspending agent, a surfactant, an emulsifier and the like.

Examples of the excipient include lactose, saccharose, glucose, starch, sucrose, microcrystalline cellulose, licorice powder, mannitol, sodium hydrogen carbonate, calcium phosphate and calcium sulfate.

Examples of the binder include a solution containing 5 to 10% by weight of starch paste, a solution containing 10 to 20% by weight of gum arabic or gelatin, a solution containing 1 to 5% by weight of tragacanth, a carboxymethylcellulose solution, a sodium alginate solution and glycerin.

Examples of the disintegrant include starch and calcium carbonate.

Examples of the lubricant include magnesium stearate, stearic acid, calcium stearate and purified talc.

Examples of the sweetener include glucose, fructose, invert sugar, sorbitol, xylitol, glycerin and simple syrup.

Examples of the surfactant include sodium lauryl sulfate, polysorbate 80, sorbitan monofatty acid ester and polyoxyl 40 stearate.

Examples of the suspending agent include gum arabic, sodium alginate, carboxymethylcellulose sodium, methylcellulose and bentonite.

Examples of the emulsifier include gum arabic, tragacanth, gelatin and polysorbate 80.

When the medicament of the present invention is, for example, tablets, the tablets can be produced according to a method known per se in the art by adding, for example, an excipient (e.g., lactose, saccharose, starch), a disintegrant (e.g., starch, calcium carbonate), a binder (e.g., starch, gum arabic, carboxymethylcellulose, polyvinylpyrrolidone, hydroxypropylcellulose) or a lubricant (e.g., talc, magnesium stearate, polyethylene glycol 6000) to the compound of the present invention and molding the mixture by compression, followed by coating, if necessary, by a method known per se in the art for the purpose of taste masking, enteric properties or durability. For example, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethyl cellulose phthalate, hydroxymethylcellulose acetate succinate, Eudragit (manufactured by Rohm GmbH, Germany, methacrylic acid-acrylic acid copolymer) and a dye (e.g., iron red, titanium dioxide) can be used as coating agents for the coating.

The injections include intravenous injections as well as subcutaneous injections, intracutaneous injections, intramuscular injections, intraperitoneal injections, drip injections and the like.

Such injections are prepared by a method known per se in the art, i.e., by dissolving, suspending or emulsifying the compound of the present invention in a sterile aqueous solution or oily solution. Examples of the aqueous solution include saline, an isotonic solution containing glucose or an additional adjuvant (e.g., D-sorbitol, D-mannitol, sodium chloride) and the like. The aqueous solution may contain an appropriate solubilizing agent, for example, an alcohol (e.g., ethanol), a polyalcohol (e.g., propylene glycol, polyethylene glycol) or a nonionic surfactant (e.g., polysorbate 80, HCO-50). Examples of the oily solution include sesame oil, soybean oil and the like. The oily solution may contain an appropriate solubilizing agent. Examples of the solubilizing agent include benzyl benzoate, benzyl alcohol and the like. The injections may be further supplemented with a buffer (e.g., a phosphate buffer solution, a sodium acetate buffer solution), a soothing agent (e.g., benzalkonium chloride, procaine hydrochloride), a stabilizer (e.g., human serum albumin, polyethylene glycol), a preservative (e.g., benzyl alcohol, phenol) or the like. Ampules can usually be filled with the prepared injection solutions.

The content of the compound of the present invention in the medicament of the present invention differs depending on the form of the preparation and is usually approximately 0.01 to approximately 100% by weight, preferably approximately 2 to approximately 85% by weight, more preferably approximately 5 to approximately 70% by weight, with respect to the whole preparation.

The content of the additive in the medicament of the present invention differs depending on the form of the preparation and is usually approximately 1 to approximately 99.9% by weight, preferably approximately 10 to approximately 90% by weight, with respect to the whole preparation.

The compound of the present invention can be used stably, low toxically and safely. The daily dose of the compound of the present invention differs depending on the status and body weight of a patient, the type of the compound, an administration route, etc. In the case of, for example, oral administration to a patient for the purpose of treating cancer, the daily dose in adult (body weight: approximately 60 kg) can be approximately 1 to approximately 1000 mg, preferably approximately 3 to approximately 300 mg, more preferably approximately 10 to approximately 200 mg, of the compound of the present invention, which can be administered in one portion or in two or three portions.

In the case of parenterally administering the compound of the present invention, the compound of the present invention is usually administered in the form of a solution (e.g., an injection). The single dose of the compound of the present invention also differs depending on a recipient, a target organ, symptoms, an administration method, etc. For example, usually approximately 0.01 to approximately 100 mg, preferably approximately 0.01 to approximately 50 mg, more preferably approximately 0.01 to approximately 20 mg, of the compound of the present invention per kg of body weight can be administered by intravenous injection.

The compound of the present invention can be used in combination with an additional drug. Specifically, the compound of the present invention can be used in combination with a drug such as a hormone therapeutic, a chemotherapeutic, an immunotherapeutic, an agent inhibiting the effects of a cell growth factor and its receptor, or the like. Hereinafter, the drug that may be used in combination with the compound of the present invention is referred to as a concomitant drug.

Examples of the "hormone therapeutic" that may be used include fosfestrol, diethylstilbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogen (e.g., tamoxifen citrate, toremifene citrate), contraceptive pills, mepitiostane, testololactone, aminoglutethimide, LH-RH agonists (e.g., goserelin acetate, buserelin, leuprorelin acetate), droloxifene, epitiostanol, ethinyl estradiol sulfonate, aromatase inhibitors (e.g., fadrozole hydrochloride, anastrozole, letrozole, exemestane, vorozole, formestane), anti-androgen (e.g., flutamide, bicalutamide, nilutamide, enzalutamide), 5α-reductase inhibitors (e.g., finasteride, epristeride, dutasteride), adrenal corticosteroid agents (e.g., dexamethasone, prednisolone, betamethasone, triamcinolone), androgen synthesis inhibitors (e.g., abiraterone), retinoid and agents delaying retinoid metabolism (e.g., liarozole), thyroid hormones and DDS (drug delivery system) preparations thereof.

Examples of the "chemotherapeutic" that may be used include an alkylating agent, an antimetabolite, an anticancer antibiotic and a plant-derived anticancer agent.

Examples of the "alkylating agent" that may be used include nitrogen mustard, nitrogen mustard-N-oxide hydrochloride, chlorambucil, cyclophosphamide, ifosfamide, thiotepa, carboquone, improsulfan tosilate, busulfan, nimustine hydrochloride, mitobronitol, melphalan, dacarbazine, ranimustine, estramustine sodium phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, Ribomustin, temozolomide, treosulfan, trofosfamide, zinostatin stimalamer, adozelesin, cystemustine, bizelesin and DDS preparations thereof.

Examples of the "antimetabolite" that may be used include mercaptopurine, 6-mercaptopurine riboside, thioinosine, methotrexate, pemetrexed, enocitabine, cytarabine, cytarabine ocfosfate, ancitabine hydrochloride, 5-FU drugs (e.g., fluorouracil, tegafur, UFT, doxifluridine, carmofur, galocitabine, emitefur, capecitabine), aminopterin, nelarabine, leucovorin calcium, tabloid, butocine, calcium folinate, calcium levofolinate, cladribine, emitefur, fludarabine, gemcitabine, hydroxycarbamide, pentostatin, piritrexim, idoxuridine, mitoguazone, tiazofurin, ambamustine, bendamustine and DDS preparations thereof.

Examples of the "anticancer antibiotic" that may be used include actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarkomycin, carzinophilin, mitotane, zorubicin hydrochloride, mitoxantrone hydrochloride, idarubicin hydrochloride and DDS preparations (e.g., PEG liposomal doxorubicin) thereof.

Examples of the "plant-derived anticancer agent" that may be used include etoposide, etoposide phosphate, vinblastine sulfate, vincristine sulfate, vindesine sulfate, teniposide, paclitaxel, docetaxel, cabazitaxel, vinorelbine and DDS preparations thereof.

Examples of the "immunotherapeutic" that may be used include picibanil, Krestin, schizophyllan, lentinan, ubenimex, interferon, interleukin, macrophage colony-stimulating factor, granulocyte colony-stimulating factor, erythropoietin, lymphotoxin, BCG vaccines, *Corynebacterium parvum*, levamisole, polysaccharide K, procodazol, anti-CTLA4 antibodies (e.g., ipilimumab, tremelimumab), anti-PD-1 antibodies (e.g., nivolumab, pembrolizumab) and anti-PD-LI antibodies.

The "cell growth factor" in the "agent inhibiting the effects of a cell growth factor and its receptor" can be any substance that promotes the growth of cells. Typical examples thereof include a factor that is a peptide having a molecular weight of 20,000 or smaller and exerts its effects at a low concentration through binding to its receptor. Specific examples of the cell growth factor that may be used include (1) EGF (epidermal growth factor) or a substance having activity substantially identical thereto [e.g., TGFα], (2) insulin or a substance having activity substantially identical thereto [e.g., insulin, IGF (insulin-like growth factor)-1, IGF-2], (3) FGF (fibroblast growth factor) or a substance having activity substantially identical thereto

[e.g., acidic FGF, basic FGF, KGF (keratinocyte growth factor), FGF-10], and (4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor), VEGF (vascular endothelial growth factor), heregulin, angiopoietin].

The "receptor of the cell growth factor" can be any receptor having the ability to bind to any of the cell growth factor described above. Specific examples of the receptor that may be used include EGF receptor, heregulin receptor (e.g., HER3), insulin receptor, IGF receptor-1, IGF receptor-2, FGF receptor-1 or FGF receptor-2, VEGF receptor, angiopoietin receptor (e.g., Tie2), PDGF receptor and the like.

Examples of the "agent inhibiting the effects of a cell growth factor and its receptor" that may be used include EGF inhibitors, TGFα inhibitors, heregulin inhibitors, insulin inhibitors, IGF inhibitors, FGF inhibitors, KGF inhibitors, CSF inhibitors, EPO inhibitors, IL-2 inhibitors, NGF inhibitors, PDGF inhibitors, TGFβ inhibitors, HGF inhibitors, VEGF inhibitors, angiopoietin inhibitors, EGF receptor inhibitors, HER2 inhibitors, HER4 inhibitors, insulin receptor inhibitors, IGF-1 receptor inhibitors, IGF-2 receptor inhibitors, FGF receptor-1 inhibitors, FGF receptor-2 inhibitors, FGF receptor-3 inhibitors, FGF receptor-4 inhibitors, VEGF receptor inhibitors, Tie-2 inhibitors, PDGF receptor inhibitors, Abl inhibitors, Raf inhibitors, FLT3 inhibitors, c-Kit inhibitors, Src inhibitors, PKC inhibitors, Smo inhibitors, ALK inhibitors, ROR1 inhibitors, Trk inhibitors, Ret inhibitors, mTOR inhibitors, Aurora inhibitors, PLK inhibitors, MEK (MEK1/2) inhibitors, MET inhibitors, CDK inhibitors, Akt inhibitors, ERK inhibitors, PI3K inhibitors and the like. More specific examples of the agent that may be used include anti-VEGF antibodies (e.g., bevacizumab, ramucirumab), anti-HER2 antibodies (e.g., trastuzumab, pertuzumab), anti-EGFR antibodies (e.g., cetuximab, panitumumab, matuzumab, nimotuzumab), anti-HGF antibodies, imatinib, erlotinib, gefitinib, sorafenib, sunitinib, dasatinib, lapatinib, vatalanib, ibrutinib, bosutinib, cabozantinib, crizotinib, alectinib, vismodegib, axitinib, motesanib, nilotinib, 6-[4-(4-ethylpiperazin-1-ylmethyl)phenyl]-N-[1(R)-phenylethyl]-7H-pyrrolo[2,3-d]pyrimidin-4-amine (AEE-788), vandetanib, temsirolimus, everolimus, enzastaurin, tozasertib, phosphoric acid 2-[N-[3-[4-[5-[N-(3-fluorophenyl)carbamoylmethyl]-1H-pyrazol-3-ylamino]quinazolin-7-yloxy]propyl]-N-ethylamino]ethyl ester (AZD-1152), 4-[9-chloro-7-(2,6-difluorophenyl)-5H-pyrimido[5,4-d][2]benzazapin-2-ylamino]benzoic acid, N-[2-methoxy-5-[(E)-2-(2,4,6-trimethoxyphenyl)vinyl sulfonylmethyl]phenyl] glycine sodium salt (ON-1910Na), volasertib, selumetinib, trametinib, N-[2(R),3-dihydroxypropoxy]-3,4-difluoro-2-(2-fluoro-4-iodophenylamino)benzamide (PD-0325901), bosutinib, regorafenib, afatinib, idelalisib, ceritinib, dabrafenib and the like.

In addition to the drugs described above, examples that may be used as the concomitant drug also include L-asparaginase, L-arginase, arginine deiminase, aceglatone, procarbazine hydrochloride, protoporphyrin-cobalt complex salt, mercury hematoporphyrin-sodium, topoisomerase I inhibitors (e.g., irinotecan, topotecan, indotecan, indimitecan), topoisomerase II inhibitors (e.g., sobuzoxane), differentiation inducers (e.g., retinoid, vitamins D), other angiogenesis inhibitors (e.g., fumagillin, shark extracts, COX-2 inhibitors), α-blockers (e.g., tamsulosin hydrochloride), bisphosphonic acids (e.g., pamidronate, zoledronate), thalidomide, lenalidomide, pomalidomide, 5-azacytidine, decitabine, proteasome inhibitors (e.g., bortezomib, carfilzomib, ixazomib), NEDD8 inhibitors (e.g., pevonedistat), UAE inhibitors, PARP inhibitors (e.g., olaparib, niraparib, veliparib), antitumor antibodies such as anti-CD20 antibodies (e.g., rituximab, obinutuzumab), anti-CCR4 antibodies (e.g., mogamulizumab) and the like, antibody-drug conjugates (e.g., trastuzumab emtansine, brentuximab vedotin), MDM2 inhibitors or the like.

The combination of the compound of the present invention and the concomitant drug can produce excellent effects such as: (1) the dose of the compound of the present invention or the concomitant drug can be reduced as compared with the administration of the compound of the present invention or the concomitant drug alone; (2) the concomitant drug can be selected for combined use with the compound of the present invention according to the symptoms (mild, serious, etc.) of a patient; (3) the period of treatment can be set longer; (4) a sustained therapeutic effect can be achieved; (5) a synergistic effect can be obtained by the combined use of the compound of the present invention and the concomitant drug; and the like.

Hereinafter, the combined use of the compound of the present invention and the concomitant drug is referred to as the "combination drug of the present invention".

For use of the combination drug of the present invention, the time of administration of the compound of the present invention and the time of administration of the concomitant drug are not limited, and the compound of the present invention and the concomitant drug may be administered simultaneously or in a staggered manner to a recipient. In the case of administration in a staggered manner, the staggered manner differs depending on active ingredients to be administered, a dosage form and an administration method. In the case of first administering, for example, the concomitant drug, the compound of the present invention can be administered within 1 minute to 3 days, preferably within 10 minutes to 1 day, more preferably within 15 minutes to 1 hour, after the administration of the concomitant drug. In the case of first administering the compound of the present invention, the concomitant drug can be administered within 1 minute to 1 day, preferably within 10 minutes to 6 hours, more preferably within 15 minutes to 1 hour, after the administration of the compound of the present invention. The dose of the concomitant drug can abide by a dose clinically used and can be appropriately selected according to a recipient, an administration route, a disease, a combination, etc.

Examples of the administration mode of the compound of the present invention and the concomitant drug used in combination include (1) the administration of a single preparation obtained by simultaneously formulating the compound of the present invention and the concomitant drug, (2) the simultaneous administration through the same administration route of two preparations obtained by separately formulating the compound of the present invention and the concomitant drug, (3) the administration through the same administration route in a staggered manner of two preparations obtained by separately formulating the compound of the present invention and the concomitant drug, (4) the simultaneous administration through different administration routes of two preparations obtained by separately formulating the compound of the present invention and the concomitant drug, and (5) the administration through different administration routes in a staggered manner of two preparations obtained by separately formulating the compound of the present invention and the concomitant drug (e.g., administration in the order of the compound of the present invention and then the concomitant drug, or in the reverse order).

The dose of the concomitant drug can be appropriately selected on the basis of a dose clinically used. The mixing ratio between the compound of the present invention and the concomitant drug can be appropriately selected according to a recipient, an administration route, a target disease, symptoms, a combination, etc. When the recipient is, for example, a human, 0.01 to 100 parts by weight of the concomitant drug can be used with respect to 1 part by weight of the compound of the present invention.

The compound of the present invention or the combination drug of the present invention can be further used in combination with a non-drug therapy. Specifically, the compound of the present invention or the combination drug of the present invention may be combined with a non-drug therapy, for example, (1) surgery, (2) induced hypertension chemotherapy using angiotensin II or the like, (3) gene therapy, (4) thermotherapy, (5) cryotherapy, (6) laser cauterization or (7) radiotherapy.

The compound of the present invention or the combination drug of the present invention is used, for example, before or after the surgery or the like or before or after treatment involving two or three of these therapies in combination to produce effects such as prevention of development of resistance, prolonged disease-free survival, inhibition of cancer metastasis or recurrence, life prolongation and the like.

Also, the treatment with the compound of the present invention or the combination drug of the present invention may be combined with supportive care [(i) the administration of an antibiotic (e.g., a β-lactam antibiotic such as Pansporin and the like, a macrolide antibiotic such as clarithromycin and the like) against various intercurrent infections, (ii) the administration of a high-calorie infusion, an amino acid preparation or multivitamin for the improvement of malnutrition, (iii) the administration of morphine for pain relief, (iv) the administration of a drug improving adverse reactions such as nausea, vomiting, anorexia, diarrhea, leukopenia, thrombocytopenia, decreased hemoglobin concentration, alopecia, liver damage, kidney damage, DIC, fever and the like and (v) the administration of a drug for inhibiting multidrug resistance of cancer, etc.].

The present invention will be described further specifically with reference to Examples, Formulation Examples and Test Examples given below. However, the present invention is not intended to be limited by them, and various changes or modifications may be made therein without departing from the scope of the present invention.

EXAMPLES

In Examples below, the term "room temperature" usually means approximately 10° C. to approximately 35° C. A ratio used for a mixed solvent represents a volume ratio unless otherwise specified. % represents % by weight unless otherwise specified.

In silica gel column chromatography, the term "NH" represents that an aminopropylsilane-bound silica gel was used, the term "Diol" represents that a 3-(2,3-dihydroxypropoxy)propylsilane-bound silica gel, was used, and the term "DiNH" represents that an N-(2-aminoethyl)-3-aminopropylsilane-bound silica gel. In HPLC (High Speed Liquid Chromatography), the term "C18" represents that an octadecyl-bound silica gel was used. A ratio used for elution solvents represents a volume ratio unless otherwise specified.

In Examples below, the following abbreviations are used:
mp: melting point
MS: mass spectrum
$[M+H]^+$, $[M-H]^-$: molecular ion peakM: molar concentration
N: normality
$CDCl_3$: deuterated chloroform
$DMSO-d_6$: deuterated dimethyl sulfoxide
$^1H$ NMR: proton nuclear magnetic resonance
LC/MS: liquid chromatograph-mass spectrometer
ESI: electrospray ionization
APCI: atmospheric pressure chemical ionization
THF: tetrahydrofuran
DME: 1,2-dimethoxyethane
DMF: N,N-dimethylformamide
DMA: N,N-dimethylacetamide
DMSO: dimethyl sulfoxide
HATU: 2-(7-azabenzotriazol-1-yl)-1,1,3,3-tetramethyluronium hexafluorophosphate
HOBt: 1-hydroxybenzotriazole
CDI: 1,1'-carbonyldiimidazole
Py: pyridine
IPE: diisopropyl ether
DIPEA: N,N'-diisopropylethylamine
DMAP: N,N-dimethyl-4-aminopyridine
IPA: isopropanol
IPE: diisopropyl ether
KHMDS: potassium bis(trimethylsilyl)amide
DIPA: diisopropylamine
NBS: N-bromosuccinimide
NMO: N-methylmorpholine N-oxide
TBAF: tetra-n-butylammonium fluoride
pTsCl: p-toluenesulfonyl chloride
TFA: trifluoroacetic acid
DIAD: diisopropyl azodicarboxylate
CPME: cyclopentyl methyl ether
EDC: 1-ethyl-3-(3-dimethylaminopropyl)carbodiimide
TLC: thin layer chromatography
IBX: 2-iodoxybenzoic acid
TBAI: tetrabutylammonium iodide
DIBAL: diisobutylaluminium hydride
AIBN: 2,2'-(E)-diazene-1,2-diylbis(2-methylpropanenitrile)

$^1H$ NMR was measured by Fourier transform NMR. ACD/SpecManager (trade name) or the like was used in analysis. No mention was made about the very broad peaks of protons of a hydroxy group, an amino group and the like.

MS was measured by LC/MS. ESI or APCI was used as an ionization method. Data was indicated by actually measured values (found). In general, molecular ion peaks ($[M+H]^+$, $[M-H]^-$ and the like) are observed. For example, in the case of a compound having a tert-butoxycarbonyl group, a fragment ion peak derived from the elimination of the tert-butoxycarbonyl group or the tert-butyl group is observed. In the case of a compound having a hydroxy group, a fragment ion peak derived from the elimination of $H_2O$ may be observed. In the case of a salt, a molecular ion peak or fragment ion peak of a free form is usually observed.

The unit of the sample concentration (c) in optical rotation (([α]D) is g/100 mL.

For the value of element analysis (Anal.), the calculated values (Calcd) and measured values (Found) are described.

Example 1

2-(azetidin-1-yl)-1-(3,5-difluorobenzyl)-6-(4-methoxy-5H-pyrrolo[3,2-d]pyrimidin-5-yl)-1H-imidazo[4,5-b]pyridine a) 4-methoxy-5H-pyrrolo[3,2-d]pyrimidine 4-chloro-5H-pyrrolo[3,2-d]pyrimidine (10 g) was suspended in methanol (50 mL), and sodium methoxide (28% methanol solution) (30 mL) was added at room temperature. Under a dry atmosphere, the mixture was stirred at 60° C. overnight. The reaction mixture was concentrated under reduced pressure. The residue was sequentially washed with water and IPA, and then dried under reduced pressure to obtain the title compound (6.44 g).

$^1$H NMR (300 MHz, DMSO-$d_6$) δ 4.07 (3H, s), 6.54 (1H, d, J=3.0 Hz), 7.65 (1H, d, J=3.0 Hz), 8.40 (1H, s), 12.01 (1H, brs).

b) 5-bromo-N3-(3,5-difluorobenzyl)pyridine-2,3-diamine

Acetic acid (5 mL) was added to a solution of 3,5-difluorobenzaldehyde (26.5 g) and 5-bromopyridine-2,3-diamine (25 g) in THF (400 mL) at room temperature. Under a dry atmosphere, the mixture was stirred at room temperature for 10 hours. The mixture was neutralized with saturated aqueous sodium hydrogen carbonate solution at 0° C., and extracted with ethyl acetate (250 mL)/toluene (250 mL). The organic layer was washed with water and a saturated brine, dried over magnesium sulfate, and then concentrated to obtain a residue. Sodium borohydride (10.06 g) was suspended in THF (200 mL), methanol (200 mL) was added at 0° C., and the mixture was stirred for 10 minutes. The obtained suspension of the residue in THF (300 mL) was added to the reaction mixture at 0° C. Under a dry atmosphere, the mixture was stirred at room temperature for 2 hours. The reaction mixture was poured into ice water at 0° C., and extracted with ethyl acetate. The organic layer was sequentially washed with water and a saturated brine, then dried over magnesium sulfate, and concentrated under reduced pressure. The residue was purified by silica gel column chromatography (ethyl acetate/hexane) to obtain the title compound (10 g).

$^1$H NMR (300 MHz, DMSO-$d_6$) δ4.35 (2H, d, J=5.8 Hz), 5.71-5.86 (3H, m), 6.56 (1H, d, J=2.1 Hz), 7.03-7.16 (3H, m), 7.32 (1H, d, J=2.1 Hz).

c) 6-bromo-1-(3,5-difluorobenzyl)-1H-imidazo[4,5-b]pyridin-2(3H)-one

Under a dry atmosphere, a mixture of 5-bromo-N3-(3,5-difluorobenzyl)pyridine-2,3-diamine (6 g), CDI (6.19 g) and THF (60 mL) was stirred at 60° C. for 16 hours. The reaction mixture was diluted with water at room temperature, and extracted with ethyl acetate. The organic layer was sequentially washed with a saturated brine, then dried over magnesium sulfate, and concentrated under reduced pressure. The residue was washed with ethyl acetate/IPE to obtain the title compound (6.4 g).

$^1$H NMR (300 MHz, DMSO-$d_6$) δ 5.04 (2H, s), 7.03-7.23 (3H, m), 7.79 (1H, d, J=2.1 Hz), 8.03 (1H, d, J=2.0 Hz), 11.97 (1H, brs).

d) 6-bromo-2-chloro-1-(3,5-difluorobenzyl)-1H-imidazo[4,5-b]pyridine

A mixture of 6-bromo-1-(3,5-difluorobenzyl)-1H-imidazo[4,5-b]pyridin-2(3H)-one (6.4 g) and phosphorus oxychloride (45 mL) was stirred under a nitrogen atmosphere at 100° C. for 22 hours. The reaction mixture was concentrated under reduced pressure. The residue was diluted with THF, neutralized with a saturated aqueous sodium hydrogen carbonate solution at 0° C., and extracted with ethyl acetate. The organic layer was washed with a saturated brine, dried over magnesium sulfate, and then concentrated. The residue was washed with ethyl acetate/IPE to obtain the title compound (4.59 g).

$^1$H NMR (300 MHz, DMSO-$d_6$) δ 5.59 (2H, s), 7.00 (2H, dd, J=8.3, 2.2 Hz), 7.22 (1H, tt, J=9.4, 2.2 Hz), 8.55 (2H, q, J=2.1 Hz).

e) 2-(azetidin-1-yl)-6-bromo-1-(3,5-difluorobenzyl)-1H-imidazo[4,5-b]pyridine A mixture of 6-bromo-2-chloro-1-(3,5-difluorobenzyl)-1H-imidazo[4,5-b]pyridine (1.00 g), azetidine (0.8 mL) and THF (8 mL) was stirred under a dry atmosphere at room temperature for 16 hours. The reaction mixture was diluted with water at room temperature, and extracted with ethyl acetate. The organic layer was washed with a saturated brine, dried over magnesium sulfate, and then concentrated. The residue was washed with ethyl acetate to obtain the title compound (0.946 g).

$^1$H NMR (300 MHz, DMSO-$d_6$) δ 2.33 (2H, quin, J=7.6 Hz), 4.19 (4H, t, J=7.6 Hz), 5.31 (2H, s), 6.79-6.90 (2H, m), 7.18 (1H, tt, J=9.4, 2.3 Hz), 7.86 (1H, d, J=2.2 Hz), 8.16 (1H, d, J=2.2 Hz).

f) 2-(azetidin-1-yl)-1-(3,5-difluorobenzyl)-6-(4-methoxy-5H-pyrrolo[3,2-d]pyrimidin-5-yl)-1H-imidazo[4,5-b]pyridine A mixture of 2-(azetidin-1-yl)-6-bromo-1-(3,5-difluorobenzyl)-1H-imidazo[4,5-b]pyridine (200 mg), 4-methoxy-5H-pyrrolo[3,2-d]pyrimidine (157 mg), sodium t-butoxide (101 mg), tris(dibenzylideneacetone)dipalladium (0) (33.8 mg), 2-di-tert-butylphosphino-2',4',6'-triisopropylbiphenyl (62.7 mg) and toluene (5 mL) was stirred under microwave irradiation at 130° C. for 2 hours. The mixture was diluted with water/methanol at room temperature, and extracted with ethyl acetate/THF. The organic layer was washed with a saturated brine, dried over magnesium sulfate, and then concentrated. The residue was purified by NH silica gel column chromatography (methanol/ethyl acetate), and the residue was washed with ethyl acetate to obtain the title compound (16.3 mg).

$^1$H NMR (300 MHz, DMSO-$d_6$) δ 2.36 (2H, quin, J=7.6 Hz), 3.74 (3H, s), 4.22 (4H, t, J=7.6 Hz), 5.32 (2H, s), 6.77 (1H, d, J=3.2 Hz), 6.86-6.94 (2H, m), 7.20 (1H, tt, J=9.4, 2.3 Hz), 7.87 (2H, dd, J=2.8, 1.7 Hz), 8.27 (1H, d, J=2.4 Hz), 8.48 (1H, s).

Example 7

1-(3,5-difluorobenzyl)-6-(4-methoxy-5H-pyrrolo[3,2-d]pyrimidin-5-yl)-2-methyl-H-imidazo[4,5-b]pyridine a) N3-(3,5-difluorobenzyl)-5-iodopyridine-2,3-diamine

A mixture of 3,5-difluorobenzaldehyde (14.4 g), 5-iodopyridine-2,3-diamine (15.4 g), acetic acid (10 mL) and THF (200 mL) was stirred under nitrogen atmosphere at room temperature for 13 hours. The reaction mixture was concentrated under reduced pressure. The residue was neutralized with a saturated aqueous sodium hydrogen carbonate solution at 0° C., and extracted with ethyl acetate/THF. The organic layer was washed with a saturated aqueous sodium hydrogen carbonate solution and a saturated brine, dried over magnesium sulfate, and then concentrated to obtain a residue. Methanol (100 mL) was added to a mixture of sodium borohydride (6.6 g) and THF (200 mL) at 0° C. The obtained solution of the residue in THF (300 mL) was added to the reaction mixture at 0° C. Under a nitrogen atmosphere, the mixture was stirred at room temperature for 2 hours. Water and a saturated aqueous ammonium chloride solution were added to the reaction mixture at 0° C. to stop the reaction, and the mixture was extracted with ethyl acetate. The organic layer was washed with a saturated brine, then dried over magnesium sulfate, and concentrated under reduced pressure. The residue was purified by silica gel column chromatography (ethyl acetate/hexane) to obtain the title compound (18.1 g).

$^1$H NMR (300 MHz, DMSO-d$_6$) δ 4.33 (2H, d, J=5.9 Hz), 5.69 (1H, t, J=5.8 Hz), 5.79 (2H, s), 6.65 (1H, d, J=1.8 Hz), 7.01-7.18 (3H, m), 7.42 (1H, d, J=1.8 Hz).

b) 1-(3,5-difluorobenzyl)-6-iodo-2-methyl-1H-imidazo[4,5-b]pyridine

Concentrated hydrochloric acid (1 mL) was added to a mixture of N3-(3,5-difluorobenzyl)-5-iodopyridine-2,3-diamine (5 g) and trimethyl orthoacetate (50 mL) at room temperature. The mixture was stirred under a dry atmosphere at room temperature for 2 hours. The mixture was neutralized with a saturated aqueous sodium hydrogen carbonate solution at room temperature, and extracted with ethyl acetate/THF. The organic layer was washed with a saturated brine, then dried over magnesium sulfate, and concentrated under reduced pressure. The residue was washed with ethyl acetate to obtain the title compound (3.46 g).

$^1$H NMR (300 MHz, DMSO-d$_6$) δ 2.55 (3H, s), 5.54 (2H, s), 6.80-6.92 (2H, m), 7.20 (1H, tt, J=9.4, 2.3 Hz), 8.39 (1H, d, J=1.9 Hz), 8.53 (1H, d, J=2.0 Hz).

c) 1-(3,5-difluorobenzyl)-6-(4-methoxy-5H-pyrrolo[3,2-d]pyrimidin-5-yl)-2-methyl-1H-imidazo[4,5-b]pyridine A mixture of 1-(3,5-difluorobenzyl)-6-iodo-2-methyl-1H-imidazo[4,5-b]pyridine (1.1 g), 4-methoxy-5H-pyrrolo[3,2-d]pyrimidine (0.554 g), potassium phosphate (1.819 g), trans-N,N'-dimethylcyclohexane-1,2-diamine (0.406 g), copper (I) iodide (0.272 g) and THF (26 mL) was stirred under microwave irradiation at 110° C. for 2 hours. The mixture was diluted with water at room temperature, and extracted with ethyl acetate. The organic layer was washed with a saturated brine, dried over magnesium sulfate, and then concentrated. The residue was purified by silica gel column chromatography (methanol/ethyl acetate), and the residue was crystallized from ethanol/IPE to obtain the title compound (0.916 g).

$^1$H NMR (300 MHz, DMSO-d$_6$) δ 2.63 (3H, s), 3.73 (3H, s), 5.57 (2H, s), 6.83 (1H, d, J 5=3.2 Hz), 6.88-6.97 (2H, m), 7.22 (1H, tt, J=9.4, 2.3 Hz), 7.97 (1H, d, J=3.2 Hz), 8.29 (1H, d, J=2.4 Hz), 8.51 (1H, s), 8.55 (1H, d, J=2.4 Hz).

Example 10

2-ethoxy-1-(3-fluorobenzyl)-6-(4-methoxy-5H-pyrrolo[3,2-d]pyrimidin-5-yl)-1H-imidazo[4,5-b]pyridine a) N3-(3-fluorobenzyl)-5-iodopyridine-2,3-diamine A mixture of 3-fluorobenzaldehyde (4.75 g), 5-iodopyridine-2,3-diamine (6 g), acetic acid (3.7 mL) and THF (80 mL) was stirred under a nitrogen atmosphere at room temperature for 3 days. The reaction mixture was concentrated under reduced pressure. The residue was neutralized with a saturated aqueous sodium hydrogen carbonate solution at 0° C., and extracted with ethyl acetate/THF. The organic layer was washed with a saturated aqueous sodium hydrogen carbonate solution and a saturated brine, dried over magnesium sulfate, and then concentrated to obtain a residue. Methanol (30 mL) was added to a mixture of sodium borohydride (2.83 g) and THF (80 mL) at 0° C. The obtained solution of the residue in THF (120 mL) was added to the reaction mixture at 0° C. Under a nitrogen atmosphere, the mixture was stirred at room temperature for 2 hours. Water and a saturated aqueous ammonium chloride solution were added to the reaction mixture at 0° C. to stop the reaction, and the mixture was extracted with ethyl acetate. The organic layer was washed with a saturated brine, then dried over magnesium sulfate, and concentrated under reduced pressure. The residue was purified by silica gel column chromatography (ethyl acetate/hexane) to obtain the title compound (4.61 g).

1H NMR (300 MHz, DMSO-d$_6$) δ 4.31 (2H, d, J=5.7 Hz), 5.67 (1H, t, J=5.7 Hz), 5.79 (2H, s), 6.65 (1H, d, J=1.8 Hz), 7.03-7.12 (1H, m), 7.13-7.23 (2H, m), 7.34-7.44 (2H, m).

b) 1-(3-fluorobenzyl)-6-iodo-1H-imidazo[4,5-b]pyridine-2(3H)-thione

Under a dry atmosphere, a mixture of N3-(3-fluorobenzyl)-5-iodopyridine-2,3-diamine (1.15 g), 1,1'-thiocarbonyldiimidazole (1.31 g) and THF (15 mL) was stirred at 60° C. for 16 hours. The reaction mixture was quenched with water at room temperature, and extracted with ethyl acetate. The organic layer was sequentially washed with a saturated aqueous ammonium chloride solution, water and a saturated brine, then dried over magnesium sulfate, and concentrated under reduced pressure. The residue was washed with ethyl acetate to obtain the title compound (1.26 g).

$^1$H NMR (300 MHz, DMSO-d$_6$) δ 5.49 (2H, s), 7.08-7.27 (3H, m), 7.39 (1H, td, J=7.9, 6.2 Hz), 8.09 (1H, d, J=1.7 Hz), 8.36 (1H, d, J=1.7 Hz), 13.69 (1H, brs).

c) 2-ethoxy-1-(3-fluorobenzyl)-6-iodo-1H-imidazo[4,5-b]pyridine

To a mixture of 1-(3-fluorobenzyl)-6-iodo-1H-imidazo[4,5-b]pyridine-2(3H)-thione (1.25 g) and DMF (2 mL) was added thionyl chloride (5 mL). Under a dry atmosphere, the mixture was stirred at 70° C. for 30 minutes. The reaction mixture was concentrated under reduced pressure. The residue was neutralized with a saturated aqueous sodium hydrogen carbonate solution at 0° C., and extracted with ethyl acetate/THF. The organic layer was washed with a saturated brine, then dried over magnesium sulfate, and concentrated under reduced pressure. The residue was suspended in ethanol (5 mL)/THF (5 mL), and sodium ethoxide (21% ethanol solution) (7 mL) was added at room temperature.

Under a dry atmosphere, the mixture was stirred at room temperature for 1 hour. The mixture was diluted with water at room temperature, and extracted with ethyl acetate. The organic layer was washed with a saturated brine, then dried over magnesium sulfate, and concentrated under reduced pressure. The residue was purified by silica gel column chromatography (ethyl acetate/hexane), and washed with IPE to obtain the title compound (0.498 g).

$^1$H NMR (300 MHz, DMSO-$d_6$) δ 1.39 (3H, t, J=7.0 Hz), 4.61 (2H, q, J=7.1 Hz), 5.27 (2H, s), 7.06 (1H, d, J=7.8 Hz), 7.10-7.18 (2H, m), 7.34-7.46 (1H, m), 8.22 (1H, d, J=1.9 Hz), 8.38 (1H, d, J=1.9 Hz).

d) 2-ethoxy-1-(3-fluorobenzyl)-6-(4-methoxy-5H-pyrrolo[3,2-d]pyrimidin-5-yl)-1H-imidazo[4,5-b]pyridine A mixture of 2-ethoxy-1-(3-fluorobenzyl)-6-iodo-1H-imidazo[4,5-b]pyridine (300 mg), 4-methoxy-5H-pyrrolo[3,2-d]pyrimidine (146 mg), potassium phosphate (481 mg), trans-N,N'-dimethylcyclohexane-1,2-diamine (107 mg), copper (I) iodide (71.9 mg) and THF (4 mL) was stirred under microwave irradiation at 110° C. for 2 hours. The mixture was diluted with water at room temperature, and extracted with ethyl acetate. The organic layer was washed with a saturated brine, dried over magnesium sulfate, and then concentrated. The residue was purified by NH silica gel column chromatography (methanol/ethyl acetate), and the residue was washed with ethyl acetate to obtain the title compound (37.2 mg).

$^1$H NMR (300 MHz, DMSO-$d_6$) δ 1.44 (3H, t, J=7.0 Hz), 3.73 (3H, s), 4.67 (2H, q, J=7.1 Hz), 5.29 (2H, s), 6.81 (1H, d, J=3.2 Hz), 7.10-7.24 (3H, m), 7.37-7.49 (1H, m), 7.92 (1H, d, J=3.2 Hz), 8.16 (1H, d, J=2.4 Hz), 8.38 (1H, d, J=2.3 Hz), 8.50 (1H, s).

Example 12

1-(3-fluorobenzyl)-6-(4-methoxy-5H-pyrrolo[3,2-d]pyrimidin-5-yl)-2-methyl-1H-imidazo[4,5-b]pyridine a) 1-(3-fluorobenzyl)-6-iodo-2-methyl-1H-imidazo[4,5-b]pyridine

Concentrated hydrochloric acid (0.5 mL) was added to a mixture of N3-(3-fluorobenzyl)-5-iodopyridine-2,3-diamine (1.5 g) and trimethyl orthoacetate (20 mL) at room temperature. The mixture was stirred under a dry atmosphere at room temperature for 2 hours. The mixture was neutralized with a saturated aqueous sodium hydrogen carbonate solution at room temperature, and extracted with ethyl acetate/THF. The organic layer was washed with a saturated brine, then dried over magnesium sulfate, and concentrated under reduced pressure. The residue was washed with ethyl acetate to obtain the title compound (1.31 g).

$^1$H NMR (300 MHz, DMSO-$d_6$) δ 2.54 (3H, s), 5.54 (2H, s), 6.91 (1H, d, J=7.6 Hz), 7.02 (1H, dt, J=9.9, 2.0 Hz), 7.14 (1H, td, J=8.5, 2.2 Hz), 7.39 (1H, td, J=8.0, 6.1 Hz), 8.39 (1H, d, J=1.9 Hz), 8.52 (1H, d, J=1.9 Hz).

b) 1-(3-fluorobenzyl)-6-(4-methoxy-5H-pyrrolo[3,2-d]pyrimidin-5-yl)-2-methyl-1H-imidazo[4,5-b]pyridine A mixture of 1-(3-fluorobenzyl)-6-iodo-2-methyl-1H-imidazo[4,5-b]pyridine (320 mg), 4-methoxy-5H-pyrrolo[3,2-d]pyrimidine (169 mg), potassium phosphate (555 mg), trans-N,N'-dimethylcyclohexane-1,2-diamine (124 mg), copper (I) iodide (83 mg) and THF (5 mL) was stirred under microwave irradiation at 110° C. for 2 hours. The mixture was diluted with water and a 28% aqueous ammonia solution at room temperature, and extracted with ethyl acetate. The organic layer was washed with a saturated brine, dried over magnesium sulfate, and then concentrated. The residue was purified by NH silica gel column chromatography (methanol/ethyl acetate), and the residue was washed with ethyl acetate to obtain the title compound (176 mg).

$^1$H NMR (300 MHz, DMSO-$d_6$) δ 2.62 (3H, s), 3.71 (3H, s), 5.57 (2H, s), 6.83 (1H, d, J=3.2 Hz), 6.99 (1H, d, J=7.7 Hz), 7.07 (1H, dt, J=9.9, 2.0 Hz), 7.16 (1H, td, J=8.5, 2.2 Hz), 7.42 (1H, td, J=7.9, 6.1 Hz), 7.96 (1H, d, J=3.2 Hz), 8.28 (1H, d, J=2.4 Hz), 8.51 (1H, s), 8.54 (1H, d, J=2.4 Hz).

Example 13

(1-(3-fluorobenzyl)-6-(4-methoxy-5H-pyrrolo[3,2-d]pyrimidin-5-yl)-1H-imidazo[4,5-b]pyridin-2-yl)methanol a) (1-(3-fluorobenzyl)-6-iodo-1H-imidazo[4,5-b]pyridin-2-yl)methanol

A mixture of N3-(3-fluorobenzyl)-5-iodopyridine-2,3-diamine (1.5 g), 2-hydroxyacetic acid (8.31 g) and THF (3 mL) was heated under microwave irradiation at 150° C. for 2 hours. The reaction mixture was poured into a saturated aqueous sodium hydrogen carbonate solution, and extracted with ethyl acetate. The organic layer was washed with a saturated brine, then dried over magnesium sulfate, and concentrated under reduced pressure. The residue was purified by silica gel column chromatography (methanol/ethyl acetate) to obtain the title compound (1.2 g).

$^1$H NMR (300 MHz, DMSO-$d_6$) δ 4.76 (2H, d, J=5.9 Hz), 5.61 (2H, s), 5.84-5.92 (1H, m), 7.00-7.18 (3H, m), 7.34-7.43 (1H, m), 8.31 (1H, d, J=2.0 Hz), 8.56 (1H, d, J=2.0 Hz).

b) (1-(3-fluorobenzyl)-6-(4-methoxy-5H-pyrrolo[3,2-d]pyrimidin-5-yl)-1H-imidazo[4,5-b]pyridin-2-yl)methanol A mixture of (1-(3-fluorobenzyl)-6-iodo-1H-imidazo[4,5-b]pyridin-2-yl)methanol (959 mg), 4-methoxy-5H-pyrrolo[3,2-d]pyrimidine (485 mg), potassium phosphate (1594 mg), trans-N,N'-dimethylcyclohexane-1,2-diamine (356 mg), copper (1) iodide (238 mg) and THF (13 mL) was stirred under microwave irradiation at 110° C. for 2 hours. The mixture was diluted with water and a 28% aqueous ammonia solution at room temperature, and extracted with ethyl acetate. The organic layer was washed with a saturated brine, dried over magnesium sulfate, and then concentrated. The residue was purified by NH silica gel column chromatography (methanol/ethyl acetate), and the residue was washed with ethyl acetate/ethanol to obtain the title compound (153 mg).

$^1$H NMR (300 MHz, DMSO-$d_6$) δ3.65 (3H, s), 4.83 (2H, d, J=5.6 Hz), 5.64 (2H, s), 5.93 (1H, t, J=5.6 Hz), 6.83 (1H, d, J=3.2 Hz), 7.07-7.21 (3H, m), 7.36-7.47 (1H, m), 7.96 (1H, d, J=3.2 Hz), 8.22 (1H, d, J=2.2 Hz), 8.50 (1H, s), 8.59 (1H, d, J=2.2 Hz).

Example 17

1-(3,4-difluorobenzyl)-6-(4-methoxy-5H-pyrrolo[3,2-d]pyrimidin-5-yl)-2-methyl-1H-imidazo[4,5-b]pyridine a)
N3-(3,4-difluorobenzyl)-5-iodopyridine-2,3-diamine A mixture of 3,4-difluorobenzaldehyde (7 g), 5-iodopyridine-2,3-diamine (7.3 g), acetic acid (5 mL) and THF (100 mL) was stirred under nitrogen atmosphere at room temperature for 13 hours. The reaction mixture was concentrated under reduced pressure. The residue was neutralized with a saturated aqueous sodium hydrogen carbonate solution at 0° C., and extracted with ethyl acetate/THF. The organic layer was washed with a saturated aqueous sodium hydrogen carbonate solution and a saturated brine, dried over magnesium sulfate, and then concentrated to obtain a residue. Methanol (50 mL) was added to a mixture of sodium borohydride (2.9 g) and THF (100 mL) at 0° C. The obtained solution of the residue in THF (50 mL) was added to the reaction mixture at 0° C. Under a nitrogen atmosphere, the mixture was stirred at room temperature for 2 hours. A saturated aqueous ammonium chloride solution was added to the reaction mixture at 0° C. to stop the reaction, and the mixture was extracted with ethyl acetate. The organic layer was washed with a saturated brine, then dried over magnesium sulfate, and concentrated under reduced pressure. The residue was purified by silica gel column chromatography (ethyl acetate/hexane) to obtain the title compound (8 g).

$^1$H NMR (300 MHz, DMSO-$d_6$) δ 4.28 (2H, d, J=5.7 Hz), 5.64 (1H, t, J=5.7 Hz), 5.78 (2H, s), 6.66 (1H, d, J=1.8 Hz), 7.15-7.25 (1H, m), 7.33-7.48 (3H, m).

b) 1-(3,4-difluorobenzyl)-6-iodo-2-methyl-1H-imidazo[4,5-b]pyridine

Concentrated hydrochloric acid (300 μL) was added to a mixture of N3-(3,4-difluorobenzyl)-5-iodopyridine-2,3-diamine (1.1 g) and trimethyl orthoacetate (5 mL) at room temperature. The mixture was stirred at room temperature for 1 hour. The reaction mixture was concentrated under reduced pressure. The residue was washed with IPE to obtain the title compound (790 mg).

$^1$H NMR (300 MHz, DMSO-$d_6$) δ 2.55 (3H, s), 5.50 (2H, s), 6.89-7.02 (1H, m), 7.25-7.50 (2H, m), 8.40 (1H, d, J=1.9 Hz), 8.52 (1H, d, J=2.0 Hz).

c) 1-(3,4-difluorobenzyl)-6-(4-methoxy-5H-pyrrolo[3,2-d]pyrimidin-5-yl)-2-methyl-1H-imidazo[4,5-b]pyridine A mixture of 1-(3,4-difluorobenzyl)-6-iodo-2-methyl-1H-imidazo[4,5-b]pyridine (202.7 mg), 4-methoxy-5H-pyrrolo[3,2-d]pyrimidine (78 mg), potassium phosphate (335 mg), trans-N,N'-dimethylcyclohexane-1,2-diamine (90 mg), copper (I) iodide (60.1 mg) and THF (2 mL) was stirred under microwave irradiation at 150° C. for 3 hours. The mixture was cooled to room temperature, and insolubles were removed. The mixture was concentrated under reduced pressure. The residue was purified by NH silica gel column chromatography (methanol/ethyl acetate), and crystallized from ethanol to obtain the title compound (66 mg).

$^1$H NMR (300 MHz, DMSO-$d_6$) δ 2.63 (3H, s), 3.74 (3H, s), 5.53 (2H, s), 6.83 (1H, d, J=3.2 Hz), 6.96-7.09 (1H, m), 7.31-7.51 (2H, m), 7.96 (1H, d, J=3.2 Hz), 8.29 (1H, d, J=2.4 Hz), 8.46-8.58 (2H, m).

Example 20

1-(2,3-difluorobenzyl)-6-(4-methoxy-5H-pyrrolo[3,2-d]pyrimidin-5-yl)-2-methyl-1H-imidazo[4,5-b]pyridine a)
N3-(2,3-difluorobenzyl)-5-iodopyridine-2,3-diamine A mixture of 2,3-difluorobenzaldehyde (13.6 g), 5-iodopyridine-2,3-diamine (15 g), acetic acid (7.31 mL) and THF (100 mL) was stirred under nitrogen atmosphere at room temperature for 13 hours. The reaction mixture was concentrated under reduced pressure. The residue was neutralized with a saturated aqueous sodium hydrogen carbonate solution at 0° C., and extracted with ethyl acetate/THF. The organic layer was washed with a saturated aqueous sodium hydrogen carbonate solution and a saturated brine, dried over magnesium sulfate, and then concentrated to obtain a residue. Methanol (50 mL) was added to a mixture of sodium borohydride (6.04 g) and THF (100 mL) at 0° C. The obtained solution of the residue in THF (300 mL) was added to the reaction mixture at 0° C. Under a nitrogen atmosphere, the mixture was stirred at room temperature for 2 hours. Water and a saturated aqueous ammonium chloride solution were added to the reaction mixture at 0° C. to stop the reaction, and the mixture was extracted with ethyl acetate. The organic layer was washed with a saturated brine, then dried over magnesium sulfate, and concentrated under reduced pressure. The residue was purified by silica gel column chromatography (ethyl acetate/hexane) to obtain the title compound (14.1 g).

$^1$H NMR (300 MHz, DMSO-$d_6$) δ 4.36 (2H, d, J=5.6 Hz), 5.54-5.66 (1H, m), 5.80 (2H, s), 6.72 (1H, d, J=1.6 Hz), 7.11-7.56 (4H, m).

b) 1-(2,3-difluorobenzyl)-6-iodo-2-methyl-1H-imidazo[4,5-b]pyridine

Concentrated hydrochloric acid (300 μL) was added to a mixture of N3-(2,3-difluorobenzyl)-5-iodopyridine-2,3-diamine (144.9 mg) and trimethyl orthoacetate (3 mL) at room temperature. The mixture was stirred at room temperature for 1 hour. The reaction mixture was concentrated under reduced pressure. The residue was purified by NH silica gel column chromatography (ethyl acetate/hexane) to obtain the title compound (105 mg).

$^1$H NMR (400 MHz, DMSO-$d_6$) δ 2.53 (3H, s), 5.64 (2H, s), 6.76 (1H, t, J=7.3 Hz), 7.13-7.22 (1H, m), 7.36-7.46 (1H, m), 8.40 (1H, d, J=2.0 Hz), 8.52 (1H, d, J=2.0 Hz).

c) 1-(2,3-difluorobenzyl)-6-(4-methoxy-5H-pyrrolo[3,2-d]pyrimidin-5-yl)-2-methyl-1H-imidazo[4,5-b]pyridine A mixture of 1-(2,3-difluorobenzyl)-6-iodo-2-methyl-1H-imidazo[4,5-b]pyridine (105.1 mg), 4-methoxy-5H-pyrrolo[3,2-d]pyrimidine (44.8 mg), potassium phosphate (174 mg), trans-N,N'-dimethylcyclohexane-1,2-diamine (46.6 mg), copper (I) iodide (31.2 mg) and THF (2 mL) was stirred under microwave irradiation at 150° C. for 3 hours. The mixture was cooled to room temperature, poured into water, and extracted with ethyl acetate. The organic layer was washed with a saturated brine, then dried over magnesium sulfate, and concentrated under reduced pressure. The residue was purified by NH silica gel column chromatography (methanol/ethyl acetate), and crystallized from ethanol/IPE to obtain the title compound (44.6 mg).

$^1$H NMR (300 MHz, DMSO-$d_6$) δ 2.61 (3H, s), 3.72 (3H, s), 5.67 (2H, s), 6.77-6.85 (2H, m), 7.15-7.25 (1H, m), 7.36-7.48 (1H, m), 7.94 (1H, d, J=3.2 Hz), 8.26 (1H, d, J=2.4 Hz), 8.51 (1H, s), 8.55 (1H, d, J=2.4 Hz).

Example 21

1-benzyl-6-(4-methoxy-5H-pyrrolo[3,2-d]pyrimidin-5-yl)-2-methyl-1H-imidazo[4,5-b]pyridine a) N3-Benzyl-5-iodopyridine-2,3-diamine Acetic acid (200 μL) was added to a solution of benzaldehyde (600 μL) and 5-iodopyridine-2,3-diamine (1.12 g) in THF (50 mL) at room temperature. The mixture was stirred overnight at room temperature. The reaction mixture was poured into a saturated aqueous sodium hydrogen carbonate solution, and extracted with ethyl acetate. The organic layer was washed with water and a saturated brine, dried over magnesium sulfate, and then concentrated. Sodium borohydride (0.27 g) was added to a solution of the residue in methanol (50 mL) at 0° C. The mixture was stirred at 0° C. for 1 hour. The reaction mixture was poured into a saturated aqueous ammonium chloride solution, and extracted with ethyl acetate. The organic layer was washed with water and a saturated brine, then dried over magnesium sulfate, and concentrated under reduced pressure. The residue was purified by NH silica gel column chromatography (ethyl acetate/hexane) to obtain the title compound (1.13 g).

$^1$H NMR (300 MHz, DMSO-$d_6$) δ 4.28 (2H, d, J=5.6 Hz), 5.64 (1H, t, J=5.6 Hz), 5.78 (2H, s), 6.65 (1H, d, J=1.8 Hz), 7.20-7.43 (6H, m).

b) 1-benzyl-6-iodo-2-methyl-1H-imidazo[4,5-b]pyridine

Concentrated hydrochloric acid (0.1 mL) was added to a mixture of N3-benzyl-5-iodopyridine-2,3-diamine (300 mg) and trimethyl orthoacetate (4 mL) at room temperature. The mixture was stirred under a dry atmosphere at room temperature for 1 hour. The mixture was neutralized with a saturated aqueous sodium hydrogen carbonate solution at room temperature, and extracted with ethyl acetate/THF. The organic layer was washed with a saturated brine, then dried over magnesium sulfate, and concentrated under reduced pressure. The residue was washed with ethyl acetate/hexane to obtain the title compound (230 mg).

$^1$H NMR (300 MHz, DMSO-$d_6$) δ 2.54 (3H, s), 5.51 (2H, s), 7.05-7.17 (2H, m), 7.23-7.44 (3H, m), 8.38 (1H, d, J=1.9 Hz), 8.51 (1H, d, J=1.9 Hz).

c) 1-benzyl-6-(4-methoxy-5H-pyrrolo[3,2-d]pyrimidin-5-yl)-2-methyl-1H-imidazo[4,5-b]pyridine A mixture of 1-benzyl-6-iodo-2-methyl-1H-imidazo[4,5-b]pyridine (200 mg), 4-methoxy-5H-pyrrolo[3,2-d]pyrimidine (111 mg), potassium phosphate (365 mg), trans-N,N'-dimethylcyclohexane-1,2-diamine (0.09 mL), copper (I) iodide (54.5 mg) and THF (5 mL) was stirred under microwave irradiation at 110° C. for 2 hours. The mixture was diluted with water and a 28% aqueous ammonia solution at room temperature, and extracted with ethyl acetate. The organic layer was washed with a saturated brine, dried over magnesium sulfate, and then concentrated. The residue was purified by NH silica gel column chromatography (methanol/ethyl acetate), and the residue was crystallized from water/ethanol to obtain the title compound (120 mg).

$^1$H NMR (300 MHz, DMSO-$d_6$) δ 2.61 (3H, s), 3.70 (3H, s), 5.55 (2H, s), 6.83 (1H, d, J=3.2 Hz), 7.13-7.24 (2H, m), 7.25-7.44 (3H, m), 7.96 (1H, d, J=3.2 Hz), 8.27 (1H, d, J=2.4 Hz), 8.50 (1H, s), 8.53 (1H, d, J=2.4 Hz).

Example 22

1-(4-fluorobenzyl)-6-(4-methoxy-5H-pyrrolo[3,2-d]pyrimidin-5-yl)-2-methyl-1H-imidazo[4,5-b]pyridine a) N3-(4-fluorobenzyl)-5-iodopyridine-2,3-diamine A mixture of 4-fluorobenzaldehyde (0.507 mL), 5-iodopyridine-2,3-diamine (1.03 g), THF (10 mL) and acetic acid (0.632 mL) was stirred overnight at room temperature. The reaction mixture was poured into a saturated aqueous sodium hydrogen carbonate solution, and extracted with ethyl acetate. The organic layer was washed with a saturated brine, dried over magnesium sulfate, and then concentrated. Sodium borohydride (0.415 g) was added to a solution of the residue in methanol (10 mL) at room temperature. The mixture was stirred overnight at room temperature. The reaction mixture was poured into water, and extracted with ethyl acetate. The organic layer was washed with a saturated brine, then dried over magnesium sulfate, and concentrated under reduced pressure. The residue was purified by silica gel column chromatography (ethyl acetate/hexane) to obtain the title compound (1.21 g).

$^1$H NMR (300 MHz, DMSO-$d_6$) δ 4.26 (2H, d, J=5.5 Hz), 5.63 (1H, t, J=5.6 Hz), 5.78 (2H, s), 6.65 (1H, d, J=1.8 Hz), 7.12-7.23 (2H, m), 7.34-7.43 (3H, m).

b) 1-(4-fluorobenzyl)-6-iodo-2-methyl-1H-imidazo[4,5-b]pyridine

Concentrated hydrochloric acid (0.1 mL) was added to a mixture of N3-(4-fluorobenzyl)-5-iodopyridine-2,3-diamine (300 mg) and trimethyl orthoacetate (4 mL) at room temperature. The mixture was stirred under a dry atmosphere at room temperature for 1 hour. The mixture was neutralized with a saturated aqueous sodium hydrogen carbonate solution at room temperature, and extracted with ethyl acetate/THF. The organic layer was washed with a saturated brine, then dried over magnesium sulfate, and concentrated under reduced pressure. The residue was washed with ethyl acetate to obtain the title compound (244 mg).

$^1$H NMR (300 MHz, DMSO-$d_6$) δ 2.54 (3H, s), 5.50 (2H, s), 7.13-7.25 (4H, m), 8.40 (1H, d, J=2.0 Hz), 8.51 (1H, d, J=2.0 Hz).

c) 1-(4-fluorobenzyl)-6-(4-methoxy-5H-pyrrolo[3,2-d]pyrimidin-5-yl)-2-methyl-1H-imidazo[4,5-b]pyridine A mixture of 1-(4-fluorobenzyl)-6-iodo-2-methyl-1H-imidazo[4,5-b]pyridine (200 mg), 4-methoxy-5H-pyrrolo[3,2-d]pyrimidine (106 mg), potassium phosphate (347 mg), trans-N,N'-dimethylcyclohexane-1,2-diamine (0.086 mL), copper (I) iodide (51.9 mg) and THF (5 mL) was stirred under microwave irradiation at 110° C. for 2 hours. The mixture was diluted with water and a 28% aqueous ammonia solution at room temperature, and extracted with ethyl acetate. The organic layer was washed with a saturated brine, dried over magnesium sulfate, and then concentrated. The residue was purified by NH silica gel column chromatography (methanol/ethyl acetate), and the residue was crystallized from water/ethanol to obtain the title compound (88 mg).

$^1$H NMR (300 MHz, DMSO-$d_6$) δ 2.62 (3H, s), 3.73 (3H, s), 5.53 (2H, s), 6.83 (1H, d, J=3.2 Hz), 7.10-7.38 (4H, m), 7.96 (1H, d, J=3.2 Hz), 8.29 (1H, d, J=2.4 Hz), 8.51 (1H, s), 8.53 (1H, d, J=2.4 Hz).

Example 23

1-(2,5-difluorobenzyl)-6-(4-methoxy-5H-pyrrolo[3,2-d]pyrimidin-5-yl)-2-methyl-1H-imidazo[4,5-b]pyridine a)
N3-(2,5-difluorobenzyl)-5-iodopyridine-2,3-diamine Acetic acid (200 μL) was added to a solution of 2,5-difluorobenzaldehyde (400 μL) and 5-iodopyridine-2,3-diamine (0.72 g) in THF (50 mL) at room temperature. The mixture was stirred overnight at room temperature. The reaction mixture was poured into a saturated aqueous sodium hydrogen carbonate solution, and extracted with ethyl acetate. The organic layer was washed with water and a saturated brine, dried over magnesium sulfate, and then concentrated. Sodium borohydride (0.174 g) was added to a solution of the residue in methanol (50 mL) at 0° C. The mixture was stirred at 0° C. for 1 hour. The reaction mixture was poured into a saturated aqueous ammonium chloride solution, and extracted with ethyl acetate. The organic layer was washed with water and a saturated brine, then dried over magnesium sulfate, and concentrated under reduced pressure. The residue was purified by NH silica gel column chromatography (ethyl acetate/hexane) to obtain the title compound (0.82 g).

$^1$H NMR (300 MHz, DMSO-$d_6$) δ 4.31 (2H, d, J=5.6 Hz), 5.56 (1H, t, J=5.6 Hz), 5.80 (2H, s), 6.72 (1H, d, J=1.8 Hz), 7.07-7.35 (3H, m), 7.44 (1H, d, J=1.8 Hz).

b) 1-(2,5-difluorobenzyl)-6-iodo-2-methyl-1H-imidazo[4,5-b]pyridine

Concentrated hydrochloric acid (0.1 mL) was added to a mixture of N3-(2,5-difluorobenzyl)-5-iodopyridine-2,3-diamine (300 mg) and trimethyl orthoacetate (4 mL) at room temperature. The mixture was stirred under a dry atmosphere at room temperature for 1 hour. The mixture was neutralized with a saturated aqueous sodium hydrogen carbonate solution at room temperature, and extracted with ethyl acetate/THF. The organic layer was washed with a saturated brine, then dried over magnesium sulfate, and concentrated under reduced pressure. The residue was washed with ethyl acetate to obtain the title compound (249 mg).

$^1$H NMR (300 MHz, DMSO-$d_6$) δ 2.54 (3H, s), 5.56 (2H, s), 6.85-7.03 (1H, m), 7.16-7.42 (2H, m), 8.30-8.58 (2H, m).

c) 1-(2,5-difluorobenzyl)-6-(4-methoxy-5H-pyrrolo[3,2-d]pyrimidin-5-yl)-2-methyl-1H-imidazo[4,5-b]pyridine A mixture of 1-(2,5-difluorobenzyl)-6-iodo-2-methyl-1H-imidazo[4,5-b]pyridine (200 mg), 4-methoxy-5H-pyrrolo[3,2-d]pyrimidine (101 mg), potassium phosphate (331 mg), trans-N,N'-dimethylcyclohexane-1,2-diamine (0.082 mL), copper (I) iodide (49.4 mg) and THF (5 mL) was stirred under microwave irradiation at 110° C. for 2 hours. The mixture was diluted with water and a 28% aqueous ammonia solution at room temperature, and extracted with ethyl acetate. The organic layer was washed with a saturated brine, dried over magnesium sulfate, and then concentrated. The residue was purified by NH silica gel column chromatography (methanol/ethyl acetate), and the residue was washed with ethyl acetate to obtain the title compound (131 mg).

$^1$H NMR (300 MHz, DMSO-$d_6$) δ 2.62 (3H, s), 3.72 (3H, s), 5.59 (2H, s), 6.83 (1H, d, J=3.3 Hz), 6.91-7.02 (1H, m), 7.17-7.42 (2H, m), 7.94 (1H, d, J=3.3 Hz), 8.25 (1H, d, J=2.4 Hz), 8.51 (1H, s), 8.54 (1H, d, J=2.4 Hz).

Example 24

1-(3-fluorobenzyl)-2-(methoxymethyl)-6-(4-methoxy-5H-pyrrolo[3,2-d]pyrimidin-5-yl)-1H-imidazo[4,5-b]pyridine a) 1-(3-fluorobenzyl)-6-iodo-2-(methoxymethyl)-1H-imidazo[4,5-b]pyridine A mixture of N3-(3-fluorobenzyl)-5-iodopyridine-2,3-diamine (251 mg), 2-methoxyacetic acid (86 mg), THF (4 mL), propylphosphonic anhydride (50% in ethyl acetate solution) (0.58 mL) and DIPEA (0.35 mL) was heated under microwave irradiation at 200° C. for 2 hours. The mixture was diluted with a saturated aqueous sodium hydrogen carbonate solution at room temperature, and extracted with ethyl acetate. The organic layer was washed with a saturated brine, dried over magnesium sulfate, and then concentrated. The residue was purified by NH silica gel column chromatography (ethyl acetate/hexane) to obtain the title compound (232 mg).

$^1$H NMR (300 MHz, DMSO-$d_6$) δ 3.31 (3H, s), 4.72 (2H, s), 5.58 (2H, s), 6.98 (1H, d, J=7.7 Hz), 7.03-7.18 (2H, m), 7.39 (1H, td, J=8.0, 6.1 Hz), 8.37 (1H, d, J=2.0 Hz), 8.60 (1H, d, J=1.9 Hz).

b) 1-(3-fluorobenzyl)-2-(methoxymethyl)-6-(4-methoxy-5H-pyrrolo[3,2-d]pyrimidin-5-yl)-1H-imidazo[4,5-b]pyridine A mixture of 1-(3-fluorobenzyl)-6-iodo-2-(methoxymethyl)-1H-imidazo[4,5-b]pyridine (226 mg), 4-methoxy-5H-pyrrolo[3,2-d]pyrimidine (110 mg), potassium phosphate (362 mg), trans-N,N'-dimethylcyclohexane-1,2-diamine (81 mg), copper (I) iodide (54.2 mg) and THF (4 mL) was stirred under microwave irradiation at 110° C. for 2 hours. The mixture was diluted with water and a 28% aqueous ammonia solution at room temperature, and extracted with ethyl acetate. The organic layer was washed with a saturated brine, dried over magnesium sulfate, and then concentrated. The residue was purified by NH silica gel column chromatography (methanol/ethyl acetate), and the residue was washed with ethyl acetate/IPE to obtain the title compound (73.8 mg).

$^1$H NMR (300 MHz, DMSO-$d_6$) δ 3.35 (3H, s), 3.68 (3H, s), 4.79 (2H, s), 5.61 (2H, s), 6.84 (1H, d, J=3.1 Hz), 7.01-7.22 (3H, m), 7.35-7.47 (1H, m), 7.96 (1H, d, J=3.1 Hz), 8.28 (1H, d, J=2.1 Hz), 8.51 (1H, s), 8.63 (1H, d, J=2.0 Hz).

Example 27

5-(1-(3-fluorobenzyl)-2-methyl-1H-imidazo[4,5-b]pyridin-6-yl)-N-methyl-5H-pyrrolo[3,2-d]pyrimidin-4-amine a) 6-(4-chloro-5H-pyrrolo[3,2-d]pyrimidin-5-yl)-1-(3-fluorobenzyl)-2-methyl-1H-imidazo[4,5-b]pyridine A mixture of 1-(3-fluorobenzyl)-6-(4-methoxy-5H-pyrrolo[3,2-d]pyrimidin-5-yl)-2-methyl-1H-imidazo[4,5-b]pyrimidine (155 mg) and phosphorus oxychloride (4.5 mL) was stirred under a nitrogen atmosphere at 100° C. for 2 hours. The reaction mixture was concentrated under reduced pressure. The residue was neutralized with a saturated aqueous sodium hydrogen carbonate solution at room temperature, and extracted with ethyl acetate. The organic layer was washed with a saturated brine, dried over magnesium sulfate, and then concentrated. The residue was purified by NH silica gel column chromatography (ethyl acetate), and washed with ethyl acetate to obtain the title compound (112 mg).
$^1$H NMR (300 MHz, DMSO-$d_6$) δ 2.64 (3H, s), 5.57 (2H, s), 6.96-7.07 (3H, m), 7.14 (1H, td, J=8.5, 2.2 Hz), 7.39 (1H, td, J=8.0, 6.1 Hz), 8.24 (1H, d, J=3.3 Hz), 8.37 (1H, d, J=2.3 Hz), 8.57 (1H, d, J=2.3 Hz), 8.75 (1H, s).

b) 5-(1-(3-fluorobenzyl)-2-methyl-1H-imidazo[4,5-b]pyridin-6-yl)-N-methyl-5H-pyrrolo[3,2-d]pyrimidin-4-amine A mixture of 6-(4-chloro-5H-pyrrolo[3,2-d]pyrimidin-5-yl)-1-(3-fluorobenzyl)-2-methyl-1H-imidazo[4,5-b]pyridine (95 mg) and methylamine (2M in THF solution) (4 mL) was stirred under microwave irradiation at 120° C. for 3 hours. The mixture was purified by NH silica gel column chromatography (ethyl acetate), and washed with ethyl acetate to obtain the title compound (42.7 mg).
$^1$H NMR (300 MHz, DMSO-$d_6$) δ 2.57 (3H, s), 2.71 (3H, d, J=4.5 Hz), 5.47 (1H, d, J=4.5 Hz), 5.57 (2H, s), 6.62 (1H, d, J=3.2 Hz), 7.04-7.19 (3H, m), 7.36-7.46 (1H, m), 7.68 (1H, d, J=3.2 Hz), 8.08 (1H, d, J=2.4 Hz), 8.29 (1H, s), 8.54 (1H, d, J=2.4 Hz).

Example 28

1-(2-fluorobenzyl)-6-(4-methoxy-5H-pyrrolo[3,2-d]pyrimidin-5-yl)-2-methyl-1H-imidazo[4,5-b]pyridine a) N3-(2-fluorobenzyl)-5-iodopyridine-2,3-diamine

Under a nitrogen atmosphere, a mixture of 2-fluorobenzaldehyde (0.792 g), 5-iodopyridine-2,3-diamine (1 g), THF (100 mL) and acetic acid (0.487 mL) was stirred at room temperature for 13 hours. The reaction mixture was concentrated under reduced pressure. The residue was neutralized with a saturated aqueous sodium hydrogen carbonate solution at 0° C., and extracted with ethyl acetate/THF. The organic layer was washed with a saturated aqueous sodium hydrogen carbonate solution and a saturated brine, dried over magnesium sulfate, and then concentrated to obtain a residue. Methanol (100 mL) was added to a mixture of sodium borohydride (0.402 g) and THF (100 mL) at 0° C. The obtained solution of the residue in THF (300 mL) was added to the reaction mixture at 0° C. Under a nitrogen atmosphere, the mixture was stirred at room temperature for 2 hours. Water and a saturated aqueous ammonium chloride solution were added to the reaction mixture at 0° C. to stop the reaction, and the mixture was extracted with ethyl acetate. The organic layer was washed with a saturated brine, then dried over magnesium sulfate, and concentrated under reduced pressure. The residue was purified by silica gel column chromatography (ethyl acetate/hexane) to obtain the title compound (1.12 g).
$^1$H NMR (300 MHz, DMSO-$d_6$) δ 4.30 (2H, d, J=5.5 Hz), 5.46-5.60 (1H, m), 5.79 (2H, s), 6.70 (1H, d, J=1.8 Hz), 7.12-7.52 (5H, m).

b) 1-(2-fluorobenzyl)-6-iodo-2-methyl-1H-imidazo[4,5-b]pyridine

Concentrated hydrochloric acid (300 μL) was added to a mixture of N3-(2-fluorobenzyl)-5-iodopyridine-2,3-diamine (500 mg) and trimethyl orthoacetate (5 mL) at room temperature. The mixture was stirred at room temperature for 1 hour. The mixture was concentrated under reduced pressure. The residue was washed with IPE to obtain the title compound (400 mg).
$^1$H NMR (300 MHz, DMSO-$d_6$) δ 2.53 (3H, s), 5.57 (2H, s), 6.94-7.48 (4H, m), 8.37 (1H, d, J=1.6 Hz), 8.51 (1H, d, J=1.9 Hz).

c) 1-(2-fluorobenzyl)-6-(4-methoxy-5H-pyrrolo[3,2-d]pyrimidin-5-yl)-2-methyl-1H-imidazo[4,5-b]pyridine A mixture of 1-(2-fluorobenzyl)-6-iodo-2-methyl-1H-imidazo[4,5-b]pyridine (200 mg), 4-methoxy-5H-pyrrolo[3,2-d]pyrimidine (81 mg), potassium phosphate (347 mg), trans-N,N'-dimethylcyclohexane-1,2-diamine (93 mg), copper (I) iodide (62.2 mg) and THF (5 mL) was stirred under microwave irradiation at 110° C. for 2 hours. The mixture was cooled to room temperature, and insolubles were removed. The mixture was concentrated under reduced pressure. The residue was purified by NH silica gel column chromatography (methanol/ethyl acetate), and washed with ethanol to obtain the title compound (80 mg).
$^1$H NMR (300 MHz, DMSO-$d_6$) δ 2.61 (3H, s), 3.71 (3H, s), 5.61 (2H, s), 6.83 (1H, d, J 10=3.2 Hz), 7.00-7.47 (4H, m), 7.94 (1H, d, J=3.2 Hz), 8.23 (1H, d, J=2.4 Hz), 8.46-8.58 (2H, m).

Example 31

1-(2,4-difluorobenzyl)-6-(4-methoxy-5H-pyrrolo[3,2-d]pyrimidin-5-yl)-2-methyl-1H-imidazo[4,5-b]pyridine a) N3-(2,4-difluorobenzyl)-5-iodopyridine-2,3-diamine

A mixture of 2,4-difluorobenzaldehyde (0.237 mL), 5-iodopyridine-2,3-diamine (392.4 mg), THF (8 mL) and acetic acid (0.482 mL) was stirred overnight at room temperature. The reaction mixture was poured into a saturated aqueous sodium hydrogen carbonate solution, and extracted with ethyl acetate. The organic layer was washed with a saturated brine, dried over magnesium sulfate, and then concentrated. Sodium borohydride (158 mg) was added to a solution of the residue in methanol (8 mL) at room temperature. The mixture was stirred at room temperature for 3 hours. The reaction mixture was poured into water, and extracted with ethyl acetate. The organic layer was washed with a saturated brine, then dried over magnesium sulfate, and concentrated under reduced pressure. The residue was purified by silica gel column chromatography (ethyl acetate/hexane) to obtain the title compound (493 mg).

$^1$H NMR (300 MHz, DMSO-d$_6$) δ 4.27 (2H, d, J=5.5 Hz), 5.52 (1H, t, J=5.6 Hz), 5.78 (2H, s), 6.71 (1H, d, J=1.8 Hz), 7.08 (1H, tdd, J=8.5, 2.6, 0.9 Hz), 7.26 (1H, ddd, J=10.5, 9.4, 2.6 Hz), 7.36-7.47 (2H, m).

b) 1-(2,4-difluorobenzyl)-6-iodo-2-methyl-1H-imidazo[4,5-b]pyridine

Concentrated hydrochloric acid (500 μL) was added to a mixture of N3-(2,4-difluorobenzyl)-5-iodopyridine-2,3-diamine (492.8 mg) and trimethyl orthoacetate (5 mL) at room temperature. The mixture was stirred at 60° C. for 3 hours. The mixture was poured into a saturated aqueous sodium hydrogen carbonate solution, and extracted with ethyl acetate. The organic layer was washed with a saturated brine, then dried over magnesium sulfate, and concentrated under reduced pressure. The residue was purified by NH silica gel column chromatography (ethyl acetate/hexane) to obtain the title compound (350 mg).

$^1$H NMR (300 MHz, DMSO-d$_6$) δ 2.54 (3H, s), 5.54 (2H, s), 7.02-7.21 (2H, m), 7.26-7.36 (1H, m), 8.38 (1H, d, J=1.9 Hz), 8.51 (1H, d, J=2.0 Hz).

c) 1-(2,4-difluorobenzyl)-6-(4-methoxy-5H-pyrrolo[3,2-d]pyrimidin-5-yl)-2-methyl-1H-imidazo[4,5-b]pyridine A mixture of 1-(2,4-difluorobenzyl)-6-iodo-2-methyl-1H-imidazo[4,5-b]pyridine (156.9 mg), 4-methoxy-5H-pyrrolo[3,2-d]pyrimidine (66.8 mg), potassium phosphate (259 mg), trans-N,N'-dimethylcyclohexane-1,2-diamine (69.5 mg), copper (I) iodide (46.6 mg) and THF (2.5 mL) was stirred under microwave irradiation at 150° C. for 3 hours. The mixture was cooled to room temperature, then poured into a saturated aqueous ammonium chloride solution, and extracted with ethyl acetate. The organic layer was washed with a saturated brine, then dried over magnesium sulfate, and concentrated under reduced pressure. The residue was purified by silica gel column chromatography (methanol/ethyl acetate), and crystallized from ethanol and IPE to obtain the title compound (82 mg).

$^1$H NMR (300 MHz, DMSO-d$_6$) δ 2.61 (3H, s), 3.74 (3H, s), 5.58 (2H, s), 6.83 (1H, d, J=3.2 Hz), 7.04-7.24 (2H, m), 7.29-7.39 (1H, m), 7.94 (1H, d, J=3.2 Hz), 8.23 (1H, d, J=2.4 Hz), 8.51 (1H, s), 8.53 (1H, d, J=2.4 Hz).

Example 32

1-(3-chlorobenzyl)-6-(4-methoxy-5H-pyrrolo[3,2-d]pyrimidin-5-yl)-2-methyl-1H-imidazo[4,5-b]pyridine a) N3-(3-chlorobenzyl)-5-iodopyridine-2,3-diamine A mixture of 3-chlorobenzaldehyde (0.234 mL), 5-iodopyridine-2,3-diamine (374.1 mg), THF (8 mL) and acetic acid (0.23 mL) was stirred overnight at room temperature. The reaction mixture was poured into a saturated aqueous sodium hydrogen carbonate solution, and extracted with ethyl acetate. The organic layer was washed with a saturated brine, dried over magnesium sulfate, and then concentrated. Sodium borohydride (151 mg) was added to a solution of the residue in methanol (5 mL) at room temperature. The mixture was stirred overnight at room temperature. The reaction mixture was poured into water, and extracted with ethyl acetate. The organic layer was washed with a saturated brine, then dried over magnesium sulfate, and concentrated under reduced pressure. The residue was purified by silica gel column chromatography (ethyl acetate/hexane) to obtain the title compound (394 mg).

$^1$H NMR (300 MHz, DMSO-d$_6$) δ 4.30 (2H, d, J=5.7 Hz), 5.67 (1H, t, J=5.8 Hz), 5.78 (2H, s), 6.65 (1H, d, J=1.8 Hz), 7.29-7.34 (2H, m), 7.35-7.44 (3H, m).

b) 1-(3-chlorobenzyl)-6-iodo-2-methyl-1H-imidazo[4,5-b]pyridine

Concentrated hydrochloric acid (500 μL) was added to a mixture of N3-(3-chlorobenzyl)-5-iodopyridine-2,3-diamine (393.8 mg) and trimethyl orthoacetate (5 mL) at room temperature. The mixture was stirred at 60° C. for 3 hours. The mixture was cooled to room temperature, poured into a saturated aqueous sodium hydrogen carbonate solution, and extracted with ethyl acetate. The organic layer was washed with a saturated brine, then dried over magnesium sulfate, and concentrated under reduced pressure. The residue was purified by NH silica gel column chromatography (ethyl acetate/hexane) to obtain the title compound (298 mg).

$^1$H NMR (300 MHz, DMSO-d$_6$) δ 2.54 (3H, s), 5.53 (2H, s), 6.97-7.04 (1H, m), 7.24-7.27 (1H, m), 7.35-7.40 (2H, m), 8.40 (1H, d, J=2.0 Hz), 8.52 (1H, d, J=1.9 Hz).

c) 1-(3-chlorobenzyl)-6-(4-methoxy-5H-pyrrolo[3,2-d]pyrimidin-5-yl)-2-methyl-1H-imidazo[4,5-b]pyridine A mixture of 1-(3-chlorobenzyl)-6-iodo-2-methyl-1H-imidazo[4,5-b]pyridine (129.3 mg), 4-methoxy-5H-pyrrolo[3,2-d]pyrimidine (52.8 mg), potassium phosphate (215 mg), trans-N,N'-dimethylcyclohexane-1,2-diamine (57.5 mg), copper (I) iodide (38.5 mg) and THF (2 mL) was stirred under microwave irradiation at 150° C. for 3 hours. The mixture was cooled to room temperature, then poured into a saturated aqueous ammonium chloride solution, and extracted with ethyl acetate. The organic layer was washed with a saturated brine, then dried over magnesium sulfate, and concentrated under reduced pressure. The residue was purified by NH silica gel column chromatography (methanol/ethyl acetate), and crystallized from ethanol/IPE to obtain the title compound (51.3 mg).

$^1$H NMR (300 MHz, DMSO-d$_6$) δ 2.61 (3H, s), 3.70 (3H, s), 5.57 (2H, s), 6.83 (1H, d, J=3.2 Hz), 7.05-7.12 (1H, m), 7.30 (1H, s), 7.35-7.45 (2H, m), 7.97 (1H, d, J=3.2 Hz), 8.28 (1H, d, J=2.3 Hz), 8.51 (1H, s), 8.55 (1H, d, J=2.3 Hz).

Example 33

6-(4-methoxy-5H-pyrrolo[3,2-d]pyrimidin-5-yl)-2-methyl-1-(3-trifluoromethoxy)benzyl)-1H-imidazo[4,5-b]pyridine a) 5-iodo-N3-(3-(trifluoromethoxy)benzyl)pyridine-2,3-diamine A mixture of 3-(trifluoromethoxy)benzaldehyde (0.336 mL), 5-iodopyridine-2,3-diamine (425 mg), THF (10 mL) and acetic acid (0.261 mL) was stirred overnight at room temperature. The reaction mixture was poured into a saturated aqueous sodium hydrogen carbonate solution, and extracted with ethyl acetate. The organic layer was washed with a saturated brine, dried over magnesium sulfate, and then concentrated. Sodium borohydride (171 mg) was added to a solution of the residue in methanol (5 mL) at room temperature. The mixture was stirred overnight at room temperature. The reaction mixture was poured into water, and extracted with ethyl acetate. The organic layer was washed with a saturated brine, then dried over magnesium sulfate, and concentrated under reduced pressure. The residue was purified by silica gel column chromatography (ethyl acetate/hexane) to obtain the title compound (673 mg).

$^1$H NMR (300 MHz, DMSO-$d_6$) δ 4.35 (2H, d, J=5.7 Hz), 5.71 (1H, t, J=5.8 Hz), 5.78 (2H, s), 6.66 (1H, d, J=1.9 Hz), 7.22-7.28 (1H, m), 7.34 (1H, s), 7.36-7.43 (2H, m), 7.45-7.53 (1H, m).

b) 6-iodo-2-methyl-1-(3-(trifluoromethoxy)benzyl)-1H-imidazo[4,5-b]pyridine

Concentrated hydrochloric acid (500 μL) was added to a mixture of 5-iodo-N3-(3-(trifluoromethoxy)benzyl)pyridine-2,3-diamine (672.9 mg) and trimethyl orthoacetate (5 mL) at room temperature. The mixture was stirred at room temperature for 1 hour. The mixture was concentrated under reduced pressure. The residue was purified by NH silica gel column chromatography (ethyl acetate/hexane) to obtain the title compound (458 mg).

$^1$H NMR (300 MHz, DMSO-$d_6$) δ 2.54 (3H, s), 5.58 (2H, s), 7.06 (1H, d, J=7.8 Hz), 7.25 (1H, s), 7.28-7.35 (1H, m), 7.44-7.52 (1H, m), 8.39 (1H, d, J=1.9 Hz), 8.52 (1H, d, J=1.9 Hz).

c) 6-(4-methoxy-5H-pyrrolo[3,2-d]pyrimidin-5-yl)-2-methyl-1-(3-trifuoromethoxy)benzyl)-1H-imidazo[4,5-b]pyri dine A mixture of 6-iodo-2-methyl-1-(3-(trifuoromethoxy)benzyl)-1H-imidazo[4,5-b]pyridine (137.5 mg), 4-methoxy-5H-pyrrolo[3,2-d]pyrimidine (49.7 mg), potassium phosphate (202 mg), trans-N,N'-dimethylcyclohexane-1,2-diamine (54.2 mg), copper (I) iodide (36.3 mg) and THF (2 mL) was stirred under microwave irradiation at 150° C. for 3 hours. The mixture was cooled to room temperature, then poured into a saturated aqueous ammonium chloride solution, and extracted with ethyl acetate. The organic layer was washed with a saturated brine, then dried over magnesium sulfate, and concentrated under reduced pressure. The residue was purified by NH silica gel column chromatography (methanol/ethyl acetate) and crystallized from ethanol/IPE to obtain the title compound (58.5 mg).

$^1$H NMR (300 MHz, DMSO-$d_6$) δ 2.61 (3H, s), 3.68 (3H, s), 5.62 (2H, s), 6.83 (1H, d, J=3.2 Hz), 7.11 (1H, d, J=7.9 Hz), 7.26-7.37 (2H, m), 7.46-7.55 (1H, m), 7.95 (1H, d, J=3.4 Hz), 8.28 (1H, d, J=2.3 Hz), 8.50 (1H, s), 8.55 (1H, d, J=2.4 Hz).

Example 34

6-(4-methoxy-5H-pyrrolo[3,2-d]pyrimidin-5-yl)-2-methyl-1-(3-trifluoromethyl)benzyl)-1H-imidazo[4,5-b]pyridine a) 5-iodo-N3-(3-(trifluoromethyl)benzyl)pyridine-2,3-diamine A mixture of 3-(trifluoromethyl)benzaldehyde (0.319 mL), 5-iodopyridine-2,3-diamine (431 mg), THF (8 mL) and acetic acid (0.264 mL) was stirred overnight at room temperature. The reaction mixture was poured into a saturated aqueous sodium hydrogen carbonate solution, and extracted with ethyl acetate. The organic layer was washed with a saturated brine, dried over magnesium sulfate, and then concentrated. Sodium borohydride (173 mg) was added to a solution of the residue in methanol (8 mL) at room temperature. The mixture was stirred overnight at room temperature. The reaction mixture was poured into water, and extracted with ethyl acetate. The organic layer was washed with a saturated brine, then dried over magnesium sulfate, and concentrated under reduced pressure. The residue was purified by silica gel column chromatography (ethyl acetate/hexane) to obtain the title compound (539 mg).

$^1$H NMR (300 MHz, DMSO-$d_6$) δ 4.39 (2H, d, J=5.7 Hz), 5.71 (1H, t, J=5.8 Hz), 5.79 (2H, s), 6.69 (1H, d, J=1.9 Hz), 7.41 (1H, d, J=1.9 Hz), 7.55-7.69 (3H, m), 7.72 (1H, s).

b) 6-iodo-2-methyl-1-(3-(trifluoromethyl)benzyl)-1H-imidazo[4,5-b]pyridine

Concentrated hydrochloric acid (500 μL) was added to a mixture of 5-iodo-N3-(3-(trifluoromethyl)benzyl)pyridine-2,3-diamine (538.5 mg) and trimethyl orthoacetate (5 mL) at room temperature. The mixture was stirred at 60° C. for 3 hours. The reaction mixture was poured into a saturated aqueous sodium hydrogen carbonate solution, and extracted with ethyl acetate. The organic layer was washed with a saturated brine, dried over magnesium sulfate, and then concentrated. The residue was purified by NH silica gel column chromatography (ethyl acetate/hexane) to obtain the title compound (397 mg).

$^1$H NMR (300 MHz, DMSO-$d_6$) δ 2.54 (3H, s), 5.63 (2H, s), 7.28 (1H, d, J=7.7 Hz), 7.53-7.61 (1H, m), 7.63 (1H, s), 7.65-7.71 (1H, m), 8.41 (1H, d, J=1.9 Hz), 8.52 (1H, d, J=2.0 Hz).

c) 6-(4-methoxy-5H-pyrrolo[3,2-d]pyrimidin-5-yl)-2-methyl-1-(3-trifluoromethyl)benzyl)-1H-imidazo[4,5-b]pyridine A mixture of 6-iodo-2-methyl-1-(3-(trifluoromethyl)benzyl)-1H-imidazo[4,5-b]pyridine (140.5 mg), 4-methoxy-5H-pyrrolo[3,2-d]pyrimidine (52.7 mg), potassium phosphate (214 mg), trans-N,N'-dimethylcyclohexane-1,2-diamine (57.5 mg), copper (I) iodide (38.5 mg) and THF (2 mL) was stirred under microwave irradiation at 150° C. for 2.5 hours. The mixture was cooled to room temperature, then poured into a saturated aqueous ammonium chloride solution, and extracted with ethyl acetate. The organic layer was washed with a saturated brine, then dried over magnesium sulfate, and concentrated under reduced pressure. The residue was purified by NH silica gel column chromatography (methanol/ethyl acetate) and crystallized from ethanol/IPE to obtain the title compound (67 mg).

$^1$H NMR (300 MHz, DMSO-$d_6$) δ 2.62 (3H, s), 3.64 (3H, s), 5.67 (2H, s), 6.83 (1H, d, J=3.2 Hz), 7.34 (1H, d, J=7.7 Hz), 7.56-7.73 (3H, m), 7.95 (1H, d, J=3.2 Hz), 8.29 (1H, d, J=2.4 Hz), 8.50 (1H, s), 8.55 (1H, d, J=2.3 Hz).

Example 35

1-(2,6-difluorobenzyl)-6-(4-methoxy-5H-pyrrolo[3,2-d]pyrimidin-5-yl)-2-methyl-1H-imidazo[4,5-b]pyridine a) N3-(2,6-difluorobenzyl)-5-iodopyridine-2,3-diamine Acetic acid (300 μL) was added to a solution of 2,6-difluorobenzaldehyde (500 μL) and 5-iodopyridine-2,3-diamine (0.7 g) in THF (50 mL) at room temperature. The mixture was stirred overnight at room temperature. The reaction mixture was poured into a saturated aqueous sodium hydrogen carbonate solution, and extracted with ethyl acetate. The organic layer was washed with water and a saturated brine, dried over magnesium sulfate, and then concentrated. Sodium borohydride (0.169 g) was added to a solution of the residue in methanol (50 mL) at 0° C. The mixture was stirred at 0° C. for 1 hour. The reaction mixture was poured into an aqueous ammonium chloride solution, and extracted with ethyl acetate. The organic layer was washed with water and a saturated brine, then dried over magnesium sulfate, and concentrated under reduced pressure. The residue was purified by NH silica gel column chromatography (ethyl acetate/hexane) to obtain the title compound (0.263 g).

$^1$H NMR (300 MHz, DMSO-$d_6$) δ 4.24 (2H, d, J=5.1 Hz), 5.33 (1H, t, J=5.1 Hz), 5.78 (2H, s), 6.89 (1H, d, J=1.8 Hz), 7.05-7.26 (2H, m), 7.35-7.55 (2H, m).

b) 1-(2,6-difluorobenzyl)-6-iodo-2-methyl-1H-imidazo[4,5-b]pyridine

Concentrated hydrochloric acid (0.1 mL) was added to a mixture of N3-(2,6-difluorobenzyl)-5-iodopyridine-2,3-diamine (262.8 mg) and trimethyl orthoacetate (4 mL) at room temperature. Under a dry atmosphere, the mixture was stirred at room temperature for 1 hour. The reaction mixture was neutralized with a saturated aqueous sodium hydrogen carbonate solution at room temperature, and extracted with ethyl acetate/THF. The organic layer was washed with a saturated brine, dried over magnesium sulfate, and then concentrated. The residue was washed with ethyl acetate to obtain the title compound (200 mg).

$^1$H NMR (300 MHz, DMSO-$d_6$) δ 2.54 (3H, s), 5.58 (2H, s), 7.09-7.26 (2H, m), 7.39-7.58 (1H, m), 8.26-8.34 (1H, m), 8.50 (1H, d, J=2.0 Hz).

c) 1-(2,6-difluorobenzyl)-6-(4-methoxy-5H-pyrrolo[3,2-d]pyrimidin-5-yl)-2-methyl-1H-imidazo[4,5-b]pyridine A mixture of 1-(2,6-difluorobenzyl)-6-iodo-2-methyl-1H-imidazo[4,5-b]pyridine (200 mg), 4-methoxy-5H-pyrrolo[3,2-d]pyrimidine (101 mg), potassium phosphate (331 mg), trans-N,N'-dimethylcyclohexane-1,2-diamine (0.082 mL), copper (I) iodide (49.4 mg) and THF (5 mL) was stirred under microwave irradiation at 110° C. for 2 hours. The mixture was diluted with an aqueous ammonia solution at room temperature, and extracted with ethyl acetate. The organic layer was washed with a saturated brine, then dried over magnesium sulfate, and concentrated under reduced pressure. The residue was purified by NH silica gel column chromatography (methanol/ethyl acetate), and washed with ethyl acetate to obtain the title compound (68.5 mg).

$^1$H NMR (300 MHz, DMSO-$d_6$) δ 2.61 (3H, s), 3.79 (3H, s), 5.62 (2H, s), 6.84 (1H, d, J=3.2 Hz), 7.12-7.26 (2H, m), 7.43-7.58 (1H, m), 7.93 (1H, d, J=3.2 Hz), 8.10 (1H, d, J=2.4 Hz), 8.44-8.60 (2H, m).

Example 38

1-(3,5-difluorobenzyl)-2-methoxy-6-(4-methoxy-5H-pyrrolo[3,2-d]pyrimidin-5-yl)-1H-imidazo[4,5-b]pyridine a) 1-(3,5-difluorobenzyl)-6-iodo-2-(isopropylthio)-1H-imidazo[4,5-b]pyridine Under a dry atmosphere, a mixture of N3-(3,5-difluorobenzyl)-5-iodopyridine-2,3-diamine (5 g), CDI (4.5 g) and THF (50 mL) was stirred at 60° C. for 16 hours. The reaction mixture was quenched with water at room temperature, and extracted with ethyl acetate. The organic layer was sequentially washed with a saturated aqueous ammonium chloride solution, water and a saturated brine, then dried over magnesium sulfate, and concentrated under reduced pressure to obtain a white solid as 1-(3,5-difluorobenzyl)-6-iodo-1H-imidazo[4,5-b]pyridin-2(3H)-one. A mixture of the obtained solid and phosphorus oxychloride (50 mL) was stirred at 100° C. for 2 days. The reaction mixture was concentrated under reduced pressure. The residue was diluted with THF, poured into a saturated aqueous sodium hydrogen carbonate solution, and extracted with ethyl acetate. The organic layer was washed with water and a saturated brine, dried over sodium sulfate, and then concentrated. The residue was diluted with THF (100 mL). To the mixture was added sodium 2-propanethiolate (1.963 g) at 0° C. Under a nitrogen atmosphere, the mixture was stirred at room temperature for 1 hour. The reaction mixture was poured into water, and extracted with ethyl acetate. The organic layer was washed with water and a saturated brine, dried over sodium sulfate, and then concentrated. The residue was purified by silica gel column chromatography (ethyl acetate/hexane) to obtain the title compound (5.73 g).

$^1$H NMR (300 MHz, DMSO-$d_6$) δ1.45 (6H, d, J=6.8 Hz), 4.05-4.17 (1H, m), 5.43 (2H, s), 6.87 (2H, dd, J=8.4, 2.2 Hz), 7.14-7.28 (1H, m), 8.42 (1H, d, J=2.0 Hz), 8.52 (1H, d, J=1.9 Hz).

b) 1-(3,5-difluorobenzyl)-2-(isopropylthio)-6-(4-methoxy-5H-pyrrolo[3,2-d]pyrimidin-5-yl)-1H-imidazo[4,5-b]pyridine A mixture of 1-(3,5-difluorobenzyl)-6-iodo-2-(isopropylthio)-1H-imidazo[4,5-b]pyridine (203 mg), 4-methoxy-5H-pyrrolo[3,2-d]pyrimidine (88 mg), potassium phosphate (290 mg), trans-N,N'-dimethylcyclohexane-1,2-diamine (0.144 mL), copper (I) iodide (87 mg) and THF (5 mL) was stirred under microwave irradiation at 100° C. for 2 hours. The mixture was diluted with water and an aqueous ammonia solution at room temperature, and extracted with ethyl acetate. The organic layer was washed with a saturated brine, then dried over magnesium sulfate, and concentrated under reduced pressure. The residue was purified by silica gel column chromatography (methanol/ethyl acetate), and washed with ethyl acetate to obtain the title compound (170 mg).

$^1$H NMR (300 MHz, DMSO-$d_6$) δ 1.49 (6H, d, J=6.8 Hz), 3.75 (3H, s), 4.10-4.25 (1H, m), 5.46 (2H, s), 6.84 (1H, d, J=3.3 Hz), 6.90-7.02 (2H, m), 7.18-7.30 (1H, m), 7.97 (1H, d, J=3.2 Hz), 8.33 (1H, d, J=2.4 Hz), 8.52 (1H, s), 8.55 (1H, d, J=2.4 Hz).

c) 1-(3,5-difluorobenzyl)-2-methoxy-6-(4-methoxy-5H-pyrrolo[3,2-d]pyrimidin-5-yl)-1H-imidazo[4,5-b]pyridine m-Chloroperbenzoic acid (55.5 mg) was added to a solution of 1-(3,5-difluorobenzyl)-2-(isopropylthio)-6-(4-methoxy-5H-pyrrolo[3,2-d]pyrimidin-5-yl)-1H-imidazo[4,5-b]pyridine (60 mg) in acetonitrile (5 mL) at 0° C. The mixture was stirred for 10 minutes, and then added to a solution of sodium methoxide (20 mg) in acetonitrile (5 mL) at 0° C. The mixture was stirred under a nitrogen atmosphere at room temperature for 5 hours. The reaction mixture was poured into a saturated aqueous ammonium chloride solution at room temperature, and extracted with ethyl acetate.

The organic layer was washed with water and a saturated brine, dried over magnesium sulfate, and then concentrated. The residue was purified by silica gel column chromatography (ethyl acetate/hexane) to obtain the title compound (47 mg).

$^1$H NMR (300 MHz, DMSO-$d_6$) δ3.74 (3H, s), 4.24 (3H, s), 5.30 (2H, s), 6.82 (1H, d, J=3.2 Hz), 7.02-7.09 (2H, m), 7.15-7.29 (1H, m), 7.93 (1H, d, J=3.2 Hz), 8.18 (1H, d, J=2.4 Hz), 8.41 (1H, d, J=2.4 Hz), 8.51 (1H, s).

Example 39

1-(3-fluorobenzyl)-2-methoxy-6-(4-methoxy-5H-pyrrolo[3,2-d]pyrimidin-5-yl)-1H-imidazo[4,5-b]pyridine a) 1-(3-fluorobenzyl)-6-iodo-1H-imidazo[4,5-b]pyridin-2(3H)-one Under a dry atmosphere, a mixture of N3-(3-fluorobenzyl)-5-iodopyridine-2,3-diamine (2.56 g), CDI (2.5 g) and THF (30 mL) was stirred at 60° C. for 16 hours. The mixture was quenched with water at room temperature, and diluted with ethyl acetate. The organic layer was sequentially washed with a saturated aqueous ammonium chloride solution, water and a saturated brine, then dried over magnesium sulfate, and concentrated under reduced pressure. The residue was washed with ethyl acetate to obtain the title compound (2.4 g).

$^1$H NMR (300 MHz, DMSO-$d_6$) δ5.02 (2H, s), 7.08-7.22 (3H, m), 7.39 (1H, td, J=7.9, 6.1 Hz), 7.80 (1H, d, J=1.8 Hz), 8.12 (1H, d, J=1.8 Hz), 11.87 (1H, s).

b) 2-chloro-1-(3-fluorobenzyl)-6-iodo-1H-imidazo[4,5-b]pyridine

A mixture of 1-(3-fluorobenzyl)-6-iodo-H-imidazo[4,5-b]pyridin-2(3H)-one (2.39 g) and phosphorus oxychloride (20 mL) was stirred under a nitrogen atmosphere at 100° C. for 18 hours. The reaction mixture was concentrated under reduced pressure. The residue was diluted with THF, neutralized with a saturated aqueous sodium hydrogen carbonate solution at room temperature, and extracted with ethyl acetate. The organic layer was washed with a saturated brine, dried over magnesium sulfate, and then concentrated. The residue was washed with ethyl acetate/IPE to obtain the title compound (1.78 g).

MS: [M+H]$^+$ 388.1.

c) 2-chloro-1-(3-fluorobenzyl)-6-(4-methoxy-5H-pyrrolo[3,2-d]pyrimidin-5-yl)-1H-imidazo[4,5-b]pyridine A mixture of 2-chloro-1-(3-fluorobenzyl)-6-iodo-1H-imidazo[4,5-b]pyridine (300 mg), 4-methoxy-5H-pyrrolo[3,2-d]pyrimidine (150 mg), potassium phosphate (493 mg), trans-N,N'-dimethylcyclohexane-1,2-diamine (0.122 mL), copper (I) iodide (73.7 mg) and THF (5 mL) was stirred under microwave irradiation at 90° C. for 2 hours. The mixture was diluted with water, and extracted with ethyl acetate. The organic layer was washed with a saturated brine, then dried over magnesium sulfate, and concentrated under reduced pressure. The residue was purified by silica gel column chromatography (methanol/ethyl acetate) to obtain the title compound (99 mg).

$^1$H NMR (300 MHz, DMSO-$d_6$) δ3.74 (3H, s), 5.61 (2H, s), 6.86 (1H, d, J=3.3 Hz), 7.04-7.12 (1H, m), 7.14-7.26 (2H, m), 7.37-7.50 (1H, m), 8.00 (1H, d, J=3.3 Hz), 8.50 (1H, d, J=2.4 Hz), 8.53 (1H, s), 8.68 (1H, d, J=2.4 Hz).

d) 1-(3-fluorobenzyl)-2-methoxy-6-(4-methoxy-5H-pyrrolo[3,2-d]pyrimidin-5-yl)-1H-imidazo[4,5-b]pyridine Sodium methoxide (28% in methanol solution) (90 mg) was added to 2-chloro-1-(3-fluorobenzyl)-6-(4-methoxy-5H-pyrrolo[3,2-d]pyrimidin-5-yl)-1H-imidazo[4,5-b]pyridine (90 mg) in THF (5 mL) at room temperature. The mixture was stirred at room temperature for 30 minutes. The reaction mixture was diluted with a saturated aqueous ammonium chloride solution at room temperature, and extracted with ethyl acetate. The organic layer was washed with water and a saturated brine, dried over magnesium sulfate, and then concentrated. The residue was purified by silica gel column chromatography (methanol/ethyl acetate), and crystallized from ethanol/water to obtain the title compound (56.8 mg).

$^1$H NMR (300 MHz, DMSO-$d_6$) δ 3.72 (3H, s), 4.24 (3H, s), 5.30 (2H, s), 6.81 (1H, d, J=3.2 Hz), 7.08-7.23 (3H, m), 7.36-7.48 (1H, m), 7.92 (1H, d, J=3.2 Hz), 8.16 (1H, d, J=2.4 Hz), 8.39 (1H, d, J=2.4 Hz), 8.50 (1H, s).

Example 44

1-(3-(difluoromethoxy)benzyl)-6-(4-methoxy-5H-pyrrolo[3,2-d]pyrimidin-5-yl)-2-methyl-1H-imidazo[4,5-b]pyridine a) N3-(3-(difluoromethoxy)benzyl)-5-iodopyridine-2,3-diamine A mixture of 3-(difluoromethoxy)benzaldehyde (429 mg), 5-iodopyridine-2,3-diamine (451 mg), THF (8 mL) and acetic acid (0.277 mL) was stirred overnight at room temperature. The reaction mixture was poured into a saturated aqueous sodium hydrogen carbonate solution, and extracted with ethyl acetate. The organic layer was washed with a saturated brine, dried over magnesium sulfate, and then concentrated. Sodium borohydride (181 mg) was added to a solution of the residue in methanol (8 mL) at room temperature. The mixture was stirred overnight at room temperature. The reaction mixture was poured into water, and extracted with ethyl acetate. The organic layer was washed with a saturated brine, then dried over magnesium sulfate, and concentrated under reduced pressure. The residue was purified by silica gel column chromatography (ethyl acetate/hexane) to obtain the title compound (660 mg).

$^1$H NMR (300 MHz, DMSO-$d_6$) δ 4.30 (2H, d, J=5.8 Hz), 5.66 (1H, t, J=5.9 Hz), 5.78 (2H, s), 6.66 (1H, d, J=1.9 Hz), 6.95-7.48 (2H, m), 7.06 (1H, dd, J=8.0, 2.2 Hz), 7.16 (1H, s), 7.37-7.44 (2H, m).

b) 1-(3-(difluoromethoxy)benzyl)-6-iodo-2-methyl-1H-imidazo[4,5-b]pyridine

Concentrated hydrochloric acid (500 μL) was added to a mixture of N3-(3-(difluoromethoxy)benzyl)-5-iodopyridine-2,3-diamine (0.66 g) and trimethyl orthoacetate (5 mL) at room temperature. The mixture was stirred at 60° C. for 3 hours. The reaction mixture was poured into a saturated aqueous sodium hydrogen carbonate solution, and extracted with ethyl acetate. The organic layer was washed with a saturated brine, dried over magnesium sulfate, and then concentrated. The residue was purified by NH silica gel column chromatography (ethyl acetate/hexane) to obtain the title compound (0.492 g).

$^1$H NMR (300 MHz, DMSO-d$_6$) δ 2.54 (3H, s), 5.53 (2H, s), 6.92 (1H, d, J=7.6 Hz), 6.96-7.49 (1H, m), 7.01 (1H, s), 7.11 (1H, dd, J=8.3, 2.2 Hz), 7.35-7.44 (1H, m), 8.39 (1H, d, J=1.9 Hz), 8.52 (1H, d, J=1.9 Hz).

c) 1-(3-(difluoromethoxy)benzyl)-6-(4-methoxy-5H-pyrrolo[3,2-d]pyrimidin-5-yl)-2-methyl-1H-imidazo[4,5-b]pyridine 1-(3-(difluoromethoxy)benzyl)-6-iodo-2-methyl-1H-imidazo[4,5-b]pyridine (157.9 mg), 4-methoxy-5H-pyrrolo[3,2-d]pyrimidine (59.6 mg), potassium phosphate (242 mg), trans-N,N'-dimethylcyclohexane-1,2-diamine (64.9 mg), copper (I) iodide (43.5 mg) and THF (2 mL) was stirred under microwave irradiation at 150° C. for 2.5 hours. The mixture was cooled to room temperature, then poured into a saturated aqueous ammonium chloride solution, and extracted with ethyl acetate. The organic layer was washed with a saturated brine, then dried over magnesium sulfate, and concentrated under reduced pressure. The residue was fractionated by NH silica gel column chromatography (methanol/ethyl acetate) and HPLC (C18, mobile phase: water/acetonitrile (0.1% TFA-containing system)) to obtain the title compound (93 mg).

$^1$H NMR (300 MHz, DMSO-d$_6$) δ2.62 (3H, s), 3.70 (3H, s), 5.57 (2H, s), 6.83 (1H, d, J=3.2 Hz), 6.91-7.50 (5H, m), 7.96 (1H, d, J=3.2 Hz), 8.29 (1H, d, J=2.4 Hz), 8.51 (1H, s), 8.54 (1H, d, J=2.4 Hz).

Example 48

1-(3,5-difluorobenzyl)-6-(4-methoxy-5H-pyrrolo[3,2-d]pyrimidin-5-yl)-1H-imidazo[4,5-b]pyridin-2-amine a) 1-(3,5-difluorobenzyl)-6-iodo-1H-imidazo[4,5-b]pyridin-2(3H)-one Under a dry atmosphere, a mixture of N3-(3,5-difluorobenzyl)-5-iodopyridine-2,3-diamine (2.2 g), CDI (1.976 g) and THF (150 mL) was stirred at 60° C. for 16 hours. The mixture was quenched with water at room temperature, and diluted with ethyl acetate. The organic layer was sequentially washed with a saturated aqueous ammonium chloride solution, water and a saturated brine, then dried over magnesium sulfate, and concentrated under reduced pressure. The residue was washed with ethyl acetate to obtain the title compound (2 g).

$^1$H NMR (300 MHz, DMSO-d$_6$) δ5.02 (2H, s), 6.99-7.25 (3H, m), 7.84 (1H, d, J=1.8 Hz), 8.13 (1H, d, J=1.8 Hz), 11.88 (1H, brs).

b) 2-chloro-1-(3,5-difluorobenzyl)-6-iodo-1H-imidazo[4,5-b]pyridine

A mixture of 1-(3,5-difluorobenzyl)-6-iodo-1H-imidazo[4,5-b]pyridin-2(3H)-one (2 g) and phosphorus oxychloride (24.13 mL) was stirred under a nitrogen atmosphere at 100° C. for 17 hours. The reaction mixture was concentrated under reduced pressure. The residue was diluted with THF, neutralized with a saturated aqueous sodium hydrogen carbonate solution at 0° C., and extracted with ethyl acetate. The organic layer was washed with a saturated brine, dried over magnesium sulfate, and then concentrated. The residue was washed with IPE to obtain the title compound (1.97 g).

$^1$H NMR (300 MHz, DMSO-d$_6$) δ 5.58 (2H, s), 6.98 (3H, d, J=6.0 Hz), 8.62 (2H, dd, J=11.5, 1.9 Hz).

c) 2-chloro-1-(3,5-difluorobenzyl)-6-(4-methoxy-5H-pyrrolo[3,2-d]pyrimidin-5-yl)-1H-imidazo[4,5-b]pyridine A mixture of 2-chloro-1-(3,5-difluorobenzyl)-6-iodo-1H-imidazo[4,5-b]pyridine (980 mg), 4-methoxy-5H-pyrrolo[3,2-d]pyrimidine (469 mg), potassium phosphate (1539 mg), trans-N,N'-dimethylcyclohexane-1,2-diamine (0.381 mL), copper (I) iodide (230 mg) and THF (5 mL) was stirred under microwave irradiation at 90° C. for 3 hours. The mixture was diluted with water and an aqueous ammonia solution at room temperature, and extracted with ethyl acetate. The organic layer was washed with a saturated brine, then dried over magnesium sulfate, and concentrated under reduced pressure. The residue was purified by NH silica gel column chromatography (methanol/ethyl acetate) to obtain the title compound (440 mg).

$^1$H NMR (300 MHz, DMSO-d$_6$) δ3.77 (3H, s), 5.61 (2H, s), 6.87 (1H, d, J=3.2 Hz), 7.04-7.26 (3H, m), 8.00 (1H, d, J=3.2 Hz), 8.47-8.59 (2H, m), 8.64-8.78 (1H, m).

d) 1-(3,5-difluorobenzyl)-6-(4-methoxy-5H-pyrrolo[3,2-d]pyrimidin-5-yl)-1H-imidazo[4,5-b]pyridin-2-amine A mixture of 2-chloro-1-(3,5-difluorobenzyl)-6-(4-methoxy-5H-pyrrolo[3,2-d]pyrimidin-5-yl)-1H-imidazo[4,5-b]pyridine (120 mg), ammonia (2 M in IPA solution) (15 mL) and THF (5 mL) was stirred under microwave irradiation at 100° C. for 5 hours. The mixture was diluted with water at room temperature, and extracted with ethyl acetate. The organic layer was washed with a saturated brine, then dried over magnesium sulfate, and concentrated under reduced pressure. The residue was purified by NH silica gel column chromatography (methanol/ethyl acetate) to obtain the title compound (41 mg).

$^1$H NMR (300 MHz, DMSO-d$_6$) δ 3.70 (3H, s), 5.32 (2H, s), 6.76 (1H, d, J=3.2 Hz), 6.91-7.00 (2H, m), 7.14-7.24 (1H, m), 7.30 (2H, s), 7.78 (1H, d, J=2.4 Hz), 7.85 (1H, d, J=3.2 Hz), 8.14 (1H, d, J=2.4 Hz), 8.47 (1H, s).

Example 68

1-(3-fluoro-5-(trifluoromethyl)benzyl)-6-(4-methoxy-5H-pyrrolo[3,2-d]pyrimidin-5-yl)-2-methyl-1H-imidazo[4,5-b]pyridine a) N3-(3-fluoro-5-(trifluoromethyl)benzyl)-5-iodopyridine-2,3-diamine A mixture of 3-fluoro-5-(trifluoromethyl)benzaldehyde (0.72 mL), 5-iodopyridine-2,3-diamine (1.01 g), THF (10 mL) and acetic acid (0.62 mL) was stirred overnight at room temperature. The reaction mixture was poured into a saturated aqueous sodium hydrogen carbonate solution, and extracted with ethyl acetate. The organic layer was washed with a saturated brine, dried over magnesium sulfate, and then concentrated. Sodium borohydride (0.406 g) was added to a solution of the residue in methanol (5 mL) at room temperature. The mixture was stirred overnight at room temperature. The reaction mixture was poured into water, and extracted with ethyl acetate. The organic layer was washed with a saturated brine, then dried over magnesium sulfate, and concentrated under reduced pressure. The residue was purified by silica gel column chromatography (ethyl acetate/hexane) to obtain the title compound (1.51 g).

$^1$H NMR (300 MHz, DMSO-d$_6$) δ 4.41 (2H, d, J=5.8 Hz), 5.71 (1H, t, J=5.7 Hz), 5.80 (2H, s), 6.71 (1H, d, J=1.7 Hz), 7.43 (1H, d, J=1.9 Hz), 7.50-7.64 (3H, m).

b) 1-(3-fluoro-5-(trifluoromethyl)benzyl)-6-iodo-2-methyl-1H-imidazo[4,5-b]pyridine Concentrated hydrochloric acid (500 µL) was added to a mixture of N3-(3-fluoro-5-(trifluoromethyl)benzyl)-5-iodopyridine-2,3-diamine (1.51 g) and trimethyl orthoacetate (5 mL) at room temperature. Under a dry atmosphere, the mixture was stirred at 60° C. for 3 hours. The reaction mixture was poured into a saturated aqueous sodium hydrogen carbonate solution, and extracted with ethyl acetate. The organic layer was washed with a saturated brine, dried over magnesium sulfate, and then concentrated. The residue was purified by NH silica gel column chromatography (ethyl acetate/hexane) to obtain the title compound (1.03 g).

$^1$H NMR (300 MHz, DMSO-d$_6$) δ 2.55 (3H, s), 5.63 (2H, s), 7.19-7.26 (1H, m), 7.45 (1H, s), 7.62-7.70 (1H, m), 8.41 (1H, d, J=2.0 Hz), 8.53 (1H, d, J=1.9 Hz).

c) 1-(3-fluoro-5-(trifluoromethyl)benzyl)-6-(4-methoxy-5H-pyrrolo[3,2-d]pyrimidin-5-yl)-2-methyl-1H-imidazo[4,5-b]pyridine A mixture of 1-(3-fluoro-5-(trifluoromethyl)benzyl)-6-iodo-2-methyl-1H-imidazo[4,5-b]pyridine (139 mg), 4-methoxy-5H-pyrrolo[3,2-d]pyrimidine (50 mg), potassium phosphate (203 mg), trans-N,N'-dimethylcyclohexane-1,2-diamine (0.06 mL), copper (I) iodide (36.5 mg) and THF (2 mL) was stirred under microwave irradiation at 100° C. for 2 hours. The mixture was cooled to room temperature, then diluted with a saturated aqueous ammonium chloride solution, and extracted with ethyl acetate. The organic layer was washed with a saturated brine, then dried over magnesium sulfate, and concentrated under reduced pressure. The residue was purified by NH silica gel column chromatography (methanol/ethyl acetate) to obtain the title compound (113 mg).

$^1$H NMR (300 MHz, DMSO-d$_6$) δ 2.63 (3H, s), 3.68 (3H, s), 5.67 (2H, s), 6.83 (1H, d, J=3.3 Hz), 7.26 (1H, d, J=9.3 Hz), 7.50 (1H, s), 7.68 (1H, d, J=8.7 Hz), 7.96 (1H, d, J=3.2 Hz), 8.29 (1H, d, J=2.4 Hz), 8.51 (1H, s), 8.56 (1H, d, J=2.4 Hz).

Example 79

1-(3-chloro-5-fluorobenzyl)-6-(4-methoxy-5H-pyrrolo[3,2-d]pyrimidin-5-yl)-2-methyl-1H-imidazo[4,5-b]pyridine a) N3-(3-chloro-5-fluorobenzyl)-5-iodopyridine-2,3-diamine A mixture of 3-chloro-5-fluorobenzaldehyde (0.623 g), 5-iodopyridine-2,3-diamine (0.77 g), THF (10 mL) and acetic acid (0.472 mL) was stirred overnight at room temperature. The reaction mixture was poured into a saturated aqueous sodium hydrogen carbonate solution, and extracted with ethyl acetate. The organic layer was washed with a saturated brine, dried over magnesium sulfate, and then concentrated. To a solution of the residue in methanol (5 mL) was added sodium borohydride (0.31 g) at room temperature. The mixture was stirred overnight at room temperature. The reaction mixture was poured into water, and extracted with ethyl acetate. The organic layer was washed with a saturated brine, then dried over magnesium sulfate, and concentrated under reduced pressure. The residue was purified by silica gel column chromatography (ethyl acetate/hexane) to obtain the title compound (1 g).

$^1$H NMR (300 MHz, DMSO-d$_6$) δ 4.32 (2H, d, J=5.8 Hz), 5.69 (1H, t, J=5.9 Hz), 5.79 (2H, s), 6.67 (1H, d, J=1.8 Hz), 7.16-7.23 (1H, m), 7.27-7.35 (2H, m), 7.43 (1H, d, J=1.9 Hz).

b) 1-(3-chloro-5-fluorobenzyl)-6-iodo-2-methyl-1H-imidazo[4,5-b]pyridine

Concentrated hydrochloric acid (500 µL) was added to a mixture of N3-(3-chloro-5-fluorobenzyl)-5-iodopyridine-2,3-diamine (1 g) and trimethyl orthoacetate (5 mL) at room temperature. The mixture was stirred at 60° C. for 3 hours. The reaction mixture was poured into a saturated aqueous sodium hydrogen carbonate solution, and extracted with ethyl acetate. The organic layer was washed with a saturated brine, dried over magnesium sulfate, and then concentrated. The residue was purified by NH silica gel column chromatography (ethyl acetate/hexane) to obtain the title compound (0.77 g).

$^1$H NMR (300 MHz, DMSO-d$_6$) δ 2.54 (3H, s), 5.54 (2H, s), 6.92-7.00 (1H, m), 7.06 (1H, s), 7.40 (1H, dt, J=8.7, 2.2 Hz), 8.40 (1H, d, J=1.9 Hz), 8.53 (1H, d, J=1.9 Hz).

c) 1-(3-chloro-5-fluorobenzyl)-6-(4-methoxy-5H-pyrrolo[3,2-d]pyrimidin-5-yl)-2-methyl-1H-imidazo[4,5-b]pyridine A mixture of 1-(3-chloro-5-fluorobenzyl)-6-iodo-2-methyl-1H-imidazo[4,5-b]pyridine (110.7 mg), 4-methoxy-5H-pyrrolo[3,2-d]pyrimidine (43.2 mg), potassium phosphate (176 mg), trans-N,N'-dimethylcyclohexane-1,2-diamine (0.052 mL), copper (I) iodide (31.5 mg) and THF (2 mL) was stirred under microwave irradiation at 100° C. for 2 hours. The mixture was cooled to room temperature, then poured into a saturated aqueous ammonium chloride solution, and extracted with ethyl acetate. The organic layer was washed with a saturated brine, then dried over magnesium sulfate, and concentrated under reduced pressure. The residue was purified by NH silica gel column chromatography (methanol/ethyl acetate) and crystallized from ethanol/IPE to obtain the title compound (54.7 mg).

$^1$H NMR (300 MHz, DMSO-d$_6$) δ 2.62 (3H, s), 3.72 (3H, s), 5.57 (2H, s), 6.83 (1H, d, J=3.2 Hz), 6.98-7.05 (1H, m), 7.10-7.14 (1H, m), 7.42 (1H, dt, J=8.7, 2.1 Hz), 7.97 (1H, d, J=3.2 Hz), 8.28 (1H, d, J=2.4 Hz), 8.51 (1H, s), 8.55 (1H, d, J=2.4 Hz).

Example 82

(1-(3,5-difluorobenzyl)-6-(4-methoxy-5H-pyrrolo[3,2-d]pyrimidin-5-yl)-1H-imidazo[4,5-b]pyridin-2-yl)methanol a) (1-(3,5-difluorobenzyl)-6-iodo-1H-imidazo[4,5-b]pyridin-2-yl)methanol A mixture of N3-(3,5-difluorobenzyl)-5-iodopyridine-2,3-diamine (9 g), glycolic acid (48 g) and THF (9 mL) was stirred under microwave irradiation at 150° C. for 1.5 hours.

The mixture was neutralized with a saturated aqueous sodium hydrogen carbonate solution at room temperature, and extracted with ethyl acetate. The organic layer was washed with a saturated brine, dried over magnesium sulfate, and then concentrated. The residue was purified by silica gel column chromatography (ethyl acetate/hexame and methanol/ethyl acetate) to obtain the title compound (4.9 g).

$^1$H NMR (300 MHz, DMSO-$d_6$) δ 4.77 (2H, s), 5.61 (2H, s), 5.79-6.07 (1H, m), 6.81-7.08 (2H, m), 7.12-7.30 (1H, m), 8.33 (1H, d, J=1.9 Hz), 8.57 (1H, d, J=2.0 Hz).

b) 2-(((tert-butyldiphenyl silyl)oxy)methyl)-1-(3,5-difluorobenzyl)-6-iodo-1H-imidazo[4,5-b]pyridine 1H-imidazole (105 mg) and tert-butylchlorodiphenylsilane (0.39 mL) were added to a solution of (1-(3,5-difluorobenzyl)-6-iodo-1H-imidazo[4,5-b]pyridin-2-yl)methanol (200 mg) in DMF (1.5 mL). The mixture was stirred at room temperature for 10 minutes. The reaction mixture was quenched with a saturated aqueous sodium hydrogen carbonate solution at 0° C., and extracted with ethyl acetate. The organic layer was washed with water and a saturated brine, dried over magnesium sulfate, and then concentrated. The residue was purified by silica gel column chromatography (ethyl acetate/hexane) to obtain the title compound (256 mg).

$^1$H NMR (300 MHz, DMSO-$d_6$) δ 0.90 (9H, s), 4.81-5.11 (2H, m), 5.54-5.83 (2H, m), 6.74-6.91 (2H, m), 7.12-7.23 (1H, m), 7.37-7.53 (6H, m), 7.57-7.65 (4H, m), 8.19-8.47 (1H, m), 8.55-8.71 (1H, m).

c) 2-(((tert-butyldiphenylsilyl)oxy)methyl)-1-(3,5-difluorobenzyl)-6-(4-methoxy-5H-pyrrolo[3,2-d]pyrimidin-5-yl)-1H-imidazo[4,5-b]pyridine A mixture of 2-(((tert-butyldiphenylsilyl)oxy)methyl)-1-(3,5-difluorobenzyl)-6-iodo-1H-imidazo[4,5-b]pyridine (4.92 g), 4-methoxy-5H-pyrrolo[3,2-d]pyrimidine (1.2 g), potassium phosphate (4.9 g), trans-N,N'-dimethylcyclohexane-1,2-diamine (2.76 mL), copper (I) iodide (1.46 g) and THF (72 mL) was stirred under microwave irradiation at 100° C. for 1.5 hours. The mixture was diluted with a saturated aqueous sodium hydrogen carbonate solution and an aqueous ammonia solution at room temperature, and extracted with ethyl acetate. The organic layer was concentrated under reduced pressure. The residue was purified by NH silica gel column chromatography (ethyl acetate/hexane) to obtain the title compound (3.23 g).

MS: [M+H]$^+$ 661.2 d) (1-(3,5-difluorobenzyl)-6-(4-methoxy-5H-pyrrolo[3,2-d]pyrimidin-5-yl)-1H-imidazo[4,5-b]pyridin-2-yl)methanol TBAF (1M in THF solution) (0.239 mL) was added to a solution of 2-(((tert-butyldiphenylsilyl)oxy)methyl)-1-(3,5-difluorobenzyl)-6-(4-methoxy-5H-pyrrolo[3,2-d]pyrimidin-5-yl)-1H-imidazo[4,5-b]pyridine (105 mg) in THF (2 mL) at room temperature. The mixture was stirred at room temperature for 30 minutes. The residue was purified by NH silica gel column chromatography (methanol/ethyl acetate) to obtain the title compound (44.3 mg).

$^1$H NMR (300 MHz, DMSO-$d_6$) δ 3.67 (3H, s), 4.66-4.96 (2H, m), 5.46-5.74 (2H, m), 5.82-6.09 (1H, m), 6.64-6.89 (1H, m), 6.93-7.09 (2H, m), 7.13-7.33 (1H, m), 7.96 (1H, d, J=3.3 Hz), 8.16-8.32 (1H, m), 8.51 (2H, s).

Example 96

1-((6-fluoropyridin-2-yl)methyl)-6-(4-methoxy-5H-pyrrolo[3,2-d]pyrimidin-5-yl)-2-methyl-1H-imidazo[4,5-b]pyridine a) N3-((6-fluoropyridin-2-yl)methyl)-5-iodopyridine-2,3-diamine A mixture of 6-fluoropicolinaldehyde (2.97 g), 5-iodopyridine-2,3-diamine (5.08 g), THF (50 mL) and acetic acid (3.12 mL) was stirred overnight at room temperature. The reaction mixture was poured into a saturated aqueous sodium hydrogen carbonate solution, and extracted with ethyl acetate. The organic layer was washed with a saturated brine, dried over magnesium sulfate, and then concentrated. To a solution of the residue in methanol (5 mL) was added sodium borohydride (2.044 g) at room temperature. The mixture was stirred overnight at room temperature. The reaction mixture was poured into water, and extracted with ethyl acetate. The organic layer was washed with a saturated brine, then dried over magnesium sulfate, and concentrated under reduced pressure. The residue was purified by silica gel column chromatography (ethyl acetate/hexane) to obtain the title compound (5.72 g).

$^1$H NMR (300 MHz, DMSO-$d_6$) δ 4.34 (2H, d, J=5.9 Hz), 5.77-5.89 (3H, m), 6.63 (1H, d, J=1.8 Hz), 7.06 (1H, dd, J=8.1, 2.4 Hz), 7.30 (1H, dd, J=7.4, 2.4 Hz), 7.41 (1H, d, J=1.9 Hz), 7.89-8.04 (1H, m).

b) 1-((6-fluoropyridin-2-yl)methyl)-6-iodo-2-methyl-1H-imidazo[4,5-b]pyridine

A mixture of N3-((6-fluoropyridin-2-yl)methyl)-5-iodopyridine-2,3-diamine (1.09 g), acetic acid (0.218 mL), DMAP (0.019 g), propylphosphonic anhydride (50% in ethyl acetate solution) (2.79 mL), DIPEA (1.106 mL) and THF (12 mL) was stirred under microwave irradiation at 180° C. for 2 hours. The reaction mixture was poured into a saturated aqueous sodium hydrogen carbonate solution, and extracted with ethyl acetate. The organic layer was washed with a saturated brine, dried over magnesium sulfate, and then concentrated. The residue was purified by NH silica gel column chromatography (ethyl acetate/hexane) to obtain the title compound (0.71 g).

$^1$H NMR (300 MHz, DMSO-$d_6$) δ 2.57 (3H, s), 5.59 (2H, s), 7.12 (1H, dd, J=8.2, 2.5 Hz), 7.28 (1H, dd, J=7.3, 2.4 Hz), 8.01 (1H, q, J=8.2 Hz), 8.40 (1H, d, J=1.9 Hz), 8.50 (1H, d, J=1.9 Hz).

c) 1-((6-fluoropyridin-2-yl)methyl)-6-(4-methoxy-5H-pyrrolo[3,2-d]pyrimidin-5-yl)-2-methyl-1H-imidazo[4,5-b]pyridine A mixture of 1-((6-fluoropyridin-2-yl)methyl)-6-iodo-2-methyl-1H-imidazo[4,5-b]pyridine (149.5 mg), 4-methoxy-5H-pyrrolo[3,2-d]pyrimidine (63.6 mg), potassium phosphate (259 mg), trans-N,N'-dimethylcyclohexane-1,2-diamine (0.128 mL), copper (1) iodide (77 mg) and THF (1 mL) was stirred under microwave irradiation at 120° C. for 2 hours. The mixture was poured into a saturated aqueous ammonium chloride solution, and extracted with ethyl acetate. The residue was purified by NH silica gel column chromatography (methanol/ethyl acetate) to obtain the title compound (75 mg).

$^1$H NMR (300 MHz, DMSO-$d_6$) δ 2.66 (3H, s), 3.70 (3H, s), 5.62 (2H, s), 6.83 (1H, d, J=3.2 Hz), 7.13 (1H, dd, J=8.0, 2.4 Hz), 7.31 (1H, dd, J=7.2, 2.4 Hz), 7.95 (1H, d, J=3.2 Hz), 7.98-8.08 (1H, m), 8.26 (1H, d, J=2.4 Hz), 8.50 (1H, s), 8.53 (1H, d, J=2.4 Hz).

Example 98

1-((6-fluoropyridin-2-yl)methyl)-2-methoxy-6-(4-methoxy-5H-pyrrolo[3,2-d]pyrimidin-5-yl)-1H-imidazo[4,5-b]pyridine a) 1-((6-fluoropyridin-2-yl)methyl)-6-1H-imidazo[4,5-b]pyridin-2(3H)-one Under a nitrogen atmosphere, a mixture of N3-((6-fluoropyridin-2-yl)methyl)-5-iodopyridine-2,3-diamine (4.62 g), CDI (4.35 g) and THF (50 mL) was stirred overnight at 60° C. The mixture was diluted with THF, sequentially washed with a saturated aqueous ammonium chloride solution and a saturated brine, then dried over magnesium sulfate, and concentrated under reduced pressure. The residue was washed with ethyl acetate to obtain the title compound (3.89 g).

$^1$H NMR (300 MHz, DMSO-$d_6$) δ 5.09 (2H, s), 7.09 (1H, dd, J=8.1, 2.3 Hz), 7.25 (1H, dd, J=7.4, 2.3 Hz), 7.78 (1H, d, J=1.7 Hz), 7.92-8.03 (1H, m), 8.13 (1H, d, J=1.8 Hz), 11.86 (1H, s).

b) 2-chloro-1-((6-fluoropyridin-2-yl)methyl)-6-iodo-1H-imidazo[4,5-b]pyridine

A mixture of 1-((6-fluoropyridin-2-yl)methyl)-6-iodo-1H-imidazo[4,5-b]pyridin-2(3H)-one (3.88 g) and phosphorus oxychloride (50 mL) was stirred under a nitrogen atmosphere at 100° C. for 21 hours. The reaction mixture was concentrated under reduced pressure. The residue was neutralized with a saturated aqueous sodium hydrogen carbonate solution at 0° C., and extracted with ethyl acetate/THF. The organic layer was washed with a saturated brine, dried over magnesium sulfate, and then concentrated. The residue was purified by NH silica gel column chromatography (ethyl acetate/hexane), and washed with ethyl acetate to obtain the title compound (1.36 g).

MS: [M+H]$^+$ 388.9 c) 2-chloro-1-((6-fluoropyridin-2-yl)methyl)-6-(4-methoxy-5H-pyrrolo[3,2-d]pyrimidin-5-yl)-1H-imidazo[4,5-b]pyridine A mixture of 2-chloro-1-((6-fluoropyridin-2-yl)methyl)-6-iodo-1H-imidazo[4,5-b]pyridine (1.18 g), 4-methoxy-5H-pyrrolo[3,2-d]pyrimidine (0.589 g), potassium phosphate (1.934 g), trans-N,N'-dimethylcyclohexane-1,2-diamine (0.864 g), copper (I) iodide (0.578 g) and THF (15 mL) was stirred under microwave irradiation at 95° C. for 90 minutes. The mixture was diluted with water at room temperature, and extracted with ethyl acetate. The organic layer was washed with a saturated brine, then dried over magnesium sulfate, and concentrated under reduced pressure. The residue was purified by silica gel column chromatography (methanol/ethyl acetate) to obtain the title compound (770 mg).

MS: [M+H]$^+$ 410.2 d) 1-((6-fluoropyridin-2-yl)methyl)-2-methoxy-6-(4-methoxy-5H-pyrrolo[3,2-d]pyrimidin-5-yl)-1H-imidazo[4,5-b]pyridine Sodium methoxide (28% in methanol solution) (0.2 mL) was added to 2-chloro-1-((6-fluoropyridin-2-yl)methyl)-6-(4-methoxy-5H-pyrrolo[3,2-d]pyrimidin-5-yl)-1H-imidazo[4,5-b]pyridine (380 mg) in THF (5 mL) at room temperature. Under a dry atmosphere, the mixture was stirred at room temperature for 30 minutes. The reaction mixture was diluted with water at room temperature, and extracted with ethyl acetate. The organic layer was washed with water and a saturated brine, dried over magnesium sulfate, and then concentrated. The residue was purified by NH silica gel column chromatography (ethyl acetate/hexane) and HPLC (C18, mobile phase: water/acetonitrile (0.1% TFA-containing system)), and washed with ethyl acetate/IPE to obtain the title compound (56.8 mg).

$^1$H NMR (300 MHz, DMSO-$d_6$) δ 3.73 (3H, s), 4.19 (3H, s), 5.39 (2H, s), 6.80 (1H, d, J=3.2 Hz), 7.12 (1H, dd, J=8.1, 2.4 Hz), 7.25 (1H, dd, J=7.4, 2.2 Hz), 7.91 (1H, d, J=3.1 Hz), 7.96-8.09 (2H, m), 8.40 (1H, d, J=2.4 Hz), 8.49 (1H, s).

Example 102

1-(3-fluorobenzyl)-6-(7-methoxy-1H-pyrrolo[3,2-b]pyridin-1-yl)-2-methyl-1H-imidazo[4,5-b]pyridine a) 7-methoxy-1H-pyrrolo[3,2-b]pyridine A mixture of 7-chloro-1H-pyrrolo[3,2-b]pyridine (1 g), methanol (20 mL) and sodium methoxide (28% in methanol solution) (1.817 mL) was stirred under microwave irradiation at 150° C. for 10 hours. The reaction mixture was poured into a saturated aqueous ammonium chloride solution at room temperature, and extracted with ethyl acetate. The organic layer was dried over magnesium sulfate, and concentrated under reduced pressure. The residue was purified by silica gel column chromatography (ethyl acetate/hexane) and NH silica gel column chromatography (ethyl acetate/hexane) to obtain the title compound (0.113 g).

$^1$H NMR (300 MHz, DMSO-$d_6$) δ 3.97 (3H, s), 6.48 (1H, dd, J=3.1, 2.1 Hz), 6.73 (1H, d, J=5.4 Hz), 7.42-7.49 (1H, m), 8.18 (1H, d, J=5.4 Hz), 11.45 (1H, brs).

b) 1-(3-fluorobenzyl)-6-(7-methoxy-1H-pyrrolo[3,2-b]pyridin-1-yl)-2-methyl-1H-imidazo[4,5-b]pyridine A mixture of 1-(3-fluorobenzyl)-6-iodo-2-methyl-1H-imidazo[4,5-b]pyridine (400 mg), 7-methoxy-1H-pyrrolo[3,2-b]pyridine (194 mg), potassium phosphate (730 mg), trans-N,N'-dimethylcyclohexane-1,2-diamine (190 mg), copper (I) iodide (125 mg) and THF (3 mL) was stirred under microwave irradiation at 130° C. for 3 hours. The mixture was poured into water at room temperature, and extracted with ethyl acetate. The organic layer was washed with a saturated brine, then dried over magnesium sulfate, and concentrated under reduced pressure. The residue was purified by NH silica gel column chromatography (methanol/ethyl acetate) and silica gel column chromatography (methanol/ethyl acetate) to obtain the title compound (154 mg).

$^1$H NMR (300 MHz, DMSO-$d_6$) δ 2.61 (3H, s), 3.55 (3H, s), 5.56 (2H, s), 6.76 (1H, d, J=3.3 Hz), 6.80 (1H, d, J=5.5 Hz), 6.98 (1H, d, J=7.7 Hz), 7.02-7.10 (1H, m), 7.11-7.21

(1H, m), 7.36-7.48 (1H, m), 7.72 (1H, d, J=3.3 Hz), 8.16 (1H, d, J=2.4 Hz), 8.29 (1H, d, J=5.5 Hz), 8.48 (1H, d, J=2.4 Hz).

Example 105

1-(1-(3-fluorobenzyl)-2-methyl-1H-imidazo[4,5-b]pyridin-6-yl)-7-methoxy-1H-pyrazolo[4,3-b]pyridine a) 7-methoxy-1H-pyrazolo[4,3-b]pyridine A mixture of 7-chloro-1H-pyrazolo[4,3-b]pyridine (300 mg), methanol (5 mL) and sodium methoxide (555 mg) was stirred under microwave irradiation at 100° C. for 3 hours and at 150° C. for 8 hours. The reaction mixture was poured into a saturated aqueous ammonium chloride solution at room temperature, and extracted with ethyl acetate. The organic layer was dried over magnesium sulfate, and concentrated under reduced pressure. The residue was purified by silica gel column chromatography (ethyl acetate), and crystallized from ethyl acetate/hexane to obtain the title compound (93 mg).
$^1$H NMR (300 MHz, DMSO-d$_6$) δ4.03 (3H, s), 6.91 (1H, d, J=5.1 Hz), 8.19 (1H, s), 8.36 (1H, d, J=5.1 Hz), 13.55 (1H, brs).

b) 1-(1-(3-fluorobenzyl)-2-methyl-1H-imidazo[4,5-b]pyridin-6-yl)-7-methoxy-1H-pyrazolo[4,3-b]pyridine A mixture of 1-(3-fluorobenzyl)-6-iodo-2-methyl-1H-imidazo[4,5-b]pyridine (224 mg), 7-methoxy-1H-pyrrolo[4,3-b]pyridine (100 mg), potassium phosphate (409 mg), trans-N,N'-dimethylcyclohexane-1,2-diamine (106 mg), copper (I) iodide (69.7 mg) and THF (3 mL) was stirred under microwave irradiation at 150° C. for 4 hours. The mixture was poured into water at room temperature, and extracted with ethyl acetate. The organic layer was washed with a saturated brine, then dried over magnesium sulfate, and concentrated under reduced pressure. The residue was purified by NH silica gel column chromatography (methanol/ethyl acetate) and silica gel column chromatography (methanol/ethyl acetate), and crystallized from ethyl acetate/heptane to obtain the title compound (41.2 mg).
$^1$H NMR (300 MHz, DMSO-d$_6$) δ2.63 (3H, s), 3.69 (3H, s), 5.59 (2H, s), 6.97 (1H, d, J=7.9 Hz), 7.03 (1H, d, J=5.2 Hz), 7.05-7.11 (1H, m), 7.12-7.21 (1H, m), 7.37-7.48 (1H, m), 8.25 (1H, d, J=2.4 Hz), 8.48 (1H, d, J=5.2 Hz), 8.53 (1H, s), 8.59 (1H, d, J=2.4 Hz).

Example 110

1-(3-fluorobenzyl)-6-(3-methoxy-5H-pyrrolo[2,3-b]pyrazin-5-yl)-2-methyl-1H-imidazo[4,5-b]pyridine a) 3-chloro-5-((2-(trimethyl silyl)ethoxy)methyl)-5H-pyrrolo[2,3-b]pyrazine Sodium hydride (60%, oil) (0.846 g) was added to a mixture of 3-chloro-5H-pyrrolo[2,3-b]pyrazine (2.5 g) and DMF (25 mL) at 0° C. The mixture was stirred for 5 minutes, and 2-(trimethylsilyl)ethoxymethyl chloride (3.75 mL) was then added to the mixture at 0° C. The mixture was stirred under an argon atmosphere at room temperature for 2 hours. The reaction mixture was poured into a saturated aqueous ammonium chloride solution at 0° C., and extracted with ethyl acetate. The organic layer was washed with water and a saturated brine, dried over sodium sulfate, and concentrated under reduced pressure. The residue was purified by silica gel column chromatography (ethyl acetate/hexane) to obtain the title compound (4.42 g).
$^1$H NMR (300 MHz, DMSO-d$_6$) δ −0.14--0.07 (9H, m), 0.76-0.88 (2H, m), 3.52 (2H, dd, J=8.5, 7.6 Hz), 5.60 (2H, s), 6.81 (1H, d, J=3.7 Hz), 8.10 (1H, d, J=3.8 Hz), 8.56 (1H, s).

b) 3-methoxy-5-((2-(trimethylsilyl)ethoxy)methyl)-5H-pyrrolo[2,3-b]pyrazine

A mixture of 3-chloro-5-((2-(trimethyl silyl)ethoxy)methyl)-5H-pyrrolo[2,3-b]pyrazine (1 g), N-methyl-2-pyrrolidone (10 mL) and sodium methoxide (28% methanol solution) (0.68 g) was stirred at 70° C. for 2 hours. The reaction mixture was poured into water, and extracted with ethyl acetate. The organic layer was washed with water and a saturated brine, dried over sodium sulfate, and concentrated under reduced pressure. The residue was purified by silica gel column chromatography (ethyl acetate/hexane) to obtain the title compound (0.693 g).
$^1$H NMR (300 MHz, DMSO-d$_6$) δ −0.17--0.07 (9H, m), 0.76-0.90 (2H, m), 3.46-3.61 (2H, m), 3.96 (3H, s), 5.56 (2H, s), 6.64 (1H, d, J=3.8 Hz), 7.70 (1H, d, J=3.7 Hz), 8.13 (1H, s).

c) 3-methoxy-5H-pyrrolo[2,3-b]pyrazine

TFA (3 mL) was added to 3-methoxy-5-((2-(trimethylsilyl)ethoxy)methyl)-5H-pyrrolo[2,3-b]pyrazine (1.02 g) at room temperature. Under a dry atmosphere, the mixture was stirred at room temperature for 1 hour. The reaction mixture was concentrated under reduced pressure. To the residue were added ethanol and ammonia (28% in aqueous solution) at 0° C. Under a dry atmosphere, the mixture was stirred at room temperature for 4 hours. The reaction mixture was concentrated under reduced pressure. The residue was washed with water and IPE, and dried under reduced pressure to obtain the title compound (0.461 g).
$^1$H NMR (300 MHz, DMSO-d$_6$) δ 3.92 (3H, s), 6.54 (1H, dd, J=3.5, 0.9 Hz), 7.49-7.54 (1H, m), 8.06 (1H, s), 11.79 (1H, brs).

d) 1-(3-fluorobenzyl)-6-(3-methoxy-5H-pyrrolo[2,3-b]pyrazin-5-yl)-2-methyl-1H-imidazo[4,5-b]pyridine A mixture of 1-(3-fluorobenzyl)-6-iodo-2-methyl-1H-imidazo[4,5-b]pyridine (222 mg), 3-methoxy-5H-pyrrolo[2,3-b]pyrazine (90 mg), potassium phosphate (384 mg), trans-N,N'-dimethylcyclohexane-1,2-diamine (0.104 mL), copper (I) iodide (63.2 mg) and THF (5 mL) was stirred under microwave irradiation at 100° C. for 3 hours. The mixture was diluted with water at room temperature, and extracted with ethyl acetate. The organic layer was washed with a saturated brine, then dried over magnesium sulfate, and concentrated under reduced pressure. The residue was purified by silica gel column chromatography (methanol/ethyl acetate), and pulverized with ethyl acetate to obtain the title compound (71.9 mg).
$^1$H NMR (300 MHz, DMSO-d$_6$) δ 2.62 (3H, s), 3.74 (3H, s), 5.62 (2H, s), 6.87 (1H, d, J=3.8 Hz), 6.94-7.20 (3H, m), 7.33-7.45 (1H, m), 8.07 (1H, d, J=3.8 Hz), 8.19 (1H, s), 8.54 (1H, d, J=2.4 Hz), 8.81 (1H, d, J=2.4 Hz).

Example 134

1-(5-(1-(3,5-difluorobenzyl)-2-methoxy-1H-imidazo[4,5-b]pyridin-6-yl)-5H-pyrrolo[2,3-b]pyrazin-3-yl)ethanol a) 1-(5-((2-(trimethylsilyl)ethoxy)methyl)-5H-pyrrolo[2,3-b]pyrazin-3-yl)ethanone A mixture of chloro(2-dicyclohexylphosphino-2',4',6'-triisopropyl-1,1'-biphenyl)[2-(2'-amino-1,1'-biphenyl)]palladium (II) (0.31 g), cesium fluoride (4.33 g), 3-chloro-5-((2-(trimethylsilyl)ethoxy)methyl)-5H-pyrrolo[2,3-b]pyrazine (3.68 g), tributyl(1-ethoxyvinyl)stannane (5.8 mL) and DME (40 mL) was stirred under an argon atmosphere at 80° C. for 3 hours. The mixture was poured into an aqueous potassium fluoride solution, insolubles were removed, and the mixture was extracted with ethyl acetate. The organic layer was washed with an aqueous potassium fluoride solution and a saturated brine, then dried over sodium sulfate, and concentrated under reduced pressure. The residue was purified by silica gel column chromatography (ethyl acetate/hexane). The obtained residue (3.86 g) was diluted with methanol (100 mL)/hydrochloric acid (2 N in aqueous solution) (25 mL) at room temperature. The mixture was stirred at room temperature for 30 minutes. The mixture was poured into water, and extracted with ethyl acetate. The organic layer was washed with water and a saturated brine, then dried over sodium sulfate, and concentrated under reduced pressure. The residue was purified by silica gel column chromatography (ethyl acetate/hexane) to obtain the title compound (3.05 g).

$^1$H NMR (300 MHz, DMSO-$d_6$) δ −0.16-−0.09 (9H, m), 0.80-0.91 (2H, m), 2.71 (3H, s), 3.53-3.64 (2H, m), 5.72 (2H, s), 6.88 (1H, d, J=3.7 Hz), 8.38 (1H, d, J=3.7 Hz), 9.05 (1H, s).

b) 1-(5H-pyrrolo[2,3-b]pyrazin-3-yl)ethanol mono-TFA salt

Sodium borohydride (0.398 g) was added to a mixture of 1-(5-((2-(trimethylsilyl)ethoxy)methyl)-5H-pyrrolo[2,3-b]pyrazin-3-yl)ethanone (3.05 g) and methanol (60 mL) at 0° C. The mixture was stirred at room temperature for 15 minutes. The mixture was poured into hydrochloric acid (0.1 N in aqueous solution), and extracted with ethyl acetate. The organic layer was washed with water and a saturated brine, then dried over sodium sulfate, and concentrated under reduced pressure. A mixture of the residue and TFA (20 mL) was stirred at room temperature for 1 hour, and concentrated under reduced pressure. The residue was diluted with ethanol/ammonia (28% in aqueous solution). The mixture was stirred at 60° C. for 15 minutes, and then concentrated under reduced pressure. The residue was purified by silica gel column chromatography (ethyl acetate/hexane) to obtain the title compound (2.22 g).

$^1$H NMR (300 MHz, DMSO-$d_6$) δ1.45 (3H, d, J=6.5 Hz), 4.87 (1H, q, J=6.5 Hz), 5.37 (1H, brs), 6.58 (1H, dd, J=3.6, 1.8 Hz), 6.86-7.34 (1H, m), 7.79 (1H, dd, J=3.5, 2.8 Hz), 8.53 (1H, s), 11.89 (1H, brs).

c) 1-(5-(1-(3,5-difluorobenzyl)-2-(isopropylthio)-1H-imidazo[4,5-b]pyridin-6-yl)-5H-pyrrolo[2,3-b]pyrazin-3-yl)ethanol A mixture of 1-(3,5-difluorobenzyl)-6-iodo-2-(isopropylthio)-1H-imidazo[4,5-b]pyridine (707 mg), a 1-(5H-pyrrolo[2,3-b]pyrazin-3-yl)ethanol mono-TFA salt (400 mg), potassium phosphate (919 mg), trans-N,N'-dimethylcyclohexane-1,2-diamine (0.249 mL), copper (I) iodide (151 mg) and THF (8 mL) was stirred under microwave irradiation at 100° C. for 3 hours. The mixture was diluted with water at room temperature, and extracted with ethyl acetate. The organic layer was washed with an aqueous ammonium chloride solution and a saturated brine, then dried over sodium sulfate, and concentrated under reduced pressure. The residue was purified by silica gel column chromatography (methanol/ethyl acetate) to obtain the title compound (610 mg).

$^1$H NMR (300 MHz, DMSO-$d_6$) δ1.39 (3H, d, J=6.5 Hz), 1.49 (6H, d, J=6.8 Hz), 4.11-4.25 (1H, m), 4.84 (1H, dd, J=6.5, 4.8 Hz), 5.44-5.60 (3H, m), 6.89-7.02 (3H, m), 7.17-7.29 (1H, m), 8.33 (1H, d, J=3.9 Hz), 8.52 (1H, d, J=2.4 Hz), 8.69 (1H, s), 8.85 (1H, d, J=2.4 Hz).

d) 1-(5-(1-(3,5-difluorobenzyl)-2-methoxy-1H-imidazo[4,5-b]pyridin-6-yl)-5H-pyrrolo[2,3-b]pyrazin-3-yl)ethanol Methachloroperbenzoic acid (0.73 g) was added to a mixture of 1-(5-(1-(3,5-difluorobenzyl)-2-(isopropylthio)-1H-imidazo[4,5-b]pyridin-6-yl)-5H-pyrrolo[2,3-b]pyrazin-3-yl)ethanol (1.18 g) and acetonitrile (30 mL) at 0° C. The mixture was stirred at 0° C. for 2 hours, and sodium methoxide (28% in methanol solution) (1.5 mL) was added at 0° C. The mixture was stirred at room temperature for 15 minutes. The reaction mixture was poured into water at room temperature, and extracted with ethyl acetate. The organic layer was washed with water and a saturated brine, dried over magnesium sulfate, and then concentrated. The residue was purified by silica gel column chromatography (methanol/ethyl acetate) to obtain the title compound (0.53 g).

$^1$H NMR (300 MHz, DMSO-$d_6$) δ1.39 (3H, d, J=6.5 Hz), 4.24 (3H, s), 4.77-4.89 (1H, m), 5.35 (2H, s), 5.50 (1H, d, J=4.8 Hz), 6.91 (1H, d, J=3.8 Hz), 7.02-7.12 (2H, m), 7.16-7.27 (1H, m), 8.29 (1H, d, J=3.8 Hz), 8.36 (1H, d, J=2.4 Hz), 8.64-8.71 (2H, m).

Example 158

(R)-1-(5-(1-(3,5-difluorobenzyl)-2-methoxy-1H-imidazo[4,5-b]pyridin-6-yl)-5H-pyrrolo[2,3-b]pyrazin-3-yl)ethanol (Optical Isomer)

A racemate of 1-(5-(1-(3,5-difluorobenzyl)-2-methoxy-1H-imidazo[4,5-b]pyridin-6-yl)-5H-pyrrolo[2,3-b]pyrazin-3-yl)ethanol (553.5 mg) was fractionated by SFC (column: CHIRALPAK ASH (LA005), 20 mm ID×250 mm L, manufactured by Daicel Chemical Industries Ltd, mobile phase: $CO_2$/ethanol (containing 0.3% diethylamine)=700/300), and crystallized from ethanol/water to obtain the title compound (0.219 g) with a smaller retention time.

$^1$H NMR (300 MHz, DMSO-$d_6$) δ1.39 (3H, d, J=6.5 Hz), 4.24 (3H, s), 4.75-4.93 (1H, m), 5.35 (2H, s), 5.50 (1H, d, J=4.8 Hz), 6.91 (1H, d, J=3.8 Hz), 7.01-7.11 (2H, m), 7.16-7.27 (1H, m), 8.29 (1H, d, J=3.8 Hz), 8.36 (1H, d, J=2.4 Hz), 8.64-8.70 (2H, m).

Example 159

(S)-1-(5-(1-(3,5-difluorobenzyl)-2-methoxy-1H-imidazo[4,5-b]pyridin-6-yl)-5H-pyrrolo[2,3-b]pyrazin-3-yl)ethanol (Optical Isomer)

A racemate of 1-(5-(1-(3,5-difluorobenzyl)-2-methoxy-1H-imidazo[4,5-b]pyridin-6-yl)-5H-pyrrolo[2,3-b]pyrazin- 3-yl)ethanol (553.5 mg) was fractionated by SFC (column: CHIRALPAK ASH (LA005), 20 mm ID×250 mm L, manufactured by Daicel Chemical Industries Ltd, mobile phase: $CO_2$/ethanol (containing 0.3% diethylamine)=700/300), and crystallized from ethanol/water to obtain the title compound (0.197 g) with a larger retention time.

$^1$H NMR (300 MHz, DMSO-$d_6$) δ1.39 (3H, d, J=6.5 Hz), 4.24 (3H, s), 4.78-4.90 (1H, m), 5.35 (2H, s), 5.50 (1H, d, J=4.7 Hz), 6.91 (1H, d, J=3.9 Hz), 7.01-7.11 (2H, m), 7.16-7.27 (1H, m), 8.29 (1H, d, J=3.9 Hz), 8.36 (1H, d, J=2.4 Hz), 8.66-8.69 (2H, m).

Example 160

1-(5-(1-(3-fluorobenzyl)-2-methoxy-1H-imidazo[4,5-b]pyridin-6-yl)-5H-pyrrolo[2,3-b]pyrazin-3-yl) ethanol (Optical Isomer)

a) 1-(3-fluorobenzyl)-6-iodo-2-(isopropylthio)-1H-imidazo[4,5-b]pyridine

Under a dry atmosphere, a mixture of N3-(3-fluorobenzyl)-5-iodopyridine-2,3-diamine (5 g), CDI (4.75 g) and THF (50 mL) was stirred at 60° C. for 16 hours. The reaction mixture was quenched with water at room temperature, and extracted with ethyl acetate. The organic layer was sequentially washed with a saturated aqueous ammonium chloride solution, water and a saturated brine, then dried over sodium sulfate, and concentrated under reduced pressure to obtain a brown solid as 1-(3-fluorobenzyl)-6-iodo-1H-imidazo[4,5-b]pyridin-2(3H)-one. A mixture of the obtained solid and phosphorus oxychloride (50 mL) was stirred at 100° C. for 2 days. The reaction mixture was concentrated under reduced pressure. The residue was diluted with THF, poured into a saturated aqueous sodium hydrogen carbonate solution, and extracted with ethyl acetate. The organic layer was washed with water and a saturated brine, dried over sodium sulfate, and then concentrated. The residue was diluted with THF (100 mL). To the mixture was added sodium 2-propanethiolate (2.066 g) at 0° C. Under a nitrogen atmosphere, the mixture was stirred overnight at room temperature. The reaction mixture was diluted with ethyl acetate. Insolubles were removed, and the mixture was concentrated under reduced pressure. The residue was purified by silica gel column chromatography (ethyl acetate/hexane) to obtain the title compound (5.87 g).

$^1$H NMR (300 MHz, DMSO-$d_6$) δ1.45 (6H, d, J=6.8 Hz), 4.05-4.16 (1H, m), 5.42 (2H, s), 6.93 (1H, d, J=7.7 Hz), 7.00-7.19 (2H, m), 7.34-7.44 (1H, m), 8.41 (1H, d, J=1.9 Hz), 8.51 (1H, d, J=1.9 Hz).

b) 1-(5-(1-(3-fluorobenzyl)-2-(isopropylthio)-1H-imidazo[4,5-b]pyridin-6-yl)-5H-pyrrolo[2,3-b]pyrazin-3-yl)ethanol A mixture of 1-(3-fluorobenzyl)-6-iodo-2-(isopropylthio)-1H-imidazo[4,5-b]pyridine (1017 mg), a 1-(5H-pyrrolo[2,3-b]pyrazin-3-yl)ethanol mono-TFA salt (600 mg), potassium phosphate (1378 mg), trans-N,N'-dimethylcyclohexane-1,2-diamine (0.374 mL), copper (I) iodide (227 mg) and THF (10 mL) was stirred under microwave irradiation at 100° C. for 3 hours. The mixture was diluted with water at room temperature, and extracted with ethyl acetate. The organic layer was washed with a saturated brine, then dried over sodium sulfate, and concentrated under reduced pressure. The residue was purified by silica gel column chromatography (methanol/ethyl acetate) to obtain the title compound (600 mg).

$^1$H NMR (300 MHz, DMSO-$d_6$) δ1.40 (3H, d, J=6.4 Hz), 1.49 (6H, d, J=6.8 Hz), 4.10-4.26 (1H, m), 4.72-4.91 (1H, m), 5.41-5.56 (3H, m), 6.93 (1H, d, J=3.8 Hz), 7.02-7.24 (3H, m), 7.35-7.48 (1H, m), 8.33 (1H, d, J=3.8 Hz), 8.53 (1H, d, J=2.4 Hz), 8.68 (1H, s), 8.83 (1H, d, J=2.3 Hz).

c) 1-(5-(1-(3-fluorobenzyl)-2-methoxy-1H-imidazo[4,5-b]pyridin-6-yl)-5H-pyrrolo[2,3-b]pyrazin-3-yl) ethanol (Optical Isomer)

Methachloroperbenzoic acid (0.79 g) was added to a mixture of 1-(5-(1-(3-fluorobenzyl)-2-(isopropylthio)-1H-imidazo[4,5-b]pyridin-6-yl)-5H-pyrrolo[2,3-b]pyrazin-3-yl) ethanol (1.24 g), DMF (5 mL) and ethyl acetate (30 mL) at 0° C. The mixture was stirred at room temperature for 3 hours, and then concentrated under reduced pressure. The residue was diluted with THF (20 mL), and sodium methoxide (28% in methanol solution) (2.8 mL) was added at 0° C. The mixture was stirred at room temperature for 10 minutes. The reaction mixture was poured into water at room temperature, and extracted with ethyl acetate. The organic layer was washed with water and a saturated brine, dried over sodium sulfate, and then concentrated. The residue was purified by silica gel column chromatography (methanol/ethyl acetate) to obtain 1-(5-(1-(3-fluorobenzyl)-2-methoxy-1H-imidazo[4,5-b]pyridin-6-yl)-5H-pyrrolo[2,3-b]pyrazin-3-yl)ethanol. A racemate of 1-(5-(1-(3-fluorobenzyl)-2-methoxy-1H-imidazo[4,5-b]pyridin-6-yl)-5H-pyrrolo[2,3-b]pyrazin-3-yl)ethanol (688 mg) was fractionated by SFC (column: CHIRALPAK ASH (S90ASHSCZ-RA001), 30 mm ID×250 mm L, manufactured by Daicel Chemical Industries Ltd, mobile phase: $CO_2$/ethanol=800/200), and a compound with a smaller retention time was crystallized from ethanol/water to obtain the title compound (335 mg).

$^1$H NMR (300 MHz, DMSO-$d_6$) δ1.40 (3H, d, J=6.5 Hz), 4.24 (3H, s), 4.84 (1H, dd, J=6.5, 4.8 Hz), 5.34 (2H, s), 5.50 (1H, d, J=4.8 Hz), 6.91 (1H, d, J=3.8 Hz), 7.10-7.25 (3H, m), 7.36-7.46 (1H, m), 8.28 (1H, d, J=3.8 Hz), 8.37 (1H, d, J=2.4 Hz), 8.64-8.70 (2H, m).

Example 161

1-(5-(1-(3-fluorobenzyl)-2-methoxy-1H-imidazo[4,5-b]pyridin-6-yl)-5H-pyrrolo[2,3-b]pyrazin-3-yl) ethanol (Optical Isomer)

A racemate of 1-(5-(1-(3-fluorobenzyl)-2-methoxy-1H-imidazo[4,5-b]pyridin-6-yl)-5H-pyrrolo[2,3-b]pyrazin-3-yl) ethanol (688 mg) was fractionated by SFC (column: CHIRALPAK ASH (S90ASHSCZ-RA001), 30 mm ID×250 mm L, manufactured by Daicel Chemical Industries Ltd, mobile phase: $CO_2$/ethanol=800/200), and a compound with a larger retention time was crystallized from ethanol/water to obtain the title compound (309 mg).

$^1$H NMR (300 MHz, DMSO-$d_6$) δ1.40 (3H, d, J=6.4 Hz), 4.24 (3H, s), 4.79-4.90 (1H, m), 5.34 (2H, s), 5.50 (1H, d, J=4.7 Hz), 6.91 (1H, d, J=3.8 Hz), 7.08-7.25 (3H, m), 7.40 (1H, d, J=6.0 Hz), 8.28 (1H, d, J=4.0 Hz), 8.37 (1H, d, J=2.4 Hz), 8.64-8.70 (2H, m).

Example 162

1-(3,5-difluorobenzyl)-6-(4-methoxypyrrolo[1,2-b] pyridin-5-yl)-2-methyl-1H-imidazo[4,5-b]pyridine a) 6-bromo-2-methyl-1H-imidazo[4,5-b]pyridine A solution of 5-bromopyridine-2,3-diamine (83.5 g) in acetic acid (500 mL) was heated and refluxed for 2 days. The reaction mixture was concentrated under reduced pressure. The residue was pulverized with IPE, and dried under reduced pressure to obtain the title compound (93 g).

$^1$H NMR (300 MHz, DMSO-$d_6$) δ 2.51-2.53 (3H, m), 8.12 (1H, d, J=2.2 Hz), 8.31 (1H, d, J=2.2 Hz), 12.96 (1H, brs).

b) 6-bromo-1-(3,5-difluorobenzyl)-2-methyl-1H-imidazo[4,5-b]pyridine

Potassium hydroxide (2.381 g) was added to a mixture of 6-bromo-2-methyl-1H-imidazo[4,5-b]pyridine (3 g), 1-(bromomethyl)-3,5-difluorobenzene (2.014 mL) and THF (40 mL) at 60° C. The reaction mixture was stirred overnight at 60° C. The reaction mixture was cooled to room temperature, then poured into water, and extracted with ethyl acetate. The organic layer was washed with a saturated brine, then dried over magnesium sulfate, and concentrated under reduced pressure. The residue was purified by silica gel column chromatography (ethyl acetate/hexane), and crystallized from ethanol/IPE. The obtained precipitate was collected by filtration, and washed with IPE to obtain the title compound (2.000 g).

$^1$H NMR (300 MHz, DMSO-$d_6$) δ 2.55 (3H, s), 5.55 (2H, s), 6.82-6.93 (2H, m), 7.20 (1H, tt, J=9.4, 2.2 Hz), 8.31 (1H, d, J=2.2 Hz), 8.43 (1H, d, J=2.2 Hz).

c) 1-(3,5-difluorobenzyl)-2-methyl-6-(4,4,5,5-tetramethyl-1,3,2-dioxaborolan-2-yl)-1H-imidazo[4,5-b]pyridine A mixture of 6-bromo-1-(3,5-difluorobenzyl)-2-methyl-1H-imidazo[4,5-b]pyridine (400 mg), bis (pinacolato)diboron (468 mg), a [1,1'-bis(diphenylphosphino)ferrocene]palladium (II) dichloride dichloromethane complex (108 mg), potassium acetate (452 mg), THF (9 mL) and DMSO (0.9 mL) was stirred under microwave irradiation at 110° C. for 1 hour. The reaction mixture was diluted with ethyl acetate, and insolubles were removed by filtration through Celite. The filtrate was poured into water, and extracted with ethyl acetate. The organic layer was washed with a saturated brine, then dried over magnesium sulfate, and concentrated under reduced pressure. The residue was collected by filtration, and washed with IPE to obtain the title compound (387 mg).

$^1$H NMR (300 MHz, DMSO-$d_6$) δ 1.31 (12H, s), 2.57 (3H, s), 5.65 (2H, s), 6.71-6.85 (2H, m), 7.19 (1H, tt, J=9.3, 2.2 Hz), 8.10 (1H, d, J=1.5 Hz), 8.60 (1H, d, J=1.5 Hz).

d) Ethyl 4-oxo-1,4-dihydropyrrolo[1,2-b]pyridazine-3-carboxylate

A mixture of 1H-pyrrol-1-amine (9.62 mL) and diethyl (ethoxymethylene)malonate (30 mL) was stirred at 125° C. for 2 hours. The reaction mixture was diluted with diphenyl ether (40 mL), and the resulting mixture was stirred at 200° C. for 3 hours. The reaction mixture was purified by silica gel column chromatography (ethyl acetate/hexane) to obtain the title compound (15.97 g).

$^1$H NMR (300 MHz, DMSO-$d_6$) δ 1.35 (3H, t, J=7.1 Hz), 4.37 (2H, q, J=7.1 Hz), 6.85 (1H, dd, J=4.4, 2.5 Hz), 6.99 (1H, dd, J=4.4, 1.6 Hz), 7.97 (1H, dd, J=2.6, 1.6 Hz), 8.32 (1H, s), 12.11 (1H, brs).

e) 4-oxo-1,4-dihydropyrrolo[1,2-b]pyridazine-3-carboxylic acid

A mixture of ethyl 4-oxo-1,4-dihydropyrrolo[1,2-b]pyridazine-3-carboxylate (15.9 g), a 8 N aqueous sodium hydroxide solution (40 mL) and ethanol (150 mL) was heated and refluxed for 6 hours. The reaction mixture was concentrated under reduced pressure. To the residue were added 6 N hydrochloric acid (65 mL) and water. The precipitate was collected by filtration, and washed with water to obtain the title compound (13.40 g).

$^1$H NMR (300 MHz, DMSO-$d_6$) δ 6.80 (1H, dd, J=4.4, 2.6 Hz), 6.89 (1H, dd, J=4.4, 1.6 Hz), 7.89 (1H, dd, J=2.6, 1.6 Hz), 8.26 (1H, s).

f) Pyrrolo[1,2-b]pyridazin-4(1H)-one

A mixture of 4-oxo-1,4-dihydropyrrolo[1,2-b]pyridazine-3-carboxylic acid (13.0 g) and DMSO (50 mL) was stirred under a nitrogen atmosphere at 150° C. for 1 hour. The reaction mixture was concentrated under reduced pressure. The residue was purified by silica gel column chromatography (ethyl acetate/hexane) to obtain the title compound (8.27 g).

$^1$H NMR (300 MHz, DMSO-$d_6$) δ 5.99 (1H, d, J=5.3 Hz), 6.56 (1H, dd, J=4.3, 1.7 Hz), 6.69 (1H, dd, J=4.2, 2.6 Hz), 7.71 (1H, dd, J=2.6, 1.7 Hz), 7.89 (1H, d, J=5.3 Hz), 11.37 (1H, s).

g) 4-methoxypyrrolo[1,2-b]pyridazine

Cesium carbonate (5.90 g) was added to a solution of pyrrolo[1,2-b]pyridazin-4(1H)-one (2.00 g) and iodomethane (1.1 mL) in THF (15 mL) and DMF (5 mL) at 0° C. The mixture was stirred at room temperature for 3 hours. The reaction mixture was poured into water, and extracted with ethyl acetate. The organic layer was washed with a saturated brine, then dried over magnesium sulfate, and concentrated under reduced pressure. The residue was purified by silica gel column chromatography (ethyl acetate/hexane) to obtain the title compound (1.846 g).

$^1$H NMR (300 MHz, DMSO-$d_6$) δ 3.98 (3H, s), 6.21 (1H, d, J=5.5 Hz), 6.53 (1H, dd, J=4.3, 1.7 Hz), 6.72 (1H, dd, J=4.2, 2.7 Hz), 7.76 (1H, dd, J=2.6, 1.7 Hz), 8.05 (1H, d, J=5.4 Hz).

h) 5,7-dibromo-4-methoxypyrrolo[1,2-b]pyridazine 1,3-dibromo-5,5-dimethylhydantoin (3.54 g) was added to a solution of 4-methoxypyrrolo[1,2-b]pyridazine (1.83 g) in THF (50 mL) at 0° C. The mixture was stirred at 0° C. for 0.5 hours. The reaction mixture was concentrated under reduced pressure. The residue was purified by silica gel column chromatography (ethyl acetate/hexane) to obtain the title compound (3.54 g).

$^1$H NMR (300 MHz, DMSO-$d_6$) δ 3.99 (3H, s), 6.37 (1H, d, J=5.6 Hz), 7.07 (1H, s), 8.23 (1H, d, J=5.6 Hz).

i) 5-bromo-4-methoxypyrrolo[1,2-b]pyridazine n-butyllithium (1.6 M in hexane solution) (7.1 mL) was added dropwise to a solution of 5,7-dibromo-4-methoxypyrrolo[1,2-b]pyridazine (3.52 g) in THF (70 mL) at −78° C. The mixture was stirred under a nitrogen atmosphere at −78° C. for 0.5 hours. Water was added to the reaction mixture at −78° C., and the temperature was elevated to room temperature, and the mixture was extracted with ethyl acetate. The organic layer was washed with a saturated brine, then dried over magnesium sulfate, and concentrated under reduced pressure. The residue was purified by silica gel column chromatography (ethyl acetate/hexane) to obtain the title compound (2.501 g).

¹H NMR (300 MHz, DMSO-d₆) δ 3.96 (3H, s), 6.25 (1H, d, J=5.6 Hz), 6.81 (1H, dd, J=2.9, 0.3 Hz), 7.79 (1H, d, J=2.9 Hz), 8.07 (1H, d, J=5.5 Hz).

j) 1-(3,5-difluorobenzyl)-6-(4-methoxypyrrolo[1,2-b]pyridin-5-yl)-2-methyl-1H-imidazo[4,5-b]pyridine A mixture of 5-bromo-4-methoxypyrrolo[1,2-b]pyridazine (80 mg), 1-(3,5-difluorobenzyl)-2-methyl-6-(4,4,5,5-tetramethyl-1,3,2-dioxaborolan-2-yl)-1H-imidazo[4,5-b]pyridine (107 mg), bis(di-tert-butyl(4-dimethylaminophenyl)phosphine)dichloropalladium (II) (20 mg), cesium carbonate (2 M in aqueous solution) (0.5 mL) and DME (10 mL) was stirred under microwave irradiation at 110° C. for 1 hour. The reaction mixture was diluted with THF. Insolubles were removed by filtration through Celite, and washed with THF. The filtrate was concentrated under reduced pressure. The residue was purified by NH silica gel column chromatography (methanol/ethyl acetate). The obtained product was collected by filtration, and washed with ethyl acetate/IPE to obtain the title compound (54 mg).

¹H NMR (300 MHz, DMSO-d₆) δ 2.59 (3H, s), 3.67 (3H, s), 5.57 (2H, s), 6.24 (1H, d, J=5.6 Hz), 6.81-6.96 (3H, m), 7.21 (1H, tt, J=9.4, 2.3 Hz), 7.88 (1H, d, J=2.8 Hz), 7.97 (1H, d, J=2.1 Hz), 8.08 (1H, d, J=5.4 Hz), 8.49 (1H, d, J=2.1 Hz).

Example 175

1-(3-fluorobenzyl)-6-(4-methoxypyrrolo[2,1-f][1,2,4]triazin-5-yl)-2-methyl-1H-imidazo[4,5-b]pyridine a) 4-methoxypyrrolo[2,1-f][1,2,4]triazine

A mixture of pyrrolo[2,1-f][1,2,4]triazin-4(3H)-one (14 g), DIPEA (18.1 mL), N,N-dimethylbenzeneamine (12.56 g), phosphoryl chloride (42.6 mL) and toluene (300 mL) was stirred at 100° C. for 12 hours. The reaction mixture was concentrated under reduced pressure. Sodium methoxide (28% in methanol solution) (140 g) was added to a suspension of the residue and THF (100 mL) at room temperature. The mixture was washed with a saturated aqueous sodium hydrogen carbonate solution at room temperature, and extracted with ethyl acetate. The organic layer was washed with a saturated brine, then dried over magnesium sulfate, and concentrated under reduced pressure. The residue was purified by silica gel column chromatography (ethyl acetate/hexane) to obtain the title compound (12.1 g).

¹H NMR (300 MHz, DMSO-d₆) δ 4.09 (3H, s), 6.73-6.91 (2H, m), 7.94 (1H, dd, J=2.5, 1.6 Hz), 8.19 (1H, s).

b) 5,7-dibromo-4-methoxypyrrolo[2,1-f][1,2,4]triazine

NBS (28.6 g) was added to a solution of 4-methoxypyrrolo[2,1-f][1,2,4]triazine (12 g) in THF (200 mL) at room temperature. The mixture was stirred under a nitrogen atmosphere at room temperature for 1 hour and at 50° C. for 1 hour. The mixture was neutralized with a saturated aqueous sodium hydrogen carbonate solution at 0° C., and extracted with ethyl acetate. The organic layer was washed with water and a saturated brine, then dried over magnesium sulfate, and concentrated under reduced pressure. The residue was washed with IPE to obtain the title compound (22.5 g).

¹H NMR (300 MHz, DMSO-d₆) δ4.10 (3H, s), 7.22 (1H, s), 8.33 (1H, s).

c) 5-bromo-4-methoxypyrrolo[2,1-f][1,2,4]triazine n-butyllithium (1.6 M in hexane solution) (64.1 mL) was added to a solution of 5,7-dibromo-4-methoxypyrrolo[2,1-f][1,2,4]triazine (22.5 g) in THF (450 mL) at −78° C. The mixture was stirred under a nitrogen atmosphere at −78° C. for 30 minutes. Water was added to the reaction mixture at −78° C., and extracted with ethyl acetate. The organic layer was sequentially washed with water and a saturated brine, then dried over magnesium sulfate, and concentrated under reduced pressure. The residue was washed with hexane to obtain the title compound (14.5 g).

¹H NMR (300 MHz, DMSO-d₆) δ4.09 (3H, s), 6.96 (1H, d, J=3.0 Hz), 7.97 (1H, d, J=2.8 Hz), 8.19 (1H, s).

d) 6-bromo-2-methyl-1H-imidazo[4,5-b]pyridine

A solution of 5-bromopyridine-2,3-diamine (83.5 g) in acetic acid (500 mL) was heated and refluxed for 2 days. The reaction mixture was concentrated under reduced pressure. The residue was pulverized with IPE, and dried under reduced pressure to obtain the title compound (93 g).

¹H NMR (300 MHz, DMSO-d₆) δ 2.51-2.53 (3H, m), 8.12 (1H, d, J=2.2 Hz), 8.31 (1H, d, J=2.2 Hz), 12.96 (1H, brs).

e) 6-bromo-1-(3-fluorobenzyl)-2-methyl-1H-imidazo[4,5-b]pyridine

Potassium hydroxide (1.984 g) was added to a mixture of 6-bromo-2-methyl-1H-imidazo[4,5-b]pyridine (2.5 g), 3-fluorobenzyl bromide (1.735 mL) and THF (30 mL) at 60° C. The mixture was stirred overnight at 60° C. The reaction solution was cooled to room temperature, then poured into water, and extracted with ethyl acetate. The organic layer was washed with a saturated brine, then dried over magnesium sulfate, and concentrated under reduced pressure. The residue was purified by NH silica gel column chromatography (ethyl acetate/hexane) to obtain the title compound (1.23 g).

¹H NMR (300 MHz, DMSO-d₆) δ 2.54 (3H, s), 5.51 (2H, s), 6.93-7.19 (3H, m), 7.31-7.44 (1H, m), 8.27 (1H, d, J=2.0 Hz), 8.40 (1H, d, J=2.0 Hz).

f) 1-(3-fluorobenzyl)-2-methyl-6-(4,4,5,5-tetramethyl-1,3,2-dioxaborolan-2-yl)-1H-imidazo[4,5-b]pyridine A mixture of 6-bromo-1-(3-fluorobenzyl)-2-methyl-1H-imidazo[4,5-b]pyridine (412 mg), a [1,1'-bis(diphenylphosphino)ferrocene]palladium (II) dichloride dichloromethane complex (107 mg), bis(pinacolato)diboron (667 mg), potassium acetate (391 mg), THF (5 mL) and DMSO (0.5 mL) was stirred under microwave irradiation at 120° C. for 40 minutes. The mixture was diluted with a saturated aqueous sodium hydrogen carbonate solution at room temperature, and extracted with ethyl acetate. The organic layer was washed with a saturated brine, dried over magnesium sulfate, and then concentrated. The residue was washed with IPE to obtain the title compound (108 mg).

MS, found: 286.1.

g) 1-(3-fluorobenzyl)-6-(4-methoxypyrrolo[2,1-f][1,2,4]triazin-5-yl)-2-methyl-1H-imidazo[4,5-b]pyridine A mixture of 5-bromo-4-methoxypyrrolo[2,1-f][1,2,4]triazine (52 mg), 1-(3-fluorobenzyl)-2-methyl-6-(4,4,5,5-tetramethyl-1,3,2-dioxaborolan-2-yl)-1H-imidazo[4,5-b]pyridine (108 mg), bis(di-tert-butyl(4-dimethylaminophenyl)phosphine)dichloropalladium (II) (14 mg), cesium carbonate (2 M in aqueous solution) (0.215 mL) and DME (1 mL) was stirred under microwave irradiation at 100° C. for 40 minutes. The reaction mixture was concentrated under reduced pressure. The residue was purified by NH silica gel column chromatography (ethyl acetate/hexane), and the residue was washed with ethyl acetate to obtain the title compound (12 mg).

$^1$H NMR (300 MHz, DMSO-$d_6$) δ 2.60 (3H, s), 3.80 (3H, s), 5.58 (2H, s), 6.96 (1H, d, J=7.6 Hz), 7.01-7.09 (2H, m), 7.15 (1H, td, J=8.8, 3.0 Hz), 7.42 (1H, td, J=8.0, 6.0 Hz), 8.05 (1H, d, J=2.7 Hz), 8.12 (1H, d, J=2.0 Hz), 8.21 (1H, s), 8.57 (1H, d, J=2.1 Hz).

Example 176

(1-(3,5-difluorobenzyl)-6-(4-methoxypyrrolo[2,1-f][1,2,4]triazin-5-yl)-1H-imidazo[4,5-b]pyridin-2-yl)methanol a) 4-methoxy-5-(4,4,5,5-tetramethyl-1,3,2-dioxaborolan-2-yl)pyrrolo[2,1-f][1,2,4]triazine A mixture of 5-bromo-4-methoxypyrrolo[2,1-f][1,2,4]triazine (10 g), a [1,1'-bis(diphenylphosphino)ferrocene]palladium (II) dichloride dichloromethane complex (3.58 g), bis(pinacolato)diboron (17.82 g), potassium acetate (17.21 g), THF (70 mL) and DMSO (10 mL) was stirred under microwave irradiation at 120° C. for 30 minutes. The mixture was quenched with a saturated aqueous sodium hydrogen carbonate solution, and extracted with ethyl acetate. The organic layer was washed with a saturated aqueous sodium hydrogen carbonate solution, dried over magnesium sulfate, and then concentrated. The residue was purified by Diol silica gel column chromatography (ethyl acetate/hexane) to obtain the title compound (3.96 g).

$^1$H NMR (300 MHz, DMSO-$d_6$) δ 1.30 (12H, s), 4.06 (3H, s), 6.90-7.01 (1H, m), 7.86-7.96 (1H, m), 8.24 (1H, s).

b) (1-(3,5-difluorobenzyl)-6-iodo-1H-imidazo[4,5-b]pyridin-2-yl)methanol

A mixture of N3-(3,5-difluorobenzyl)-5-iodopyridine-2,3-diamine (1 g), glycolic acid (5 g) and THF (1 mL) was stirred under microwave irradiation at 150° C. for 2.5 hours. The mixture was diluted with ethyl acetate and water, neutralized with a 8 N aqueous sodium hydroxide solution, basified with a saturated aqueous sodium hydrogen carbonate solution, and extracted with ethyl acetate. The organic layer was washed with a saturated brine, dried over magnesium sulfate, and then concentrated. The residue was purified by silica gel column chromatography (ethyl acetate/hexane and methanol/ethyl acetate) and NH silica gel column chromatography (ethyl acetate/hexane and methanol/ethyl acetate) to obtain the title compound (0.65 g).

$^1$H NMR (300 MHz, DMSO-$d_6$) δ 4.77 (2H, d, J=5.9 Hz), 5.61 (2H, s), 5.84-5.95 (1H, m), 6.91-7.04 (2H, m), 7.19 (1H, tt, J=9.3, 2.4 Hz), 8.33 (1H, d, J=2.0 Hz), 8.58 (1H, d, J=2.0 Hz).

c) (1-(3,5-difluorobenzyl)-6-(4-methoxypyrrolo[2,1-f][1,2,4]triazin-5-yl)-1H-imidazo[4,5-b]pyridin-2-yl)methanol A mixture of (1-(3,5-difluorobenzyl)-6-iodo-1H-imidazo[4,5-b]pyridin-2-yl)methanol (0.915 g), 4-methoxy-5-(4,4,5,5-tetramethyl-1,3,2-dioxaborolan-2-yl)pyrrolo[2,1-f][1,2,4]triazine (2 g), bis(di-tert-butyl(4-dimethylaminophenyl)phosphine)dichloropalladium (II) (0.137 g), cesium carbonate (2 M in aqueous solution) (3.05 mL) and DME (14 mL) was stirred under microwave irradiation at 100° C. for 40 minutes. The reaction mixture was concentrated under reduced pressure. The residue was purified by NH silica gel column chromatography (methanol/ethyl acetate), and the residue was crystallized from ethanol/water to obtain the title compound (0.35 g).

$^1$H NMR (300 MHz, DMSO-$d_6$) δ 3.79 (3H, s), 4.83 (2H, d, J=3.0 Hz), 5.65 (2H, s), 5.91 (1H, brs), 6.95-7.09 (3H, m), 7.15-7.29 (1H, m), 8.02-8.10 (2H, m), 8.22 (1H, s), 8.62 (1H, d, J=1.9 Hz).

Example 179

6-(4-methoxypyrrolo[2,1-f][1,2,4]triazin-5-yl)-2-methyl-1-((1-methyl-1H-pyrazol-5-yl)methyl)-1H-imidazo[4,5-b]pyridine a) 6-bromo-2-methyl-1-((1-methyl-1H-pyrazol-5-yl)methyl)-1H-imidazo[4,5-b]pyridine Acetic acid (0.4 mL) was added to a solution of 2-methyl-2H-pyrazole-3-carbaldehyde (0.8 g) and 5-bromopyridine-2,3-diamine (1 g) in THF (20 mL) at room temperature. The mixture was stirred overnight at room temperature. The mixture was poured into a saturated aqueous sodium hydrogen carbonate solution, and extracted with ethyl acetate. The organic layer was washed with water and a saturated brine, dried over magnesium sulfate, and then concentrated to obtain a residue. Sodium borohydride (300 mg) was added to a solution of the residue in THF (20 mL)/methanol (50 mL) at 0° C., and the mixture was stirred for 1 hour. The reaction mixture was poured into a saturated aqueous ammonium chloride solution, and extracted with ethyl acetate. The organic layer was sequentially washed with water and a saturated brine, then dried over magnesium sulfate, and concentrated under reduced pressure. The residue was purified by NH silica gel column chromatography (ethyl acetate/hexane) to obtain a pale yellow solid as 5-bromo-N3-((1-methyl-1H-pyrazol-5-yl)methyl)pyridine-2,3-diamine (0.38 g). A mixture of the obtained pale yellow solid (300 mg), acetic acid (0.1 mL), DMAP (10 mg), propylphosphonic anhydride (50% in ethyl acetate solution) (0.938 mL), DIPEA (0.464 mL) and THF (10 mL) was stirred under microwave irradiation at 200° C. for 2 hours. The mixture was purified by NH silica gel column chromatography (methanol/ethyl acetate) to obtain the title compound (188 mg).

$^1$H NMR (300 MHz, DMSO-$d_6$) δ 2.55 (3H, s), 3.81 (3H, s), 5.63 (2H, s), 5.70 (1H, d, J=1.9 Hz), 7.30 (1H, d, J=1.9 Hz), 8.24 (1H, d, J=2.2 Hz), 8.42 (1H, d, J=2.2 Hz).

b) 6-(4-methoxypyrrolo[2,1-f][1,2,4]triazin-5-yl)-2-methyl-1-((1-methyl-1H-pyrazol-5-yl)methyl)-1H-imidazo[4,5-b]pyridine A mixture of 6-bromo-2-methyl-1-((1-methyl-1H-pyrazol-5-yl)methyl)-1H-imidazo[4,5-b]pyridine (61 mg), 4-methoxy-5-(4,4,5,5-tetramethyl-1,3,2-dioxaborolan-2-yl)pyrrolo[2,1-f][1,2,4]triazine (151 mg), bis(di-tert-butyl(4-dimethylaminophenyl)phosphine)dichloropalladium (II) (11 mg), cesium carbonate (2 M in aqueous solution) (0.2 mL) and DME (3 mL) was stirred under microwave irradiation at 100° C. for 40 minutes. The mixture was purified by NH silica gel column chromatography (methanol/ethyl acetate), and the residue was crystallized from ethanol/ethyl acetate/heptane to obtain the title compound (33 mg).
$^1$H NMR (300 MHz, DMSO-$d_6$) δ 2.60 (3H, s), 3.83 (3H, s), 3.86 (3H, s), 5.65 (2H, s), 5.72 (1H, d, J=2.0 Hz), 7.03 (1H, d, J=2.7 Hz), 7.31 (1H, d, J=2.0 Hz), 8.02-8.08 (2H, m), 8.21 (1H, s), 8.56 (1H, d, J=2.0 Hz).

Example 186

6-(4-methoxypyrrolo[2,1-f][1,2,4]triazin-5-yl)-2-methyl-1-((3-methyl-1,2,4-oxadiazol-5-yl)methyl)-1H-imidazo[4,5-b]pyridine a) tert-butyl 2-(6-bromo-2-methyl-1H-imidazo[4,5-b]pyridin-1-yl)acetate Sodium hydride (60%, oil) (15.09 g) was added to a solution of 6-bromo-2-methyl-1H-imidazo[4,5-b]pyridine (40 g) in DMF (300 mL) at 0° C. The mixture was stirred at 0° C. for 30 minutes, and tert-butyl chloroacetate (40.6 mL) was then added to the mixture. The mixture was stirred at 0° C. for 1 hour. The reaction was stopped with acetic acid (20 mL) and water at 0° C., and the mixture was extracted with ethyl acetate. The organic layer was washed with a saturated aqueous sodium hydrogen carbonate solution and a saturated brine, dried over magnesium sulfate, and then concentrated under reduced pressure to reduce the amount by half. The precipitate was collected by filtration, and washed with IPE to obtain the title compound (21.11 g).
$^1$H NMR (300 MHz, DMSO-$d_6$) δ 1.43 (9H, s), 2.49 (3H, s), 5.15 (2H, s), 8.33 (1H, d, J=2.2 Hz), 8.41 (1H, d, J=2.2 Hz).

b) 5-((6-bromo-2-methyl-1H-imidazo[4,5-b]pyridin-1-yl)methyl)-3-methyl-1,2,4-oxadiazole A solution of tert-butyl 2-(6-bromo-2-methyl-1H-imidazo[4,5-b]pyridin-1-yl)acetate (3.00 g) in TFA (10 mL) was stirred at room temperature for 1 hour. The mixture was concentrated under reduced pressure to obtain a brown oil. A mixture of the obtained brown oil, propylphosphonic anhydride (50% in ethyl acetate solution) (14.40 mL), (Z)—N'-hydroxyacetimidamide (1.00 g), DIPEA (8 mL) and ethyl acetate (10 mL) was stirred at 80° C. for 4 hours. The residue was purified by NH silica gel column chromatography (methanol/ethyl acetate) to obtain the title compound (1.980 g).
$^1$H NMR (300 MHz, DMSO-$d_6$) δ 2.28 (3H, s), 2.58 (3H, s), 5.97 (2H, s), 8.39 (1H, d, J=2.2 Hz), 8.45 (1H, d, J=2.2 Hz).

c) 6-(4-methoxypyrrolo[2,1-f][1,2,4]triazin-5-yl)-2-methyl-1-((3-methyl-1,2,4-oxadiazol-5-yl)methyl)-1H-imidazo[4,5-b]pyridine A mixture of 4-methoxy-5-(4,4,5,5-tetramethyl-1,3,2-dioxaborolan-2-yl)pyrrolo[2,1-f][1,2,4]triazine (680 mg), 5-((6-bromo-2-methyl-1H-imidazo[4,5-b]pyridin-1-yl)methyl)-3-methyl-1,2,4-oxadiazole (576 mg), bis(di-tert-butyl(4-dimethylaminophenyl)phosphine)dichloropalladium (II) (105 mg), cesium carbonate (2 M in aqueous solution) (2.336 mL) and DME (14 mL) was stirred under microwave irradiation at 100° C. for 40 minutes. The mixture was concentrated under reduced pressure. The residue was purified by NH silica gel column chromatography (methanol/ethyl acetate), and the obtained solid was crystallized from THF/ethyl acetate/heptane to obtain the title compound (310 mg).
$^1$H NMR (300 MHz, DMSO-$d_6$) δ 2.29 (3H, s), 2.63 (3H, s), 3.94 (3H, s), 6.00 (2H, s), 7.06 (1H, d, J=2.7 Hz), 8.06 (1H, d, J=2.7 Hz), 8.14-8.30 (2H, m), 8.59 (1H, d, J=2.1 Hz).

Example 191

6-(4-methoxypyrrolo[2,1-f][1,2,4]triazin-5-yl)-2-methyl-1-(1,3-thiazol-2-ylmethyl)-1H-imidazo[4,5-b]pyridine a) 5-bromo-N3-(thiazol-2-ylmethyl)pyridine-2,3-diamine Acetic acid (0.4 mL) was added to a solution of 2-thiazolecarboxyaldehyde (1.553 mL) and 5-bromopyridine-2,3-diamine (3 g) in THF (50 mL) at room temperature. The mixture was stirred overnight at room temperature. The mixture was poured into a saturated aqueous sodium hydrogen carbonate solution, and extracted with ethyl acetate. The organic layer was washed with water and a saturated brine, dried over magnesium sulfate, and then concentrated. Sodium borohydride (4 g) was added to a solution of the residue in THF (20 mL)/methanol (50 mL) at 0° C., and the mixture was stirred for 10 minutes. The reaction mixture was poured into a saturated aqueous ammonium chloride solution, and extracted with ethyl acetate. The organic layer was sequentially washed with water and a saturated brine, then dried over magnesium sulfate, and concentrated under reduced pressure. The residue was purified by silica gel column chromatography (ethyl acetate/hexane) to obtain the title compound (2.32 g).
$^1$H NMR (300 MHz, DMSO-$d_6$) δ 4.65 (2H, d, J=5.9 Hz), 5.81 (2H, s), 6.13 (1H, t, J=5.9 Hz), 6.66 (1H, d, J=2.1 Hz), 7.34 (1H, d, J=2.1 Hz), 7.63 (1H, d, J=3.3 Hz), 7.77 (1H, d, J=3.3 Hz).

b) 2-((6-bromo-2-methyl-1H-imidazo[4,5-b]pyridin-1-yl)methyl)thiazole

A mixture of 5-bromo-N3-(thiazol-2-ylmethyl)pyridine-2,3-diamine (620 mg), acetic acid (0.162 mL), DMAP (20 mg), propylphosphonic anhydride (50% in ethyl acetate solution) (1.918 mL), DIPEA (843 mg) and THF (10 mL) was stirred under microwave irradiation at 200° C. for 2 hours. The mixture was purified by NH silica gel column chromatography (ethyl acetate/hexane) to obtain the title compound (540 mg).
$^1$H NMR (300 MHz, DMSO-$d_6$) δ 2.63 (3H, s), 5.92 (2H, s), 7.70-7.81 (2H, m), 8.37-8.45 (2H, m).

c) 6-(4-methoxypyrrolo[2,1-f][1,2,4]triazin-5-yl)-2-methyl-1-(1,3-thiazol-2-ylmethyl)-1H-imidazo[4,5-b]pyridine A mixture of 2-((6-bromo-2-methyl-1H-imidazo[4,5-b]pyridin-1-yl)methyl)thiazole (100 mg), 4-methoxy-5-(4,4,5, 5-tetramethyl-1,3,2-dioxaborolan-2-yl)pyrrolo[2,1-f][1,2,4]triazine (125 mg), bis(di-tert-butyl(4-dimethylaminophenyl)phosphine)dichloropalladium (II) (20 mg), cesium carbonate (2 M in aqueous solution) (0.3 mL) and DME (4 mL) was stirred under microwave irradiation at 100° C. for 1 hour. The mixture was purified by NH silica gel column chromatography (methanol/ethyl acetate), and the obtained solid was crystallized from ethanol/ethyl acetate/heptane to obtain the title compound (47 mg).

$^1$H NMR (300 MHz, DMSO-$d_6$) δ 2.66 (3H, s), 3.88 (3H, s), 5.93 (2H, s), 7.05 (1H, d, J 10=2.7 Hz), 7.73 (1H, d, J=3.3 Hz), 7.80 (1H, d, J=3.3 Hz), 8.06 (1H, d, J=2.7 Hz), 8.20 (1H, d, J=2.1 Hz), 8.22 (1H, s), 8.57 (1H, d, J=2.1 Hz).

Example 193

6-(4-methoxypyrrolo[2,1-f][1,2,4]triazin-5-yl)-2-methyl-1-((5-methyl-1,3,4-oxadiazol-2-yl)methyl)-1H-imidazo[4,5-b]pyridine a) 2-((6-bromo-2-methyl-1H-imidazo[4,5-b]pyridin-1-yl)methyl)-5-methyl-1,3,4-oxadiazole Potassium hydroxide (2.00 g) was added to a solution of 6-bromo-2-methyl-1H-imidazo[4,5-b]pyridine (5.80 g), 2-(chloromethyl)-5-methyl-1,3,4-oxadiazole (3.70 g) and TBAI (1.01 g) in THF (80 mL) at room temperature. The mixture was stirred at 60° C. for 2 hours. The mixture was poured into water at room temperature, and extracted with ethyl acetate. The organic layer was washed with water and a saturated brine, dried over magnesium sulfate, and then concentrated under reduced pressure. The residue was purified by NH silica gel column chromatography (methanol/ethyl acetate) to obtain the title compound (1.550 g).

$^1$H NMR (300 MHz, DMSO-$d_6$) δ 2.47 (3H, s), 2.61 (3H, s), 5.86 (2H, s), 8.36 (1H, d, J=2.2 Hz), 8.44 (1H, d, J=2.2 Hz).

b) 2-((6-bromo-2-methyl-1H-imidazo[4,5-b]pyridin-1-yl)methyl)-5-methyl-1,3,4-oxadiazole A mixture of 4-methoxy-5-(4,4,5,5-tetramethyl-1,3,2-dioxaborolan-2-yl)pyrrolo[2,1-f][1,2,4]triazine (550 mg), 2-((6-bromo-2-methyl-1H-imidazo[4,5-b]pyridin-1-yl)methyl)-5-methyl-1,3,4-oxadiazole (450 mg), bis(di-tert-butyl(4-dimethylaminophenyl)phosphine)dichloropalladium (II) (50 mg), cesium carbonate (2 M in aqueous solution) (1.3 mL) and DME (10 mL) was stirred under microwave irradiation at 100° C. for 1 hour. The residue was purified by NH silica gel column chromatography (methanol/ethyl acetate) and silica gel column chromatography (methanol/ethyl acetate). The obtained solid was crystallized from ethyl acetate/ethanol/heptane to obtain the title compound (255 mg).

$^1$H NMR (300 MHz, DMSO-$d_6$) δ 2.47 (3H, s), 2.66 (3H, s), 3.97 (3H, s), 5.88 (2H, s), 7.07 (1H, d, J=2.7 Hz), 8.07 (1H, d, J=2.7 Hz), 8.20 (1H, d, J=2.1 Hz), 8.23 (1H, s), 8.58 (1H, d, J=2.1 Hz).

Example 199

6-(4-methoxypyrrolo[2,1-f][1,2,4]triazin-5-yl)-2-methyl-1-((2-methyl-1,3-oxadiazol-4-yl)methyl)-1H-imidazo[4,5-b]pyridine a) 4-((6-bromo-2-methyl-1H-imidazo[4,5-b]pyridin-1-yl)methyl)-2-methyloxazole Potassium hydroxide (0.287 g) was added to a mixture of 6-bromo-2-methyl-1H-imidazo[4,5-b]pyridine (0.361 g), 4-(bromomethyl)-2-methyloxazole (0.30 g) and THF (10 mL) at 60° C. The mixture was stirred under a nitrogen atmosphere at 60° C. for 4 hours. The reaction mixture was poured into water, and extracted with ethyl acetate. The organic layer was washed with water and a saturated brine, then dried over sodium sulfate, and concentrated under reduced pressure. The residue was purified by NH silica gel column chromatography (ethyl acetate/hexane) to obtain the title compound (0.124 g).

$^1$H NMR (300 MHz, DMSO-$d_6$) δ 2.32 (3H, s), 2.67 (3H, s), 5.33 (2H, s), 8.09 (1H, s), 8.34-8.37 (1H, m), 8.37-8.40 (1H, m).

b) 6-(4-methoxypyrrolo[2,1-f][1,2,4]triazin-5-yl)-2-methyl-1-((2-methyl-1,3-oxadiazol-4-yl)methyl)-1H-imidazo[4,5-b]pyridine A mixture of 4-methoxy-5-(4,4,5,5-tetramethyl-1,3,2-dioxaborolan-2-yl)pyrrolo[2,1-f][1,2,4]triazine (120 mg), 4-((6-bromo-2-methyl-1H-imidazo[4,5-b]pyridin-1-yl)methyl)-2-methyloxazole (79.5 mg), bis(di-tert-butyl(4-dimethylaminophenyl)phosphine)dichloropalladium (II) (13 mg), cesium carbonate (2 M in aqueous solution) (0.200 mL) and DME (3.0 mL) was stirred under microwave irradiation at 100° C. for 15 minutes. The reaction mixture was purified by silica gel column chromatography (ethyl acetate/hexane and methanol/ethyl acetate), and the residue was crystallized from ethanol/ethyl acetate/heptane to obtain the title compound (57.9 mg).

$^1$H NMR (300 MHz, DMSO-$d_6$) δ 2.33 (3H, s), 2.71 (3H, s), 3.96 (3H, s), 5.34 (2H, s), 7.05 (1H, d, J=2.7 Hz), 8.07 (1H, d, J=2.7 Hz), 8.12 (1H, s), 8.17 (1H, d, J=2.1 Hz), 8.23 (1H, s), 8.52 (1H, d, J=2.1 Hz).

Example 203

6-(4-methoxypyrrolo[2,1-f][1,2,4]triazin-5-yl)-2-methyl-1-((1-methyl-1H-pyrazol-3-yl)methyl)-1H-imidazo[4,5-b]pyridine a) 5-iodo-N3-((1-methyl-1H-pyrazol-3-yl)methyl)pyridine-2,3-diamine A mixture of 1-methyl-1H-pyrazole-3-carbaldehyde (0.516 g) and 5-iodopyridine-2,3-diamine (1 g), acetic acid (0.256 mL) and THF (20 mL) was stirred at room temperature for 21 hours. The mixture was neutralized with a saturated aqueous sodium hydrogen carbonate solution, and extracted with THF and ethyl acetate. The organic layer was washed with a saturated aqueous sodium hydrogen carbonate solution and a saturated brine, dried over magnesium sulfate, and then concentrated to obtain a residue. Sodium borohydride (0.485 g) was added to a solution of the residue in THF (40 mL)/methanol (10 mL) at 0° C., and the mixture was stirred at room temperature for 1 hour. The reaction was stopped with water and a saturated aqueous ammonium chloride solution at room temperature, and the mixture was basified, and extracted with ethyl acetate. The organic layer was washed with a saturated brine, then dried over magnesium sulfate, and concentrated under reduced pressure. The residue was purified by silica gel column chromatography (ethyl acetate/methanol) to obtain the title compound (0.325 g).

MS: [M+H]$^+$ 330.1.

b) 6-iodo-2-methyl-1-((1-methyl-1H-pyrazol-3-yl)methyl)-1H-imidazo[4,5-b]pyridine A mixture of 5-iodo-N3-((1-methyl-1H-pyrazol-3-yl)methyl)pyridine-2,3-diamine (325.1 mg), acetic acid (0.075 mL), DMAP (18 mg), propylphosphonic anhydride (1.7 M in ethyl acetate solution) (0.99 mL), DIPEA (0.346 mL) and THF (3 mL) was stirred under microwave irradiation at 160° C. for 1 hour. The residue was purified by NH silica gel column chromatography (hexane/ethyl acetate), and the obtained solid was washed with IPE to obtain the title compound (240 mg).

MS: [M+H]$^+$ 354.0.

c) 6-(4-methoxypyrrolo[2,1-f][1,2,4]triazin-5-yl)-2-methyl-1-((1-methyl-1H-pyrazol-3-yl)methyl)-1H-imidazo[4,5-b]pyridine A mixture of 6-iodo-2-methyl-1-((1-methyl-1H-pyrazol-3-yl)methyl)-1H-imidazo[4,5-b]pyridine (81 mg), 4-methoxy-5-(4,4,5,5-tetramethyl-1,3,2-dioxaborolan-2-yl)pyrrolo[2,1-f][1,2,4]triazine (175 mg), bis(di-tert-butyl(4-dimethylaminophenyl)phosphine)dichloropalladium (II) (12 mg), cesium carbonate (2 M in aqueous solution) (0.195 mL) and DME (1 mL) was stirred under microwave irradiation at 100° C. for 1 hour. The solvent was distilled off, the residue was then purified by NH silica gel column chromatography (methanol/ethyl acetate), and the obtained solid was washed with IPE to obtain the title compound (31.3 mg).

$^1$H NMR (300 MHz, DMSO-d$_6$) δ 2.67 (3H, s), 3.76 (3H, s), 3.95 (3H, s), 5.41 (2H, s), 6.21 (1H, d, J=2.3 Hz), 7.05 (1H, d, J=2.7 Hz), 7.62 (1H, d, J=2.2 Hz), 8.06 (1H, d, J=2.7 Hz), 8.15 (1H, d, J=2.1 Hz), 8.22 (1H, s), 8.52 (1H, d, J=2.1 Hz).

Example 204

6-(4-methoxypyrrolo[2,1-f][1,2,4]triazin-5-yl)-2-methyl-1-((2-methyl-1,3-thiazol-4-yl)methyl)-1H-imidazo[4,5-b]pyridine a) 5-iodo-N3-((2-methylthiazol-4-yl)methyl)pyridine-2,3-diamine

A mixture of 2-methylthiazole-4-carbaldehyde (390 mg) and 5-iodopyridine-2,3-diamine (770 mg), acetic acid (0.198 mL) and THF (15 mL) was stirred under a nitrogen atmosphere at room temperature for 21 hours. The mixture was concentrated under reduced pressure. The residue was neutralized with a saturated aqueous sodium hydrogen carbonate solution at 0° C., and extracted with THF and ethyl acetate. The organic layer was washed with a saturated aqueous sodium hydrogen carbonate solution and a saturated brine, dried over magnesium sulfate, and then concentrated to obtain a residue. Sodium borohydride (311 mg) was added to a solution of the residue in THF (40 mL)/methanol (10 mL) at 0° C., and the mixture was stirred at room temperature for 30 min. The reaction was stopped with water and a saturated aqueous ammonium chloride solution at room temperature, and the mixture was basified, and extracted with ethyl acetate. The organic layer was washed with a saturated brine, then dried over magnesium sulfate, and concentrated under reduced pressure. The residue was purified by silica gel column chromatography (ethyl acetate/methanol) to obtain the title compound (708 mg).

MS: [M+H]$^+$ 347.1.

b) 4-((6-iodo-2-methyl-1H-imidazo[4,5-b]pyridin-1-yl)methyl)-2-methylthiazole A mixture of 5-iodo-N3-((2-methylthiazol-4-yl)methyl)pyridine-2,3-diamine (300 mg), acetic acid (0.075 mL), DMAP (16 mg), propylphosphonic anhydride (1.7 M in ethyl acetate solution) (0.868 mL), DIPEA (0.304 mL) and THF (2.5 mL) was stirred under microwave irradiation at 160° C. for 1 hour. The residue was purified by NH silica gel column chromatography (hexane/ethyl acetate), and the obtained solid was washed with IPE to obtain the title compound (265 mg).

MS: [M+H]$^+$ 370.9.

c) 6-(4-methoxypyrrolo[2,1-f][1,2,4]triazin-5-yl)-2-methyl-1-((2-methyl-1,3-thiazol-4-yl)methyl)-1H-imidazo[4,5-b]pyridine A mixture of 4-((6-iodo-2-methyl-1H-imidazo[4,5-b]pyridin-1-yl)methyl)-2-methylthiazole (94 mg), 4-methoxy-5-(4,4,5,5-tetramethyl-1,3,2-dioxaborolan-2-yl)pyrrolo[2,1-f][1,2,4]triazine (175 mg), bis(di-tert-butyl(4-dimethylaminophenyl)phosphine)dichloropalladium (II) (13 mg), cesium carbonate (2 M in aqueous solution) (0.218 mL) and DME (1 mL) was stirred under microwave irradiation at 100° C. for 1 hour. The solvent was distilled off, the residue was then purified by NH silica gel column chromatography (methanol/ethyl acetate), and the obtained solid was washed with IPE to obtain the title compound (57.3 mg).

$^1$H NMR (300 MHz, DMSO-d$_6$) δ 2.58 (3H, s), 2.71 (3H, s), 3.93 (3H, s), 5.51 (2H, s), 7.04 (1H, d, J=2.7 Hz), 7.52 (1H, s), 8.06 (1H, d, J=2.7 Hz), 8.18 (1H, d, J=2.1 Hz), 8.22 (1H, s), 8.53 (1H, d, J=2.1 Hz).

Example 205

6-(4-methoxypyrrolo[2,1-f][1,2,4]triazin-5-yl)-2-methyl-1-(1,3-oxazol-2-ylmethyl)-1H-imidazo[4,5-b]pyridine a) N-(2-amino-5-iodopyridin-3-yl)oxazole-2-carboxamide

A mixture of 5-iodopyridine-2,3-diamine (1 g), oxazole-2-carboxylic acid (0.482 g), HATU (2.27 g), Et3N (1.78 mL) and DMF (10 mL) was stirred at 0° C. for 1 hour, and then stirred overnight at room temperature. The mixture was diluted with a saturated aqueous sodium hydrogen carbonate solution, and extracted with ethyl acetate. The organic layer was washed with a saturated brine, then dried over magnesium sulfate, and concentrated under reduced pressure. The residue was purified by silica gel column chromatography (ethyl acetate/hexane) to obtain the title compound (0.781 g). The title compound was used for the subsequent reaction without being further purified.

MS: [M+H]$^+$ 330.9.

b) 5-iodo-N3-(oxazol-2-ylmethyl)pyridine-2,3-diamine

A BH3-THF complex (1M in THF solution) (9 mL) was added dropwise to a solution of N-(2-amino-5-iodopyridin-3-yl)oxazole-2-carboxamide (750 mg) in THF (6 mL) at room temperature. The mixture was stirred under a nitrogen atmosphere at 60° C. for 2 hours. The reaction was stopped with water at room temperature, and the mixture was then acidified with HCl (1 N in aqueous solution). The mixture was stirred at 60° C. for 30 minutes. The mixture was neutralized with a saturated aqueous sodium hydrogen carbonate solution at room temperature, and then extracted with ethyl acetate. The organic layer was washed with a saturated brine, then dried over magnesium sulfate, and concentrated under reduced pressure. The residue was purified by silica gel column chromatography (ethyl acetate/hexane) to obtain the title compound (153 mg).

MS: [M+H]$^+$ 316.9.

c) 2-((6-iodo-2-methyl-1H-imidazo[4,5-b]pyridin-1-yl)methyl)oxazole

A mixture of 5-iodo-N3-(oxazol-2-ylmethyl)pyridine-2,3-diamine (152.8 mg), acetic acid (0.045 mL), DMAP (9 mg), propylphosphonic anhydride (1.7 M in ethyl acetate solution) (0.484 mL), DIPEA (0.195 mL) and THF (1.5 mL) was stirred under microwave irradiation at 160° C. for 1 hour. The residue was purified by NH silica gel column chromatography (hexane/ethyl acetate), and the obtained solid was washed with IPE to obtain the title compound (99 mg).

MS: [M+H]$^+$ 341.0.

d) 6-(4-methoxypyrrolo[2,1-f][1,2,4]triazin-5-yl)-2-methyl-1-(1,3-oxazol-2-ylmethyl)-1H-imidazo[4,5-b]pyridine A mixture of 2-((6-iodo-2-methyl-1H-imidazo[4,5-b]pyridin-1-yl)methyl)oxazole (98 mg), 4-methoxy-5-(4,4,5,5-tetramethyl-1,3,2-dioxaborolan-2-yl)pyrrolo[2,1-f][1,2,4]triazine (210 mg), bis(di-tert-butyl(4-dimethylaminophenyl)phosphine)dichloropalladium (II) (16 mg), cesium carbonate (2 M in aqueous solution) (0.261 mL) and DME (1.2 mL) was stirred under microwave irradiation at 100° C. for 1 hour. The solvent was distilled off, the residue was then purified by NH silica gel column chromatography (methanol/ethyl acetate), and the obtained solid was washed with IPE to obtain the title compound (44.1 mg).

$^1$H NMR (300 MHz, DMSO-d$_6$) δ 2.64 (3H, s), 3.95 (3H, s), 5.77 (2H, s), 7.06 (1H, d, J=2.8 Hz), 7.22 (1H, d, J=0.8 Hz), 8.06 (1H, d, J=2.7 Hz), 8.14 (1H, d, J=0.8 Hz), 8.18 (1H, d, J=2.1 Hz), 8.23 (1H, s), 8.57 (1H, d, J=2.0 Hz).

Example 206

6-(4-methoxypyrrolo[2,1-f][1,2,4]triazin-5-yl)-2-methyl-1-((1-methyl-1H-1,2,3-triazol-4-yl)methyl)-1H-imidazo[4,5-b]pyridine a) N-(2-amino-5-iodopyridin-3-yl)-1-methyl-1H-1,2,3-triazole-4-carboxamide

A mixture of 5-iodopyridine-2,3-diamine (1 g), 1-methyl-1H-1,2,3-triazole-4-carboxylic acid (0.54 g), HATU (2.27 g), Et3N (1.78 mL) and DMF (10 mL) was stirred at 0° C. for 1 hour, and then stirred overnight at room temperature. The mixture was diluted with a saturated aqueous sodium hydrogen carbonate solution, and extracted with ethyl acetate. The organic layer was washed with a saturated brine, then dried over magnesium sulfate, and concentrated under reduced pressure. The residue was purified by silica gel column chromatography (ethyl acetate/hexane) to obtain the title compound (0.987 g). The title compound was used for the subsequent reaction without being further purified.

MS: [M+H]$^+$ 344.9.

b) 5-iodo-N3-((1-methyl-1H-1,2,3-triazol-4-yl)methyl)pyridine-2,3-diamine

A BH3-THF complex (1M in THF solution) (11 mL) was added dropwise to a solution of N-(2-amino-5-iodopyridin-3-yl)-1-methyl-1H-1,2,3-triazole-4-carboxamide (985 mg) in THF (8 mL) at room temperature. The mixture was stirred under a nitrogen atmosphere at 60° C. for 2 hours. The reaction was stopped with water at room temperature, and the mixture was then acidified with HCl (1 N in aqueous solution). The mixture was stirred at 60° C. for 30 minutes. The mixture was neutralized with a saturated aqueous sodium hydrogen carbonate solution at room temperature, and then extracted with ethyl acetate. The organic layer was washed with a saturated brine, then dried over magnesium sulfate, and concentrated under reduced pressure. The residue was purified by silica gel column chromatography (ethyl acetate/methanol) to obtain the title compound (682 mg).

MS: [M+H]$^+$ 331.0.

c) 6-iodo-2-methyl-1-((1-methyl-1H-1,2,3-triazol-4-yl)methyl)-1H-imidazo[4,5-b]pyridine A mixture of 5-iodo-N3-((1-methyl-1H-1,2,3-triazol-4-yl)methyl)pyridine-2,3-diamine (300 mg), acetic acid (0.084 mL), DMAP (16 mg), propylphosphonic anhydride (1.7 M in ethyl acetate solution) (0.910 mL), DIPEA (0.350 mL) and THF (2.5 mL) was stirred under microwave irradiation at 160° C. for 1 hour. The residue was purified by NH silica gel column chromatography (methanol/ethyl acetate), and the obtained solid was washed with IPE to obtain the title compound (167 mg).

MS: [M+H]$^+$ 355.0.

d) 6-(4-methoxypyrrolo[2,1-f][1,2,4]triazin-5-yl)-2-methyl-1-((1-methyl-1H-1,2,3-triazol-4-yl)methyl)-1H-imidazo[4,5-b]pyridine A mixture of 6-iodo-2-methyl-1-((1-methyl-1H-1,2,3-triazol-4-yl)methyl)-1H-imidazo[4,5-b]pyridine (97 mg), 4-methoxy-5-(4,4,5,5-tetramethyl-1,3,2-dioxaborolan-2-yl)pyrrolo[2,1-f][1,2,4]triazine (200 mg), bis(di-tert-butyl(4-dimethylaminophenyl)phosphine)dichloropalladium (II) (15 mg), cesium carbonate (2 M in aqueous solution) (0.249 mL) and DME (1 mL) was stirred under microwave irradiation at 100° C. for 1 hour, and then stirred at 120° C. for 20 minutes. The solvent was distilled off, the residue was then purified by NH silica gel column chromatography (methanol/ethyl acetate), and the obtained solid was washed with IPE to obtain the title compound (59.0 mg).

$^1$H NMR (300 MHz, DMSO-d$_6$) δ 2.72 (3H, s), 3.97 (3H, s), 3.99 (3H, s), 5.56 (2H, s), 7.07 (1H, d, J=2.7 Hz), 8.07 (1H, d, J=2.8 Hz), 8.14 (1H, s), 8.21 (1H, d, J=2.0 Hz), 8.23 (1H, s), 8.53 (1H, d, J=2.1 Hz).

Example 207

6-(4-methoxypyrrolo[2,1-f][1,2,4]triazin-5-yl)-2-methyl-1-((2-methyl-1,3-oxadiazol-5-yl)methyl)-1H-imidazo[4,5-b]pyridine a) 5-((6-bromo-2-methyl-1H-imidazo[4,5-b]pyridin-1-yl)methyl)-2-methyloxazole Potassium hydroxide (3.60 g) was added to a mixture of 6-bromo-2-methyl-1H-imidazo[4,5-b]pyridine (4.53 g), 5-(bromomethyl)-2-methyloxazole (3.76 g) and THF (100 mL) at room temperature. The mixture was stirred under a nitrogen atmosphere overnight at 60° C. Insolubles were removed by filtration through a filter, and the filtrate was concentrated under reduced pressure. The residue was purified by NH silica gel column chromatography (ethyl acetate/hexane) to obtain the title compound (2.030 g).

$^1$H NMR (300 MHz, DMSO-$d_6$) δ 2.32 (3H, s), 2.66 (3H, s), 5.57 (2H, s), 7.19 (1H, s), 8.41 (2H, d, J=0.7 Hz).

b) 6-(4-methoxypyrrolo[2,1-f][1,2,4]triazin-5-yl)-2-methyl-1-((2-methyl-1,3-oxadiazol-5-yl)methyl)-1H-imidazo[4,5-b]pyridine A mixture of 4-methoxy-5-(4,4,5,5-tetramethyl-1,3,2-dioxaborolan-2-yl)pyrrolo[2,1-f][1,2,4]triazine (203 mg), 5-((6-bromo-2-methyl-1H-imidazo[4,5-b]pyridin-1-yl)methyl)-2-methyloxazole (140 mg), bis(di-tert-butyl(4-dimethylaminophenyl)phosphine)dichloropalladium (II) (18 mg), cesium carbonate (2 M in aqueous solution) (0.30 mL) and DME (3.0 mL) was stirred under microwave irradiation at 100° C. for 20 minutes. The reaction mixture was purified by silica gel column chromatography (ethyl acetate/hexane and methanol/ethyl acetate), and the residue was crystallized from ethanol/ethyl acetate/heptane to obtain the title compound (78 mg).

$^1$H NMR (300 MHz, DMSO-$d_6$) δ 2.34 (3H, s), 2.70 (3H, s), 3.97 (3H, s), 5.58 (2H, s), 7.06 (1H, d, J=2.7 Hz), 7.21 (1H, s), 8.07 (1H, d, J=2.7 Hz), 8.20-8.26 (2H, m), 8.54 (1H, d, J=2.1 Hz).

Example 208

6-(4-methoxypyrrolo[2,1-f][1,2,4]triazin-5-yl)-2-methyl-1-(pyrazin-2-ylmethyl)-1H-imidazo[4,5-b]pyridine a) 6-bromo-2-methyl-1-(pyrazin-2-ylmethyl)-1H-imidazo[4,5-b]pyridine 6-bromo-2-methyl-1H-imidazo[4,5-b]pyridine (600 mg) was dissolved in THF (20 mL) at 60° C., and potassium hydroxide (476 mg) and 2-(bromomethyl)pyrazine (490 mg) were added. The mixture was stirred at 60° C. for 16 hours. The reaction solution was cooled to room temperature, then diluted with water, and extracted with ethyl acetate. The organic layer was washed with a saturated brine, then dried over magnesium sulfate, and concentrated under reduced pressure. The residue was purified by NH silica gel column chromatography (ethyl acetate/hexane), and the obtained solid was washed with ethyl acetate/IPE to obtain the title compound (88.3 mg).

$^1$H NMR (300 MHz, DMSO-$d_6$) δ 2.59 (3H, s), 5.71 (2H, s), 8.34 (1H, d, J=2.2 Hz), 8.40 (1H, d, J=2.2 Hz), 8.53 (1H, dd, J=2.5, 1.6 Hz), 8.59 (1H, d, J=2.5 Hz), 8.82 (1H, d, J=1.5 Hz).

b) 6-(4-methoxypyrrolo[2,1-f][1,2,4]triazin-5-yl)-2-methyl-1-(pyrazin-2-ylmethyl)-1H-imidazo[4,5-b]pyridine A mixture of 6-bromo-2-methyl-1-(pyrazin-2-ylmethyl)-1H-imidazo[4,5-b]pyridine (82 mg), 4-methoxy-5-(4,4,5,5-tetramethyl-1,3,2-dioxaborolan-2-yl)pyrrolo[2,1-f][1,2,4]triazine (100 mg), bis(di-tert-butyl(4-dimethylaminophenyl)phosphine)dichloropalladium (II) (15.16 mg), cesium carbonate (2 M in aqueous solution) (0.3 mL) and DME (3 mL) was stirred under microwave irradiation at 100° C. for 1 hour. The mixture was diluted with water, and extracted with ethyl acetate. The organic layer was washed with a saturated brine, dried over magnesium sulfate, and then concentrated. The residue was purified by NH silica gel column chromatography (methanol/ethyl acetate), and the obtained solid was washed with ethyl acetate/IPE to obtain the title compound (45.9 mg).

$^1$H NMR (300 MHz, DMSO-$d_6$) δ 2.66 (3H, s), 3.83 (3H, s), 5.73 (2H, s), 7.03 (1H, d, J=2.7 Hz), 8.05 (1H, d, J=2.7 Hz), 8.15 (1H, d, J=2.0 Hz), 8.21 (1H, s), 8.54 (1H, d, J=2.1 Hz), 8.57-8.62 (2H, m), 8.83 (1H, d, J=1.3 Hz).

Example 209

6-(4-methoxypyrrolo[2,1-f][1,2,4]triazin-5-yl)-2-methyl-1-(pyrimidin-2-ylmethyl)-1H-imidazo[4,5-b]pyridine a) 6-bromo-2-methyl-1-(pyrimidin-2-ylmethyl)-1H-imidazo[4,5-b]pyridine 6-bromo-2-methyl-1H-imidazo[4,5-b]pyridine (700 mg) was dissolved in THF (20 mL) at 60° C., and potassium hydroxide (741 mg), tetrabutylammonium iodide (1829 mg) and 2-(chloromethyl)pyrimidine hydrochloride (599 mg) were added. The mixture was stirred at 60° C. for 3 hours. The reaction solution was cooled to room temperature, then diluted with water, and extracted with ethyl acetate. The organic layer was washed with a saturated brine, then dried over magnesium sulfate, and concentrated under reduced pressure. The residue was purified by NH silica gel column chromatography (ethyl acetate/hexane), and the obtained solid was washed with ethyl acetate/IPE to obtain the title compound (199 mg).

$^1$H NMR (300 MHz, DMSO-$d_6$) δ 2.50 (3H, s), 5.76 (2H, s), 7.45 (1H, t, J=4.9 Hz), 8.26 (1H, d, J=2.2 Hz), 8.40 (1H, d, J=2.2 Hz), 8.76 (1H, s), 8.77 (1H, s).

b) 6-(4-methoxypyrrolo[2,1-f][1,2,4]triazin-5-yl)-2-methyl-1-(pyrimidin-2-ylmethyl)-1H-imidazo[4,5-b]pyridine A mixture of 6-bromo-2-methyl-1-(pyrimidin-2-ylmethyl)-1H-imidazo[4,5-b]pyridine (82 mg), 4-methoxy-5-(4,4,5,5-tetramethyl-1,3,2-dioxaborolan-2-yl)pyrrolo[2,1-f][1,2,4]triazine (100 mg), bis(di-tert-butyl(4-dimethylaminophenyl)phosphine)dichloropalladium (II) (15.16 mg), cesium carbonate (2 M in aqueous solution) (0.3 mL) and DME (3 mL) was stirred under microwave irradiation at 100° C. for 1 hour. The mixture was diluted with water, and extracted with ethyl acetate. The organic layer was washed with a saturated brine, dried over magnesium sulfate, and then concentrated. The residue was purified by NH silica gel column chromatography (methanol/ethyl acetate), and the obtained solid was washed with ethyl acetate/IPE to obtain the title compound (33.8 mg).

$^1$H NMR (300 MHz, DMSO-$d_6$) δ 2.57 (3H, s), 3.82 (3H, s), 5.77 (2H, s), 7.04 (1H, d, J=2.6 Hz), 7.45 (1H, t, J=4.9 Hz), 8.01-8.11 (2H, m), 8.20 (1H, s), 8.54 (1H, s), 8.79 (2H, d, J=5.0 Hz).

Example 210

6-(4-methoxypyrrolo[2,1-f][1,2,4]triazin-5-yl)-2-methyl-1-(pyridin-4-ylmethyl)-1H-imidazo[4,5-b]pyridine a) 5-iodo-N3-(pyridin-4-ylmethyl)pyridine-2,3-diamine Acetic acid (0.6 mL) was added to a solution of isonicotinaldehyde (1.34 g) and 5-iodopyridine-2,3-diamine (2 g) in THF (20 mL) at room temperature. The mixture was stirred at room temperature for 21 hours. The mixture was concentrated, a saturated aqueous sodium hydrogen carbonate solution was added to the residue at 0° C., and the mixture was extracted with THF/ethyl acetate. The organic layer was washed with a saturated aqueous sodium hydrogen carbonate solution and a saturated brine, dried over magnesium sulfate, and then concentrated. Sodium borohydride (0.644 g) was added to a solution of the residue in THF (30 mL)/methanol (3 mL) at 0° C., and the mixture was stirred at room temperature for 1 hour. An aqueous ammonium chloride solution was added to the reaction mixture at 0° C., and the mixture was extracted with ethyl acetate. The organic layer was sequentially washed with water and a saturated brine, then dried over magnesium sulfate, and concentrated under reduced pressure. The residue was purified by silica gel column chromatography (methanol/ethyl acetate) to obtain the title compound (933 mg).

$^1$H NMR (300 MHz, DMSO-$d_6$) δ 4.35 (2H, d, J=5.8 Hz), 5.76 (1H, t, J=5.9 Hz), 5.81 (2H, s), 6.59 (1H, d, J=1.8 Hz), 7.32-7.35 (2H, m), 7.41 (1H, d, J=1.8 Hz), 8.49-8.54 (2H, m).

b) 6-bromo-2-methyl-1-(pyridin-4-ylmethyl)-1H-imidazo[4,5-b]pyridine

A mixture of 5-iodo-N3-(pyridin-4-ylmethyl)pyridine-2,3-diamine (917 mg), acetic acid (0.209 mL), DMAP (51.5 mg), propylphosphonic anhydride (50% in ethyl acetate solution) (2.98 mL), DIPEA (0.982 mL) and THF (15 mL) was stirred under microwave irradiation at 160° C. for 1 hour. The mixture was diluted with a saturated aqueous sodium hydrogen carbonate solution, and extracted with ethyl acetate. The organic layer was washed with a saturated brine, dried over magnesium sulfate, and then concentrated. The residue was purified by NH silica gel column chromatography (ethyl acetate/hexane), and the obtained solid was washed with IPE to obtain the title compound (606 mg).

$^1$H NMR (300 MHz, DMSO-$d_6$) δ 2.51 (3H, s), 5.59 (2H, s), 7.05 (2H, d, J=6.0 Hz), 8.38 (1H, d, J=1.9 Hz), 8.49-8.57 (3H, m).

c) 6-(4-methoxypyrrolo[2,1-f][1,2,4]triazin-5-yl)-2-methyl-1-(pyridin-4-ylmethyl)-1H-imidazo[4,5-b]pyridine A mixture of 6-iodo-2-methyl-1-(pyridin-4-ylmethyl)-1H-imidazo[4,5-b]pyridine (95 mg), 4-methoxy-5-(4,4,5,5-tetramethyl-1,3,2-dioxaborolan-2-yl)pyrrolo[2,1-f][1,2,4]triazine (100 mg), bis(di-tert-butyl(4-dimethylaminophenyl)phosphine)dichloropalladium (II) (15.16 mg), cesium carbonate (2 M in aqueous solution) (0.3 mL) and DME (3 mL) was stirred under microwave irradiation at 100° C. for 1 hour. The mixture was diluted with water, and extracted with ethyl acetate. The organic layer was washed with a saturated brine, dried over magnesium sulfate, and then concentrated. The residue was purified by NH silica gel column chromatography (methanol/ethyl acetate), and the obtained solid was washed with ethyl acetate/IPE to obtain the title compound (46.1 mg).

$^1$H NMR (300 MHz, DMSO-$d_6$) δ 2.58 (3H, s), 3.74 (3H, s), 5.63 (2H, s), 7.05 (1H, d, J=2.6 Hz), 7.10 (2H, d, J=5.7 Hz), 8.04 (1H, d, J=2.6 Hz), 8.09 (1H, d, J=1.8 Hz), 8.20 (1H, s), 8.53-8.60 (3H, m).

Example 211

6-(4-methoxypyrrolo[2,1-f][1,2,4]triazin-5-yl)-2-methyl-1-(pyridin-3-ylmethyl)-1H-imidazo[4,5-b]pyridine a) 6-bromo-2-methyl-1-(pyridin-3-ylmethyl)-1H-imidazo[4,5-b]pyridine 6-bromo-2-methyl-1H-imidazo[4,5-b]pyridine (600 mg) was dissolved in THF (20 mL) at 60° C., and potassium hydroxide (635 mg) and 3-(bromomethyl)pyridine (787 mg) were added. The mixture was stirred at 60° C. for 3 hours. The reaction solution was cooled to room temperature, then diluted with water, and extracted with ethyl acetate. The organic layer was washed with a saturated brine, then dried over magnesium sulfate, and concentrated under reduced pressure. The residue was purified by NH silica gel column chromatography (ethyl acetate/hexane), and the obtained solid was washed with ethyl acetate/IPE to obtain the title compound (382 mg).

$^1$H NMR (300 MHz, DMSO-$d_6$) δ 2.58 (3H, s), 5.58 (2H, s), 7.36 (1H, ddd, J=7.9, 4.8, 0.8 Hz), 7.52 (1H, dt, J=8.2, 1.9 Hz), 8.36 (1H, d, J=2.2 Hz), 8.42 (1H, d, J=2.2 Hz), 8.49-8.55 (2H, m).

b) 6-(4-methoxypyrrolo[2,1-f][1,2,4]triazin-5-yl)-2-methyl-1-(pyridin-3-ylmethyl)-1H-imidazo[4,5-b]pyridine A mixture of 6-bromo-2-methyl-1-(pyridin-3-ylmethyl)-1H-imidazo[4,5-b]pyridine (82 mg), 4-methoxy-5-(4,4,5,5-tetramethyl-1,3,2-dioxaborolan-2-yl)pyrrolo[2,1-f][1,2,4]triazine (100 mg), bis(di-tert-butyl(4-dimethylaminophenyl)phosphine)dichloropalladium (II) (15.16 mg), cesium carbonate (2 M in aqueous solution) (0.3 mL) and DME (3 mL) was stirred under microwave irradiation at 100° C. for 1 hour. The mixture was diluted with water, and extracted with ethyl acetate. The organic layer was washed with a saturated brine, dried over magnesium sulfate, and then concentrated. The residue was purified by NH silica gel column chromatography (methanol/ethyl acetate), and the obtained solid was washed with ethyl acetate/IPE to obtain the title compound (49.6 mg).

$^1$H NMR (300 MHz, DMSO-$d_6$) δ 2.63 (3H, s), 3.82 (3H, s), 5.61 (2H, s), 7.05 (1H, d, J=2.8 Hz), 7.39 (1H, dd, J=7.6, 4.5 Hz), 7.53-7.61 (1H, m), 8.05 (1H, d, J=2.7 Hz), 8.17 (1H, d, J=2.0 Hz), 8.21 (1H, s), 8.52 (1H, dd, J=4.7, 1.5 Hz), 8.56 (2H, d, J=1.9 Hz).

Example 212

6-(4-methoxypyrrolo[2,1-f][1,2,4]triazin-5-yl)-2-methyl-1-((5-methyl-1,2-oxadiazol-3-yl)methyl)-1H-imidazo[4,5-b]pyridine a) 3-((6-bromo-2-methyl-1H-imidazo[4,5-b]pyridin-1-yl)methyl)-5-methylisoxazole Potassium hydroxide (1.081 g) was added to a mixture of 6-bromo-2-methyl-1H-imidazo[4,5-b]pyridine (1.361 g), 3-(bromomethyl)-5-methylisoxazole (1.13 g) and THF (30 mL) at room temperature. The mixture was stirred under a nitrogen atmosphere at 60° C. for 4 hours. The reaction mixture was poured into water at room temperature, and extracted with ethyl acetate. The organic layer was washed with water and a saturated brine, then dried over sodium sulfate, and concentrated under reduced pressure. The residue was purified by NH silica gel column chromatography (ethyl acetate/hexane), and the residue was washed with IPE to obtain the title compound (0.819 g).

$^1$H NMR (300 MHz, DMSO-$d_6$) δ2.35 (3H, d, J=0.8 Hz), 2.59 (3H, s), 5.58 (2H, s), 6.21 (1H, d, J=0.8 Hz), 8.34 (1H, d, J=2.2 Hz), 8.42 (1H, d, J=2.2 Hz).

b) 6-(4-methoxypyrrolo[2,1-f][1,2,4]triazin-5-yl)-2-methyl-1-((5-methyl-1,2-oxadiazol-3-yl)methyl)-1H-imidazo[4,5-b]pyridine A mixture of 4-methoxy-5-(4,4,5,5-tetramethyl-1,3,2-dioxaborolan-2-yl)pyrrolo[2,1-f][1,2,4]triazine (144 mg), 3-((6-bromo-2-methyl-1H-imidazo[4,5-b]pyridin-1-yl)methyl)-5-methylisoxazole (100 mg), bis(di-tert-butyl(4-dimethylaminophenyl)phosphine)dichloropalladium (II) (22 mg), cesium carbonate (2 M in aqueous solution) (0.330 mL) and DME (2.0 mL) was stirred under microwave irradiation at 100° C. for 40 minutes. The reaction mixture was purified by silica gel column chromatography (methanol/ethyl acetate), and the residue was washed with ethyl acetate/heptane to obtain the title compound (63.8 mg).

$^1$H NMR (300 MHz, DMSO-$d_6$) δ 2.35 (3H, s), 2.64 (3H, s), 3.94 (3H, s), 5.59 (2H, s), 6.21 (1H, s), 7.07 (1H, d, J=2.8 Hz), 8.07 (1H, d, J=2.6 Hz), 8.16 (1H, d, J=1.9 Hz), 8.23 (1H, s), 8.56 (1H, d, J=1.7 Hz).

Example 213

6-(4-methoxypyrrolo[2,1-f][1,2,4]triazin-5-yl)-2-methyl-1-((2-methyl-1,3-thiazol-5-yl)methyl)-1H-imidazo[4,5-b]pyridine a) 5-((6-bromo-2-methyl-1H-imidazo[4,5-b]pyridin-1-yl)methyl)-2-methylthiazole Potassium hydroxide (0.709 g) was added to a mixture of 6-bromo-2-methyl-1H-imidazo[4,5-b]pyridine (0.893 g), 5-(bromomethyl)-2-methylthiazole (0.809 g) and THF (20 mL) at room temperature. The mixture was stirred under a nitrogen atmosphere at 60° C. for 4 hours. The reaction mixture was poured into water, and extracted with ethyl acetate. The organic layer was washed with water and a saturated brine, then dried over sodium sulfate, and concentrated under reduced pressure. The residue was purified by NH silica gel column chromatography (ethyl acetate/hexane) to obtain the title compound (0.0953 g).

$^1$H NMR (300 MHz, CDCl$_3$) δ 2.67 (3H, s), 2.69-2.72 (3H, m), 5.40 (2H, s), 7.52 (1H, s), 7.73 (1H, d, J=2.1 Hz), 8.55 (1H, d, J=2.1 Hz).

b) 6-(4-methoxypyrrolo[2,1-f][1,2,4]triazin-5-yl)-2-methyl-1-((2-methyl-1,3-thiazol-5-yl)methyl)-1H-imidazo[4,5-b]pyridine A mixture of 4-methoxy-5-(4,4,5,5-tetramethyl-1,3,2-dioxaborolan-2-yl)pyrrolo[2,1-f][1,2,4]triazine (131 mg), 5-((6-bromo-2-methyl-1H-imidazo[4,5-b]pyridin-1-yl)methyl)-2-methylthiazole (95.3 mg), bis(di-tert-butyl(4-dimethylaminophenyl)phosphine)dichloropalladium (II) (20.0 mg), cesium carbonate (2 M in aqueous solution) (0.300 mL) and DME (2.0 mL) was stirred under microwave irradiation at 100° C. for 40 minutes. The residue was purified by silica gel column chromatography (methanol/ethyl acetate), and the residue was washed with ethyl acetate/heptane to obtain the title compound (51.5 mg).

$^1$H NMR (300 MHz, DMSO-$d_6$) δ 2.57 (3H, s), 2.66 (3H, s), 3.95 (3H, s), 5.73 (2H, s), 7.05 (1H, d, J=2.7 Hz), 7.76 (1H, s), 8.07 (1H, d, J=2.7 Hz), 8.21-8.27 (2H, m), 8.55 (1H, d, J=2.0 Hz).

Example 214

6-(4-methoxypyrrolo[2,1-f][1,2,4]triazin-5-yl)-2-methyl-1-((5-methyl-1,2,4-oxadiazol-3-yl)methyl)-1H-imidazo[4,5-b]pyridine a) 3-((6-bromo-2-methyl-1H-imidazo[4,5-b]pyridin-1-yl)methyl)-5-methyl-1,2,4-oxadiazole Potassium hydroxide (1.270 g) was added to a mixture of 6-bromo-2-methyl-1H-imidazo[4,5-b]pyridine (1.600 g), 3-(chloromethyl)-5-methyl-1,2,4-oxadiazole (1 g), TBAI (2.79 g) and THF (10 mL) at 60° C. The mixture was stirred under a nitrogen atmosphere at 60° C. for 2 hours. The mixture was poured into water at room temperature, and extracted with ethyl acetate. The organic layer was washed with water and a saturated brine, dried over magnesium sulfate, and concentrated under reduced pressure. The residue was purified by NH silica gel column chromatography (ethyl acetate/hexane) to obtain the title compound (0.430 g).

$^1$H NMR (300 MHz, DMSO-$d_6$) δ2.54 (3H, s), 2.60 (3H, s), 5.73 (2H, s), 8.33 (1H, d, J=2.2 Hz), 8.43 (1H, d, J=2.2 Hz).

b) 6-(4-methoxypyrrolo[2,1-f][1,2,4]triazin-5-yl)-2-methyl-1-((5-methyl-1,2,4-oxadiazol-3-yl)methyl)-1H-imidazo[4,5-b]pyridine A mixture of 4-methoxy-5-(4,4,5,5-tetramethyl-1,3,2-dioxaborolan-2-yl)pyrrolo[2,1-f][1,2,4]triazine (595 mg), 3-((6-bromo-2-methyl-1H-imidazo[4,5-b]pyridin-1-yl)methyl)-5-methyl-1,2,4-oxadiazole (420 mg), bis(di-tert-butyl(4-dimethylaminophenyl)phosphine)dichloropalladium (II) (45.8 mg), cesium carbonate (2 M in aqueous solution) (2.045 mL) and DME (12 mL) was stirred under microwave irradiation at 100° C. for 40 minutes. The mixture was poured into ice water at room temperature, and extracted with ethyl acetate. The organic layer was washed with water and a saturated brine, dried over magnesium sulfate, and concentrated under reduced pressure. The residue was purified by NH silica gel column chromatography (methanol/ethyl acetate) to obtain a solid. The obtained solid was washed with ethyl acetate/IPE to obtain the title compound (171 mg).

$^1$H NMR (300 MHz, DMSO-$d_6$) δ2.55 (3H, s), 2.66 (3H, s), 3.97 (3H, s), 5.73 (2H, s), 7.06 (1H, d, J=2.8 Hz), 8.06 (1H, d, J=2.7 Hz), 8.17 (1H, d, J=2.0 Hz), 8.23 (1H, s), 8.57 (1H, d, J=2.1 Hz).

Example 215

6-(4-methoxypyrrolo[2,1-f][1,2,4]triazin-5-yl)-2-methyl-1-((3-methyl-1,2-oxadiazol-5-yl)methyl)-1H-imidazo[4,5-b]pyridine a) 5-((6-bromo-2-methyl-1H-imidazo[4,5-b]pyridin-1-yl)methyl)-3-methylisoxazole Potassium hydroxide (1.588 g) was added to a solution of 6-bromo-2-methyl-1H-imidazo[4,5-b]pyridine (2 g), 5-(bromomethyl)-3-methylisoxazole (1.8 g) and TBAI (3.48 g) in THF at 60° C. The mixture was stirred under a nitrogen atmosphere at 60° C. for 2 hours. The reaction mixture was poured into water, and extracted with ethyl acetate. The organic layer was sequentially washed with water and a saturated brine, then dried over sodium sulfate, and concentrated under reduced pressure. The residue was purified by NH silica gel column chromatography (hexane/ethyl acetate) to obtain the title compound (0.89 g).

$^1$H NMR (300 MHz, DMSO-$d_6$) δ 2.18 (3H, s), 2.63 (3H, s), 5.71 (2H, s), 6.38 (1H, s), 8.40-8.42 (1H, m), 8.42-8.46 (1H, m).

b) 6-(4-methoxypyrrolo[2,1-f][1,2,4]triazin-5-yl)-2-methyl-1-((3-methyl-1,2-oxadiazol-5-yl)methyl)-1H-imidazo[4,5-b]pyridine A mixture of 5-((6-bromo-2-methyl-1H-imidazo[4,5-b]pyridin-1-yl)methyl)-3-methylisoxazole (644.5 mg), 4-methyl-5-(4,4,5,5-tetramethyl-1,3,2-dioxaborolan-2-yl)pyrrolo[2,1-f][1,2,4]triazine (502 mg), bis(di-tert-butyl(4-dimethylaminophenyl)phosphine)dichloropalladium (II) (129 mg), cesium carbonate (2 M in aqueous solution) (1.825 mL) and DME (12 mL) was stirred under microwave irradiation at 100° C. for 1 hour. The mixture was purified by NH silica gel column chromatography (methanol/ethyl acetate), and the residue was crystallized from ethanol/water to obtain the title compound (138 mg).

$^1$H NMR (300 MHz, DMSO-$d_6$) δ 2.19 (3H, s), 2.66 (3H, s), 3.96 (3H, s), 5.72 (2H, s), 6.40 (1H, s), 7.07 (1H, d, J=2.8 Hz), 8.07 (1H, d, J=2.7 Hz), 8.21-8.25 (2H, m), 8.57 (1H, d, J=2.1 Hz).

Example 220 b) 6-(4-methoxypyrrolo[2,1-f][1,2,4]triazin-5-yl)-2-methyl-1-((5-methyl-1,3,4-thiadiazol-2-yl)methyl)-1H-imidazo[4,5-b]pyridine a) 2-((6-bromo-2-methyl-1H-imidazo[4,5-b]pyridin-1-yl)methyl)-5-methyl-1,3,4-thiadiazole Potassium hydroxide (600 mg) was added to a mixture of 6-bromo-2-methyl-1H-imidazo[4,5-b]pyridine (720 mg), 2-(chloromethyl)-5-methyl-1,3,4-thiadiazole (550 mg), TBAI (1254 mg) and THF (10 mL) at room temperature. The mixture was stirred at 60° C. for 2 hours. The mixture was poured into water at room temperature, and extracted with ethyl acetate. The organic layer was washed with water and a saturated brine, dried over magnesium sulfate, and concentrated under reduced pressure. The residue was purified by NH silica gel column chromatography (methanol/ethyl acetate) to obtain the title compound (182 mg).

$^1$H NMR (300 MHz, DMSO-$d_6$) δ 2.62 (3H, s), 2.68 (3H, s), 6.00 (2H, s), 8.39-8.46 (2H, m).

b) 6-(4-methoxypyrrolo[2,1-f][1,2,4]triazin-5-yl)-2-methyl-1-(5-methyl-1,3,4-thiadiazol-2-yl)methyl)-1H-imidazo[4,5-b]pyridine A mixture of 4-methoxy-5-(4,4,5,5-tetramethyl-1,3,2-dioxaborolan-2-yl)pyrrolo[2,1-f][1,2,4]triazine (100 mg), 2-((6-bromo-2-methyl-1H-imidazo[4,5-b]pyridin-1-yl)methyl)-5-methyl-1,3,4-thiadiazole (80 mg), bis(di-tert-butyl(4-dimethylaminophenyl)phosphine)dichloropalladium (II) (11 mg), cesium carbonate (2 M in aqueous solution) (0.250 mL) and DME (3 mL) was stirred under microwave irradiation at 100° C. for 40 minutes. The residue was purified by NH silica gel column chromatography (methanol/ethyl acetate) to obtain a solid. The obtained solid was crystallized from ethanol/THF/heptane to obtain the title compound (33.5 mg).

$^1$H NMR (300 MHz, DMSO-$d_6$) δ 2.66 (3H, s), 2.67 (3H, s), 3.94 (3H, s), 6.02 (2H, s), 7.05 (1H, d, J=2.8 Hz), 8.07 (1H, d, J=2.8 Hz), 8.20-8.25 (2H, m), 8.58 (1H, d, J=2.0 Hz).

Example 229

6-(4-methoxypyrrolo[2,1-f][1,2,4]triazin-5-yl)-2-methyl-1-((3-methyl-1,2,4-thiadiazol-5-yl)methyl)-1H-imidazo[4,5-b]pyridine a) 2-(6-bromo-2-methyl-1H-imidazo[4,5-b]pyridin-1-yl)acetonitrile A mixture of potassium tert-butoxide (11 g), 6-bromo-2-methyl-1H-imidazo[4,5-b]pyridine (20 g) and THF (200 mL) was stirred at 50° C. for 30 minutes. To the mixture was added dropwise a solution of bromoacetonitrile (7.00 mL) in THF (20 mL) at 50° C. The mixture was stirred at 50° C. for 2 hours, and then cooled to 5° C. The mixture was diluted with water (100 mL), and stirred at 5° C. for 30 minutes. The precipitate was collected by filtration, and washed with water (100 mL) and ethyl acetate (50 mL) to obtain a solid (13.3 g). A suspension of the obtained solid (13.3 g) in ethyl acetate (260 mL) was stirred at 70° C. for 60 minutes. The suspension was cooled to 40° C., and the precipitate was then collected by filtration, and washed with ethyl acetate (100 mL) to obtain the title compound (7.52 g).

$^1$H NMR (300 MHz, DMSO-$d_6$) δ 2.66 (3H, s), 5.63 (2H, s), 8.45-8.47 (1H, m), 8.47-8.50 (1H, m).

b) 2-(6-bromo-2-methyl-1H-imidazo[4,5-b]pyridin-1-yl)ethanethioamide

Diethyl phosphorodithioic acid (3.00 mL) was added to a solution of 2-(6-bromo-2-methyl-1H-imidazo[4,5-b]pyridin-1-yl)acetonitrile (2.40 g) in THF (40 mL)/water (4 mL) at room temperature. The mixture was stirred at 70° C. for 3 hours. The mixture was cooled, and the residue was purified by NH silica gel column chromatography (methanol/ethyl acetate) to obtain the title compound (2.150 g).

$^1$H NMR (300 MHz, DMSO-$d_6$) δ 2.50 (3H, s), 5.16 (2H, s), 8.20 (1H, d, J=2.2 Hz), 8.38 (1H, d, J=2.2 Hz), 9.51 (1H, brs), 9.94 (1H, brs).

c) 5-((6-bromo-2-methyl-1H-imidazo[4,5-b]pyridin-1-yl)methyl)-3-methyl-1,2,4-thiadiazole N,N-dimethylacetamide dimethylacetal (900 μL) was added to a suspension of 2-(6-bromo-2-methyl-1H-imidazo[4,5-b]pyridin-1-yl)ethanethioamide (1.40 g) in acetonitrile (50 mL) at room temperature. The mixture was stirred at 40° C. for 3 hours, and then concentrated under reduced pressure to obtain a brown oil. Pyridine (1.00 mL) was added to a solution of the obtained oil in methanol (10 mL) at 0° C. The mixture was stirred at 0° C. for 10 minutes, and a solution of hydroxylamine-O-sulfonic acid (600 mg) in methanol (15 mL) was then added dropwise to the mixture. The mixture was stirred overnight at room temperature. The precipitate was collected by filtration, and washed with IPA and water to obtain the title compound (644 mg). The filtrate was poured into a saturated aqueous sodium hydrogen carbonate solution, and extracted twice with ethyl acetate. The organic layer was washed with water and a saturated brine, dried over magnesium sulfate, and then concentrated. The residue was purified by NH silica gel column chromatography (ethyl acetate/hexane) to obtain the title compound (660 mg).

$^1$H NMR (300 MHz, DMSO-$d_6$) δ 2.51 (3H, s), 2.62 (3H, s), 6.08 (2H, s), 8.40-8.42 (1H, m), 8.43-8.45 (1H, m).

d) 6-(4-methoxypyrrolo[2,1-f][1,2,4]triazin-5-yl)-2-methyl-1-(3-methyl-1,2,4-thiadiazol-5-yl)methyl)-1H-imidazo[4,5-b]pyridine A mixture of 4-methoxy-5-(4,4,5,5-tetramethyl-1,3,2-dioxaborolan-2-yl)pyrrolo[2,1-f][1,2,4]triazine (1867 mg), 5-((6-bromo-2-methyl-1H-imidazo[4,5-b]pyridin-1-yl)methyl)-3-methyl-1,2,4-thiadiazole (550 mg), bis(di-tert-butyl(4-dimethylaminophenyl)phosphine)dichloropalladium (II) (57.1 mg), cesium carbonate (2 M in aqueous solution) (2.54 mL) and DME (12 mL) was stirred under microwave irradiation at 100° C. for 40 minutes. The mixture was poured into ice water at room temperature, and extracted with ethyl acetate. The organic layer was washed with water and a saturated brine, dried over magnesium sulfate, and concentrated under reduced pressure. The residue was purified by NH silica gel column chromatography (methanol/ethyl acetate) to obtain a solid. The obtained solid was washed with ethyl acetate/IPE to obtain the title compound (210 mg).

$^1$H NMR (300 MHz, DMSO-$d_6$) δ2.54 (3H, s), 2.66 (3H, s), 3.86 (3H, s), 6.11 (2H, s), 7.05 (1H, d, J=2.8 Hz), 8.06 (1H, d, J=2.8 Hz), 8.15-8.28 (2H, m), 8.58 (1H, d, J=2.1 Hz).

Example 230

6-(4-methoxypyrrolo[2,1-f][1,2,4]triazin-5-yl)-2-methyl-1-((1-methyl-1H-pyrazol-4-yl)methyl)-1H-imidazo[4,5-b]pyridine a) 6-bromo-2-methyl-1-((1-methyl-1H-pyrazol-4-yl)methyl)-1H-imidazo[4,5-b]pyridine di-TFA salt 6-bromo-2-methyl-1H-imidazo[4,5-b]pyridine (700 mg) was dissolved in THF (20 mL) at 60° C., and KOH (742 mg), TBAI (123 mg) and 4-(chloromethyl)-1-methyl-1H-pyrazole hydrochloride (663 mg) were added at 60° C. The mixture was stirred at 60° C. for 2 hours. The mixture was diluted with water at room temperature, and extracted with ethyl acetate. The organic layer was washed with a saturated brine, then dried over magnesium sulfate, and concentrated under reduced pressure. The residue was purified by NH silica gel column chromatography (ethyl acetate/methanol), the obtained solid was further fractionated by HPLC (C18, mobile phase: water/acetonitrile (0.1% TFA-containing system)), and the fraction was concentrated to obtain the title compound (305 mg).

MS: [M+H]$^+$ 306.0.

b) 6-(4-methoxypyrrolo[2,1-f][1,2,4]triazin-5-yl)-2-methyl-1-((1-methyl-1H-pyrazol-4-yl)methyl)-1H-imidazo[4,5-b]pyridine A mixture of 6-bromo-2-methyl-1-((1-methyl-1H-pyrazol-4-yl)methyl)-1H-imidazo[4,5-b]pyridine di-TFA salt (200 mg), 4-methoxy-5-(4,4,5,5-tetramethyl-1,3,2-dioxaborolan-2-yl)pyrrolo[2,1-f][1,2,4]triazine (140 mg), bis(di-tert-butyl(4-dimethylaminophenyl)phosphine)dichloropalladium (II) (21 mg), cesium carbonate (2 M in aqueous solution) (0.330 mL) and DME (1.5 mL) was stirred under microwave irradiation at 100° C. for 1 hour, and then stirred at 120° C. for 20 minutes. The mixture was purified by NH silica gel column chromatography (methanol/ethyl acetate), and the obtained solid was washed with IPE to obtain the title compound (90 mg).

$^1$H NMR (300 MHz, DMSO-$d_6$) δ 2.68 (3H, s), 3.75 (3H, s), 3.93 (3H, s), 5.32 (2H, s), 7.07 (1H, d, J=2.8 Hz), 7.49 (1H, s), 7.74 (1H, s), 8.07 (1H, d, J=2.8 Hz), 8.18 (1H, d, J=2.0 Hz), 8.23 (1H, s), 8.52 (1H, d, J=2.0 Hz).

Example 231

6-(4-methoxypyrrolo[2,1-f][1,2,4]triazin-5-yl)-2-methyl-1-((1-methyl-1H-1,2,4-triazol-3-yl)methyl)-1H-imidazo[4,5-b]pyridine a) N-(2-amino-5-bromopyridin-3-yl)-1-methyl-1H-1,2,4-triazole-3-carboxamide A mixture of 5-bromopyridine-2,3-diamine (1.5 g), 1-methyl-1H-1,2,4-triazole-3-carboxylic acid (1.02 g), HATU (4.26 g), Et3N (3.4 mL) and DMF (16 mL) was stirred overnight at room temperature. The mixture was diluted with a saturated aqueous sodium hydrogen carbonate solution, and extracted with ethyl acetate. The organic layer was washed with a saturated brine, then dried over magnesium sulfate, and concentrated under reduced pressure. The residue was purified by silica gel column chromatography (ethyl acetate/methanol) to obtain the title compound (0.663 g). The title compound was used for the subsequent reaction without being further purified.

MS: [M+H]$^+$ 297.0.

b) 5-bromo-N3-((1-methyl-1H-1,2,4-triazol-3-yl)methyl)pyridine-2,3-diamine

A BH3-THF complex (1M in THF solution) (7.7 mL) was added dropwise to a solution of N-(2-amino-5-bromopyridin-3-yl)-1-methyl-1H-1,2,4-triazole-3-carboxamide (662.7 mg) in THF (6 mL) at room temperature. The mixture was stirred under a nitrogen atmosphere at 60° C. for 2 hours. The reaction was stopped with water at room temperature, and the mixture was then acidified with HCl (1 N in aqueous solution). The mixture was stirred at 60° C. for 30 minutes. The mixture was neutralized with a saturated aqueous sodium hydrogen carbonate solution at room temperature, and then extracted with ethyl acetate. The organic layer was washed with a saturated brine, then dried over magnesium sulfate, and concentrated under reduced pressure. The residue was purified by silica gel column chromatography (ethyl acetate/methanol) to obtain the title compound (348 mg).

MS: [M+H]$^+$ 283.1.

c) 6-bromo-2-methyl-1-((1-methyl-1H-1,2,4-triazol-3-yl)methyl)-1H-imidazo[4,5-b]pyridine A mixture of 5-bromo-N3-((1-methyl-1H-1,2,4-triazol-3-yl)methyl)pyridine-2,3-diamine (348 mg), acetic acid (0.09 mL), DMAP (22 mg), propylphosphonic anhydride (1.7 M in ethyl acetate solution) (1.1 mL), DIPEA (0.43 mL) and THF (2.5 mL) was stirred under microwave irradiation at 160° C. for 50 minutes. The residue was purified by NH silica gel column chromatography (methanol/ethyl acetate) to obtain the title compound (301 mg).

MS: [M+H]$^+$ 307.0.

d) 6-(4-methoxypyrrolo[2,1-f][1,2,4]triazin-5-yl)-2-methyl-1-((1-methyl-1H-1,2,4-triazol-3-yl)methyl)-1H-imidazo[4,5-b]pyridine A mixture of 6-bromo-2-methyl-1-((1-methyl-1H-1,2,4-triazol-3-yl)methyl)-1H-imidazo[4,5-b]pyridine (90 mg), 4-methoxy-5-(4,4,5,5-tetramethyl-1,3,2-dioxaborolan-2-yl)pyrrolo[2,1-f][1,2,4]triazine (120 mg), bis(di-tert-butyl(4-dimethylaminophenyl)phosphine)dichloropalladium (II) (18 mg), cesium carbonate (2 M in aqueous solution) (0.285 mL) and DME (1.5 mL) was stirred under microwave irradiation at 120° C. for 1 hour. The mixture was purified by NH silica gel column chromatography (methanol/ethyl acetate), and the obtained solid was washed with IPE to obtain the title compound (45.0 mg).

$^1$H NMR (300 MHz, DMSO-$d_6$) δ 2.68 (3H, s), 3.80 (3H, s), 3.97 (3H, s), 5.53 (2H, s), 7.06 (1H, d, J=2.7 Hz), 8.06 (1H, d, J=2.7 Hz), 8.14 (1H, d, J=2.1 Hz), 8.22 (1H, s), 8.42 (1H, s), 8.54 (1H, d, J=2.0 Hz).

Example 237

6-(4-methoxypyrrolo[2,1-f][1,2,4]triazin-5-yl)-2-methyl-1-(pyridin-2-ylmethyl)-1H-imidazo[4,5-b]pyridine a)
5-iodo-N3-(pyridin-2-ylmethyl)pyridine-2,3-diamine Acetic acid (0.657 mL) was added to a solution of picolinaldehyde (0.476 mL) and 5-bromopyridine-2,3-diamine (1.07 g) in THF (10 mL) at room temperature. The mixture was stirred overnight at room temperature. The mixture was poured into a saturated aqueous sodium hydrogen carbonate solution, and extracted twice with ethyl acetate. The organic layers were combined, washed with a saturated brine, dried over magnesium sulfate, and then concentrated to obtain a residue. To a solution of the residue in methanol (10 mL) was added sodium borohydride (0.431 g) at room temperature, and the mixture was stirred overnight. The reaction mixture was poured into water, and extracted twice with ethyl acetate. The organic layers were combined, then washed with a saturated brine, dried over sodium sulfate, and concentrated under reduced pressure. The residue was purified by silica gel column chromatography (ethyl acetate/hexane/methanol) to obtain the title compound (0.26 g).

$^1$H NMR (300 MHz, DMSO-$d_6$) δ 4.37 (2H, d, J=5.8 Hz), 5.72-5.90 (3H, m), 6.63 (1H, d, J=1.9 Hz), 7.28 (1H, ddd, J=7.5, 4.8, 1.1 Hz), 7.35 (1H, d, J=7.8 Hz), 7.40 (1H, d, J=1.9 Hz), 7.77 (1H, td, J=7.7, 1.8 Hz), 8.51-8.58 (1H, m).

b) 6-bromo-2-methyl-1-(pyridin-2-ylmethyl)-1H-imidazo[4,5-b]pyridine

A mixture of 5-iodo-N3-(pyridin-2-ylmethyl)pyridine-2,3-diamine (0.26 g), acetic acid (0.055 mL), DMAP (4.87 mg), propylphosphonic anhydride (50% in ethyl acetate solution) (0.703 mL), DIPEA (0.278 mL) and THF (3 mL) was stirred under microwave irradiation at 180° C. for 4 hours. The mixture was purified by NH silica gel column chromatography (hexane/ethyl acetate) to obtain the title compound (0.154 g).

$^1$H NMR (300 MHz, DMSO-$d_6$) δ 2.56 (3H, s), 5.60 (2H, s), 7.27-7.39 (2H, m), 7.81 (1H, td, J=7.7, 1.8 Hz), 8.38 (1H, d, J=1.9 Hz), 8.45-8.50 (2H, m).

c) 6-(4-methoxypyrrolo[2,1-f][1,2,4]triazin-5-yl)-2-methyl-1-(pyridin-2-ylmethyl)-1H-imidazo[4,5-b]pyridine A mixture of 6-iodo-2-methyl-1-(pyridin-2-ylmethyl)-1H-imidazo[4,5-b]pyridine (153.6 mg), 4-methyl-5-(4,4,5,5-tetramethyl-1,3,2-dioxaborolan-2-yl)pyrrolo[2,1-f][1,2,4]triazine (127 mg), bis(di-tert-butyl(4-dimethylaminophenyl)phosphine)dichloropalladium (II) (31.1 mg), cesium carbonate (2 M in aqueous solution) (0.439 mL) and DME (2 mL) was stirred under microwave irradiation at 100° C. for 1 hour. The mixture was purified by NH silica gel column chromatography (methanol/ethyl acetate), and the residue was crystallized from ethanol/water to obtain the title compound (74.2 mg).

$^1$H NMR (300 MHz, DMSO-$d_6$) δ 2.63 (3H, s), 3.80 (3H, s), 5.63 (2H, s), 7.04 (1H, d, J=2.8 Hz), 7.29-7.37 (2H, m), 7.82 (1H, td, J=7.7, 1.8 Hz), 8.04 (1H, d, J=2.8 Hz), 8.11 (1H, d, J=2.1 Hz), 8.20 (1H, s), 8.49-8.53 (1H, m), 8.54 (1H, d, J=2.1 Hz).

Example 242

1-((5-(difluoromethyl)-1,3,4-oxadiazol-2-yl)methyl)-6-(4-methoxypyrrolo[2,1-f][1,2,4]triazin-5-yl)-2-methyl-1H-imidazo[4,5-b]pyridine a) methyl 2-(6-bromo-2-methyl-1H-imidazo[4,5-b]pyridin-1-yl)acetate A mixture of potassium tert-butoxide (11.1 g), 6-bromo-2-methyl-1H-imidazo[4,5-b]pyridine (20.0 g) and THF (200 mL) was stirred at 50° C. for 20 minutes. Methyl 2-bromoacetate (17.4 g) was added to the mixture. The mixture was stirred at 50° C. for 1 hour. The reaction was stopped with acetic acid/water (1/10) at 0° C., and the mixture was diluted with ethyl acetate (100 mL) and a saturated aqueous sodium hydrogen carbonate solution (100 mL). The precipitate was collected by filtration, and the obtained solid was washed with water (100 mL) and ethyl acetate (50 mL) to obtain the title compound (13.10 g).

$^1$H NMR (300 MHz, DMSO-$d_6$) δ 2.52 (3H, s), 3.73 (3H, s), 5.27 (2H, s), 8.33 (1H, d, J=2.2 Hz), 8.41 (1H, d, J=2.2 Hz).

b) 2-(6-bromo-2-methyl-1H-imidazo[4,5-b]pyridin-1-yl)acetohydrazide

A suspension of methyl 2-(6-bromo-2-methyl-1H-imidazo[4,5-b]pyridin-1-yl)acetate (6.43 g) in ethanol (130 mL)/water (13 mL) was stirred at 70° C. for 10 minutes. Hydrazine monohydrate (10 mL) was added to the mixture, and the mixture was stirred at 70° C. for 1 hour, and then stirred at 0° C. for 2 hours. The precipitate was collected by filtration, and washed with ethanol (30 mL) to obtain the title compound (5.17 g).

$^1$H NMR (300 MHz, DMSO-$d_6$) δ 2.53 (3H, s), 4.36 (2H, brs), 4.87 (2H, s), 8.22 (1H, d, J=2.2 Hz), 8.39 (1H, d, J=2.2 Hz), 9.49 (1H, brs).

c) 2-((6-bromo-2-methyl-1H-imidazo[4,5-b]pyridin-1-yl)methyl)-5-(difluoromethyl)-1,3,4-oxadiazole Propylphosphonic anhydride (50% in ethyl acetate solution) (8.0 mL) was added to a suspension of triethylamine (3.00 mL), 2-(6-bromo-2-methyl-1H-imidazo[4,5-b]pyridin-1-yl)acetohydrazide (1.70 g) and difluoroacetic acid (500 μL) in ethyl acetate (55 mL) at room temperature. The mixture was stirred at 50° C. for 20 minutes, and then stirred under microwave irradiation at 140° C. for 60 minutes. Insolubles were removed by filtration, and the filtrate was concentrated under reduced pressure. The residue was purified by NH silica gel column chromatography (ethyl acetate/hexane) to obtain a solid. The obtained solid was washed with ethyl acetate/hexane to obtain the title compound (0.730 g).
$^1$H NMR (300 MHz, DMSO-$d_6$) δ 2.63 (3H, s), 5.99 (2H, s), 7.19-7.73 (1H, m), 8.39 (1H, d, J=2.2 Hz), 8.45 (1H, d, J=2.2 Hz).

d) 1-((5-(difluoromethyl)-1,3,4-oxadiazol-2-yl)methyl)-6-(4-methoxypyrrolo[2,1-f][1,2,4]triazin-5-yl)-2-methyl-1H-imidazo[4,5-b]pyridine A mixture of 4-methoxy-5-(4,4,5,5-tetramethyl-1,3,2-dioxaborolan-2-yl)pyrrolo[2,1-f][1,2,4]triazine (900 mg), 2-((6-bromo-2-methyl-1H-imidazo[4,5-b]pyridin-1-yl)methyl)-5-(difluoromethyl)-1,3,4-oxadiazole (305 mg), bis(di-tert-butyl(4-dimethylaminophenyl)phosphine)dichloropalladium (II) (30 mg), cesium carbonate (2 M in aqueous solution) (850 μL) and DME (8 mL) was stirred under microwave irradiation at 100° C. for 1 hour. The residue was purified by silica gel column chromatography (methanol/ethyl acetate) to obtain a solid. The obtained solid was crystallized from ethanol/water to obtain the title compound (88 mg).
$^1$H NMR (300 MHz, DMSO-$d_6$) δ 2.67 (3H, s), 3.96 (3H, s), 6.02 (2H, s), 7.05 (1H, d, J=2.7 Hz), 7.25-7.69 (1H, m), 8.07 (1H, d, J=2.7 Hz), 8.21-8.25 (2H, m), 8.59 (1H, d, J=2.1 Hz).

Example 243

1-((5-(1,1-difluoroethyl)-1,2,4-oxadiazol-3-yl)methyl)-6-(4-methoxypyrrolo[2,1-f][1,2,4]triazin-5-yl)-2-methyl-1H-imidazo[4,5-b]pyridine a) 3-((6-bromo-2-methyl-1H-imidazo[4,5-b]pyridin-1-yl)methyl)-5-(1,1-difluoroethyl)-1,2,4-oxadiazole Sodium carbonate (1.266 g) was added to a mixture of hydroxylamine monohydrochloride (0.850 g) and water (5.0 ml) at room temperature. The mixture was stirred for 10 minutes. Thereafter, to the mixture was added a mixture of 2-(6-bromo-2-methyl-1H-imidazo[4,5-b]pyridin-1-yl)acetonitrile (2.00 g) and ethanol (30 ml), and the resulting mixture was stirred under a nitrogen atmosphere at 70° C. for 1 hour. The reaction mixture was concentrated under reduced pressure, and diluted with water. Insolubles were collected by filtration, and washed with IPE to obtain a brown solid (1.589 g) as 2-(6-bromo-2-methyl-1H-imidazo[4,5-b]pyridin-1-yl)-N'-hydroxyacetimidamide. The obtained solid (500 mg) was added to a mixture of DIEA (0.867 ml), 2,2-difluoropropanoic acid (140 mg), propylphosphonic anhydride (50% in ethyl acetate solution) (1.477 ml) and ethyl acetate (4 ml) at room temperature, and the resulting mixture was stirred at room temperature for 2 days. The reaction mixture was concentrated under reduced pressure, and the residue was purified by NH silica gel column chromatography (ethyl acetate/hexane) to obtain the title compound (77 mg).

$^1$H NMR (300 MHz, DMSO-$d_6$) δ 2.14 (3H, t, J=19.8 Hz), 2.62 (3H, s), 5.88 (2H, s), 8.37 (1H, d, J=2.1 Hz), 8.44 (1H, d, J=2.1 Hz).

b) 1-((5-(1,1-difluoroethyl)-1,2,4-oxadiazol-3-yl)methyl)-6-(4-methoxypyrrolo[2,1-f][1,2,4]triazin-5-yl)-2-methyl-1H-imidazo[4,5-b]pyridine A mixture of 3-((6-bromo-2-methyl-1H-imidazo[4,5-b]pyridin-1-yl)methyl)-5-(1,1-difluoroethyl)-1,2,4-oxadiazole (77.0 mg), 4-methoxy-5-(4,4,5,5-tetramethyl-1,3,2-dioxaborolan-2-yl)pyrrolo[2,1-f][1,2,4]triazine (99 mg) bis(di-tert-butyl(4-dimethylaminophenyl)phosphine)dichloropalladium (II) (15 mg), cesium carbonate (2 M in aqueous solution) (0.20 mL) and DME (2.0 mL) was stirred under microwave irradiation at 100° C. for 30 minutes. The reaction mixture was purified by silica gel column chromatography (ethyl acetate/hexane and methanol/ethyl acetate), and the residue was crystallized from ethanol/ethyl acetate/heptane to obtain the title compound (19.00 mg).
$^1$H NMR (300 MHz, DMSO-$d_6$) δ 2.14 (3H, t, J=19.8 Hz), 2.67 (3H, s), 3.96 (3H, s), 5.90 (2H, s), 7.06 (1H, d, J=2.7 Hz), 8.07 (1H, d, J=2.7 Hz), 8.20-8.25 (2H, m), 8.58 (1H, d, J=2.0 Hz).

Example 250

6-(4-methoxypyrrolo[2,1-f][1,2,4]triazin-5-yl)-2-methyl-1-((5-(trifluoromethyl)-1,3,4-oxadiazol-2-yl)methyl)-1H-imidazo[4,5-b]pyridine a) 2-((6-bromo-2-methyl-1H-imidazo[4,5-b]pyridin-1-yl)methyl)-5-(trifluoromethyl)-1,3,4-oxadiazole A mixture of potassium tert-butoxide (2.80 g), 6-bromo-2-methyl-1H-imidazo[4,5-b]pyridine (5.00 g) and THF (60 mL) was stirred at 45° C. for 30 minutes. To the mixture were added TBAI (8.71 g) and 2-(chloromethyl)-5-(trifluoromethyl)-1,3,4-oxadiazole (5.00 g), and the resulting mixture was stirred at 45° C. for 1 hour. The mixture was neutralized with aqueous acetic acid, and extracted with ethyl acetate. The organic layer was washed with a saturated aqueous sodium hydrogen carbonate solution and a saturated brine, dried over magnesium sulfate, and then concentrated under reduced pressure. The residue was purified by NH silica gel column chromatography (ethyl acetate/hexane) to obtain the title compound (0.094 g).
$^1$H NMR (300 MHz, DMSO-$d_6$) δ 2.64 (3H, s), 6.00 (2H, s), 8.37 (1H, d, J=2.2 Hz), 8.45 (1H, d, J=2.2 Hz).

b) 6-(4-methoxypyrrolo[2,1-f][1,2,4]triazin-5-yl)-2-methyl-1-((5-(trifluoromethyl)-1,3,4-oxadiazol-2-yl)methyl)-1H-imidazo[4,5-b]pyridine A mixture of 4-methoxy-5-(4,4,5,5-tetramethyl-1,3,2-dioxaborolan-2-yl)pyrrolo[2,1-f][1,2,4]triazine (100 mg), 2-((6-bromo-2-methyl-1H-imidazo[4,5-b]pyridin-1-yl)methyl)-5-(trifluoromethyl)-1,3,4-oxadiazole (94 mg), bis(di-tert-butyl(4-dimethylaminophenyl)phosphine)dichloropalladium (II) (10 mg), cesium carbonate (2 M in aqueous solution) (250 μL) and DME (4 mL) was stirred under microwave irradiation at 100° C. for 40 minutes. The residue was purified by NH silica gel column chromatography (methanol/ethyl acetate) to obtain a solid. The obtained solid was crystallized from ethyl acetate/ethanol/heptane to obtain the title compound (18.50 mg).

$^1$H NMR (300 MHz, DMSO-d$_6$) δ 2.68 (3H, s), 3.97 (3H, s), 6.02 (2H, s), 7.05 (1H, d, J=2.7 Hz), 8.07 (1H, d, J=2.7 Hz), 8.19-8.27 (2H, m), 8.59 (1H, d, J=2.1 Hz).

Example 252

1-((5-ethyl-1,3,4-oxadiazol-2-yl)methyl)-6-(4-methoxypyrrolo[2,1-f][1,2,4]triazin-5-yl)-2-methyl-1H-imidazo[4,5-b]pyridine a) 2-((6-bromo-2-methyl-1H-imidazo[4,5-b]pyridin-1-yl)methyl)-5-ethyl-1,3,4-oxadiazole A solution of tert-butyl 2-(6-bromo-2-methyl-1H-imidazo[4,5-b]pyridin-1-yl)acetate (580 mg) in TFA (5 mL) was stirred at room temperature for 1 hour, and concentrated under reduced pressure. To a solution of the residue in ethyl acetate (6 ml) were added TEA (1.239 ml), propionohydrazide (220 mg) and propylphosphonic anhydride (50% in ethyl acetate solution) (3.70 ml) at room temperature, and the mixture was stirred overnight at 80° C., and stirred under microwave irradiation at 150° C. for 2 hours. The residue was purified by NH silica gel column chromatography (methanol/ethyl acetate) to obtain the title compound (325 mg).
$^1$H NMR (300 MHz, DMSO-d$_6$) δ 1.23 (3H, t, J=7.6 Hz), 2.61 (3H, s), 2.83 (2H, q, J=7.6 Hz), 5.86 (2H, s), 8.36 (1H, d, J=2.2 Hz), 8.44 (1H, d, J=2.2 Hz).

b) 1-((5-ethyl-1,3,4-oxadiazol-2-yl)methyl)-6-(4-methoxypyrrolo[2,1-f][1,2,4]triazin-5-yl)-2-methyl-1H-imidazo[4,5-b]pyridine A mixture of 2-((6-bromo-2-methyl-1H-imidazo[4,5-b]pyridin-1-yl)methyl)-5-ethyl-1,3,4-oxadiazole (100 mg), 4-methoxy-5-(4,4,5,5-tetramethyl-1,3,2-dioxaborolan-2-yl)pyrrolo[2,1-f][1,2,4]triazine (149 mg), bis(di-tert-butyl(4-dimethylaminophenyl)phosphine)dichloropalladium (II) (22 mg), cesium carbonate (2 M in aqueous solution) (0.24 mL) and DME (2.0 mL) was stirred under microwave irradiation at 100° C. for 20 minutes. The reaction mixture was purified by silica gel column chromatography (ethyl acetate/hexane acetate and methanol/ethyl acetate), and the residue was crystallized from ethanol/ethyl acetate/heptane to obtain the title compound (66.8 mg).
$^1$H NMR (300 MHz, DMSO-d$_6$) δ 1.22 (3H, t, J=7.5 Hz), 2.66 (3H, s), 2.78-2.89 (2H, m), 3.97 (3H, s), 5.88 (2H, s), 7.06 (1H, d, J=2.8 Hz), 8.07 (1H, d, J=2.6 Hz), 8.20 (1H, d, J=2.1 Hz), 8.23 (1H, s), 8.58 (1H, d, J=1.9 Hz).

Example 253

1-((5-cyclopropyl-1,3,4-oxadiazol-2-yl)methyl)-6-(4-methoxypyrrolo[2,1-f][1,2,4]triazin-5-yl)-2-methyl-1H-imidazo[4,5-b]pyridine a) 2-((6-bromo-2-methyl-1H-imidazo[4,5-b]pyridin-1-yl)methyl)-5-cyclopropyl-1,3,4-oxadiazole A solution of tert-butyl 2-(6-bromo-2-methyl-1H-imidazo[4,5-b]pyridin-1-yl)acetate (500 mg) in TFA (5.0 mL) was stirred at room temperature for 1 hour, and concentrated under reduced pressure. To a solution of the residue in ethyl acetate (2 ml) were added TEA (1.068 ml), cyclopropanecarbohydrazide (220 mg) and propylphosphonic anhydride (50% in ethyl acetate solution) (3.19 ml) at room temperature, and the mixture was stirred at room temperature for 1 hour, and stirred under microwave irradiation at 150° C. for 2 hours. The residue was purified by NH silica gel column chromatography (methanol/ethyl acetate) to obtain the title compound (61.2 mg).
$^1$H NMR (300 MHz, DMSO-d$_6$) δ 0.92-0.99 (2H, m), 1.07-1.15 (2H, m), 2.15-2.25 (1H, m), 2.60 (3H, s), 5.80 (2H, s), 8.35 (1H, d, J=2.2 Hz), 8.44 (1H, d, J=2.2 Hz).

b) 1-((5-cyclopropyl-1,3,4-oxadiazol-2-yl)methyl)-6-(4-methoxypyrrolo[2,1-f][1,2,4]triazin-5-yl)-2-methyl-1H-imidazo[4,5-b]pyridine A mixture of 2-((6-bromo-2-methyl-1H-imidazo[4,5-b]pyridin-1-yl)methyl)-5-cyclopropyl-1,3,4-oxadiazole (61.2 mg), 4-methoxy-5-(4,4,5,5-tetramethyl-1,3,2-dioxaborolan-2-yl)pyrrolo[2,1-f][1,2,4]triazine (88 mg), bis(di-tert-butyl(4-dimethylaminophenyl)phosphine)dichloropalladium (II) (13 mg), cesium carbonate (2 M in aqueous solution) (0.15 mL) and DME (2.0 mL) was stirred under microwave irradiation at 100° C. for 20 minutes. The reaction mixture was purified by silica gel column chromatography (ethyl acetate/hexane acetate and methanol/ethyl acetate), and the residue was crystallized from ethanol/ethyl acetate/heptane to obtain the title compound (28.0 mg).
$^1$H NMR (300 MHz, DMSO-d$_6$) δ 0.91-1.00 (2H, m), 1.04-1.16 (2H, m), 2.15-2.25 (1H, m), 2.65 (3H, s), 3.97 (3H, s), 5.83 (2H, s), 7.06 (1H, d, J=2.7 Hz), 8.07 (1H, d, J=2.7 Hz), 8.19 (1H, d, J=2.1 Hz), 8.23 (1H, s), 8.58 (1H, d, J=2.1 Hz).

Example 267

1-((5-isopropyl-1,3,4-oxadiazol-2-yl)methyl)-6-(4-methoxypyrrolo[2,1-f][1,2,4]triazin-5-yl)-2-methyl-1H-imidazo[4,5-b]pyridine a) 2-((6-bromo-2-methyl-1H-imidazo[4,5-b]pyridin-1-yl)methyl)-5-isopropyl-1,3,4-oxadiazole A mixture of isobutyric acid (180 μL), TEA (1.10 mL), 2-(6-bromo-2-methyl-1H-imidazo[4,5-b]pyridin-1-yl)acetohydrazide (450 mg), propylphosphonic anhydride (50% in ethyl acetate solution) (3.30 ml) and ethyl acetate (2.0 ml) was stirred under microwave irradiation at 150° C. for 30 minutes. The reaction mixture was purified by NH silica gel column chromatography (methanol/ethyl acetate) to obtain the title compound (337 mg).
$^1$H NMR (300 MHz, DMSO-d$_6$) δ 1.27 (6H, d, J=7.0 Hz), 2.61 (3H, s), 3.10-3.24 (1H, m), 5.86 (2H, s), 8.36 (1H, d, J=2.2 Hz), 8.44 (1H, d, J=2.2 Hz).

b) 1-((5-isopropyl-1,3,4-oxadiazol-2-yl)methyl)-6-(4-methoxypyrrolo[2,1-f][1,2,4]triazin-5-yl)-2-methyl-1H-imidazo[4,5-b]pyridine A mixture of 2-((6-bromo-2-methyl-1H-imidazo[4,5-b]pyridin-1-yl)methyl)-5-isopropyl-1,3,4-oxadiazole (100 mg), 4-methoxy-5-(4,4,5,5-tetramethyl-1,3,2-dioxaborolan-2-yl)pyrrolo[2,1-f][1,2,4]triazine (143 mg), bis(di-tert-butyl(4-dimethylaminophenyl)phosphine)dichloropalladium (II) (20 mg), cesium carbonate (2 M in aqueous solution) (0.24 mL) and DME (2.0 mL) was stirred under microwave irradiation at 100° C. for 20 minutes. The reaction mixture was purified by silica gel column chromatography (ethyl acetate/hexane and methanol/ethyl acetate), and the residue was crystallized from ethanol/ethyl acetate/heptane to obtain the title compound (61.1 mg).

¹H NMR (300 MHz, DMSO-d₆) δ 1.26 (6H, d, J=6.9 Hz), 2.66 (3H, s), 3.12-3.23 (1H, m), 3.96 (3H, s), 5.88 (2H, s), 7.06 (1H, d, J=2.7 Hz), 8.07 (1H, d, J=2.7 Hz), 8.20 (1H, d, J=2.0 Hz), 8.23 (1H, s), 8.58 (1H, d, J=2.0 Hz).

Example 268

1-((5-cyclobutyl-1,3,4-oxadiazol-2-yl)methyl)-6-(4-methoxypyrrolo[2,1-f][1,2,4]triazin-5-yl)-2-methyl-1H-imidazo[4,5-b]pyridine a) 2-((6-bromo-2-methyl-1H-imidazo[4,5-b]pyridin-1-yl)methyl)-5-cyclobutyl-1,3,4-oxadiazole A mixture of cyclobutanecarboxylic acid (130 μL), TEA (0.73 ml), 2-(6-bromo-2-methyl-1H-imidazo[4,5-b]pyridin-1-yl)acetohydrazide (300 mg), propylphosphonic anhydride (50% in ethyl acetate solution) (2.10 ml) and ethyl acetate (2.0 ml) was stirred under microwave irradiation at 150° C. for 30 minutes. The reaction mixture was purified by NH silica gel column chromatography (methanol/ethyl acetate), and the residue was washed with ethyl acetate/heptane to obtain the title compound (210 mg).
¹H NMR (300 MHz, DMSO-d₆) δ 2.02 (2H, s), 2.20-2.41 (4H, m), 2.61 (3H, s), 3.67-3.82 (1H, m), 5.85 (2H, s), 8.37 (1H, d, J=2.2 Hz), 8.44 (1H, d, J=2.2 Hz).

b) 1-((5-cyclobutyl-1,3,4-oxadiazol-2-yl)methyl)-6-(4-methoxypyrrolo[2,1-f][1,2,4]triazin-5-yl)-2-methyl-1H-imidazo[4,5-b]pyridine A mixture of 2-((6-bromo-2-methyl-1H-imidazo[4,5-b]pyridin-1-yl)methyl)-5-cyclobutyl-1,3,4-oxadiazole (100 mg), 4-methoxy-5-(4,4,5,5-tetramethyl-1,3,2-dioxaborolan-2-yl)pyrrolo[2,1-f][1,2,4]triazine (138 mg), bis(di-tert-butyl(4-dimethylaminophenyl)phosphine)dichloropalladium (II) (20 mg), cesium carbonate (2 M in aqueous solution) (0.24 mL) and DME (2.0 mL) was stirred under microwave irradiation at 100° C. for 20 minutes. The reaction mixture was purified by silica gel column chromatography (ethyl acetate/hexane and methanol/ethyl acetate), and the residue was crystallized from ethanol/ethyl acetate/heptane to obtain the title compound (67.1 mg).
¹H NMR (300 MHz, DMSO-d₆) δ 1.84-2.11 (2H, m), 2.21-2.39 (4H, m), 2.66 (3H, s), 3.66-3.82 (1H, m), 3.96 (3H, s), 5.88 (2H, s), 7.06 (1H, d, J=2.7 Hz), 8.07 (1H, d, J=2.7 Hz), 8.20 (1H, d, J=2.1 Hz), 8.23 (1H, s), 8.58 (1H, d, J=2.1 Hz).

Example 269

1-((5-(3,3-difluorocyclobutyl)-1,3,4-oxadiazol-2-yl)methyl)-6-(4-methoxypyrrolo[2,1-f][1,2,4]triazin-5-yl)-2-methyl-1H-imidazo[4,5-b]pyridine a) 2-((6-bromo-2-methyl-1H-imidazo[4,5-b]pyridin-1-yl)methyl)-5-(3,3-difluorocyclobutyl)-1,3,4-oxadiazole A mixture of 3,3-difluorocyclobutanecarboxylic acid (180 mg), TEA (0.73 ml), 2-(6-bromo-2-methyl-1H-imidazo[4,5-b]pyridin-1-yl)acetohydrazide (300 mg), propylphosphonic anhydride (50% in ethyl acetate solution) (2.10 ml) and ethyl acetate (2.0 ml) was stirred under microwave irradiation at 150° C. for 20 minutes. The reaction mixture was purified by NH silica gel column chromatography (methanol/ethyl acetate) to obtain the title compound (209 mg).
¹H NMR (300 MHz, DMSO-d₆) δ 2.62 (3H, s), 2.83-3.21 (4H, m), 3.62-3.80 (1H, m), 5.86 (2H, s), 8.36 (1H, d, J=2.2 Hz), 8.44 (1H, d, J=2.2 Hz).

b) 1-((5-(3,3-difluorocyclobutyl)-1,3,4-oxadiazol-2-yl)methyl)-6-(4-methoxypyrrolo[2,1-f][1,2,4]triazin-5-yl)-2-methyl-1H-imidazo[4,5-b]pyridine A mixture of 2-((6-bromo-2-methyl-1H-imidazo[4,5-b]pyridin-1-yl)methyl)-5-(3,3-difluorocyclobutyl)-1,3,4-oxadiazole (100 mg), 4-methoxy-5-(4,4,5,5-tetramethyl-1,3,2-dioxaborolan-2-yl)pyrrolo[2,1-f][1,2,4]triazine (315 mg) bis(di-tert-butyl(4-dimethylaminophenyl)phosphine) dichloropalladium (II) (20 mg), cesium carbonate (2 M in aqueous solution) (0.20 mL) and DME (2.0 mL) was stirred under microwave irradiation at 100° C. for 20 minutes. The reaction mixture was purified by silica gel column chromatography (ethyl acetate/hexane and methanol/ethyl acetate), and the residue was crystallized from ethanol/ethyl acetate/heptane to obtain the title compound (61.1 mg).
¹H NMR (300 MHz, DMSO-d₆) δ 2.67 (3H, s), 2.85-3.17 (4H, m), 3.72 (1H, d, J=7.9 Hz), 3.97 (3H, s), 5.89 (2H, s), 7.06 (1H, d, J=2.8 Hz), 8.07 (1H, d, J=2.8 Hz), 8.21 (1H, d, J=2.1 Hz), 8.23 (1H, s), 8.58 (1H, d, J=2.1 Hz).

Example 273

6-(4-methoxypyrrolo[2,1-f][1,2,4]triazin-5-yl)-1,2-dimethyl-1H-imidazo[4,5-b]pyridine a) 6-bromo-1,2-dimethyl-1H-imidazo[4,5-b]pyridine Potassium hydroxide (15.88 g) was added to a solution of 6-bromo-2-methyl-1H-imidazo[4,5-b]pyridine (15 g) and iodomethane (5.31 mL) in THF (150 mL) at room temperature. Under a nitrogen atmosphere, the mixture was stirred at 60° C. for 3 hours. The reaction mixture was poured into hydrochloric acid (1N in aqueous solution) at room temperature, and extracted with ethyl acetate. The organic layer was washed with water and a saturated brine, dried over magnesium sulfate, and then concentrated. The residue was purified by NH silica gel column chromatography (ethyl acetate/hexane) to obtain the title compound (8.3 g).
¹H NMR (300 MHz, DMSO-d₆) δ 2.57 (3H, s), 3.75 (3H, s), 8.29 (1H, d, J=2.26 Hz), 8.37 (1H, d, J=2.26 Hz).

b) 6-(4-methoxypyrrolo[2,1-f][1,2,4]triazin-5-yl)-1,2-dimethyl-1H-imidazo[4,5-b]pyridine A mixture of 6-bromo-1,2-dimethyl-1H-imidazo[4,5-b]pyridine (70 mg), 4-methoxy-5-(4,4,5,5-tetramethyl-1,3,2-dioxaborolan-2-yl)pyrrolo[2,1-f][1,2,4]triazine (135 mg), bis(di-tert-butyl(4-dimethylaminophenyl)phosphine)dichloropalladium (II) (10.41 mg), cesium carbonate (2 M in aqueous solution) (0.464 mL) and DME (12 mL) was stirred under microwave irradiation at 100° C. for 40 minutes. The reaction mixture was poured into ice water at room temperature, and extracted with ethyl acetate. The organic layer was sequentially washed with water and a saturated brine, then dried over magnesium sulfate, and concentrated under reduced pressure. The mixture was purified by NH silica gel column chromatography (methanol/ethyl acetate), and the residue was washed with ethyl acetate/IPE to obtain the title compound (27 mg).
¹H NMR (300 MHz, DMSO-d₆) δ2.60 (3H, s), 3.80 (3H, s), 4.02 (3H, s), 7.08 (1H, d, J 5=2.7 Hz), 7.99-8.12 (2H, m), 8.23 (1H, s), 8.53 (1H, d, J=2.1 Hz).

Example 274

1-((5-(1,1-(difluoroethyl)-1,3,4-oxadiazol-2-yl)methyl)-6-(4-methoxypyrrolo[2,1-f][1,2,4]triazin-5-yl)-2-methyl-1H-imidazo[4,5-b]pyridine a) 2-((6-bromo-2-methyl-1H-imidazo[4,5-b]pyridin-1-yl)methyl)-5-(1,1-difluoroethyl)-1,3,4-oxadiazole Propylphosphonic anhydride (50% in ethyl acetate solution) (2.57 mL) was added to a suspension of triethylamine (0.859 mL), 2-(6-bromo-2-methyl-1H-imidazo[4,5-b]pyridin-1-yl)acetohydrazide (350 mg) and 2,2-difluoropropanoic acid (200 mg) in ethyl acetate (2 mL) at room temperature. The mixture was stirred under microwave irradiation at 150° C. for 30 minutes. The residue was purified by NH silica gel column chromatography (ethyl acetate/hexane) to obtain the title compound (135 mg).

$^1$H NMR (300 MHz, DMSO-d$_6$) δ 2.15 (3H, t, J=19.5 Hz), 2.63 (3H, s), 5.97 (2H, s), 8.39 (1H, d, J=2.2 Hz), 8.45 (1H, d, J=2.2 Hz).

b) 1-((5-(1,1-difluoroethyl)-1,3,4-oxadiazol-2-yl)methyl)-6-(4-methoxypyrrolo[2,1-f][1,2,4]triazin-5-yl)-2-methyl-1H-imidazo[4,5-b]pyridine A mixture of 4-methoxy-5-(4,4,5,5-tetramethyl-1,3,2-dioxaborolan-2-yl)pyrrolo[2,1-f][1,2,4]triazine (135 mg), 2-((6-bromo-2-methyl-1H-imidazo[4,5-b]pyridin-1-yl)methyl)-5-(1,1-difluoroethyl)-1,3,4-oxadiazole (130 mg), bis (di-tert-butyl(4-dimethylaminophenyl)phosphine)dichloropalladium (II) (15 mg), cesium carbonate (2 M in aqueous solution) (300 µL) and DME (4 mL) was stirred under microwave irradiation at 100° C. for 40 minutes. The residue was purified by NH silica gel column chromatography (methanol/ethyl acetate) and silica gel column chromatography (methanol/ethyl acetate) to obtain a solid. The solid was purified by preparative HPLC (C18, mobile phase: water/acetonitrile (10 mM ammonium hydrogen carbonate-containing system)), and the target fraction was concentrated under reduced pressure, and then crystallized from ethanol/water to obtain the title compound (38.8 mg).

$^1$H NMR (300 MHz, DMSO-d$_6$) δ 2.15 (3H, t, J=19.5 Hz), 2.67 (3H, s), 3.96 (3H, s), 6.01 (2H, s), 7.05 (1H, d, J=2.7 Hz), 8.07 (1H, d, J=2.7 Hz), 8.23 (1H, s), 8.24 (1H, d, J=2.1 Hz), 8.59 (1H, d, J=2.1 Hz).

Example 276

1-((5-(2,2-difluorocyclopropyl)-1,3,4-oxadiazol-2-yl)methyl)-6-(4-methoxypyrrolo[2,1-f][1,2,4]triazin-5-yl)-2-methyl-1H-imidazo[4,5-b]pyridine a) 2-((6-bromo-2-methyl-1H-imidazo[4,5-b]pyridin-1-yl)methyl)-5-(2,2-difluorocyclopropyl)-1,3,4-oxadiazole Propylphosphonic anhydride (50% in ethyl acetate solution) (2.200 mL) was added to a suspension of triethylamine (0.736 mL), 2-(6-bromo-2-methyl-1H-imidazo[4,5-b]pyridin-1-yl)acetohydrazide (300 mg) and 2,2-difluorocyclopropanecarboxylic acid (150 mg) in ethyl acetate (6 mL) at room temperature. The mixture was stirred under microwave irradiation at 150° C. for 30 minutes. The residue was purified by NH silica gel column chromatography (methanol/ethyl acetate) to obtain the title compound (230 mg).

$^1$H NMR (300 MHz, DMSO-d$_6$) δ 2.04-2.23 (1H, m), 2.25-2.44 (1H, m), 2.61 (3H, s), 3.41-3.60 (1H, m), 5.89 (2H, s), 8.37 (1H, d, J=2.1 Hz), 8.44 (1H, d, J=2.1 Hz).

b) 1-((5-(2,2-difluorocyclopropyl)-1,3,4-oxadiazol-2-yl)methyl)-6-(4-methoxypyrrolo[2,1-f][1,2,4]triazin-5-yl)-2-methyl-1H-imidazo[4,5-b]pyridine A mixture of 4-methoxy-5-(4,4,5,5-tetramethyl-1,3,2-dioxaborolan-2-yl)pyrrolo[2,1-f][1,2,4]triazine (550 mg), 2-((6-bromo-2-methyl-1H-imidazo[4,5-b]pyridin-1-yl)methyl)-5-(2,2-difluorocyclopropyl)-1,3,4-oxadiazole (220 mg), bis (di-tert-butyl(4-dimethylaminophenyl)phosphine)dichloropalladium (II) (20 mg), cesium carbonate (2 M in aqueous solution) (300 µL) and DME (4 mL) was stirred under microwave irradiation at 100° C. for 40 minutes. The residue was purified by silica gel column chromatography (ethyl acetate/hexane and methanol/ethyl acetate) to obtain the title compound (98 mg).

$^1$H NMR (300 MHz, DMSO-d$_6$) δ 2.09-2.23 (1H, m), 2.28-2.39 (1H, m), 2.66 (3H, s), 3.42-3.57 (1H, m), 3.96 (3H, s), 5.92 (2H, s), 7.06 (1H, d, J=2.7 Hz), 8.07 (1H, d, J=2.7 Hz), 8.21 (1H, d, J=2.1 Hz), 8.23 (1H, s), 8.58 (1H, d, J=2.1 Hz).

Example 277

1-((5-(2-fluoropropan-2-yl)-1,3,4-oxadiazol-2-yl)methyl)-6-(4-methoxypyrrolo[2,1-f][1,2,4]triazin-5-yl)-2-methyl-1H-imidazo[4,5-b]pyridine a) 2-((6-bromo-2-methyl-1H-imidazo[4,5-b]pyridin-1-yl)methyl)-5-(2-fluoropropan-2-yl)-1,3,4-oxadiazole Propylphosphonic anhydride (50% in ethyl acetate solution) (2.200 mL) was added to a suspension of triethylamine (0.736 mL), 2-(6-bromo-2-methyl-1H-imidazo[4,5-b]pyridin-1-yl)acetohydrazide (300 mg) and 2-fluoro-2-methylpropanoic acid (127 mg) in ethyl acetate (6 mL) at room temperature. The mixture was stirred under microwave irradiation at 130° C. for 30 minutes. The residue was purified by NH silica gel column chromatography (methanol/ethyl acetate) to obtain the title compound (224 mg).

$^1$H NMR (300 MHz, DMSO-d$_6$) δ 1.79 (6H, d, J=21.9 Hz), 2.62 (3H, s), 5.93 (2H, s), 8.39 (1H, d, J=2.2 Hz), 8.45 (1H, d, J=2.2 Hz).

b) 1-((5-(2-fluoropropan-2-yl)-1,3,4-oxadiazol-2-yl)methyl)-6-(4-methoxypyrrolo[2,1-f][1,2,4]triazin-5-yl)-2-methyl-1H-imidazo[4,5-b]pyridine A mixture of 4-methoxy-5-(4,4,5,5-tetramethyl-1,3,2-dioxaborolan-2-yl)pyrrolo[2,1-f][1,2,4]triazine (300 mg), 2-((6-bromo-2-methyl-1H-imidazo[4,5-b]pyridin-1-yl)methyl)-5-(2-fluoropropan-2-yl)-1,3,4-oxadiazole (110 mg), bis (di-tert-butyl(4-dimethylaminophenyl)phosphine)dichloropalladium (II) (10 mg), cesium carbonate (2 M in aqueous solution) (300 µL) and DME (4 mL) was stirred under microwave irradiation at 100° C. for 40 minutes. The residue was purified by silica gel column chromatography (ethyl acetate/hexane and methanol/ethyl acetate) to obtain a solid. The obtained solid was crystallized from ethyl acetate/ethanol/heptane to obtain the title compound (47.0 mg).

¹H NMR (300 MHz, DMSO-d₆) δ 1.78 (6H, d, J=21.9 Hz), 2.67 (3H, s), 3.95 (3H, s), 5.97 (2H, s), 7.05 (1H, d, J=2.7 Hz), 8.07 (1H, d, J=2.7 Hz), 8.18-8.27 (2H, m), 8.59 (1H, d, J=2.0 Hz).

Example 279

1-((5-(1-fluoroethyl)-1,3,4-oxadiazol-2-yl)methyl)-6-(4-methoxypyrrolo[2,1-f][1,2,4]triazin-5-yl)-2-methyl-1H-imidazo[4,5-b]pyridine a) 2-((6-bromo-2-methyl-1H-imidazo[4,5-b]pyridin-1-yl)methyl)-5-(1-fluoroethyl)-1,3,4-oxadiazole A mixture of 2-fluoropropanoic acid (137 mg), Et3N (0.86 mL), propylphosphonic anhydride (50% in ethyl acetate solution) (2.2 mL), 2-(6-bromo-2-methyl-1H-imidazo[4,5-b]pyridin-1-yl)acetohydrazide (350 mg) and ethyl acetate (2.0 mL) was stirred under microwave irradiation at 135° C. for 30 minutes. The mixture was purified by NH silica gel column chromatography (methanol/ethyl acetate) to obtain the title compound (188 mg).
MS: [M+H]⁺ 340.0.

b) 1-((5-(1-fluoroethyl)-1,3,4-oxadiazol-2-yl)methyl)-6-(4-methoxypyrrolo[2,1-f][1,2,4]triazin-5-yl)-2-methyl-1H-imidazo[4,5-b]pyridine A mixture of 2-((6-bromo-2-methyl-1H-imidazo[4,5-b]pyridin-1-yl)methyl)-5-(1-fluoroethyl)-1,3,4-oxadiazole (186 mg), 4-methoxy-5-(4,4,5,5-tetramethyl-1,3,2-dioxaborolan-2-yl)pyrrolo[2,1-f][1,2,4]triazine (500 mg) bis(di-tert-butyl(4-dimethylaminophenyl)phosphine)dichloropalladium (II) (30 mg), cesium carbonate (2 M in aqueous solution) (0.478 mL) and DME (2.5 mL) was stirred under microwave irradiation at 100° C. for 1 hour. The mixture was purified by NH silica gel column chromatography (hexane/ethyl acetate), and the obtained solid was washed with IPE to obtain the title compound (80 mg).
¹H NMR (300 MHz, DMSO-d₆) δ 1.60-1.81 (3H, m), 2.67 (3H, s), 3.96 (3H, s), 5.85-6.13 (3H, m), 7.06 (1H, d, J=2.7 Hz), 8.07 (1H, d, J=2.8 Hz), 8.18-8.27 (2H, m), 8.59 (1H, d, J=2.1 Hz).

Example 280

6-(4-methoxypyrrolo[2,1-f][1,2,4]triazin-5-yl)-2-methyl-1-(1,2,3-thiazol-4-ylmethyl)-1H-imidazo[4,5-b]pyridine a) N-(2-amino-5-bromopyridin-3-yl)-1,2,3-thiadiazole-4-carboxamide A mixture of 5-bromopyridine-2,3-diamine (723 mg), 1,2,3-thiadiazole-4-carboxylic acid (500 mg), HATU (2050 mg), Et3N (1.6 mL) and DMF (8 mL) was stirred overnight at room temperature. The mixture was diluted with a saturated aqueous sodium hydrogen carbonate solution, and extracted with ethyl acetate. The organic layer was washed with a saturated brine, then dried over magnesium sulfate, and concentrated under reduced pressure. The residue was purified by silica gel column chromatography (ethyl acetate/hexane) to obtain the title compound (754 mg). The title compound was used for the subsequent reaction without being further purified.
MS: [M+H]⁺ 299.9.

b) N3-((1,2,3-thiadiazol-4-yl)methyl)-5-bromopyridine-2,3-diamine

A BH3-THF complex (1M in THF solution) (10 mL) was added dropwise to a solution of N-(2-amino-5-bromopyridin-3-yl)-1,2,3-thiadiazole-4-carboxamide (754 mg) in THF (10 mL) at room temperature. The mixture was stirred under a nitrogen atmosphere at 60° C. for 2 hours. The reaction was stopped with water at room temperature, and the mixture was then acidified with HCl (1 N in aqueous solution). The mixture was stirred at 60° C. for 30 minutes. The mixture was neutralized with a saturated aqueous sodium hydrogen carbonate solution at room temperature, and then extracted with ethyl acetate. The organic layer was washed with a saturated brine, then dried over magnesium sulfate, and concentrated under reduced pressure. The residue was purified by silica gel column chromatography (ethyl acetate/methanol) to obtain the title compound (135 mg).
MS: [M+H]⁺ 286.2.

c) 4-((6-bromo-2-methyl-1H-imidazo[4,5-b]pyridin-1-yl)methyl)-1,2,3-thiadiazole

A mixture of N3-((1,2,3-thiadiazol-4-yl)methyl)-5-bromopyridine-2,3-diamine (135 mg), acetic acid (0.045 mL), DMAP (8 mg), propylphosphonic anhydride (1.7 M in ethyl acetate solution) (0.505 mL), DIPEA (0.164 mL) and THF (1.5 mL) was stirred under microwave irradiation at 140° C. for 50 minutes. The residue was purified by NH silica gel column chromatography (methanol/ethyl acetate) to obtain the title compound (90 mg).
MS: [M+H]⁺ 309.9.

d) 6-(4-methoxypyrrolo[2,1-f][1,2,4]triazin-5-yl)-2-methyl-1-(1,2,3-thiazol-4-ylmethyl)-1H-imidazo[4,5-b]pyridine A mixture of 4-((6-bromo-2-methyl-1H-imidazo[4,5-b]pyridin-1-yl)methyl)-1,2,3-thiadiazole (89 mg), 4-methoxy-5-(4,4,5,5-tetramethyl-1,3,2-dioxaborolan-2-yl)pyrrolo[2,1-f][1,2,4]triazine (317 mg), bis(di-tert-butyl(4-dimethylaminophenyl)phosphine)dichloropalladium (II) (19 mg), cesium carbonate (2 M in aqueous solution) (0.30 mL) and DME (1.5 mL) was stirred under microwave irradiation at 100° C. for 1 hour. The mixture was purified by NH silica gel column chromatography (hexane/ethyl acetate), and the obtained solid was washed with IPE to obtain the title compound (32.0 mg).
¹H NMR (300 MHz, DMSO-d₆) δ 2.75 (3H, s), 3.92 (3H, s), 6.01 (2H, s), 7.05 (1H, d, J=2.8 Hz), 8.06 (1H, d, J=2.7 Hz), 8.22 (1H, s), 8.27 (1H, d, J=2.1 Hz), 8.55 (1H, d, J=2.0 Hz), 9.29 (1H, s).

Example 281

6-(4-methoxypyrrolo[2,1-f][1,2,4]triazin-5-yl)-2-methyl-1-((5-(2,2,2-trifluoroethyl)-1,3,4-oxadiazol-2-yl)methyl)-1H-imidazo[4,5-b]pyridine a) N'-(2-(6-bromo-2-methyl-1H-imidazo[4,5-b]pyridin-1-yl)acetyl)-3,3,3-trifluoropropanehydrazide 3,3,3-trifluoropropanoyl chloride (185 mg) was added to a solution of 2-(6-bromo-2-methyl-1H-imidazo[4,5-b]pyridin-1-yl)acetohydrazide (300 mg) in DMA (3 mL) at room temperature, and the mixture was stirred for 1 hour. The reaction mixture was purified by NH silica gel column chromatography (methanol/ethyl acetate) to obtain the title compound (370 mg).
MS: [M+H]$^+$ 393.9.

b) 2-((6-bromo-2-methyl-1H-imidazo[4,5-b]pyridin-1-yl)methyl)-5-(2,2,2-trifluoroethyl)-1,3,4-oxadiazole pTsCl (470 mg) was added to a mixture of TEA (600 µl), trimethylamine monohydrochloride (198 mg), N'-(2-(6-bromo-2-methyl-1H-imidazo[4,5-b]pyridin-1-yl)acetyl)-3,3,3-trifluoropropanehydrazide (369.9 mg) and acetonitrile (10 ml) at room temperature, and the mixture was stirred overnight at room temperature. The reaction mixture was purified by silica gel column chromatography (ethyl acetate/hexame and methanol/ethyl acetate) to obtain the title compound (210 mg).
$^1$H NMR (300 MHz, DMSO-d$_6$) δ 2.61 (3H, s), 4.32 (2H, d, J=10.6 Hz), 5.95 (2H, s), 8.37 (1H, d, J=2.2 Hz), 8.45 (1H, d, J=2.2 Hz).

c) 6-(4-methoxypyrrolo[2,1-f][1,2,4]triazin-5-yl)-2-methyl-1-((5-(2,2,2-trifluoroethyl)-1,3,4-oxadiazol-2-yl)methyl)-1H-imidazo[4,5-b]pyridine A mixture of 2-((6-bromo-2-methyl-1H-imidazo[4,5-b]pyridin-1-yl)methyl)-5-(2,2,2-trifluoroethyl)-1,3,4-oxadiazole (210 mg), 4-methoxy-5-(4,4,5,5-tetramethyl-1,3,2-dioxaborolan-2-yl)pyrrolo[2,1-f][1,2,4]triazine (676 mg) bis(di-tert-butyl(4-dimethylaminophenyl)phosphine)dichloropalladium (II) (20 mg), cesium carbonate (2 M in aqueous solution) (0.40 mL) and DME (4.0 mL) was stirred under microwave irradiation at 100° C. for 20 minutes. The reaction mixture was purified by silica gel column chromatography (ethyl acetate/hexane and methanol/ethyl acetate), and the residue was crystallized from ethanol/ethyl acetate/heptane to obtain the title compound (49.6 mg).
$^1$H NMR (300 MHz, DMSO-d$_6$) δ 2.66 (3H, s), 3.95 (3H, s), 4.27-4.41 (2H, m), 5.98 (2H, s), 7.06 (1H, d, J=2.7 Hz), 8.07 (1H, d, J=2.7 Hz), 8.21 (1H, d, J=2.1 Hz), 8.23 (1H, s), 8.59 (1H, d, J=2.1 Hz).

Example 282

6-(4-methoxypyrrolo[2,1-f][1,2,4]triazin-5-yl)-2-methyl-1-(1,2,3-thiazol-5-ylmethyl)-1H-imidazo[4,5-b]pyridine a) N-(2-amino-5-bromopyridin-3-yl)-1,2,3-thiadiazole-5-carboxamide TEA (2.4 ml) was added to a mixture of 5-bromopyridine-2,3-diamine (1.08 g), 1,2,3-thiadiazole-5-carboxylic acid (760 mg), HATU (2.93 g) and DMF (12 ml) at room temperature, and the mixture was stirred overnight. The reaction mixture was diluted with a saturated aqueous sodium hydrogen carbonate solution, and extracted with ethyl acetate. The organic layer was washed with a saturated brine, dried over sodium sulfate, and concentrated under reduced pressure. The residue was purified by silica gel column chromatography (ethyl acetate/hexane) to obtain the title compound (0.900 g).
$^1$H NMR (300 MHz, DMSO-d$_6$) δ 6.36 (2H, s), 7.74 (1H, d, J=2.3 Hz), 7.98 (1H, d, J=2.3 Hz), 9.49 (1H, s), 10.34 (1H, s).

b) N3-((1,2,3-thiadiazol-5-yl)methyl)-5-bromopyridine-2,3-diamine

A borane-THF complex (1.0 M) (10 ml) was added to a mixture of N-(2-amino-5-bromopyridin-3-yl)-1,2,3-thiadiazole-5-carboxamide (0.90 g) and THF (10 ml) at 0° C., and the mixture was stirred overnight under a nitrogen atmosphere at room temperature. To the reaction mixture were added methanol and hydrochloric acid (1N) at 0° C., and the mixture was stirred at room temperature for 3 hours, and concentrated under reduced pressure. The residue was poured into an aqueous potassium carbonate solution, and extracted with ethyl acetate. The organic layer was washed with water and a saturated brine, dried over sodium sulfate, and concentrated under reduced pressure. The residue was purified by silica gel column chromatography (ethyl acetate/hexane) to obtain the title compound (0.330 g).
$^1$H NMR (300 MHz, DMSO-d$_6$) δ 4.83 (2H, d, J=5.9 Hz), 5.77 (2H, s), 5.96 (1H, t, J=5.9 Hz), 6.76 (1H, d, J=2.1 Hz), 7.37 (1H, d, J=2.1 Hz), 8.92 (1H, s).

c) 5-((6-bromo-2-methyl-1H-imidazo[4,5-b]pyridin-1-yl)methyl)-1,2,3-thiadiazole

A mixture of acetic acid (130 µl), DMAP (5.0 mg), DIEA (0.403 ml), N3-((1,2,3-thiadiazol-5-yl)methyl)-5-bromopyridine-2,3-diamine (330 mg), propylphosphonic anhydride (50% in ethyl acetate solution) (1.2 ml) and THF (6.0 ml) was stirred under microwave irradiation at 150° C. for 1 hour. The residue was purified by silica gel column chromatography (ethyl acetate/hexane and methanol/ethyl acetate) to obtain the title compound (220 mg).
$^1$H NMR (300 MHz, DMSO-d$_6$) δ 2.61 (3H, s), 6.04 (2H, d, J=0.7 Hz), 8.44 (2H, d, J=1.3 Hz), 8.90 (1H, s).

d) 6-(4-methoxypyrrolo[2,1-f][1,2,4]triazin-5-yl)-2-methyl-1-(1,2,3-thiazol-5-ylmethyl)-1H-imidazo[4,5-b]pyridine A mixture of 5-((6-bromo-2-methyl-1H-imidazo[4,5-b]pyridin-1-yl)methyl)-1,2,3-thiadiazole (210 mg), 4-methoxy-5-(4,4,5,5-tetramethyl-1,3,2-dioxaborolan-2-yl)pyrrolo[2,1-f][1,2,4]triazine (820 mg), bis(di-tert-butyl(4-dimethylaminophenyl)phosphine)dichloropalladium (II) (40 mg), cesium carbonate (2 M in aqueous solution) (0.45 mL) and DME (4.0 mL) was stirred under microwave irradiation at 100° C. for 50 minutes. The reaction mixture was purified by silica gel column chromatography (ethyl acetate/hexane and methanol/ethyl acetate) and NH silica gel column chromatography (methanol/ethyl acetate), and the residue was crystallized from ethanol/ethyl acetate/heptane to obtain the title compound (49.6 mg).
$^1$H NMR (300 MHz, DMSO-d$_6$) δ 2.66 (3H, s), 3.85 (3H, s), 6.08 (2H, s), 7.06 (1H, d, J=2.8 Hz), 8.07 (1H, d, J=2.7 Hz), 8.20-8.23 (2H, m), 8.58 (1H, d, J=2.0 Hz), 8.92 (1H, s).

Example 283

1-((5-(1-fluorocyclopropyl)-1,3,4-oxadiazol-2-yl)methyl)-6-(4-methoxypyrrolo[2,1-f][1,2,4]triazin-5-yl)-2-methyl-1H-imidazo[4,5-b]pyridine a) 2-((6-bromo-2-methyl-1H-imidazo[4,5-b]pyridin-1-yl)methyl)-5-(1-fluorocyclopropyl)-1,3,4-oxadiazole Propylphosphonic anhydride (50% in ethyl acetate solution) (0.917 mL) was added to a suspension of triethylamine (0.307 mL), 2-(6-bromo-2-methyl-1H-imidazo[4,5-b]pyridin-1-yl)acetohydrazide (125 mg) and 1-fluorocyclopropanecarboxylic acid (50 mg) in ethyl acetate (2 mL) at room temperature. The mixture was stirred under microwave irradiation at 150° C. for 30 minutes. The residue was purified by NH silica gel column chromatography (ethyl acetate/hexane) to obtain the title compound (84 mg).

$^1$H NMR (300 MHz, DMSO-$d_6$) δ 1.32-1.44 (2H, m), 1.61-1.77 (2H, m), 2.62 (3H, s), 5.90 (2H, s), 8.38 (1H, d, J=2.2 Hz), 8.44 (1H, d, J=2.2 Hz).

b) 2-((6-bromo-2-methyl-1H-imidazo[4,5-b]pyridin-1-yl)methyl)-5-(1-fluorocyclopropyl)-1,3,4-oxadiazole A mixture of 4-methoxy-5-(4,4,5,5-tetramethyl-1,3,2-dioxaborolan-2-yl)pyrrolo[2,1-f][1,2,4]triazine (245 mg), 2-((6-bromo-2-methyl-1H-imidazo[4,5-b]pyridin-1-yl)methyl)-5-(1-fluorocyclopropyl)-1,3,4-oxadiazole (84 mg), bis (di-tert-butyl(4-dimethylaminophenyl)phosphine)dichloropalladium (II) (20 mg), cesium carbonate (2 M in aqueous solution) (220 μL) and DME (4 mL) was stirred under microwave irradiation at 100° C. for 40 minutes. The residue was purified by NH silica gel column chromatography (ethyl acetate/hexane and methanol/ethyl acetate) to obtain a solid. The obtained solid was washed with ethyl acetate/hexane to obtain the title compound (32.0 mg).

$^1$H NMR (300 MHz, DMSO-$d_6$) δ 1.31-1.45 (2H, m), 1.61-1.76 (2H, m), 2.66 (3H, s), 3.97 (3H, s), 5.93 (2H, s), 7.06 (1H, d, J=2.7 Hz), 8.07 (1H, d, J=2.7 Hz), 8.20-8.27 (2H, m), 8.59 (1H, d, J=2.1 Hz).

Example 284

1-((5-(1-fluorocyclobutyl)-1,3,4-oxadiazol-2-yl)methyl)-6-(4-methoxypyrrolo[2,1-f][1,2,4]triazin-5-yl)-2-methyl-1H-imidazo[4,5-b]pyridine a) 2-((6-bromo-2-methyl-1H-imidazo[4,5-b]pyridin-1-yl)methyl)-5-(1-fluorocyclobutyl)-1,3,4-oxadiazole Propylphosphonic anhydride (50% in ethyl acetate solution) (0.917 mL) was added to a suspension of triethylamine (0.307 mL), 2-(6-bromo-2-methyl-1H-imidazo[4,5-b]pyridin-1-yl)acetohydrazide (125 mg) and 1-fluorocyclobutanecarboxylic acid (50 mg) in ethyl acetate (2 mL) at room temperature. The mixture was stirred under microwave irradiation at 150° C. for 30 minutes. The residue was purified by NH silica gel column chromatography (ethyl acetate/hexane) to obtain the title compound (101 mg).

$^1$H NMR (300 MHz, DMSO-$d_6$) δ 1.57-1.76 (1H, m), 1.86-2.04 (1H, m), 2.57-2.77 (7H, m), 5.93 (2H, s), 8.39 (1H, d, J=2.2 Hz), 8.45 (1H, d, J=2.2 Hz).

b) 1-((5-(1-fluorocyclobutyl)-1,3,4-oxadiazol-2-yl)methyl)-6-(4-methoxypyrrolo[2,1-f][1,2,4]triazin-5-yl)-2-methyl-1H-imidazo[4,5-b]pyridine A mixture of 4-methoxy-5-(4,4,5,5-tetramethyl-1,3,2-dioxaborolan-2-yl)pyrrolo[2,1-f][1,2,4]triazine (283 mg), 2-((6-bromo-2-methyl-1H-imidazo[4,5-b]pyridin-1-yl)methyl)-5-(1-fluorocyclobutyl)-1,3,4-oxadiazole (101 mg), bis (di-tert-butyl(4-dimethylaminophenyl)phosphine)dichloropalladium (II) (10 mg), cesium carbonate (2 M in aqueous solution) (250 μL) and DME (4 mL) was stirred under microwave irradiation at 100° C. for 40 minutes. The residue was purified by NH silica gel column chromatography (ethyl acetate/hexane and methanol/ethyl acetate) to obtain a solid. The obtained solid was washed with ethyl acetate/hexane to obtain the title compound (42.0 mg).

$^1$H NMR (300 MHz, DMSO-$d_6$) δ 1.55-1.76 (1H, m), 1.84-2.05 (1H, m), 2.58-2.76 (7H, m), 3.95 (3H, s), 5.96 (2H, s), 7.05 (1H, d, J=2.7 Hz), 8.07 (1H, d, J=2.7 Hz), 8.19-8.27 (2H, m), 8.59 (1H, d, J=2.0 Hz).

Example 286

1-((5-((1R)-1-fluoroethyl)-1,3,4-oxadiazol-2-yl)methyl)-6-(4-methoxypyrrolo[2,1-f][1,2,4]triazin-5-yl)-2-methyl-1H-imidazo[4,5-b]pyridine (Optical Isomer)

a) 2-((6-bromo-2-methyl-1H-imidazo[4,5-b]pyridin-1-yl)methyl)-5-(1-fluoroethyl)-1,3,4-oxadiazole Propylphosphonic anhydride (50% in ethyl acetate solution) (6.0 mL) was added to a mixture of 2-fluoropropionic acid (0.58 mL), DIEA (3.0 mL), 2-(6-bromo-2-methyl-1H-imidazo[4,5-b]pyridin-1-yl)acetohydrazide (1.33 g) and ethyl acetate (40 ml) at room temperature, and the resulting mixture was stirred at 50° C. for 1 hour. The mixture was stirred under microwave irradiation at 140° C. for 2.5 hours. Insolubles were removed by filtration through a filter, and the filtrate was concentrated. The residue was purified by NH silica gel column chromatography (methanol/ethyl acetate), and washed with IPE to obtain the title compound (0.644 g).

$^1$H NMR (300 MHz, DMSO-$d_6$) δ 1.64-1.77 (3H, m), 2.62 (3H, s), 5.86-6.12 (3H, m), 8.38 (1H, d, J=2.2 Hz), 8.45 (1H, d, J=2.2 Hz).

b) 1-((5-(1-fluoroethyl)-1,3,4-oxadiazol-2-yl)methyl)-6-(4-methoxypyrrolo[2,1-f][1,2,4]triazin-5-yl)-2-methyl-1H-imidazo[4,5-b]pyridine A mixture of 2-((6-bromo-2-methyl-1H-imidazo[4,5-b]pyridin-1-yl)methyl)-5-(1-fluoroethyl)-1,3,4-oxadiazole (186 mg), 4-methoxy-5-(4,4,5,5-tetramethyl-1,3,2-dioxaborolan-2-yl)pyrrolo[2,1-f][1,2,4]triazine (500 mg), bis(di-tert-butyl(4-dimethylaminophenyl)phosphine)dichloropalladium (II) (30 mg), cesium carbonate (2 M in aqueous solution) (0.478 ml) and DME (2.5 ml) was stirred under microwave irradiation at 100° C. for 1 hour. The reaction mixture was purified by NH silica gel column chromatography (ethyl acetate/hexane), and the residue was washed with IPE to obtain the title compound (80 mg).

$^1$H NMR (300 MHz, DMSO-$d_6$) δ 1.56-1.86 (3H, m), 2.67 (3H, s), 3.96 (3H, s), 5.98 (3H, s), 7.06 (1H, d, J=2.7 Hz), 8.07 (1H, d, J=2.8 Hz), 8.19-8.35 (2H, m), 8.59 (1H, d, J=2.1 Hz).

c) 1-((5-((1R)-1-fluoroethyl)-1,3,4-oxadiazol-2-yl)methyl)-6-(4-methoxypyrrolo[2,1-f][1,2,4]triazin-5-yl)-2-methyl-1H-imidazo[4,5-b]pyridine (Optical Isomer)

A racemate of 1-((5-(1-fluoroethyl)-1,3,4-oxadiazol-2-yl)methyl)-6-(4-methoxypyrrolo[2,1-f][1,2,4]triazin-5-yl)-2-methyl-1H-imidazo[4,5-b]pyridine (66.5 mg) was fractionated by SFC (column: CHIRALPAK ASH (LA005) 20×250 mm, 5 μm, mobile phase: $CO_2$/methanol=800/200), and a compound with a smaller retention time was crystallized with ethanol/ethyl acetate/heptane to obtain the title compound (12.8 mg).

¹H NMR (300 MHz, CDCl₃) δ 1.72-1.89 (3H, m), 2.84 (3H, s), 4.06 (3H, s), 5.57 (2H, s), 5.61-5.87 (1H, m), 6.87 (1H, d, J=2.8 Hz), 7.77 (1H, d, J=2.7 Hz), 7.95 (1H, d, J=2.0 Hz), 8.07 (1H, s), 8.75 (1H, d, J=2.0 Hz).

Another method for producing 1-((5-((1R)-1-fluoroethyl)-1,3,4-oxadiazol-2-yl)methyl)-6-(4-methoxypyrrolo[2,1-f][1,2,4]triazin-5-yl)-2-methyl-1H-imidazo[4,5-b]pyridine monohydrate (identical to the title compound in Example 286) is shown below.

a) (4-methoxypyrrolo[2,1-f][1,2,4]triazin-5-yl)boronic acid

To a solution of 5-bromo-4-methoxypyrrolo[2,1-f][1,2,4]triazine (60 g) and 2-isopropoxy-4,4,5,5-tetramethyl-1,3,2-dioxaborolane (243 mL) in THF (3000 mL) was added dropwise n-butyllithium (1.6 M in hexane solution) (411 mL) under an argon atmosphere at −78° C. to −60° C. over 45 minutes. The mixture was stirred at −70° C. to −60° C. for 30 minutes under an argon atmosphere. To the reaction mixture were added water (140 mL) and hydrochloric acid (2 N in aqueous solution) (600 mL), and the mixture was warmed to room temperature. The aqueous layer was extracted with isopropyl acetate. The organic layer was inversely extracted with a 2N aqueous sodium hydroxide solution (700 mL) and water (300 mL). The aqueous layer was acidified with hydrochloric acid (2N in aqueous solution) (7100 mL) at 10° C., and the suspension was filtered. The obtained residue was washed with water to obtain the title compound (40.5 g).

¹H NMR (300 MHz, DMSO-d₆) δ 4.13 (3H, s), 7.07 (1H, d, J=2.3 Hz), 7.68 (2H, s), 7.94 (1H, d, J=2.6 Hz), 8.24 (1H, s).

b) (R)-2-fluoropropanoic acid (R)-Ethyl 2-fluoropropanoate (95 g) was suspended in 10% sulfuric acid (950 mL), and heated and refluxed for 3 hours. After cooled, sodium chloride was added to saturate the aqueous layer, and the aqueous layer was extracted with t-butyl methyl ether (900 mL×4). The obtained organic layer was dried over magnesium sulfate, and concentrated under reduced pressure to obtain the title compound (124 g, containing t-butyl methyl ether).

¹H NMR (300 MHz, DMSO-d₆) δ 1.35-1.56 (3H, m), 4.91-5.21 (1H, m), 13.19 (1H, brs).

c) (S)-2-amino-3-phenylpropane-1-ol (R)-2-fluoropropanoate

To a solution of (S)-2-amino-3-phenylpropan-1-ol (119 g) in ethanol (360 mL) and acetonitrile (1090 mL) was added dropwise a solution of (R)-2-fluoropropanoic acid (72.7 g) in acetonitrile (1090 mL) at 65° C. to 70° C. The mixture was stirred at 60° C. for 1 hour, and further stirred at room temperature for 1 hour. Precipitated crystals were collected by filtration, and washed with acetonitrile (500 mL) to obtain white crystals (170 g). The obtained crystals (140 g) were dissolved in ethanol (700 mL) at 60° C., and to the solution was added acetonitrile (4200 mL) at 58° C. to 65° C. The mixture was stirred at 60° C. for 1 hour. The mixture was cooled to room temperature, and then stirred overnight at room temperature. The obtained solid was collected by filtration, and washed with acetonitrile to obtain the title compound (109 g).

d) (R)-2-((6-bromo-2-methyl-1H-imidazo[4,5-b]pyridin-1-yl)methyl)-5-(1-fluoroethyl)-1,3,4-oxadiazole (S)-2-Amino-3-phenylpropan-1-ol (R)-2-fluoropropanoate (109 g) was dissolved in hydrochloric acid (1N in aqueous solution) (1500 mL) and a saturated brine (1500 mL), and the solution was extracted with t-butyl methyl ether (1000 mL×4). The organic layer was dried over magnesium sulfate, and concentrated under reduced pressure to obtain a colorless oil. Propylphosphonic anhydride (50% in ethyl acetate solution) (419 mL) was added to a suspension of the obtained oil, 2-(6-bromo-2-methyl-1H-imidazo[4,5-b]pyridin-1-yl)acetohydrazide (100 g), DIPEA (246 mL) and butyl acetate (3000 mL) at room temperature. The mixture was stirred at 50° C. for 30 minutes, propylphosphonic anhydride (50% in ethyl acetate solution) (210 mL) was added to the mixture, and the resulting mixture was heated and refluxed for 3 hours. The mixture was cooled, a saturated aqueous sodium hydrogen carbonate solution (3000 mL) was then added to the mixture, and insolubles were removed. The liquid layer was extracted twice with ethyl acetate (1500 mL×2), and the organic layer was washed with water and a saturated brine. The organic layer was purified with NH silica gel (ethyl acetate). The residue was concentrated under reduced pressure, and the obtained solid was washed with IPE (3000 mL) to obtain the title compound (57.8 g).

¹H NMR (300 MHz, DMSO-d₆) δ 1.62-1.79 (3H, m), 2.62 (3H, s), 5.83-6.14 (3H, m), 8.38 (1H, d, J=1.9 Hz), 8.45 (1H, d, J=1.9 Hz).

e) 1-((5-((1R)-1-fluoroethyl)-1,3,4-oxadiazol-2-yl)methyl)-6-(4-methoxypyrrolo[2,1-f][1,2,4]triazin-5-yl)-2-methyl-1H-imidazo[4,5-b]pyridine monohydrate A mixture of (4-methoxypyrrolo[2,1-f][1,2,4]triazin-5-yl)boronic acid (79 g), (R)-2-((6-bromo-2-methyl-1H-imidazo[4,5-b]pyridin-1-yl)methyl)-5-(1-fluoroethyl)-1,3,4-oxadiazole (100 g), bis(di-tert-butyl(4-dimethylaminophenyl)phosphine)dichloropalladium (II) (2.00 g), cesium carbonate (2 M in aqueous solution) (295 mL) and DME (2000 mL) was stirred at 80° C. for 1 hour. The mixture was cooled to 50° C., and then diluted with THF (1000 mL). The mixture was poured into an aqueous sodium hydrogen carbonate solution (1600 mL), and extracted with ethyl acetate (1000 mL×3). The organic layer was washed with a 5% aqueous ammonia solution (1600 mL×2) and a saturated brine (1600 mL), dried over magnesium sulfate, and concentrated under reduced pressure to obtain a yellow solid. NH silica gel (2400 g) was added to a solution of the obtained solid in THF (8000 mL) and water (200 mL), and the mixture was stirred at room temperature for 3.5 hours. Insolubles were removed, and washed with THF (15 L). The obtained solution was concentrated under reduced pressure to obtain a yellow solid. The obtained solid was washed with t-butyl methyl ether to obtain pale yellow crystals (98 g).

A mixture of the obtained crystals (115 g), activated carbon (Ecosorb) (33 g), ethanol/water=9/1 (2200 mL) and water (1100 mL) was stirred at 55° C. for 1 hour. Insolubles were removed, and washed with ethanol (550 mL). The obtained solution was diluted with water (1600 mL) at 55° C., and stirred overnight at room temperature. The mixture was cooled to 5° C., and then stirred for 3 hours. The obtained solid was collected by filtration, and washed with ethanol/water=1/1 (1000 mL) to obtain the title compound (88 g).

¹H NMR (300 MHz, DMSO-d₆) δ 1.60-1.83 (3H, m), 2.67 (3H, s), 3.96 (3H, s), 5.83-6.19 (3H, m), 7.06 (1H, d, J=2.5 Hz), 8.06 (1H, d, J=2.5 Hz), 8.17-8.30 (2H, m), 8.59 (1H, d, J=2.0 Hz).

Example 287

1-((5-((1 S)-1-fluoroethyl)-1,3,4-oxadiazol-2-yl)methyl)-6-(4-methoxypyrrolo[2,1-f][1,2,4]triazin-5-yl)-2-methyl-1H-imidazo[4,5-b]pyridine (Optical Isomer)

A racemate of 1-((5-(1-fluoroethyl)-1,3,4-oxadiazol-2-yl)methyl)-6-(4-methoxypyrrolo[2,1-f][1,2,4]triazin-5-yl)-2-methyl-1H-imidazo[4,5-b]pyridine (66.5 mg) was fractionated by SFC (column: CHIRALPAK ASH (LA005) 20×50 mm, 5 μm, mobile phase: CO₂/methanol=800/200), and a compound with a larger retention time was crystallized with ethanol/ethyl acetate/heptane to obtain the title compound (15.7 mg).

¹H NMR (300 MHz, CDCl₃) δ 1.72-1.87 (3H, m), 2.84 (3H, s), 4.06 (3H, s), 5.57 (2H, s), 5.62-5.87 (1H, m), 6.87 (1H, d, J=2.8 Hz), 7.77 (1H, d, J=2.7 Hz), 7.94 (1H, d, J=1.9 Hz), 8.07 (1H, s), 8.75 (1H, d, J=1.9 Hz).

Example 288

1-((5-(difluoromethyl)-1,3,4-oxadiazol-2-yl)methyl)-6-(4-methoxypyrrolo[1,2-b]pyridazin-5-yl)-2-methyl-1H-imidazo[4,5-b]pyridine a) 4-methoxy-5-(4,4,5,5-tetramethyl-1,3,2-dioxaborolan-2-yl)pyrrolo[1,2-b]pyridazine n-butyllithium (1.6 M in hexane solution) (4.5 mL) was added dropwise to a solution of 5-bromo-4-methoxypyrrolo[1,2-b]pyridazine (1.20 g) in THF (30 mL) under a nitrogen atmosphere at −78° C. The mixture was stirred at −78° C. for 20 minutes, and 2-isopropoxy-4,4,5,5-tetramethyl-1,3,2-dioxaborolane (1.8 mL) was then added. The mixture was warmed to room temperature, and stirred for 30 minutes. The reaction mixture was poured into water, and extracted with ethyl acetate. The organic layer was washed with a saturated brine, then dried over magnesium sulfate, and concentrated under reduced pressure. The residue was purified by silica gel column chromatography (ethyl acetate/hexane) to obtain the title compound (0.707 g).

¹H NMR (300 MHz, DMSO-d₆) δ 1.28 (12H, s), 3.94 (3H, s), 6.30 (1H, d, J=5.5 Hz), 6.87 (1H, d, J=2.5 Hz), 7.75 (1H, d, J=2.6 Hz), 8.11 (1H, d, J=5.5 Hz).

b) 1-((5-(difluoromethyl)-1,3,4-oxadiazol-2-yl)methyl)-6-(4-methoxypyrrolo[1,2-b]pyridazin-5-yl)-2-methyl-1H-imidazo[4,5-b]pyridine A mixture of 4-methoxy-5-(4,4,5,5-tetramethyl-1,3,2-dioxaborolan-2-yl)pyrrolo[2,1-b]pyridazine (91 mg), 2-((6-bromo-2-methyl-1H-imidazo[4,5-b]pyridin-1-yl)methyl)-5-(difluoromethyl)-1,3,4-oxadiazole (120 mg), bis(di-tert-butyl(4-dimethylaminophenyl)phosphine)dichloropalladium (11 mg), cesium carbonate (2 M in aqueous solution) (0.350 mL) and DME (3 mL) was stirred under microwave irradiation at 100° C. for 40 minutes. The residue was purified by silica gel column chromatography (ethyl acetate/hexane and methanol/ethyl acetate) to obtain a solid. The obtained solid was crystallized from ethanol/ethyl acetate/heptane to obtain the title compound (57 mg).

¹H NMR (300 MHz, DMSO-d₆) δ 2.65 (3H, s), 3.81 (3H, s), 6.00 (2H, s), 6.27 (1H, d, J=5.6 Hz), 6.91 (1H, d, J=2.8 Hz), 7.21-7.70 (1H, m), 7.90 (1H, d, J=2.8 Hz), 8.04-8.13 (2H, m), 8.50 (1H, d, J=2.0 Hz).

Example 289

1-((5-(difluoromethyl)-1,3,4-thiadiazol-2-yl)methyl)-6-(4-methoxypyrrolo[2,1-f][1,2,4]triazin-5-yl)-2-methyl-1H-imidazo[4,5-b]pyridine a) 2-((6-bromo-2-methyl-1H-imidazo[4,5-b]pyridin-1-yl)methyl)-5-(difluoromethyl)-1,3,4-thiadiazole A mixture of triethylamine (4.00 mL), difluoroacetic acid (0.50 mL), propylphosphonic anhydride (50% in ethyl acetate solution) (10.00 mL), 2-(6-bromo-2-methyl-1H-imidazo[4,5-b]pyridin-1-yl)acetohydrazide (1.72 g), diphosphorus pentasulfide (3.33 g) and ethyl acetate (50 mL) was heated overnight at 80° C. The mixture was purified by NH silica gel column chromatography (ethyl acetate). The obtained residue was purified by NH silica gel column chromatography (ethyl acetate/hexane) to obtain the title compound (0.711 g).

¹H NMR (300 MHz, DMSO-d₆) δ 2.63 (3H, s), 6.15 (2H, s), 7.33-7.78 (1H, m), 8.41-8.50 (2H, m).

b) 1-((5-(difluoromethyl)-1,3,4-thiadiazol-2-yl)methyl)-6-(4-methoxypyrrolo[2,1-f][1,2,4]triazin-5-yl)-2-methyl-1H-imidazo[4,5-b]pyridine A mixture of 4-methoxy-5-(4,4,5,5-tetramethyl-1,3,2-dioxaborolan-2-yl)pyrrolo[2,1-f][1,2,4]triazine (430 mg), 2-((6-bromo-2-methyl-1H-imidazo[4,5-b]pyridin-1-yl)methyl)-5-(difluoromethyl)-1,3,4-thiadiazole (150 mg), bis(di-tert-butyl(4-dimethylaminophenyl)phosphine)dichloropalladium (II) (25 mg), cesium carbonate (2 M in aqueous solution) (500 μL) and DME (10 mL) was stirred under microwave irradiation at 100° C. for 2 hours. The residue was purified by silica gel column chromatography (ethyl acetate/hexane and methanol/ethyl acetate) to obtain a solid. The obtained solid was washed with ethanol/ethyl acetate/heptane to obtain the title compound (48.0 mg).

¹H NMR (300 MHz, DMSO-d₆) δ 2.68 (3H, s), 3.90 (3H, s), 6.18 (2H, s), 7.05 (1H, d, J=2.7 Hz), 7.34-7.78 (1H, m), 8.06 (1H, d, J=2.7 Hz), 8.22 (1H, s), 8.24 (1H, d, J=2.0 Hz), 8.58 (1H, d, J=2.0 Hz).

The compounds of Examples 2 to 6, 8 and 9, 11, 14 to 16, 18 and 19, 25 and 26, 29 and 30, 36 and 37, 40 to 43, 45 to 47, 49 to 67, 69 to 78, 80 and 81, 83 to 95, 97, 99 to 101, 103 and 104, 106 to 109, 111 to 133, 135 to 155, 157, 163 to 174, 177 and 178, 180 to 185, 187 to 190, 192, 194 to 198, 200 to 202, 216 to 219, 221 to 228, 232 to 236, 238 to 241, 244 to 249, 251, 254 to 266, 270 to 272, 275, 278, 285 and 290 in the table below were produced in accordance with the methods shown in the above-described examples, or similar methods. The example compounds are shown in the table below. MS in the table indicates a measured value.

TABLE 1

| Example | IUPAC NAME | CHEMICAL STRUCTURE | Salt | MS |
|---|---|---|---|---|
| 1 | 2-(azetidin-1-yl)-1-(3,5-difluorobenzyl)-6-(4-methoxy-5H-pyrrolo[3,2-d]pyrimidin-5-yl)-1H-imidazo[4,5-b]pyridine | 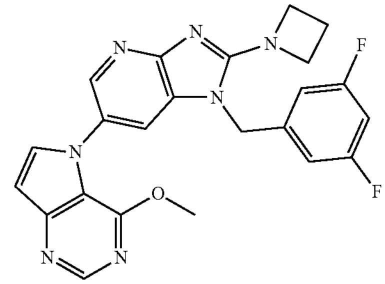 [SMILES: COc1ncnc2ccn(-c3cnc4nc(N5CCC5)n(Cc5cc(F)cc(F)c5)c4c3)c12] | | 448.2 |
| 2 | 1-(3,4-difluorobenzyl)-6-(4-methoxy-5H-pyrrolo[3,2-d]pyrimidin-5-yl)-N-methyl-1H-imidazo[4,5-b]pyridin-2-amine | 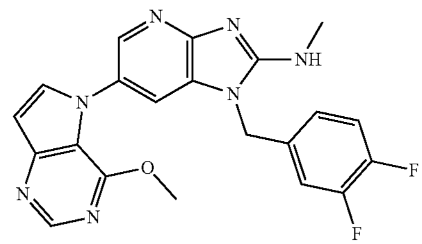 [SMILES: CNc1nc2ncc(-n3ccc4ncnc(OC)c43)cc2n1Cc1ccc(F)c(F)c1] | | 422.2 |
| 3 | 1-(3,4-difluorobenzyl)-2-ethoxy-6-(4-methoxy-5H-pyrrolo[3,2-d]pyrimidin-5-yl)-1H-imidazo[4,5-b]pyridine | 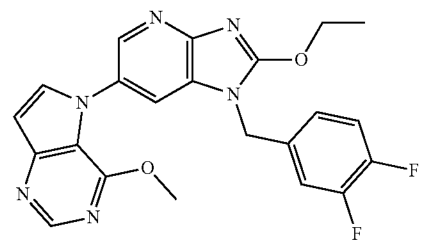 [SMILES: CCOc1nc2ncc(-n3ccc4ncnc(OC)c43)cc2n1Cc1ccc(F)c(F)c1] | | 437.2 |
| 4 | 2-(1,1-difluoroethyl)-1-(3-fluorobenzyl)-6-(4-methoxy-5H-pyrrolo[3,2-d]pyrimidin-5-yl)-1H-imidazo[4,5-b]pyridine | 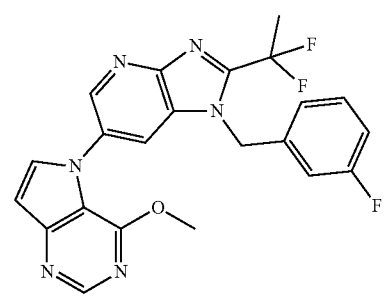 [SMILES: COc1ncnc2ccn(-c3cnc4nc(C(C)(F)F)n(Cc5cccc(F)c5)c4c3)c12] | | 439.2 |
| 5 | 1-(3,4-difluorobenzyl)-N-methyl-6-(5H-pyrrolo[3,2-d]pyrimidin-5-yl)-1H-imidazo[4,5-b]pyridin-2-amine | 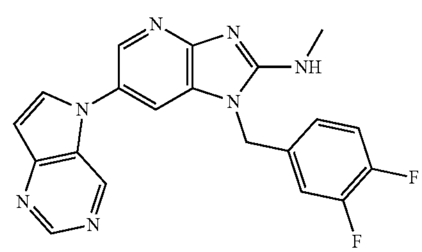 [SMILES: CNc1nc2ncc(-n3ccc4ncncc43)cc2n1Cc1ccc(F)c(F)c1] | | 392.2 |

TABLE 1-continued

| Example | IUPAC NAME | CHEMICAL STRUCTURE | Salt | MS |
|---|---|---|---|---|
| 6 | 2-(azetidin-1-yl)-1-(2,5-difluorobenzyl)-6-(4-methoxy-5H-pyrrolo[3,2-d]pyrimidin-5-yl)-1H-imidazo[4,5-b]pyridine | 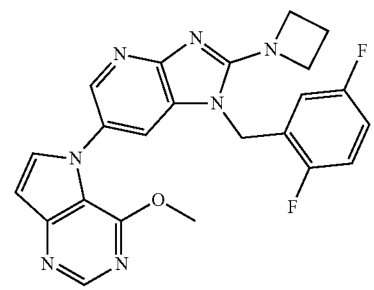 [SMILES: COc1ncnc2ccn(-c3cnc4nc(N5CCC5)n(Cc5cc(F)ccc5F)c4c3)c12] | | 448.2 |
| 7 | 1-(3,5-difluorobenzyl)-6-(4-methoxy-5H-pyrrolo[3,2-d]pyrimidin-5-yl)-2-methyl-1H-imidazo[4,5-b]pyridine | 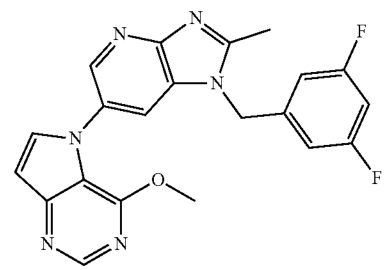 [SMILES: COc1ncnc2ccn(-c3cnc4nc(C)n(Cc5cc(F)cc(F)c5)c4c3)c12] | | 407.1 |
| 8 | 1-(3,5-difluorobenzyl)-N-(2,2-difluoroethyl)-6-(4-methoxy-5H-pyrrolo[3,2-d]pyrimidin-5-yl)-1H-imidazo[4,5-b]pyridin-2-amine | 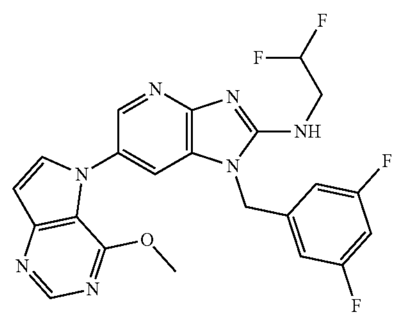 [SMILES: COc1ncnc2ccn(-c3cnc4nc(NCC(F)F)n(Cc5cc(F)cc(F)c5)c4c3)c12] | | 472.1 |
| 9 | 2-(3,3-difluoroazetidin-1-yl)-1-(3,5-difluorobenzyl)-6-(4-methoxy-5H-pyrrolo[3,2-d]pyrimidin-5-yl)-1H-imidazo[4,5-b]pyridine | 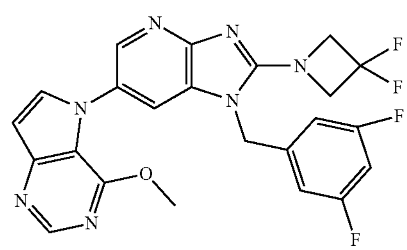 [SMILES: COc1ncnc2ccn(-c3cnc4nc(N5CC(F)(F)C5)n(Cc5cc(F)cc(F)c5)c4c3)c12] | | 484.2 |
| 10 | 2-ethoxy-1-(3-fluorobenzyl)-6-(4-methoxy-5H-pyrrolo[3,2-d]pyrimidin-5-yl)-1H-imidazo[4,5-b]pyridine | 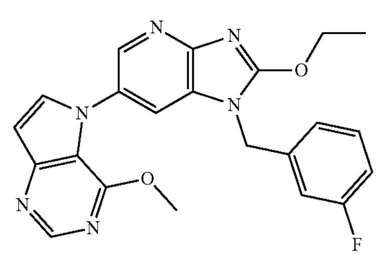 [SMILES: CCOc1nc2ncc(-n3ccc4ncnc(OC)c43)cc2n1Cc1cccc(F)c1] | | 419.1 |

TABLE 1-continued

| Example | IUPAC NAME | CHEMICAL STRUCTURE | Salt | MS |
|---|---|---|---|---|
| 11 | 2-ethoxy-1-((5-fluoropyridin-3-yl)methyl)-6-(4-methoxy-5H-pyrrolo[3,2-d]pyrimidin-5-yl)-1H-imidazo[4,5-b]pyridine | 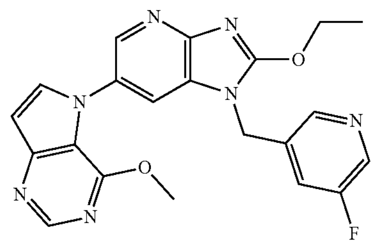 [SMILES: CCOc1nc2ncc(-n3ccc4ncnc(OC)c43)cc2n1Cc1cncc(F)c1] | | 420.2 |
| 12 | 1-(3-fluorobenzyl)-6-(4-methoxy-5H-pyrrolo[3,2-d]pyrimidin-5-yl)-2-methyl-1H-imidazo[4,5-b]pyridine | 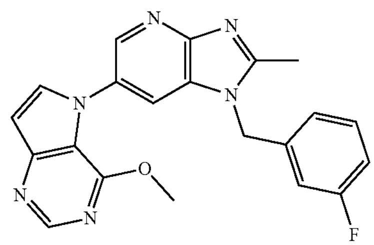 [SMILES: COc1ncnc2ccn(-c3cnc4nc(C)n(Cc5cccc(F)c5)c4c3)c12] | | 389.2 |
| 13 | (1-(3-fluorobenzyl)-6-(4-methoxy-5H-pyrrolo[3,2-d]pyrimidin-5-yl)-1H-imidazo[4,5-b]pyridin-2-yl)methanol | 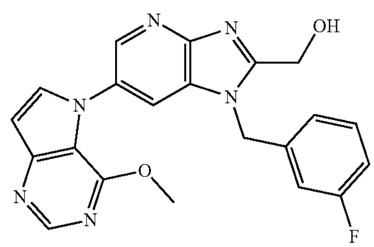 [SMILES: COc1ncnc2ccn(-c3cnc4nc(CO)n(Cc5cccc(F)c5)c4c3)c12] | | 405.2 |
| 14 | 3-(1-(3-fluorobenzyl)-6-(4-methoxy-5H-pyrrolo[3,2-d]pyrimidin-5-yl)-1H-imidazo[4,5-b]pyridin-2-yl)propanenitrile | 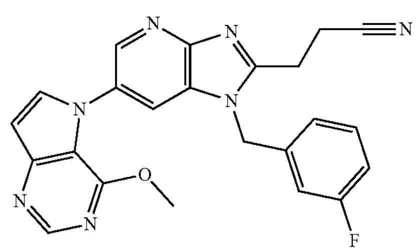 [SMILES: COc1ncnc2ccn(-c3cnc4nc(CCC#N)n(Cc5cccc(F)c5)c4c3)c12] | | 428.3 |
| 15 | 1-(4-(difluoromethoxy)benzyl)-6-(4-methoxy-5H-pyrrolo[3,2-d]pyrimidin-5-yl)-2-methyl-1H-imidazo[4,5-b]pyridine | 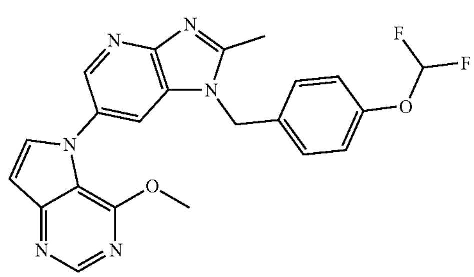 [SMILES: COc1ncnc2ccn(-c3cnc4nc(C)n(Cc5ccc(OC(F)F)cc5)c4c3)c12] | | 437.2 |
| 16 | 1-(3-fluorobenzyl)-6-(4-methoxy-5H-pyrrolo[3,2-d]pyrimidin-5-yl)-2-(1-methyl-1H-pyrazol-4-yl)-1H-imidazo[4,5-b]pyridine | 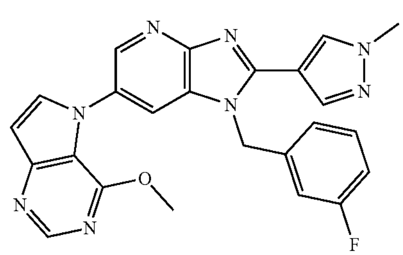 [SMILES: COc1ncnc2ccn(-c3cnc4nc(-c5cnn(C)c5)n(Cc5cccc(F)c5)c4c3)c12] | | 455.2 |

TABLE 1-continued

| Example | IUPAC NAME | CHEMICAL STRUCTURE | Salt | MS |
|---|---|---|---|---|
| 17 | 1-(3,4-difluorobenzyl)-6-(4-methoxy-5H-pyrrolo[3,2-d]pyrimidin-5-yl)-2-methyl-1H-imidazo[4,5-b]pyridine | 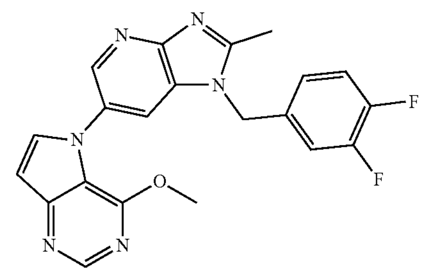 [SMILES: COc1ncnc2ccn(-c3cnc4nc(C)n(Cc5ccc(F)c(F)c5)c4c3)c12] | | 407.1 |
| 18 | 1-(1-(3-fluorobenzyl)-6-(4-methoxy-5H-pyrrolo[3,2-d]pyrimidin-5-yl)-1H-imidazo[4,5-b]pyridin-2-yl)azetidin-3-ol | 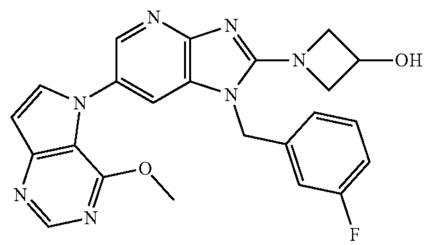 [SMILES: COc1ncnc2ccn(-c3cnc4nc(N5CC(O)C5)n(Cc5cccc(F)c5)c4c3)c12] | | 446.3 |
| 19 | 2-(3-fluoroazetidin-1-yl)-1-(3-fluorobenzyl)-6-(4-methoxy-5H-pyrrolo[3,2-d]pyrimidin-5-yl)-1H-imidazo[4,5-b]pyridine | 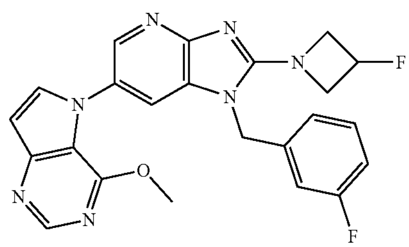 [SMILES: COc1ncnc2ccn(-c3cnc4nc(N5CC(F)C5)n(Cc5cccc(F)c5)c4c3)c12] | | 448.2 |
| 20 | 1-(2,3-difluorobenzyl)-6-(4-methoxy-5H-pyrrolo[3,2-d]pyrimidin-5-yl)-2-methyl-1H-imidazo[4,5-b]pyridine | 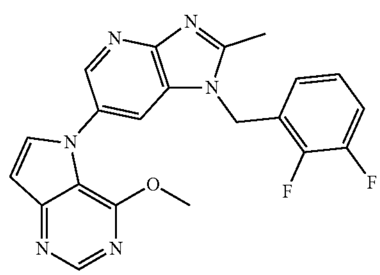 [SMILES: COc1ncnc2ccn(-c3cnc4nc(C)n(Cc5cccc(F)c5F)c4c3)c12] | | 407.1 |
| 21 | 1-benzyl-6-(4-methoxy-5H-pyrrolo[3,2-d]pyrimidin-5-yl)-2-methyl-1H-imidazo[4,5-b]pyridine | 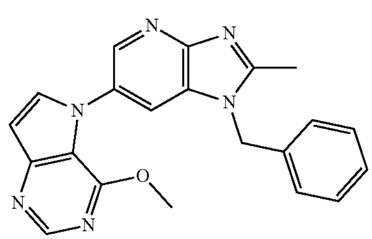 [SMILES: COc1ncnc2ccn(-c3cnc4nc(C)n(Cc5ccccc5)c4c3)c12] | | 371.2 |
| 22 | 1-(4-fluorobenzyl)-6-(4-methoxy-5H-pyrrolo[3,2-d]pyrimidin-5-yl)-2-methyl-1H-imidazo[4,5-b]pyridine | 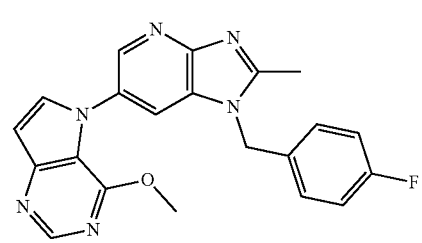 [SMILES: COc1ncnc2ccn(-c3cnc4nc(C)n(Cc5ccc(F)cc5)c4c3)c12] | | 389.1 |

TABLE 1-continued

| Example | IUPAC NAME | CHEMICAL STRUCTURE | Salt | MS |
|---|---|---|---|---|
| 23 | 1-(2,5-difluorobenzyl)-6-(4-methoxy-5H-pyrrolo[3,2-d]pyrimidin-5-yl)-2-methyl-1H-imidazo[4,5-b]pyridine | 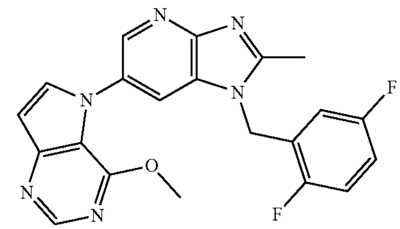 [SMILES: COc1ncnc2ccn(-c3cnc4nc(C)n(Cc5cc(F)ccc5F)c4c3)c12] | | 407.1 |
| 24 | 1-(3-fluorobenzyl)-2-(methoxymethyl)-6-(4-methoxy-5H-pyrrolo[3,2-d]pyrimidin-5-yl)-1H-imidazo[4,5-b]pyridine | 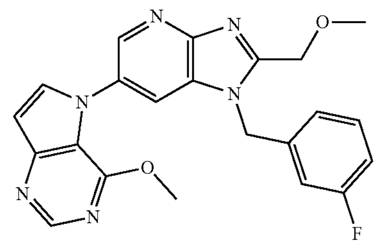 [SMILES: COCc1nc2ncc(-n3ccc4ncnc(OC)c43)cc2n1Cc1cccc(F)c1] | | 419.2 |
| 25 | 6-(4-chloro-5H-pyrrolo[3,2-d]pyrimidin-5-yl)-1-(3-fluorobenzyl)-2-methyl-1H-imidazo[4,5-b]pyridine | 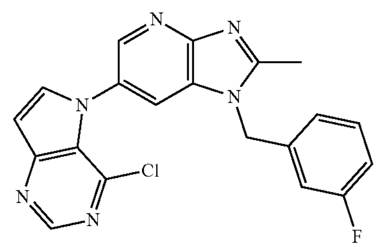 [SMILES: Cc1nc2ncc(-n3ccc4ncnc(Cl)c43)cc2n1Cc1cccc(F)c1] | | 393.1 |
| 26 | 2-((1-(3-fluorobenzyl)-6-(4-methoxy-5H-pyrrolo[3,2-d]pyrimidin-5-yl)-1H-imidazo[4,5-b]pyridine-2-yl)oxy)ethanol | 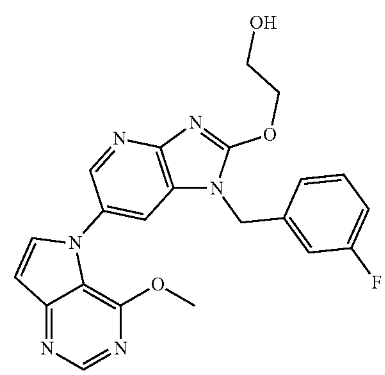 [SMILES: COc1ncnc2ccn(-c3cnc4nc(OCCO)n(Cc5cccc(F)c5)c4c3)c12] | | 435.2 |
| 27 | 5-(1-(3-fluorobenzyl)-2-methyl-1H-imidazo[4,5-b]pyridin-6-yl)-N-methyl-5H-pyrrolo[3,2-d]pyrimidin-4-amine | 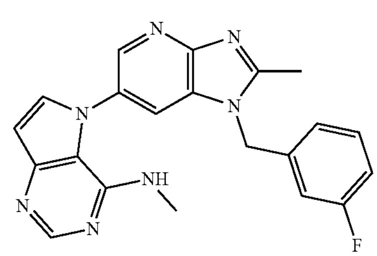 [SMILES: CNc1ncnc2ccn(-c3cnc4nc(C)n(Cc5cccc(F)c5)c4c3)c12] | | 388.2 |

TABLE 1-continued

| Example | IUPAC NAME | CHEMICAL STRUCTURE | Salt | MS |
|---|---|---|---|---|
| 28 | 1-(2-fluorobenzyl)-6-(4-methoxy-5H-pyrrolo[3,2-d]pyrimidin-5-yl)-2-methyl-1H-imidazo[4,5-b]pyridine | 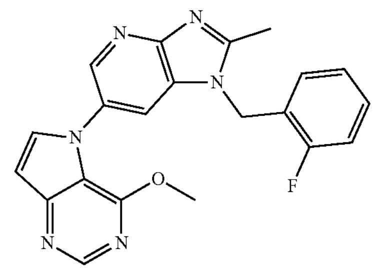 [SMILES: COc1ncnc2ccn(-c3cnc4nc(C)n(Cc5ccccc5F)c4c3)c12] | | 389.2 |
| 29 | 1-(1-(3-fluorobenzyl)-6-(4-methoxy-5H-pyrrolo[3,2-d]pyrimidin-5-yl)-1H-imidazo[4,5-b]pyridin-2-yl)ethanol | 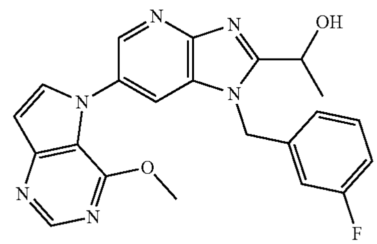 [SMILES: COc1ncnc2ccn(-c3cnc4nc(C(C)O)n(Cc5cccc(F)c5)c4c3)c12] | | 419.3 |
| 30 | 6-(4-methoxy-5H-pyrrolo[3,2-d]pyrimidin-5-yl)-2-methyl-1-(3-nitrobenzyl)-1H-imidazo[4,5-b]pyridine | 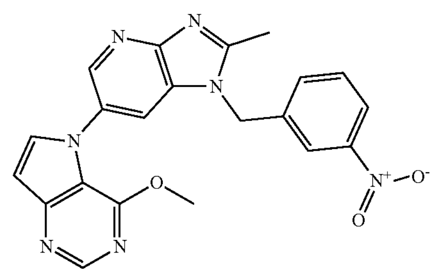 [SMILES: COc1ncnc2ccn(-c3cnc4nc(C)n(Cc5cccc([N+](=O)[O-])c5)c4c3)c12] | | 416.2 |
| 31 | 1-(2,4-difluorobenzyl)-6-(4-methoxy-5H-pyrrolo[3,2-d]pyrimidin-5-yl)-2-methyl-1H-imidazo[4,5-b]pyridine | 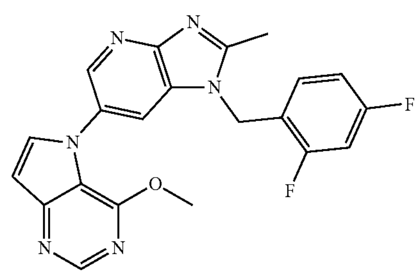 [SMILES: COc1ncnc2ccn(-c3cnc4nc(C)n(Cc5ccc(F)cc5F)c4c3)c12] | | 407.1 |
| 32 | 1-(3-chlorobenzyl)-6-(4-methoxy-5H-pyrrolo[3,2-d]pyrimidin-5-yl)-2-methyl-1H-imidazo[4,5-b]pyridine | 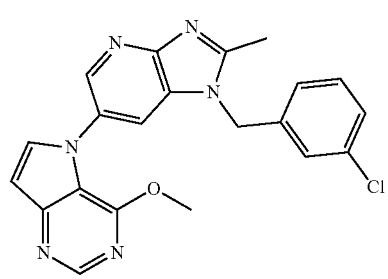 [SMILES: COc1ncnc2ccn(-c3cnc4nc(C)n(Cc5cccc(Cl)c5)c4c3)c12] | | 405.1 |
| 33 | 6-(4-methoxy-5H-pyrrolo[3,2-d]pyrimidin-5-yl)-2-methyl-1-(3-(trifluoromethoxy)benzyl)-1H-imidazo[4,5-b]pyridine | 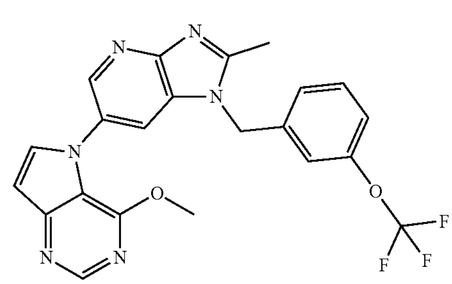 [SMILES: COc1ncnc2ccn(-c3cnc4nc(C)n(Cc5cccc(OC(F)(F)F)c5)c4c3)c12] | | 455.2 |

TABLE 1-continued

| Example | IUPAC NAME | CHEMICAL STRUCTURE | Salt | MS |
|---|---|---|---|---|
| 34 | 6-(4-methoxy-5H-pyrrolo[3,2-d]pyrimidin-5-yl)-2-methyl-1-(3-(trifluoromethyl)benzyl)-1H-imidazo[4,5-b]pyridine | 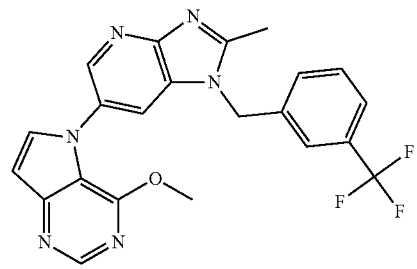 [SMILES: COc1ncnc2ccn(-c3cnc4nc(C)n(Cc5cccc(C(F)(F)F)c5)c4c3)c12] | | 439.1 |
| 35 | 1-(2,6-difluorobenzyl)-6-(4-methoxy-5H-pyrrolo[3,2-d]pyrimidin-5-yl)-2-methyl-1H-imidazo[4,5-b]pyridine | 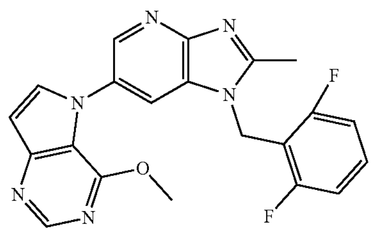 [SMILES: COc1ncnc2ccn(-c3cnc4nc(C)n(Cc5c(F)cccc5F)c4c3)c12] | | 407.1 |
| 36 | 6-(4-methoxy-5H-pyrrolo[3,2-d]pyrimidin-5-yl)-2-methyl-1-(2,3,4-trifluorobenzyl)-1H-imidazo[4,5-b]pyridine | 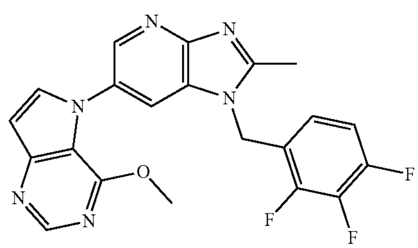 [SMILES: COc1ncnc2ccn(-c3cnc4nc(C)n(Cc5ccc(F)c(F)c5F)c4c3)c12] | | 425.1 |
| 37 | 1-(2,3-difluorobenzyl)-2-ethoxy-6-(4-methoxy-5H-pyrrolo[3,2-d]pyrimidin-5-yl)-1H-imidazo[4,5-b]pyridine | 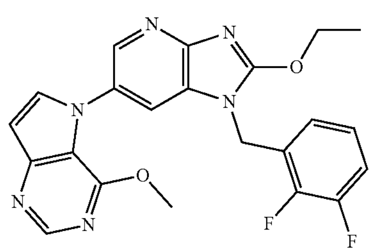 [SMILES: CCOc1nc2ncc(-n3ccc4ncnc(OC)c43)cc2n1Cc1cccc(F)c1F] | | 437.2 |
| 38 | 1-(3,5-difluorobenzyl)-2-methoxy-6-(4-methoxy-5H-pyrrolo[3,2-d]pyrimidin-5-yl)-1H-imidazo[4,5-b]pyridine | 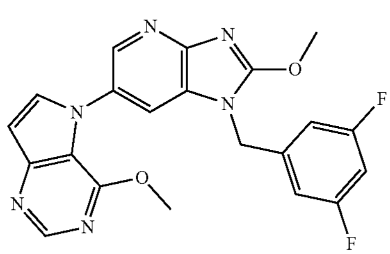 [SMILES: COc1ncnc2ccn(-c3cnc4nc(OC)n(Cc5cc(F)cc(F)c5)c4c3)c12] | | 423.1 |
| 39 | 1-(3-fluorobenzyl)-2-methoxy-6-(4-methoxy-5H-pyrrolo[3,2-d]pyrimidin-5-yl)-1H-imidazo[4,5-b]pyridine | 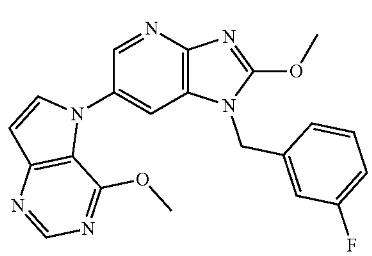 [SMILES: COc1ncnc2ccn(-c3cnc4nc(OC)n(Cc5cccc(F)c5)c4c3)c12] | | 405.1 |

TABLE 1-continued

| Example | IUPAC NAME | CHEMICAL STRUCTURE | Salt | MS |
|---|---|---|---|---|
| 40 | 2-((1-(3,5-difluorobenzyl)-6-(4-methoxy-5H-pyrrolo[3,2-d]pyrimidin-5-yl)-1H-imidazo[4,5-b]pyridin-2-yl)amino)ethanol | 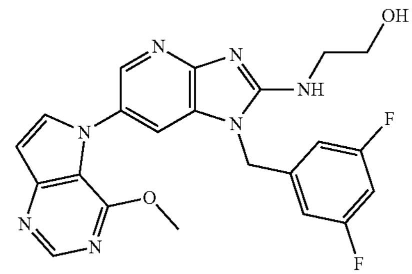 [SMILES: COc1ncnc2ccn(-c3cnc4nc(NCCO)n(Cc5cc(F)cc(F)c5)c4c3)c12] | | 452.1 |
| 41 | 1-(3,4-difluorobenzyl)-2-methoxy-6-(4-methoxy-5H-pyrrolo[3,2-d]pyrimidin-5-yl)-1H-imidazo[4,5-b]pyridine | 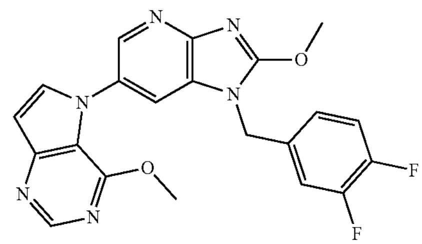 [SMILES: COc1ncnc2ccn(-c3cnc4nc(OC)n(Cc5ccc(F)c(F)c5)c4c3)c12] | | 423.1 |
| 42 | 1-(3,4-difluorobenzyl)-N-(2-methoxyethyl)-6-(4-methoxy-5H-pyrrolo[3,2-d]pyrimidin-5-yl)-1H-imidazo[4,5-b]pyridin-2-amine | 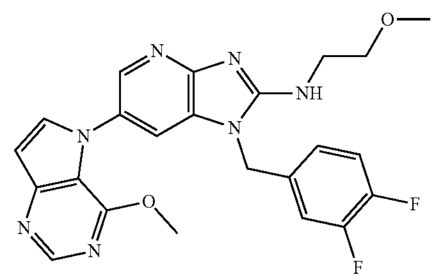 [SMILES: COCCNc1nc2ncc(-n3ccc4ncnc(OC)c43)cc2n1Cc1ccc(F)c(F)c1] | | 466.2 |
| 43 | 1-((1-(3,4-difluorobenzyl)-6-(4-methoxy-5H-pyrrolo[3,2-d]pyrimidin-5-yl)-1H-imidazo[4,5-b]pyridin-2-yl)pyrrolidin-3-ol | 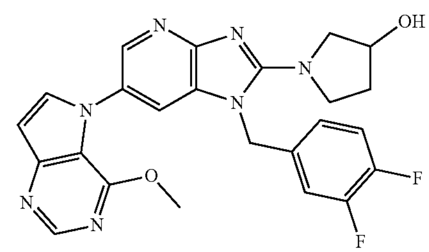 [SMILES: COc1ncnc2ccn(-c3cnc4nc(N5CCC(O)C5)n(Cc5ccc(F)c(F)c5)c4c3)c12] | | 478.2 |
| 44 | 1-(3-(difluoromethoxy)benzyl)-6-(4-methoxy-5H-pyrrolo[3,2-d]pyrimidin-5-yl)-2-methyl-1H-imidazo[4,5-b]pyridine | 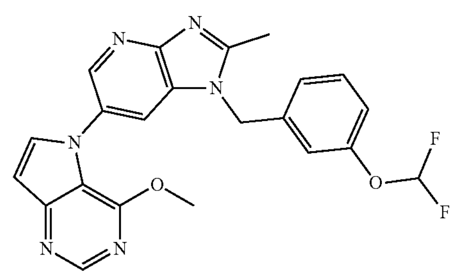 [SMILES: COc1ncnc2ccn(-c3cnc4nc(C)n(Cc5cccc(OC(F)F)c5)c4c3)c12] | | 437.2 |
| 45 | tert-butyl (3-((6-(4-methoxy-5H-pyrrolo[3,2-d]pyrimidin-5-yl)-2-methyl-1H-imidazo[4,5-b]pyridin-1-yl)methyl)phenyl)carbamate | 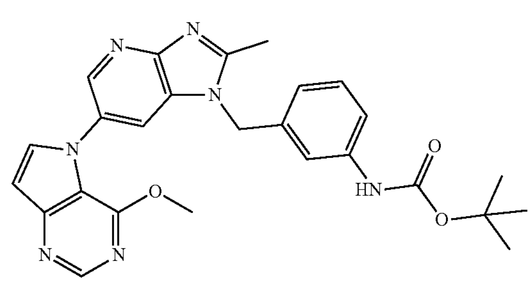 [SMILES: COc1ncnc2ccn(-c3cnc4nc(C)n(Cc5cccc(NC(=O)OC(C)(C)C)c5)c4c3)c12] | | 486.1 |

TABLE 1-continued

| Example | IUPAC NAME | CHEMICAL STRUCTURE | Salt | MS |
|---|---|---|---|---|
| 46 | 3-((6-(4-methoxy-5H-pyrrolo[3,2-d]pyrimidin-5-yl)-2-methyl-1H-imidazo[4,5-b]pyridin-1-yl)methyl)aniline | 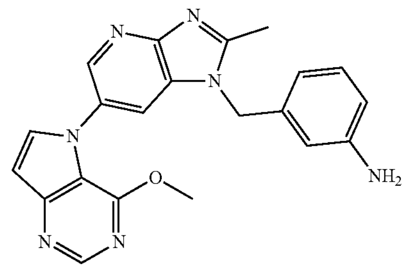 [SMILES: COc1ncnc2ccn(-c3cnc4nc(C)n(Cc5cccc(N)c5)c4c3)c12] | | 386.1 |
| 47 | 6-(4-methoxy-5H-pyrrolo[3,2-d]pyrimidin-5-yl)-2-methyl-1-(pyridin-2-ylmethyl)-1H-imidazo[4,5-b]pyridine | 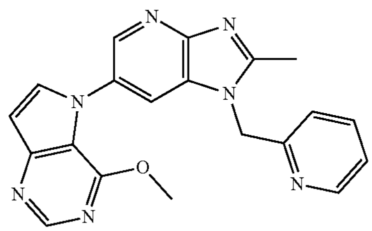 [SMILES: COc1ncnc2ccn(-c3cnc4nc(C)n(Cc5ccccn5)c4c3)c12] | | 372.2 |
| 48 | 1-(3,5-difluorobenzyl)-6-(4-methoxy-5H-pyrrolo[3,2-d]pyrimidin-5-yl)-1H-imidazo[4,5-b]pyridin-2-amine | 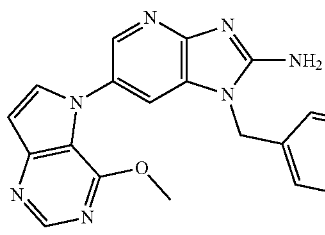 | | 408.2 |
| 49 | 1-((1-(3,5-difluorobenzyl)-6-(4-methoxy-5H-pyrrolo[3,2-d]pyrimidin-5-yl)-1H-imidazo[4,5-b]pyridin-2-yl)amino)-2-methylpropan-2-ol | 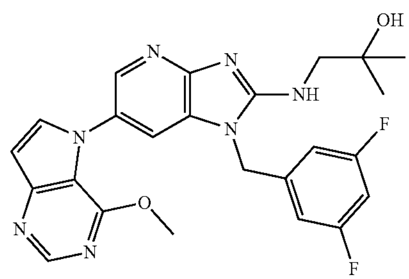 [SMILES: COc1ncnc2ccn(-c3cnc4nc(NCC(C)(C)O)n(Cc5cc(F)cc(F)c5)c4c3)c12] | | 480.2 |
| 50 | 1-(3,5-difluorobenzyl)-6-(4-(difluoromethoxy)-5H-pyrrolo[3,2-d]pyrimidin-5-yl)-N-methyl-1H-imidazo[4,5-b]pyridin-2-amine | 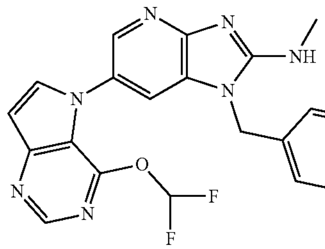 | | 458.1 |
| 51 | 1-((5-fluoropyridin-3-yl)methyl)-6-(4-methoxy-5H-pyrrolo[3,2-d]pyrimidin-5-yl)-2-methyl-1H-imidazo[4,5-b]pyridine | 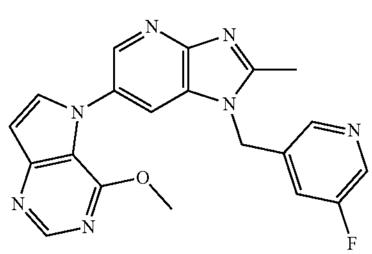 [SMILES: COc1ncnc2ccn(-c3cnc4nc(C)n(Cc5cncc(F)c5)c4c3)c12] | | 390.2 |

TABLE 1-continued

| Example | IUPAC NAME | CHEMICAL STRUCTURE | Salt | MS |
|---|---|---|---|---|
| 52 | 1-((2-fluoropyridin-4-yl)methyl)-6-(4-methoxy-5H-pyrrolo[3,2-d]pyrimidin-5-yl)-2-methyl-1H-imidazo[4,5-b]pyridine | 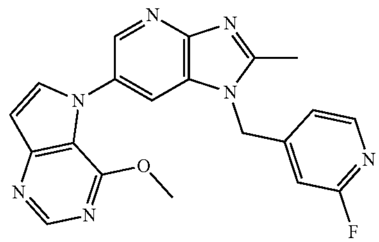 [SMILES: COc1ncnc2ccn(-c3cnc4nc(C)n(Cc5ccnc(F)c5)c4c3)c12] | | 390.2 |
| 53 | 1-(3-chloro-4-fluorobenzyl)-6-(4-methoxy-5H-pyrrolo[3,2-d]pyrimidin-5-yl)-2-methyl-1H-imidazo[4,5-b]pyridine | 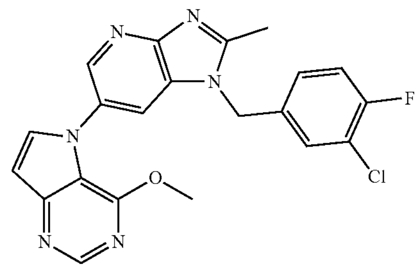 [SMILES: COc1ncnc2ccn(-c3cnc4nc(C)n(Cc5ccc(F)c(Cl)c5)c4c3)c12] | | 423.1 |
| 54 | 1-(4-chloro-3-fluorobenzyl)-6-(4-methoxy-5H-pyrrolo[3,2-d]pyrimidin-5-yl)-2-methyl-1H-imidazo[4,5-b]pyridine | 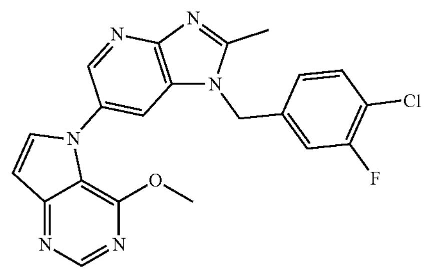 [SMILES: COc1ncnc2ccn(-c3cnc4nc(C)n(Cc5ccc(Cl)c(F)c5)c4c3)c12] | | 423.1 |
| 55 | methyl 3-((6-(4-methoxy-5H-pyrrolo[3,2-d]pyrimidin-5-yl)-2-methyl-1H-imidazo[4,5-b]pyridin-1-yl)methyl)benzoate | 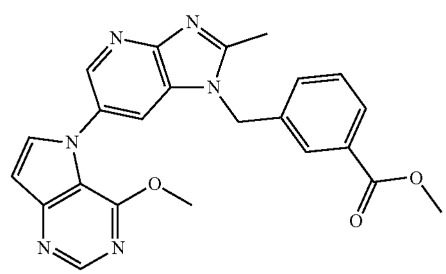 [SMILES: COC(=O)c1cccc(Cn2c(C)nc3ncc(-n4ccc5ncnc(OC)c54)cc32)c1] | | 429.2 |
| 56 | 3-((6-(4-methoxy-5H-pyrrolo[3,2-d]pyrimidin-5-yl)-2-methyl-1H-imidazo[4,5-b]pyridin-1-yl)methyl)benzoic acid | 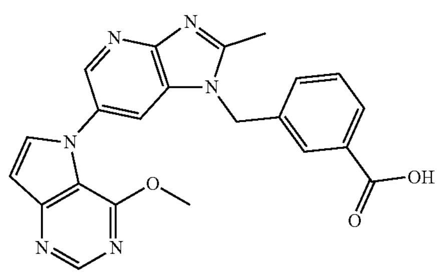 [SMILES: COc1ncnc2ccn(-c3cnc4nc(C)n(Cc5cccc(C(=O)O)c5)c4c3)c12] | | 415.2 |
| 57 | 3-((6-(4-methoxy-5H-pyrrolo[3,2-d]pyrimidin-5-yl)-2-methyl-1H-imidazo[4,5-b]pyridin-1-yl)methyl)-N-methylaniline | 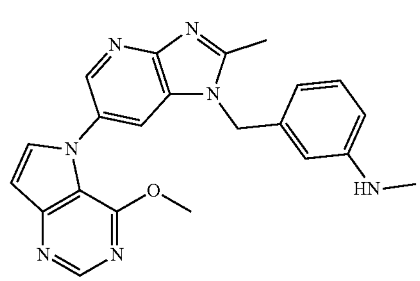 [SMILES: CNc1cccc(Cn2c(C)nc3ncc(-n4ccc5ncnc(OC)c54)cc32)c1] | | 400.2 |

TABLE 1-continued

| Example | IUPAC NAME | CHEMICAL STRUCTURE | Salt | MS |
|---|---|---|---|---|
| 58 | 3-((6-(4-methoxy-5H-pyrrolo[3,2-d]pyrimidin-5-yl)-2-methyl-1H-imidazo[4,5-b]pyridin-1-yl)methyl)-N-methylbenzamide | 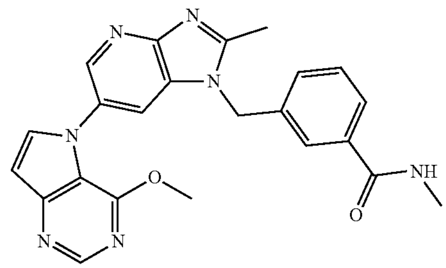 [SMILES: CNC(=O)c1cccc(Cn2c(C)nc3ncc(-n4ccc5ncnc(OC)c54)cc32)c1] | | 428.2 |
| 59 | 2-(3-((6-(4-methoxy-5H-pyrrolo[3,2-d]pyrimidin-5-yl)-2-methyl-1H-imidazo[4,5-b]pyridin-1-yl)methyl)phenyl)propan-2-ol | 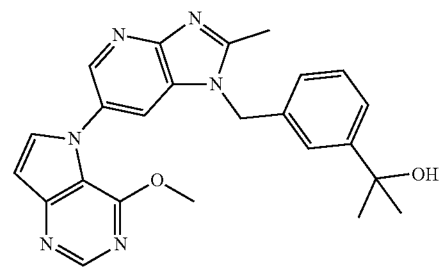 [SMILES: COc1ncnc2ccn(-c3cnc4nc(C)n(Cc5cccc(C(C)(C)O)c5)c4c3)c12] | | 429.2 |
| 60 | 2-methoxy-6-(4-methoxy-5H-pyrrolo[3,2-d]pyrimidin-5-yl)-1-(2,4,5-trifluorobenzyl)-1H-imidazo[4,5-b]pyridine | 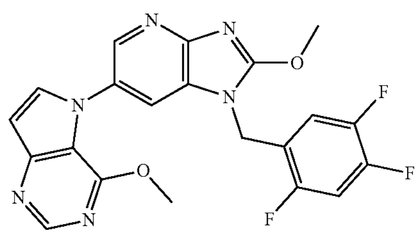 [SMILES: COc1ncnc2ccn(-c3cnc4nc(OC)n(Cc5cc(F)c(F)cc5F)c4c3)c12] | | 441.1 |
| 61 | 1-benzyl-2-methoxy-6-(4-methoxy-5H-pyrrolo[3,2-d]pyrimidin-5-yl)-1H-imidazo[4,5-b]pyridine | 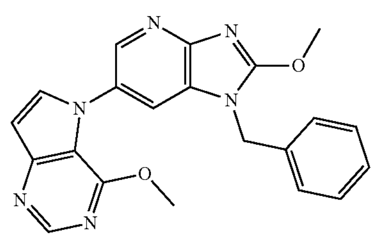 [SMILES: COc1ncnc2ccn(-c3cnc4nc(OC)n(Cc5ccccc5)c4c3)c12] | | 387.2 |
| 62 | 1-(2,5-difluorobenzyl)-2-methoxy-6-(4-methoxy-5H-pyrrolo[3,2-d]pyrimidin-5-yl)-1H-indazo[4,5-b]pyridine | 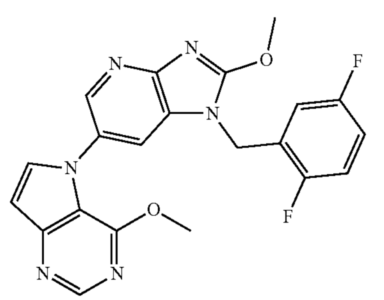 [SMILES: COc1ncnc2ccn(-c3cnc4nc(OC)n(Cc5cc(F)ccc5F)c4c3)c12] | | 423.1 |
| 63 | 1-(2,3-difluorobenzyl)-2-methoxy-6-(4-methoxy-5H-pyrrolo[3,2-d]pyrimidin-5-yl)-1H-indazo[4,5-b]pyridine | 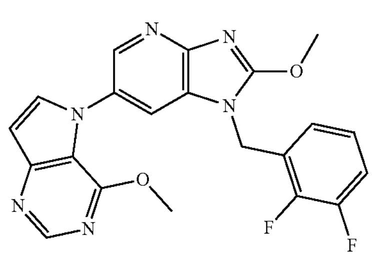 [SMILES: COc1ncnc2ccn(-c3cnc4nc(OC)n(Cc5cccc(F)c5F)c4c3)c12] | | 423.1 |

TABLE 1-continued

| Example | IUPAC NAME | CHEMICAL STRUCTURE | Salt | MS |
|---|---|---|---|---|
| 64 | 2-methoxy-6-(4-methoxy-5H-pyrrolo[3,2-d]pyrimidin-5-yl)-1-(2,3,4-trifluorobenzyl)-1H-imidazo[4,5-b]pyridine | 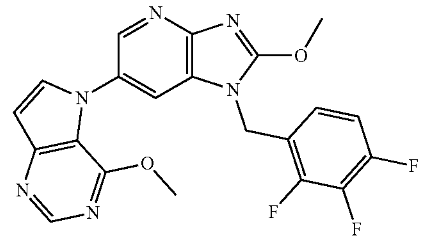 [SMILES: COc1ncnc2ccn(-c3cnc4nc(OC)n(Cc5ccc(F)c(F)c5F)c4c3)c12] | | 441.1 |
| 65 | 2-methoxy-6-(4-methoxy-5H-pyrrolo[3,2-d]pyrimidin-5-yl)-1-(2,3,6-trifluorobenzyl)-1H-imidazo[4,5-b]pyridine | 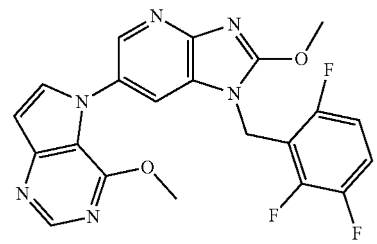 [SMILES: COc1ncnc2ccn(-c3cnc4nc(OC)n(Cc5c(F)ccc(F)c5F)c4c3)c12] | | 441.1 |
| 66 | (3-((6-(4-methoxy-5H-pyrrolo[3,2-d]pyrimidin-5-yl)-2-methyl-1H-imidazo[4,5-b]pyridin-1-yl)methyl)phenyl)methanol | 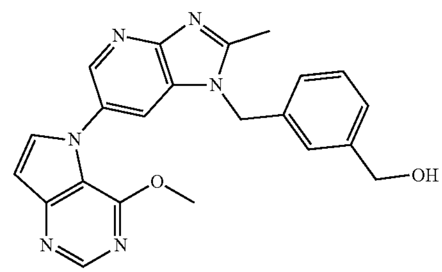 [SMILES: COc1ncnc2ccn(-c3cnc4nc(C)n(Cc5cccc(CO)c5)c4c3)c12] | | 401.2 |
| 67 | 1-(3,5-difluorobenzyl)-6-(4-methoxy-5H-pyrrolo[3,2-d]pyrimidin-5-yl)-2-(1-methyl-1H-pyrazol-4-yl)-1H-imidazo[4,5-b]pyridine | 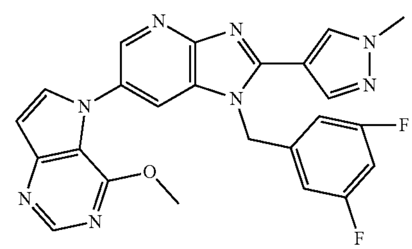 [SMILES: COc1ncnc2ccn(-c3cnc4nc(-c5cnn(C)c5)n(Cc5cc(F)cc(F)c5)c4c3)c12] | | 473.2 |
| 68 | 1-(3-fluoro-5-(trifluoromethyl)benzyl)-6-(4-methoxy-5H-pyrrolo[3,2-d]pyrimidin-5-yl)-2-methyl-1H-imidazo[4,5-b]pyridine | 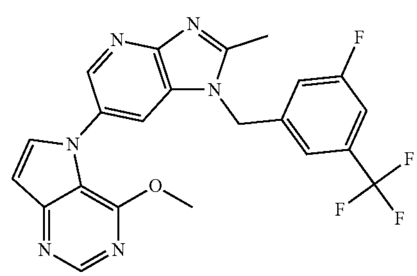 [SMILES: COc1ncnc2ccn(-c3cnc4nc(C)n(Cc5cc(F)cc(C(F)(F)F)c5)c4c3)c12] | | 457.1 |
| 69 | 1-(3,5-dichlorobenzyl)-6-(4-methoxy-5H-pyrrolo[3,2-d]pyrimidin-5-yl)-2-methyl-1H-imidazo[4,5-b]pyridine | 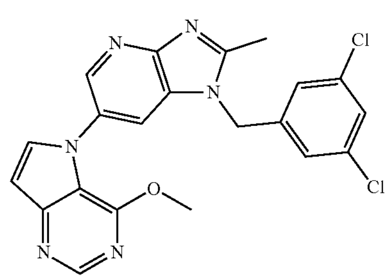 [SMILES: COc1ncnc2ccn(-c3cnc4nc(C)n(Cc5cc(Cl)cc(Cl)c5)c4c3)c12] | | 439.1 |

TABLE 1-continued

| Example | IUPAC NAME | CHEMICAL STRUCTURE | Salt | MS |
|---|---|---|---|---|
| 70 | 1-(3-fluoro-5-nitrobenzyl)-6-(4-methoxy-5H-pyrrolo[3,2-d]pyrimidin-5-yl)-2-methyl-1H-imidazo[4,5-b]pyridine | 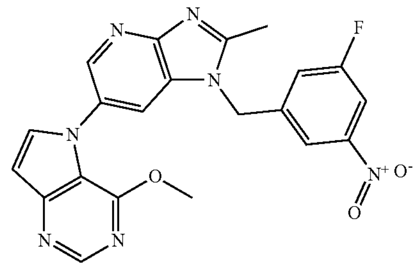 | | 434.1 |
| 71 | 3-fluoro-5-((6-(4-methoxy-5H-pyrrolo[3,2-d]pyrimidin-5-yl)-2-methyl-1H-imidazo[4,5-b]pyridin-1-yl)methyl)aniline | 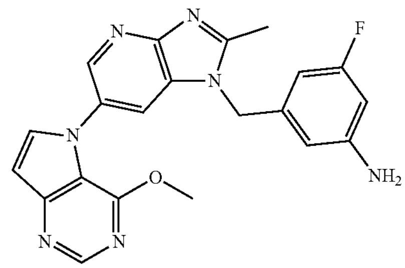 [SMILES: COc1ncnc2ccn(-c3cnc4nc(C)n(Cc5cc(N)cc(F)c5)c4c3)c12] | | 404.2 |
| 72 | 1-(3,5-difluorobenzyl)-2-(1-(difluoromethyl)-1H-pyrazol-4-yl)-6-(4-methoxy-5H-pyrrolo[3,2-d]pyrimidin-5-yl)-1H-imidazo[4,5-b]pyridine | 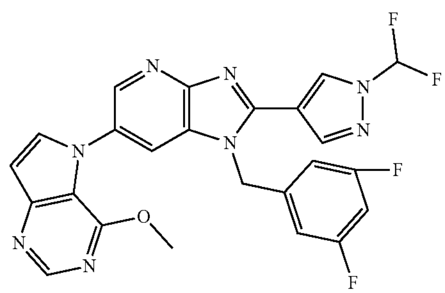 [SMILES: COc1ncnc2ccn(-c3cnc4nc(-c5cnn(C(F)F)c5)n(Cc5cc(F)cc(F)c5)c4c3)c12] | | 507.2 |
| 73 | 2-methoxy-6-(4-methoxy-5H-pyrrolo[3,2-d]pyrimidin-5-yl)-1-(2,3,5-trifluorobenzyl)-1H-imidazo[4,5-b]pyridine | 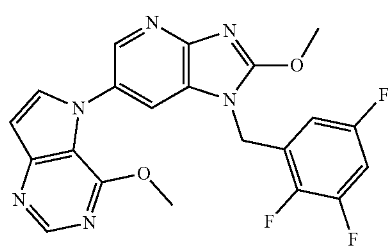 [SMILES: COc1ncnc2ccn(-c3cnc4nc(OC)n(Cc5cc(F)cc(F)c5F)c4c3)c12] | | 441.1 |
| 74 | 2-fluoro-4-((6-(4-methoxy-5H-pyrrolo[3,2-d]pyrimidin-5-yl)-2-methyl-1H-imidazo[4,5-b]pyridin-1-yl)methyl)benzonitrile | 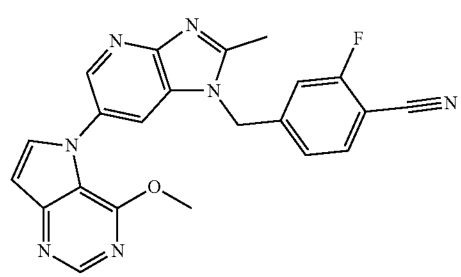 [SMILES: COc1ncnc2ccn(-c3cnc4nc(C)n(Cc5ccc(C#N)c(F)c5)c4c3)c12] | | 414.1 |

TABLE 1-continued

| Example | IUPAC NAME | CHEMICAL STRUCTURE | Salt | MS |
|---|---|---|---|---|
| 75 | 1-(5-fluoro-2-methoxybenzyl)-6-(4-methoxy-5H-pyrrolo[3,2-d]pyrimidin-5-yl)-2-methyl-1H-imidazo[4,5-b]pyridine | 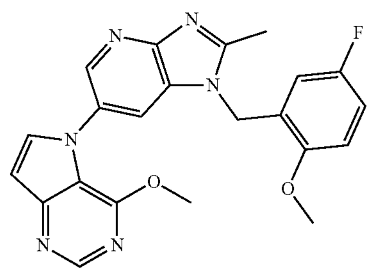 [SMILES: COc1ccc(F)cc1Cn1c(C)nc2ncc(-n3ccc4ncnc(OC)c43)cc21] | | 419.1 |
| 76 | 1-(3,5-difluorobenzyl)-6-(4-methoxy-5H-pyrrolo[3,2-d]pyrimidin-5-yl)-2-(tetrahydrofuran-3-ylmethoxy)-1H-imidazo[4,5-b]pyridine | 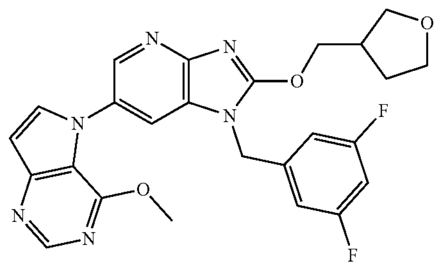 [SMILES: COc1ncnc2ccn(-c3cnc4nc(OCC5CCOC5)n(Cc5cc(F)cc(F)c5)c4c3)c12] | | 493.2 |
| 77 | 1-(3,5-difluorobenzyl)-6-(4-methoxy-5H-pyrrolo[3,2-d]pyrimidin-5-yl)-2-((1-methyl-1H-pyrazol-4-yl)methoxy)-1H-imidazo[4,5-b]pyridine | 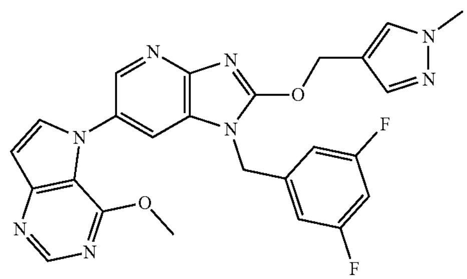 [SMILES: COc1ncnc2ccn(-c3cnc4nc(OCc5cnn(C)c5)n(Cc5cc(F)cc(F)c5)c4c3)c12] | | 503.1 |
| 78 | 1-(3,5-difluorobenzyl)-2-(difluoromethyl)-6-(4-methoxy-5H-pyrrolo[3,2-d]pyrimidin-5-yl)-1H-imidazo[4,5-b]pyridine | 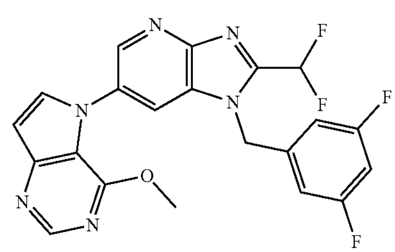 [SMILES: COc1ncnc2ccn(-c3cnc4nc(C(F)F)n(Cc5cc(F)cc(F)c5)c4c3)c12] | | 441.1 |
| 79 | 1-(3-chloro-5-fluorobenzyl)-6-(4-methoxy-5H-pyrrolo[3,2-d]pyrimidin-5-yl)-2-methyl-1H-imidazo[4,5-b]pyridine | 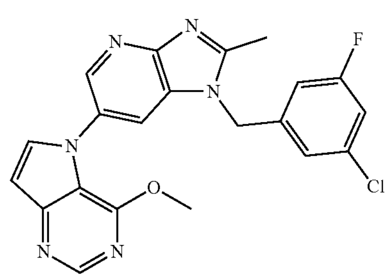 [SMILES: COc1ncnc2ccn(-c3cnc4nc(C)n(Cc5cc(F)cc(Cl)c5)c4c3)c12] | | 423.1 |

TABLE 1-continued

| Example | IUPAC NAME | CHEMICAL STRUCTURE | Salt | MS |
|---|---|---|---|---|
| 80 | 1-(3-fluoro-4-(trifluoromethyl)benzyl)-6-(4-methoxy-5H-pyrrolo[3,2-d]pyrimidin-5-yl)-2-methyl-1H-imidazo[4,5-b]pyridine | 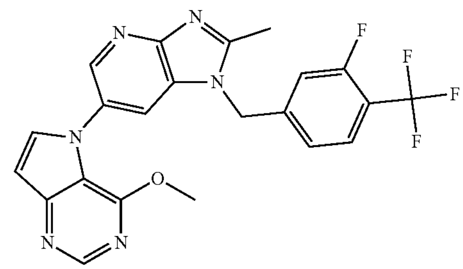 [SMILES: COc1ncnc2ccn(-c3cnc4nc(C)n(Cc5ccc(C(F)(F)F)c(F)c5)c4c3)c12] | | 457.1 |
| 81 | 2-((3,3-difluoroazetidin-1-yl)methyl)-1-(3,5-difluorobenzyl)-6-(4-methoxy-5H-pyrrolo[3,2-d]pyrimidin-5-yl)-1H-imidazo[4,5-b]pyridine | 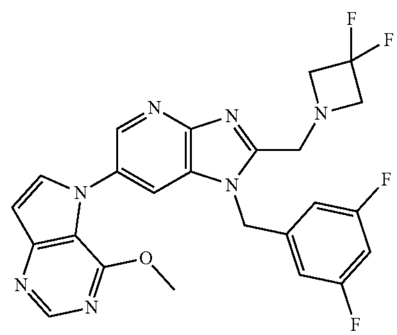 [SMILES: COc1ncnc2ccn(-c3cnc4nc(CN5CC(F)(F)C5)n(Cc5cc(F)cc(F)c5)c4c3)c12] | | 498.1 |
| 82 | (1-(3,5-difluorobenzyl)-6-(4-methoxy-5H-pyrrolo[3,2-d]pyrimidin-5-yl)-1H-imidazo[4,5-b]pyridin-2-yl)methanol | 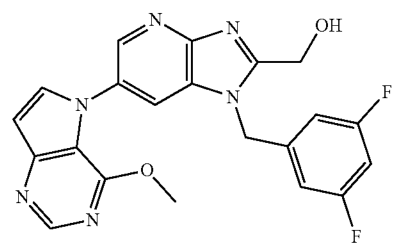 [SMILES: COc1ncnc2ccn(-c3cnc4nc(CO)n(Cc5cc(F)cc(F)c5)c4c3)c12] | | 423.1 |
| 83 | 1-((6-methoxypyridin-2-yl)methyl)-6-(4-methoxy-5H-pyrrolo[3,2-d]pyrimidin-5-yl)-2-methyl-1H-imidazo[4,5-b]pyridine | 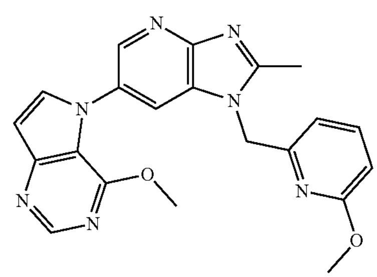 [SMILES: COc1cccc(Cn2c(C)nc3ncc(-n4ccc5ncnc(OC)c54)cc32)n1] | | 402.2 |
| 84 | 1-((6-chloropyridin-2-yl)methyl)-6-(4-methoxy-5H-pyrrolo[3,2-d]pyrimidin-5-yl)-2-methyl-1H-imidazo[4,5-b]pyridine | 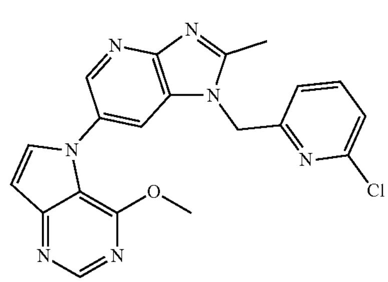 [SMILES: COc1ncnc2ccn(-c3cnc4nc(C)n(Cc5cccc(Cl)n5)c4c3)c12] | | 406.1 |

TABLE 1-continued

| Example | IUPAC NAME | CHEMICAL STRUCTURE | Salt | MS |
|---|---|---|---|---|
| 85 | (1-(2,3-difluorobenzyl)-6-(4-methoxy-5H-pyrrolo[3,2-d]pyrimidin-5-yl)-1H-imidazo[4,5-b]pyridin-2-yl)methanol | 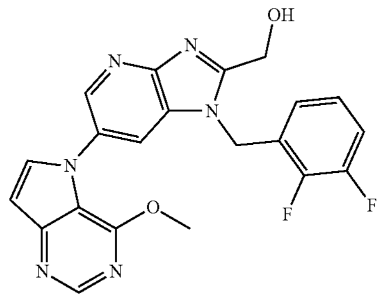 [SMILES: COc1ncnc2ccn(-c3cnc4nc(CO)n(Cc5cccc(F)c5F)c4c3)c12] | | 423.1 |
| 86 | 1-(3,5-difluorobenzyl)-6-(4-(fluoromethoxy)-5H-pyrrolo[3,2-d]pyrimidin-5-yl)-2-methyl-1H-imidazo[4,5-b]pyridine | 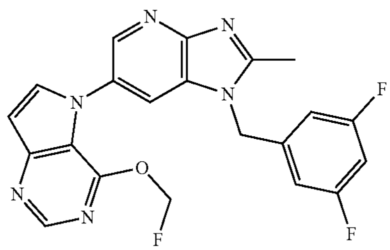 [SMILES: Cc1nc2ncc(-n3ccc4ncnc(OCF)c43)cc2n1Cc1cc(F)cc(F)c1] | | 425.1 |
| 87 | 1-(3,5-difluorobenzyl)-6-(4-methoxy-5H-pyrrolo[3,2-d]pyrimidin-5-yl)-2-(1,3-oxazol-5-yl)-1H-imidazo[4,5-b]pyridine | 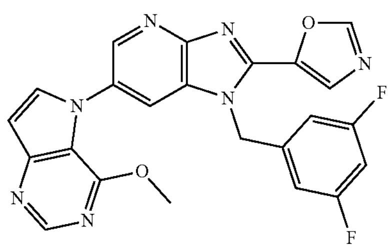 [SMILES: COc1ncnc2ccn(-c3cnc4nc(-c5cnco5)n(Cc5cc(F)cc(F)c5)c4c3)c12] | | 460.2 |
| 88 | 2-((1-((3,5-difluorobenzyl)-6-(4-methoxy-5H-pyrrolo[3,2-d]pyrimidin-5-yl)-1H-imidazo[4,5-b]pyridin-2-yl)methoxy)ethanol | 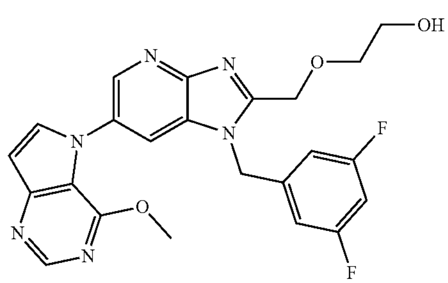 [SMILES: COc1ncnc2ccn(-c3cnc4nc(COCCO)n(Cc5cc(F)cc(F)c5)c4c3)c12] | | 467.1 |
| 89 | 1-(3,5-difluorobenzyl)-6-(4-methoxy-5H-pyrrolo[3,2-d]pyrimidin-5-yl)-2-((2,2,2-trifluoroethoxy)methyl)-1H-imidazo[4,5-b]pyridine | 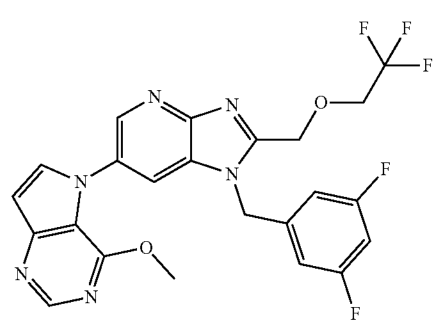 [SMILES: COc1ncnc2ccn(-c3cnc4nc(COCC(F)(F)F)n(Cc5cc(F)cc(F)c5)c4c3)c12] | | 505.1 |

TABLE 1-continued

| Example | IUPAC NAME | CHEMICAL STRUCTURE | Salt | MS |
|---|---|---|---|---|
| 90 | 1-(3,5-difluorobenzyl)-2-((2,2-difluoroethoxy)methyl)-6-(4-methoxy-5H-pyrrolo[3,2-d]pyrimidin-5-yl)-1H-imidazo[4,5-b]pyridine | 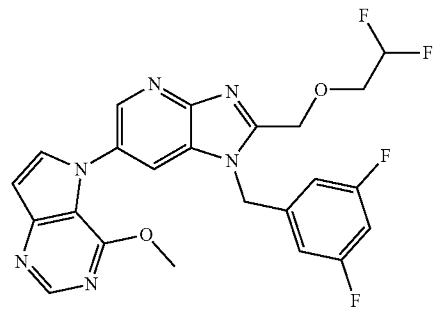 [SMILES: COc1ncnc2ccn(-c3cnc4nc(COCC(F)F)n(Cc5cc(F)cc(F)c5)c4c3)c12] | | 487.1 |
| 91 | 1-(2-furylmethyl)-6-(4-methoxy-5H-pyrrolo[3,2-d]pyrimidin-5-yl)-2-methyl-1H-imidazo[4,5-b]pyridine | 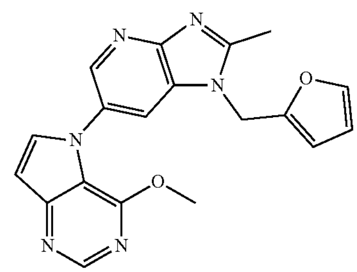 [SMILES: COc1ncnc2ccn(-c3cnc4nc(C)n(Cc5ccco5)c4c3)c12] | | 361.1 |
| 92 | 1-(3-fluorobenzyl)-2-(3-methoxyazetidin-1-yl)-6-(4-methoxy-5H-pyrrolo[3,2-d]pyrimidin-5-yl)-1H-imidazo[4,5-b]pyridine | 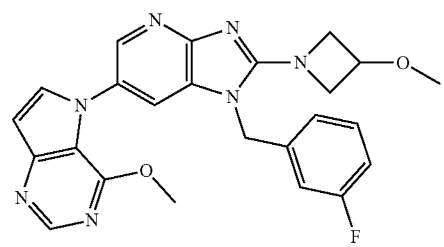 [SMILES: COc1ncnc2ccn(-c3cnc4nc(N5CC(OC)C5)n(Cc5cccc(F)c5)c4c3)c12] | | 460.2 |
| 93 | 1-(3-furylmethyl)-6-(4-methoxy-5H-pyrrolo[3,2-d]pyrimidin-5-yl)-2-methyl-1H-imidazo[4,5-b]pyridine | 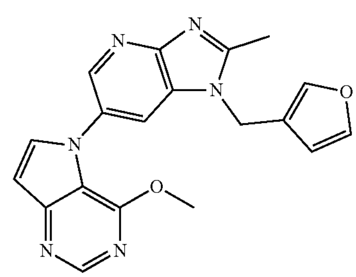 [SMILES: COc1ncnc2ccn(-c3cnc4nc(C)n(Cc5ccoc5)c4c3)c12] | | 361.1 |
| 94 | 6-(4-methoxy-5H-pyrrolo[3,2-d]pyrimidin-5-yl)-2-methyl-1-((6-(trifluoromethyl)pyridin-2-yl)methyl)-1H-imidazo[4,5-b]pyridine | 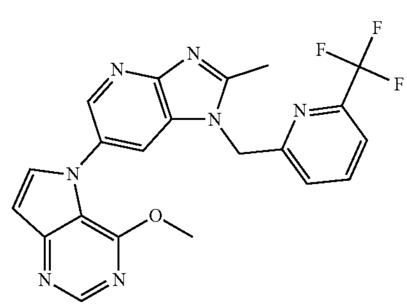 [SMILES: COc1ncnc2ccn(-c3cnc4nc(C)n(Cc5cccc(C(F)(F)F)n5)c4c3)c12] | | 440.1 |

TABLE 1-continued

| Example | IUPAC NAME | CHEMICAL STRUCTURE | Salt | MS |
|---|---|---|---|---|
| 95 | 2-(2-fluoro-4-((6-(4-methoxy-5H-pyrrolo[3,2-d]pyrimidin-5-yl)-2-methyl-1H-imidazo[4,5-b]pyridin-1-yl)methyl)phenoxy)ethanol | 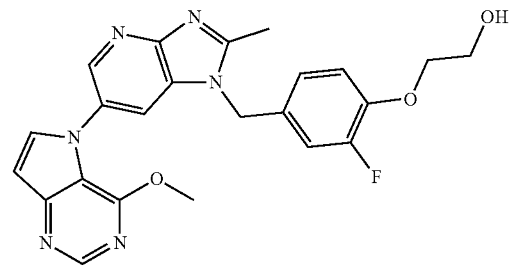 [SMILES: COc1ncnc2ccn(-c3cnc4nc(C)n(Cc5ccc(OCCO)c(F)c5)c4c3)c12] | | 449.1 |
| 96 | 1-((6-fluoropyridin-2-yl)methyl)-6-(4-methoxy-5H-pyrrolo[3,2-d]pyrimidin-5-yl)-2-methyl-1H-imidazo[4,5-b]pyridine | 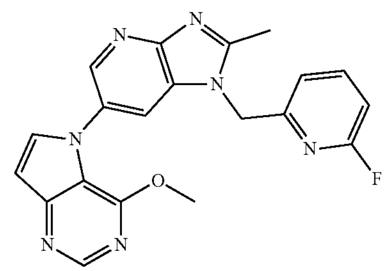 [SMILES: COc1ncnc2ccn(-c3cnc4nc(C)n(Cc5cccc(F)n5)c4c3)c12] | | 390.1 |
| 97 | 1-((2-chloro-6-methylpyridin-4-yl)methyl)-6-(4-methoxy-5H-pyrrolo[3,2-d]pyrimidin-5-yl)-2-methyl-1H-imidazo[4,5-b]pyridine | 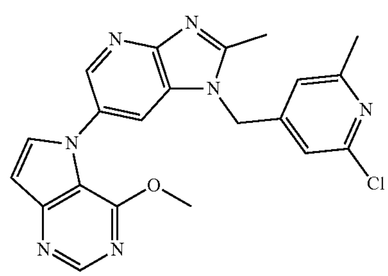 [SMILES: COc1ncnc2ccn(-c3cnc4nc(C)n(Cc5cc(C)nc(Cl)c5)c4c3)c12] | | 418.0 |
| 98 | 1-((6-fluoropyridin-2-yl)methyl)-2-methoxy-6-(4-methoxy-5H-pyrrolo[3,2-d]pyrimidin-5-yl)-1H-imidazo[4,5-b]pyridine | 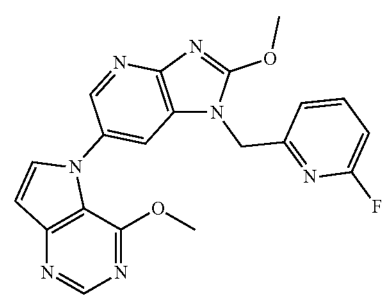 [SMILES: COc1ncnc2ccn(-c3cnc4nc(OC)n(Cc5cccc(F)n5)c4c3)c12] | | 406.2 |
| 99 | 1-(3,4-difluorobenzyl)-N-methyl-6-(1H-pyrrolo[3,2-b]pyridin-1-yl)-1H-imidazo[4,5-b]pyridin-2-amine | 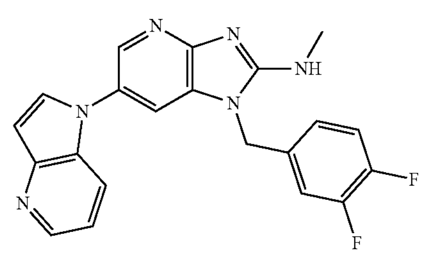 [SMILES: CNc1nc2ncc(-n3ccc4ncccc43)cc2n1Cc1ccc(F)c(F)c1] | | 391.2 |
| 100 | 1-(3,5-difluorobenzyl)-6-(7-methoxy-1H-pyrrolo[3,2-b]pyridin-1-yl)-N-methyl-1H-imidazo[4,5-b]pyridin-2-amine | 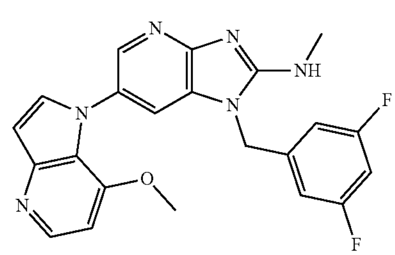 [SMILES: CNc1nc2ncc(-n3ccc4nccc(OC)c43)cc2n1Cc1cc(F)cc(F)c1] | | 421.2 |

TABLE 1-continued

| Example | IUPAC NAME | CHEMICAL STRUCTURE | Salt | MS |
|---|---|---|---|---|
| 101 | 1-(3,5-difluorobenzyl)-2-ethoxy-6-(7-methoxy-1H-pyrrolo[3,2-b]pyridin-1-yl)-1H-imidazo[4,5-b]pyridine | 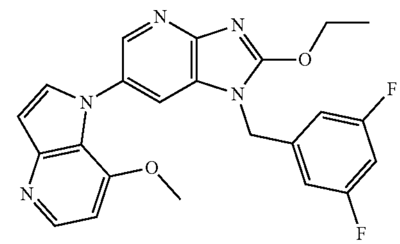 [SMILES: CCOc1nc2ncc(-n3ccc4nccc(OC)c43)cc2n1Cc1cc(F)cc(F)c1] | | 436.2 |
| 102 | 1-(3-fluorobenzyl)-6-(7-methoxy-1H-pyrrolo[3,2-b]pyridin-1-yl)-2-methyl-1H-imidazo[4,5-b]pyridine | 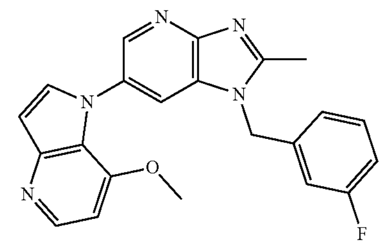 [SMILES: COc1ccnc2ccn(-c3cnc4nc(C)n(Cc5cccc(F)c5)c4c3)c12] | | 388.2 |
| 103 | 1-(3,4-difluorobenzyl)-N-methyl-6-(1H-pyrazolo[4,3-b]pyridin-1-yl)-1H-imidazo[4,5-b]pyridin-2-amine | 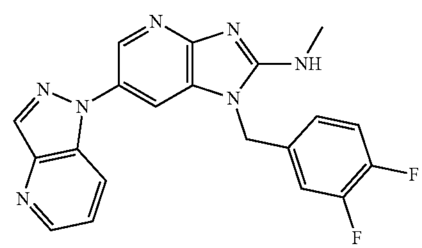 [SMILES: CNc1nc2ncc(-n3ncc4ncccc43)cc2n1Cc1ccc(F)c(F)c1] | | 392.2 |
| 104 | 1-(3,4-difluorobenzyl)-6-(7-methoxy-1H-pyrazolo[4,3-b]pyridin-1-yl)-N-methyl-1H-imidazo[4,5-b]pyridin-2-amine | 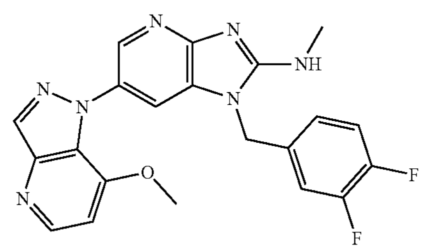 [SMILES: CNc1nc2ncc(-n3ncc4nccc(OC)c43)cc2n1Cc1ccc(F)c(F)c1] | | 422.2 |
| 105 | 1-(1-(3-fluorobenzyl)-2-methyl-1H-imidazo[4,5-b]pyridin-6-yl)-7-methoxy-1H-pyrazolo[4,3-b]pyridine | 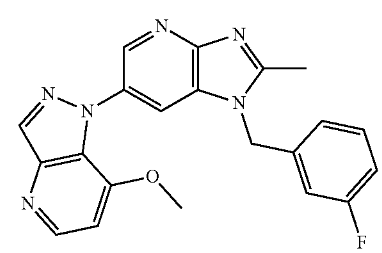 [SMILES: COc1ccnc2cnn(-c3cnc4nc(C)n(Cc5cccc(F)c5)c4c3)c12] | | 389.2 |
| 106 | 1-(3,5-difluorobenzyl)-6-(3-methoxy-5H-pyrrolo[2,3-b]pyrazin-5-yl)-N-methyl-1H-imidazo[4,5-b]pyridin-2-amine | 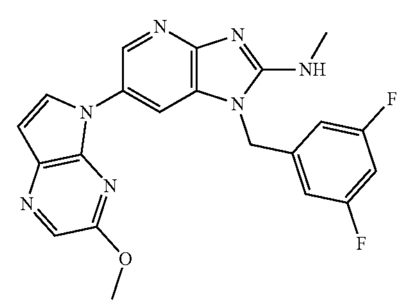 [SMILES: CNc1nc2ncc(-n3ccc4ncc(OC)nc43)cc2n1Cc1cc(F)cc(F)c1] | | 422.1 |

TABLE 1-continued

| Example | IUPAC NAME | CHEMICAL STRUCTURE | Salt | MS |
|---|---|---|---|---|
| 107 | 1-(3,5-difluorobenzyl)-N-methyl-6-(5H-pyrrolo[2,3-b]pyrazin-5-yl)-1H-imidazo[4,5-b]pyridin-2-amine | 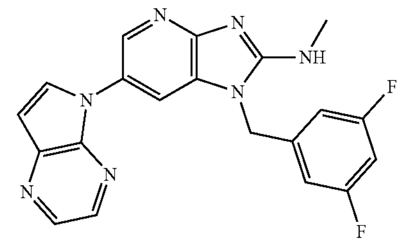 [SMILES: CNc1nc2ncc(-n3ccc4nccnc43)cc2n1Cc1cc(F)cc(F)c1] | | 392.1 |
| 108 | (1-(3-fluorobenzyl)-6-(3-methoxy-5H-pyrrolo[2,3-b]pyrazin-5-yl)-1H-imidazo[4,5-b]pyridin-2-yl)-methanol | 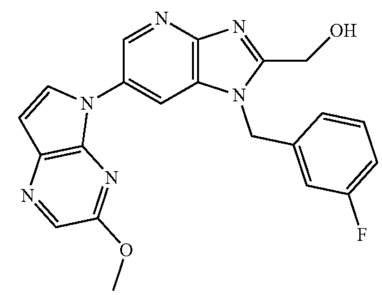 [SMILES: COc1cnc2ccn(-c3cnc4nc(CO)n(Cc5cccc(F)c5)c4c3)c2n1] | | 405.1 |
| 109 | (1-(3,5-difluorobenzyl)-6-(3-methoxy-5H-pyrrolo[2,3-b]pyrazin-5-yl)-1H-imidazo[4,5-b]pyridin-2-yl)-methanol | 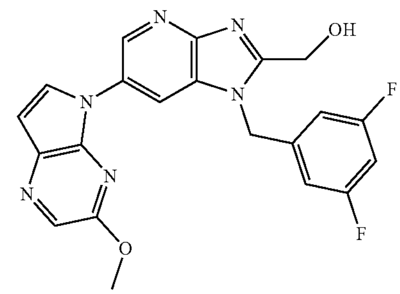 [SMILES: COc1cnc2ccn(-c3cnc4nc(CO)n(Cc5cc(F)cc(F)c5)c4c3)c2n1] | | 423.1 |
| 110 | 1-(3-fluorobenzyl)-6-(3-methoxy-5H-pyrrolo[2,3-b]pyrazin-5-yl)-2-methyl-1H-imidazo[4,3-b]pyridine | 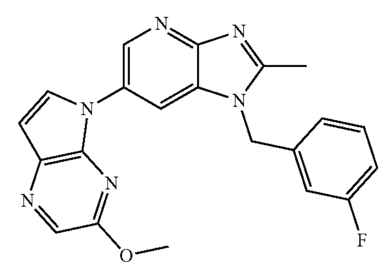 [SMILES: COc1cnc2ccn(-c3cnc4nc(C)n(Cc5cccc(F)c5)c4c3)c2n1] | | 389.2 |
| 111 | 2-(5-(1-(3-fluorobenzyl)-2-methyl-1H-imidazo[4,5-b]pyridin-6-yl)-5H-pyrrolo[2,3-b]pyrazin-3-yl)propan-2-ol | 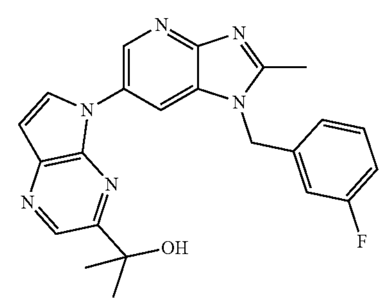 [SMILES: Cc1nc2ncc(-n3ccc4ncc(C(C)(C)O)nc43)cc2n1Cc1cccc(F)c1] | | 417.1 |

TABLE 1-continued

| Example | IUPAC NAME | CHEMICAL STRUCTURE | Salt | MS |
|---|---|---|---|---|
| 112 | 1-(3-fluorobenzyl)-2-methyl-6-(5H-pyrrolo[2,3-b]pyrazin-5-yl)-1H-imidazo[4,5-b]pyridine | 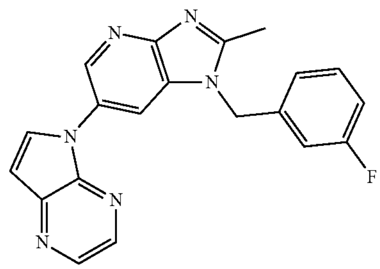 [SMILES: Cc1nc2ncc(-n3ccc4nccnc43)cc2n1Cc1cccc(F)c1] | | 359.1 |
| 113 | 1-(5-(1-(3-fluorobenzyl)-2-methyl-1H-imidazo[4,5-b]pyridin-6-yl)-5H-pyrrolo[2,3-b]pyrazin-3-yl)ethanone | 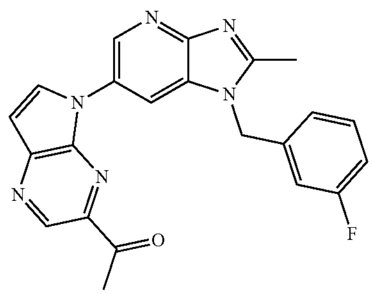 [SMILES: CC(=O)c1cnc2ccn(-c3cnc4nc(C)n(Cc5cccc(F)c5)c4c3)c2n1] | | 401.2 |
| 114 | 6-(3-chloro-5H-pyrrolo[2,3-b]pyrazin-5-yl)-1-(3-fluorobenzyl)-2-methyl-1H-imidazo[4,5-b]pyridine | 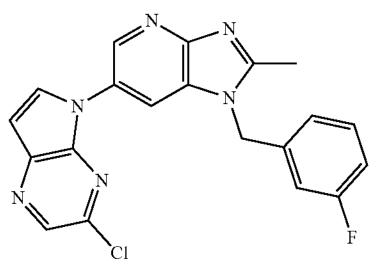 [SMILES: Cc1nc2ncc(-n3ccc4ncc(Cl)nc43)cc2n1Cc1cccc(F)c1] | | 393.1 |
| 115 | 1-(3-fluorobenzyl)-2-methyl-6-(3-(1-methyl-1H-pyrazol-4-yl)-5H-pyrrolo[2,3-b]pyrazin-5-yl)-1H-imidazo[4,5-b]pyridine | 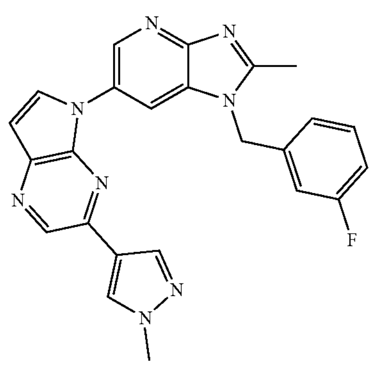 [SMILES: Cc1nc2ncc(-n3ccc4ncc(-c5cnn(C)c5)nc43)cc2n1Cc1cccc(F)c1] | | 439.2 |
| 116 | 5-(1-(3-fluorobenzyl)-2-methyl-1H-imidazo[4,5-b]pyridin-6-yl)-5H-pyrrolo[2,3-b]pyrazin-3-ol | 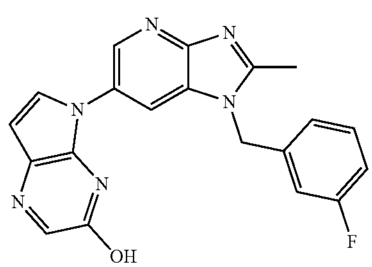 [SMILES: Cc1nc2ncc(-n3ccc4ncc(O)nc43)cc2n1Cc1cccc(F)c1] | | 375.2 |

TABLE 1-continued

| Example | IUPAC NAME | CHEMICAL STRUCTURE | Salt | MS |
|---|---|---|---|---|
| 117 | 1-(3-fluorobenzyl)-2-methyl-6-(3-methyl-5H-pyrrolo[2,3-b]pyrazin-5-yl)-1H-imidazo[4,5-b]pyridine | 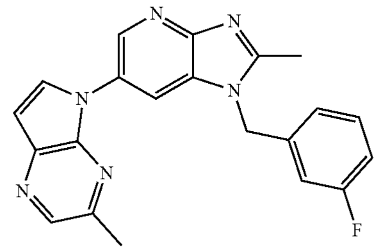 [SMILES: Cc1cnc2ccn(-c3cnc4nc(C)n(Cc5cccc(F)c5)c4c3)c2n1] | | 373.2 |
| 118 | N-(2,2-difluoroethyl)-5-(1-(3-fluorobenzyl)-2-methyl-1H-imidazo[4,5-b]pyridin-6-yl)-5H-pyrrolo[2,3-b]pyrazin-3-amine | 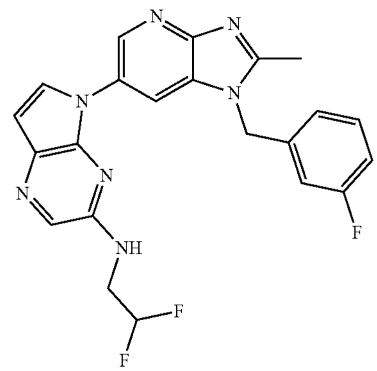 [SMILES: Cc1nc2ncc(-n3ccc4ncc(NCC(F)F)nc43)cc2n1Cc1cccc(F)c1] | | 438.2 |
| 119 | 2-(5-(1-(3,5-difluorobenzyl)-2-methyl-1H-imidazo[4,5-b]pyridin-6-yl)-5H-pyrrolo[2,3-b]pyrazin-3-yl)propan-2-ol | 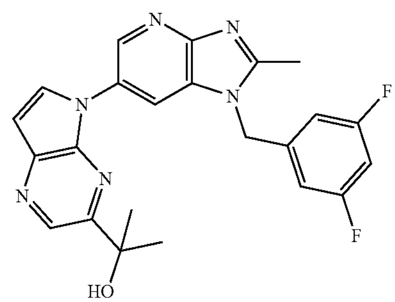 [SMILES: Cc1nc2ncc(-n3ccc4ncc(C(C)(C)O)nc43)cc2n1Cc1cc(F)cc(F)c1] | | 435.2 |
| 120 | 1-(5-(1-(3,5-difluorobenzyl)-2-methyl-1H-imidazo[4,5-b]pyridin-6-yl)-5H-pyrrolo[2,3-b]pyrazin-3-yl)ethanol | 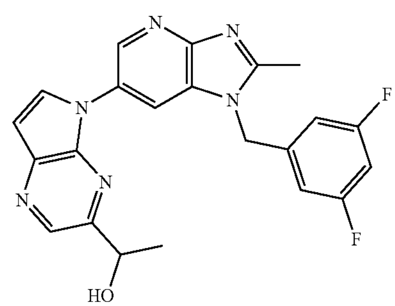 [SMILES: Cc1nc2ncc(-n3ccc4ncc(C(C)O)nc43)cc2n1Cc1cc(F)cc(F)c1] | | 421.1 |
| 121 | 5-(1-(3-fluorobenzyl)-2-methyl-1H-imidazo[4,5-b]pyridin-6-yl)-5H-pyrrolo[2,3-b]pyrazine-3-carbonitrile | 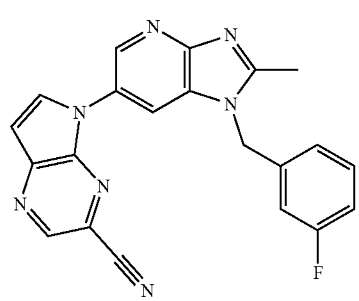 [SMILES: Cc1nc2ncc(-n3ccc4ncc(C#N)nc43)cc2n1Cc1cccc(F)c1] | | 384.1 |

TABLE 1-continued

| Example | IUPAC NAME | CHEMICAL STRUCTURE | Salt | MS |
|---|---|---|---|---|
| 122 | 2-(5-(1-(3,5-difluorobenzyl)-2-methoxy-1H-imidazo[4,5-b]pyridin-6-yl)-5H-pyrrolo[2,3-b]pyrazin-3-yl)propan-2-ol | 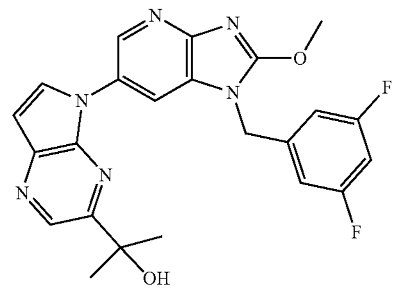 [SMILES: COc1nc2ncc(-n3ccc4ncc(C(C)(C)O)nc43)cc2n1Cc1cc(F)cc(F)c1] | | 451.2 |
| 123 | 1-(3,5-difluorobenzyl)-N-(2,2-difluoroethyl)-6-(5H-pyrrolo[2,3-b]pyrazin-5-yl)-1H-imidazo[4,5-b]pyridin-2-amine | 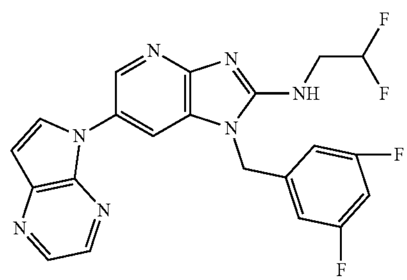 [SMILES: Fc1cc(F)cc(Cn2c(NCC(F)F)nc3ncc(-n4ccc5nccnc54)cc32)c1] | | 442.1 |
| 124 | 1-(3,5-difluorobenzyl)-2-methoxy-6-(5H-pyrrolo[2,3-b]pyrazin-5-yl)-1H-imidazo[4,5-b]pyridine | 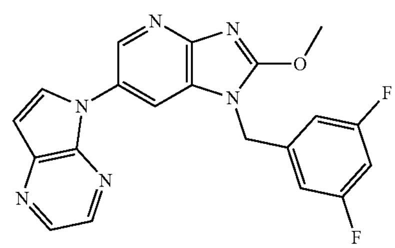 [SMILES: COc1nc2ncc(-n3ccc4nccnc43)cc2n1Cc1cc(F)cc(F)c1] | | 393.1 |
| 125 | 1-(3,5-difluorobenzyl)-6-(5H-pyrrolo[2,3-b]pyrazin-5-yl)-1H-imidazo[4,5-b]pyridin-2-amine | 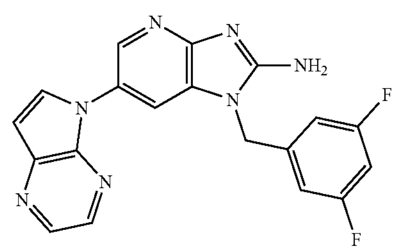 [SMILES: Nc1nc2ncc(-n3ccc4nccnc43)cc2n1Cc1cc(F)cc(F)c1] | | 378.2 |
| 126 | 6-(3-(1-difluoromethyl)-1H-pyrazol-4-yl)-5H-pyrrolo[2,3-b]pyrazin-5-yl)-1-(3-fluorobenzyl)-2-methyl-1H-imidazo[4,5-b]pyridine | 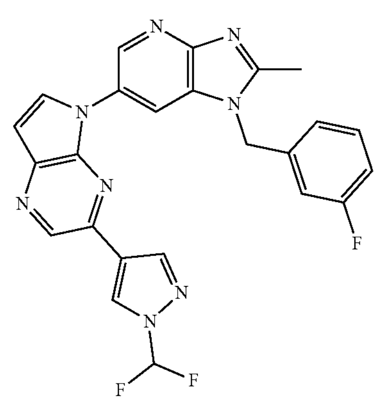 [SMILES: Cc1nc2ncc(-n3ccc4ncc(-c5cnn(C(F)F)c5)nc43)cc2n1Cc1cccc(F)c1] | | 475.2 |

TABLE 1-continued

| Example | IUPAC NAME | CHEMICAL STRUCTURE | Salt | MS |
|---|---|---|---|---|
| 127 | 1-(3,5-difluorobenzyl)-2-methyl-6-(5H-pyrrolo[2,3-b]pyrazin-5-yl)-1H-imidazo[4,5-b]pyridine | 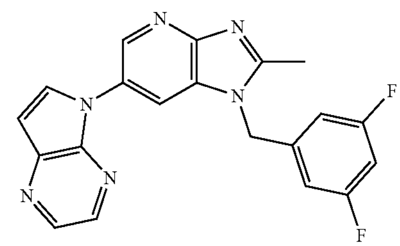 [SMILES: Cc1nc2ncc(-n3ccc4nccnc43)cc2n1Cc1cc(F)cc(F)c1] | | 377.2 |
| 128 | 1-(3,5-difluorobenzyl)-2-methyl-6-(3-((1-methyl-1H-pyrazol-4-yl)oxy)-5H-pyrrolo[2,3-b]pyrazin-5-yl)-1H-imidazo[4,5-b]pyridine | 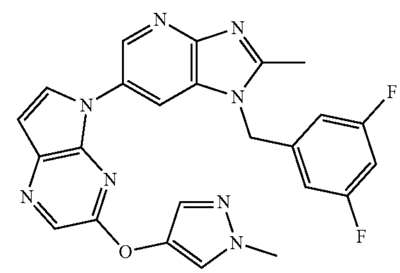 [SMILES: Cc1nc2ncc(-n3ccc4ncc(Oc5cnn(C)c5)nc43)cc2n1Cc1cc(F)cc(F)c1] | | 473.1 |
| 129 | 1-(3,5-difluorobenzyl)-6-(3-(3-fluoroazetidin-1-yl)-5H-pyrrolo[2,3-b]pyrazin-5-yl)-2-methyl-1H-imidazo[4,5-b]pyridine | 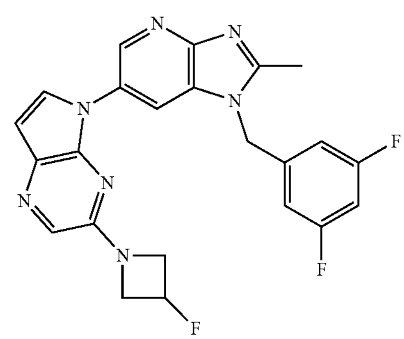 [SMILES: Cc1nc2ncc(-n3ccc4ncc(N5CC(F)C5)nc43)cc2n1Cc1cc(F)cc(F)c1] | | 450.1 |
| 130 | 1-(5-(1-(3,5-difluorobenzyl)-2-methyl-1H-imidazo[4,5-b]pyridin-6-yl)-5H-pyrrolo[2,3-b]pyrazin-3-yl)pyrrolidin-2-one | 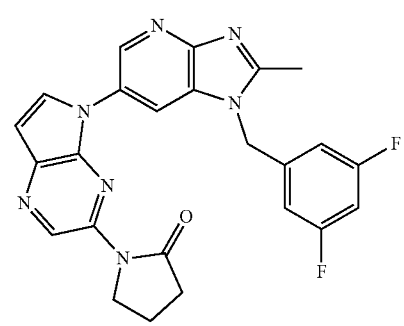 [SMILES: Cc1nc2ncc(-n3ccc4ncc(N5CCCC5=O)nc43)cc2n1Cc1cc(F)cc(F)c1] | | 460.3 |
| 131 | 1-(3,5-difluorobenzyl)-6-(3-(3,6-dihydro-2H-pyran-4-yl)-5H-pyrrolo[2,3-b]pyrazin-5-yl)-2-methyl-1H-imidazo[4,5-b]pyridine | 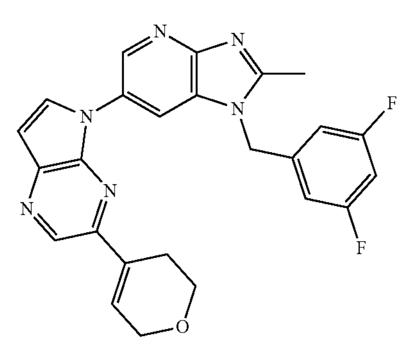 [SMILES: Cc1nc2ncc(-n3ccc4ncc(C5=CCOCC5)nc43)cc2n1Cc1cc(F)cc(F)c1] | | 459.2 |

| Example | IUPAC NAME | CHEMICAL STRUCTURE | Salt | MS |
|---|---|---|---|---|
| 132 | 1-(3,5-difluorobenzyl)-2-methyl-6-(3-(1H-pyrazol-1-yl)-5H-pyrrolo[2,3-b]pyrazin-5-yl)-1H-imidazo[4,5-b]pyridine | 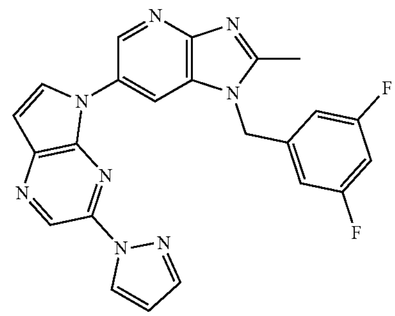 [SMILES: Cc1nc2ncc(-n3ccc4ncc(-n5cccn5)nc43)cc2n1Cc1cc(F)cc(F)c1] | | 443.2 |
| 133 | 1-(3,5-difluorobenzyl)-2-methyl-6-(3-tetrahydro-2H-pyran-4-yl)-5H-pyrrolo[2,3-b]pyrazin-5-yl)-1H-imidazo[4,5-b]pyridine | 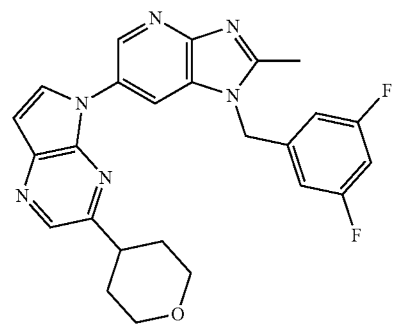 [SMILES: Cc1nc2ncc(-n3ccc4ncc(C5CCOCC5)nc43)cc2n1Cc1cc(F)cc(F)c1] | | 461.2 |
| 134 | 1-(5-(1-(3,5-difluorobenzyl)-2-methoxy-1H-imidazo[4,5-b]pyridin-6-yl)-5H-pyrrolo[2,3-b]pyrazin-3-yl)ethanol | 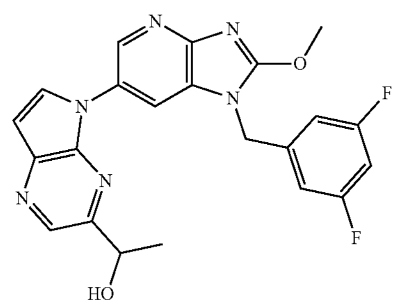 [SMILES: COc1nc2ncc(-n3ccc4ncc(C(C)O)nc43)cc2n1Cc1cc(F)cc(F)c1] | | 437.2 |
| 135 | 1-(3,5-difluorobenzyl)-2-methyl-6-(3-(pyridin-2-yl)-5H-pyrrolo[2,3-b]pyrazin-5-yl)-1H-imidazo[4,5-b]pyridine | 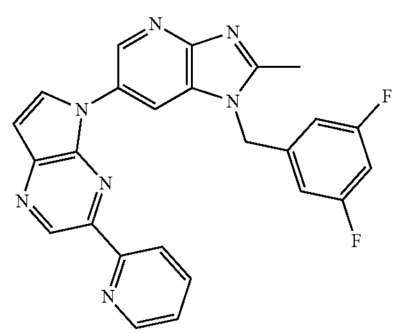 [SMILES: Cc1nc2ncc(-n3ccc4ncc(-c5ccccn5)nc43)cc2n1Cc1cc(F)cc(F)c1] | | 454.2 |
| 136 | 1-(3,5-difluorobenzyl)-2-methyl-6-(3-(pyridin-4-yl)-5H-pyrrolo[2,3-b]pyrazin-5-yl)-1H-imidazo[4,5-b]pyridine | 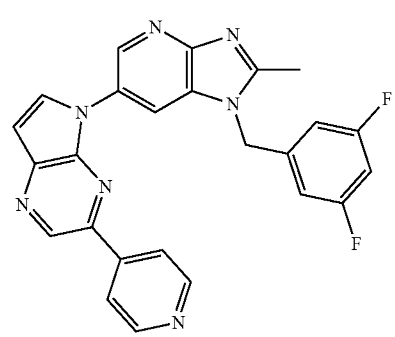 [SMILES: Cc1nc2ncc(-n3ccc4ncc(-c5ccncc5)nc43)cc2n1Cc1cc(F)cc(F)c1] | | 454.2 |

TABLE 1-continued

| Example | IUPAC NAME | CHEMICAL STRUCTURE | Salt | MS |
|---|---|---|---|---|
| 137 | 1-(3,5-difluorobenzyl)-2-methyl-6-(3-(pyridin-3-yl)-5H-pyrrolo[2,3-b]pyrazin-5-yl)-1H-imidazo[4,5-b]pyridine | 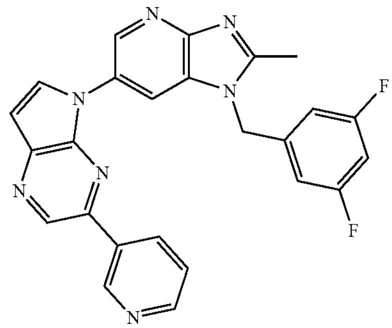 [SMILES: Cc1nc2ncc(-n3ccc4ncc(-c5cccnc5)nc43)cc2n1Cc1cc(F)cc(F)c1] | | 454.2 |
| 138 | 4-(5-(1-(3,5-difluorobenzyl)-2-methyl-1H-imidazo[4,5-b]pyridin-6-yl)-5H-pyrrolo[2,3-b]pyrazin-3-yl)benzonitrile | 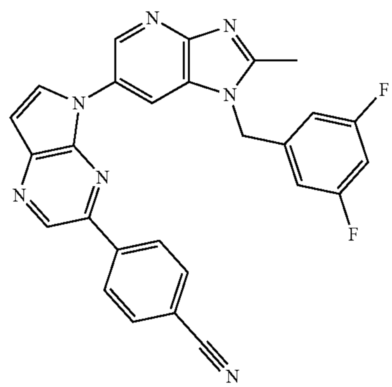 [SMILES: Cc1nc2ncc(-n3ccc4ncc(-c5ccc(C#N)cc5)nc43)cc2n1Cc1cc(F)cc(F)c1] | | 478.2 |
| 139 | 3-(5-(1-(3,5-difluorobenzyl)-2-methyl-1H-imidazo[4,5-b]pyridin-6-yl)-5H-pyrrolo[2,3-b]pyrazin-3-yl)benzonitrile | 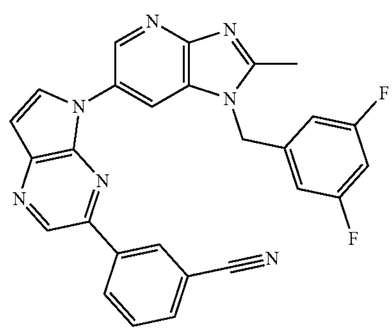 [SMILES: Cc1nc2ncc(-n3ccc4ncc(-c5cccc(C#N)c5)nc43)cc2n1Cc1cc(F)cc(F)c1] | | 478.2 |
| 140 | 1-(3,5-difluorobenzyl)-2-methyl-6-(3-(1-(2-(morpholin-4-yl)ethyl)-1H-pyrazol-4-yl)-5H-pyrrolo[2,3-b]pyrazin-5-yl)-1H-imidazo[4,5-b]pyridine | 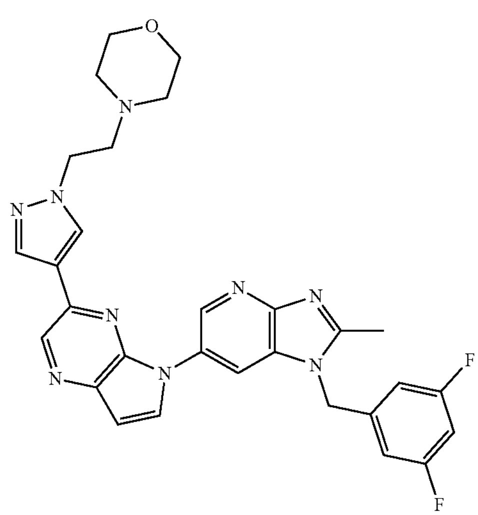 [SMILES: Cc1nc2ncc(-n3ccc4ncc(-c5cnn(CCN6CCOCC6)c5)nc43)cc2n1Cc1cc(F)cc(F)c1] | | 556.3 |

TABLE 1-continued

| Example | IUPAC NAME | CHEMICAL STRUCTURE | Salt | MS |
|---|---|---|---|---|
| 141 | 1-(3,5-difluorobenzyl)-2-methyl-6-(3-(1-(pyridin-2-ylmethyl)-1H-pyrazol-4-yl)-5H-pyrrolo[2,3-b]pyrazin-5-yl)-1H-imidazo[4,5-b]pyridine | 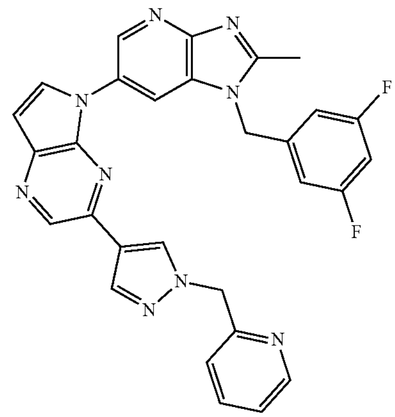 [SMILES: Cc1nc2ncc(-n3ccc4ncc(-c5cnn(Cc6ccccn6)c5)nc43)cc2n1Cc1cc(F)cc(F)c1] | | 534.2 |
| 142 | 1-(3,5-difluorobenzyl)-2-methyl-6-(3-(1-(pyridin-3-ylmethyl)-1H-pyrazol-4-yl)-5H-pyrrolo[2,3-b]pyrazin-5-yl)-1H-imidazo[4,5-b]pyridine | 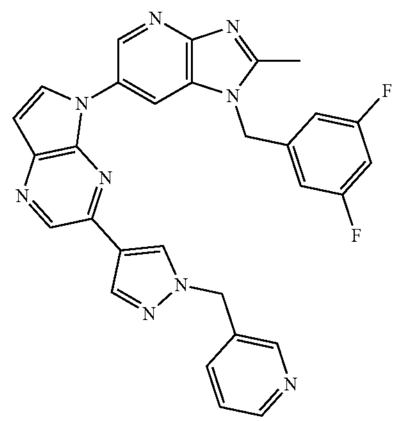 [SMILES: Cc1nc2ncc(-n3ccc4ncc(-c5cnn(Cc6cccnc6)c5)nc43)cc2n1Cc1cc(F)cc(F)c1] | | 534.2 |
| 143 | 1-(3,5-difluorobenzyl)-2-methyl-6-(3-(1-methyl-1H-pyrazol-3-yl)-5H-pyrrolo[2,3-b]pyrazin-5-yl)-1H-imidazo[4,5-b]pyridine | 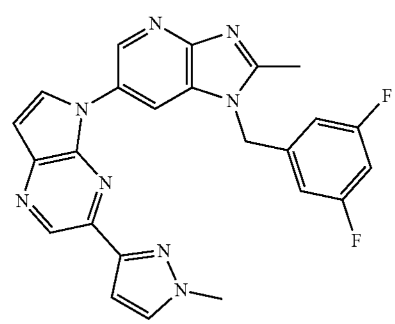 [SMILES: Cc1nc2ncc(-n3ccc4ncc(-c5ccn(C)n5)nc43)cc2n1Cc1cc(F)cc(F)c1] | | 457.2 |
| 144 | 1-(3,5-difluorobenzyl)-6-(3-(1,3-dimethyl-1H-pyrazol-4-yl)-5H-pyrrolo[2,3-b]pyrazin-5-yl)-2-methyl-1H-imidazo[4,5-b]pyridine | 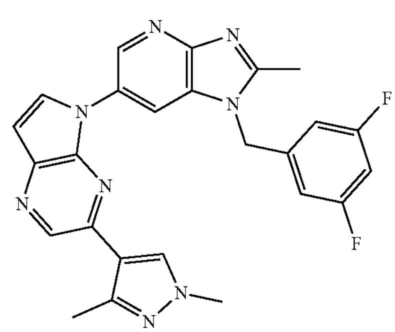 [SMILES: Cc1nn(C)cc1-c1cnc2ccn(-c3cnc4nc(C)n(Cc5cc(F)cc(F)c5)c4c3)c2n1] | | 471.2 |

TABLE 1-continued

| Example | IUPAC NAME | CHEMICAL STRUCTURE | Salt | MS |
|---|---|---|---|---|
| 145 | 1-(3,5-difluorobenzyl)-2-methyl-6-(3-(1-methyl-3-(trifluoromethyl)-1H-pyrazol-5-yl)-5H-pyrrolo[2,3-b]pyrazin-5-yl)-1H-imidazo[4,5-b]pyridine | 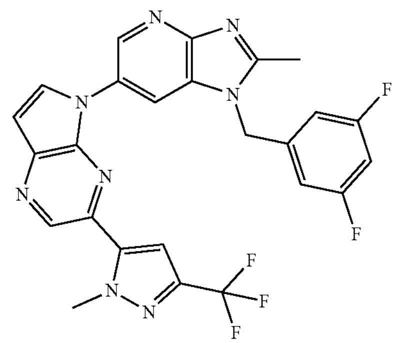 [SMILES: Cc1nc2ncc(-n3ccc4ncc(-c5cc(C(F)(F)F)nn5C)nc43)cc2n1Cc1cc(F)cc(F)c1] | | 525.2 |
| 146 | 1-(3,5-difluorobenzyl)-6-(3-(3,5-dimethyl-1,2-oxazol-4-yl)-5H-pyrrolo[2,3-b]pyrazin-5-yl)-2-methyl-1H-imidazo[4,5-b]pyridine | 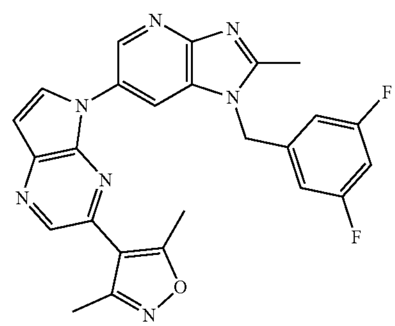 [SMILES: Cc1noc(C)c1-c1cnc2ccn(-c3cnc4nc(C)n(Cc5cc(F)cc(F)c5)c4c3)c2n1] | | 472.2 |
| 147 | 1-(3,5-difluorobenzyl)-2-methyl-6-(3-vinyl-5H-pyrrolo[2,3-b]pyrazin-5-yl)-1H-imidazo[4,5-b]pyridine | 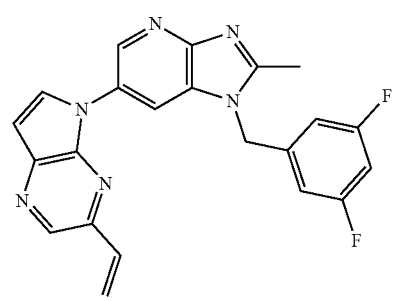 [SMILES: C=Cc1cnc2ccn(-c3cnc4nc(C)n(Cc5cc(F)cc(F)c5)c4c3)c2n1] | | 403.1 |
| 148 | 1-(3,5-difluorobenzyl)-6-(3-((1Z)-3-methoxyprop-1-en-1-yl)-5H-pyrrolo[2,3-b]pyrazin-5-yl)-2-methyl-1H-imidazo[4,5-b]pyridine | 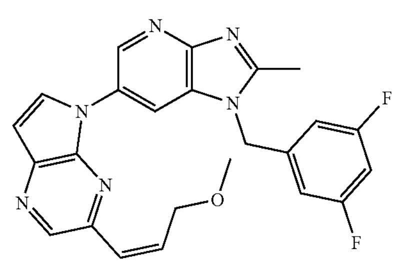 [SMILES: COC/C=C\c1cnc2ccn(-c3cnc4nc(C)n(Cc5cc(F)cc(F)c5)c4c3)c2n1] | | 447.2 |
| 149 | (5-(1-(3,5-difluorobenzyl)-2-methyl-1H-imidazo[4,5-b]pyridin-6-yl)-5H-pyrrolo[2,3-b]pyrazin-3-yl)methyl pivalate | 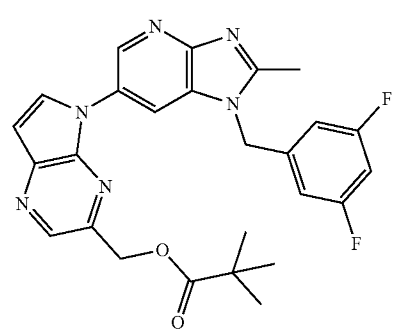 [SMILES: Cc1nc2ncc(-n3ccc4ncc(COC(=O)C(C)(C)C)nc43)cc2n1Cc1cc(F)cc(F)c1] | | 491.2 |

TABLE 1-continued

| Example | IUPAC NAME | CHEMICAL STRUCTURE | Salt | MS |
|---|---|---|---|---|
| 150 | 1-(3,5-difluorobenzyl)-6-(3-(1-methoxyethyl)-5H-pyrrolo[2,3-b]pyrazin-5-yl)-2-methyl-1H-imidazo[4,5-b]pyridine | 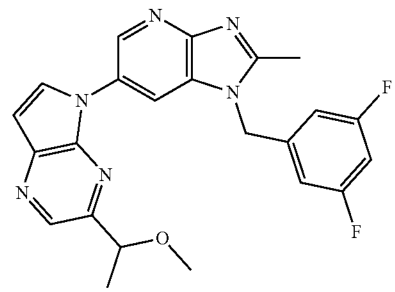 [SMILES: COC(C)c1cnc2ccn(-c3cnc4nc(C)n(Cc5cc(F)cc(F)c5)c4c3)c2n1] | | 435.1 |
| 151 | (5-(1-(3,5-difluorobenzyl)-2-methyl-1H-imidazo[4,5-b]pyridin-6-yl)-5H-pyrrolo[2,3-b]pyrazin-3-yl)methanol | 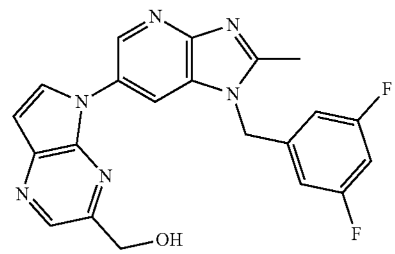 [SMILES: Cc1nc2ncc(-n3ccc4ncc(CO)nc43)cc2n1Cc1cc(F)cc(F)c1] | | 407.1 |
| 152 | 1-(3,5-difluorobenzyl)-6-(3-(methoxymethyl)-5H-pyrrolo[2,3-b]pyrazin-5-yl)-2-methyl-1H-imidazo[4,5-b]pyridine | 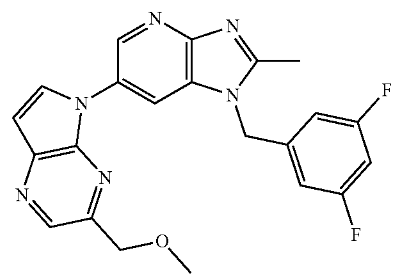 [SMILES: COCc1cnc2ccn(-c3cnc4nc(C)n(Cc5cc(F)cc(F)c5)c4c3)c2n1] | | 421.2 |
| 153 | 1-(3,5-difluorobenzyl)-6-(3-(difluoromethyl)-5H-pyrrolo[2,3-b]pyrazin-5-yl)-2-methyl-1H-imidazo[4,5-b]pyridine | 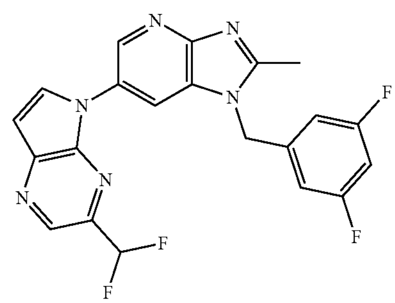 [SMILES: Cc1nc2ncc(-n3ccc4ncc(C(F)F)nc43)cc2n1Cc1cc(F)cc(F)c1] | | 427.1 |
| 154 | 1-(3,5-difluorobenzyl)-6-(3-ethynyl-5H-pyrrolo[2,3-b]pyrazin-5-yl)-2-methyl-1H-imidazo[4,5-b]pyridine | 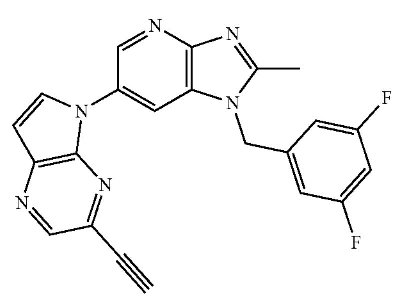 [SMILES: C#Cc1cnc2ccn(-c3cnc4nc(C)n(Cc5cc(F)cc(F)c5)c4c3)c2n1] | | 401.1 |

TABLE 1-continued

| Example | IUPAC NAME | CHEMICAL STRUCTURE | Salt | MS |
|---|---|---|---|---|
| 155 | 1-(3,5-difluorobenzyl)-6-(3-((2-methoxyethoxy)methyl)-5H-pyrrolo[2,3-b]pyrazin-5-yl)-2-methyl-1H-imidazo[4,5-b]pyridine | 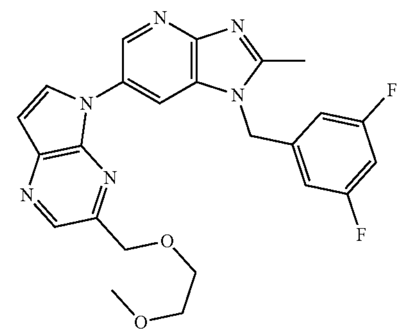 [SMILES: COCCOCc1cnc2ccn(-c3cnc4nc(C)n(Cc5cc(F)cc(F)c5)c4c3)c2n1] | | 465.1 |
| 157 | 1-(3,5-difluorobenzyl)-6-(3-(3-methoxyoxetan-3-yl)-5H-pyrrolo[2,3-b]pyrazin-5-yl)-2-methyl-1H-imidazo[4,5-b]pyridine | 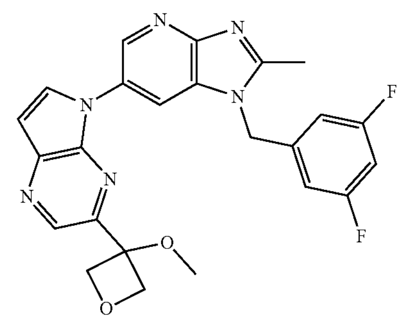 [SMILES: COC1(c2cnc3ccn(-c4cnc5nc(C)n(Cc6cc(F)cc(F)c6)c5c4)c3n2)COC1] | | 463.1 |
| 159 | (R)-1-(5-(1-(3,5-difluorobenzyl)-2-methoxy-1H-imidazo[4,5-b]pyridin-6-yl)-5H-pyrrolo[2,3-b]pyrazin-3-yl)ethanol | | | 437.2 |
| 159 | (S)-1-(5-(1-(3,5-difluorobenzyl)-2-methoxy-1H-imidazo[4,5-b]pyridin-6-yl)-5H-pyrrolo[2,3-b]pyrazin-3-yl)ethanol | | | 437.2 |
| 160 | 1-(5-(1-(3-fluorobenzyl)-2-methoxy-1H-imidazo[4,5-b]pyridin-6-yl)-5H-pyrrolo[2,3-b]pyrazin-3-yl)ethanol | 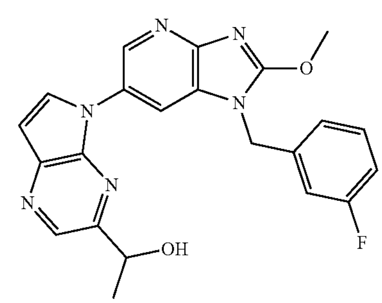 [SMILES: COc1nc2ncc(-n3ccc4ncc(C(C)O)nc43)cc2n1Cc1cccc(F)c1] | | 419.2 |

TABLE 1-continued

| Example | IUPAC NAME | CHEMICAL STRUCTURE | Salt | MS |
|---|---|---|---|---|
| 161 | 1-(5-(1-(3-fluorobenzyl)-2-methoxy-1H-imidazo[4,5-b]pyridin-6-yl)-5H-pyrrolo[2,3-b]pyrazin-3-yl)ethanol | 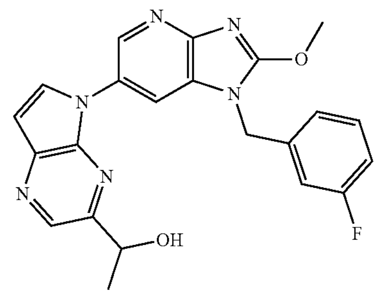 [SMILES: COc1nc2ncc(-n3ccc4ncc(C(C)O)nc43)cc2n1Cc1cccc(F)c1] | | 419.1 |
| 162 | 1-(3,5-difluorobenzyl)-6-(4-methoxypyrrolo[1,2-b]pyridazin-5-yl)-2-methyl-1H-imidazo[4,5-b]pyridine | 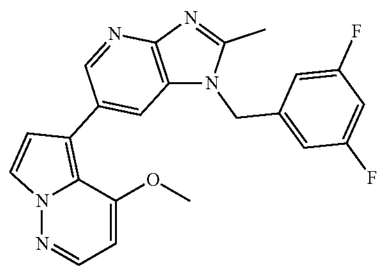 [SMILES: COc1ccnn2ccc(-c3cnc4nc(C)n(Cc5cc(F)cc(F)c5)c4c3)c12] | | 406.1 |
| 163 | 1-((2-fluoropyridin-4-yl)methyl)-6-(4-methoxypyrrolo[1,2-b]pyridazin-5-yl)-2-methyl-1H-imidazo[4,5-b]pyridine | 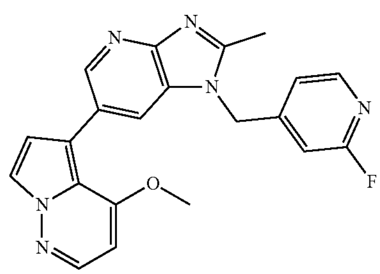 [SMILES: COc1ccnn2ccc(-c3cnc4nc(C)n(Cc5ccnc(F)c5)c4c3)c12] | | 389.2 |
| 164 | 6-(4-methoxypyrrolo[1,2-b]pyridazin-5-yl)-2-methyl-1-((3-methyl-1,2,4-oxadiazol-5-yl)methyl)-1H-imidazo[4,5-b]pyridine | 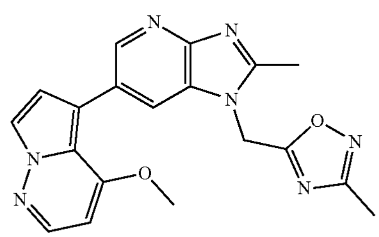 [SMILES: COc1ccnn2ccc(-c3cnc4nc(C)n(Cc5nc(C)no5)c4c3)c12] | | 376.1 |
| 165 | 1-(3,5-difluorobenzyl)-6-(4-methoxypyrrolo[1,2-b]pyridazin-5-yl)-2-(1-methyl-1H-pyrazol-4-yl)-1H-imidazo[4,5-b]pyridine | 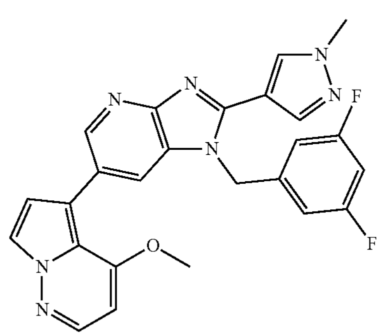 [SMILES: COc1ccnn2ccc(-c3cnc4nc(-c5cnn(C)c5)n(Cc5cc(F)cc(F)c5)c4c3)c12] | | 472.2 |

TABLE 1-continued

| Example | IUPAC NAME | CHEMICAL STRUCTURE | Salt | MS |
|---|---|---|---|---|
| 166 | 6-(4-methoxypyrrolo[1,2-b]pyridazin-5-yl)-2-methyl-1-((1-methyl-1H-pyrazol-5-yl)methyl)-1H-imidazo[4,5-b]pyridine | 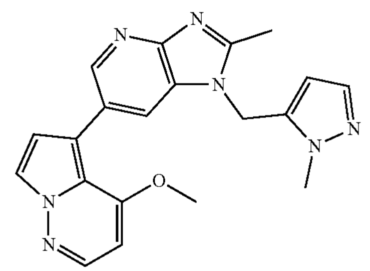 [SMILES: COc1ccnn2ccc(-c3cnc4nc(C)n(Cc5ccnn5C)c4c3)c12] | | 374.2 |
| 167 | (1-(3,5-difluorobenzyl)-6-(4-methoxypyrrolo[1,2-b]pyridazin-5-yl)-1H-imidazo[4,5-b]pyridin-2-yl)methanol | 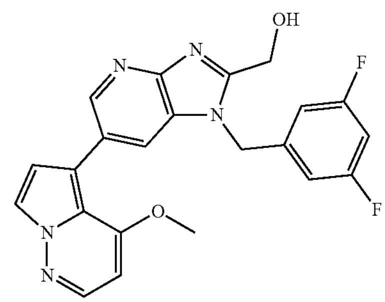 [SMILES: COc1ccnn2ccc(-c3cnc4nc(CO)n(Cc5cc(F)cc(F)c5)c4c3)c12] | | 422.1 |
| 168 | (1S)-1-(1-(3,5-difluorobenzyl)-6-(4-methoxypyrrolo[1,2-b]pyridazin-5-yl)-1H-imidazo[4,5-b]pyridin-2-yl)ethanol | 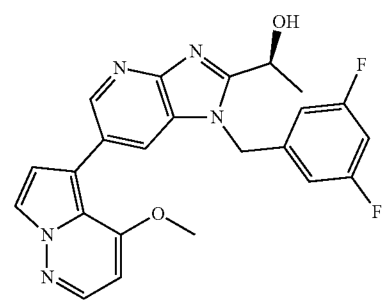 [SMILES: COc1ccnn2ccc(-c3cnc4nc([C@H](C)O)n(Cc5cc(F)cc(F)c5)c4c3)c12] | | 436.2 |
| 169 | 1-(1-(3,5-difluorobenzyl)-6-(4-methoxypyrrolo[1,2-b]pyridazin-5-yl)-1H-imidazo[4,5-b]pyridin-2-yl)azetidin-3-ol | 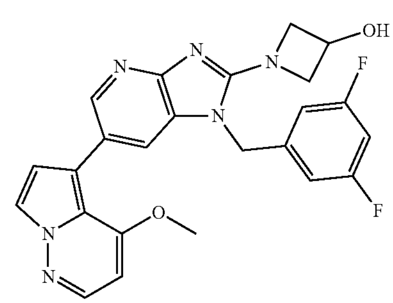 [SMILES: COc1ccnn2ccc(-c3cnc4nc(N5CC(O)C5)n(Cc5cc(F)cc(F)c5)c4c3)c12] | | 463.2 |
| 170 | (1R)-1-(1-(3,5-difluorobenzyl)-6-(4-methoxypyrrolo[1,2-b]pyridazin-5-yl)-1H-imidazo[4,5-b]pyridin-2-yl)ethanol | 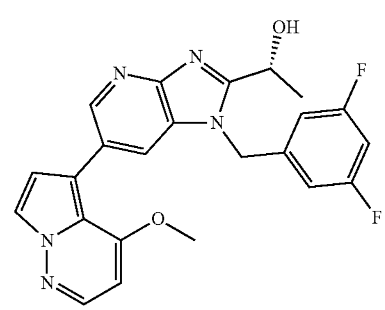 [SMILES: COc1ccnn2ccc(-c3cnc4nc([C@@H](C)O)n(Cc5cc(F)cc(F)c5)c4c3)c12] | | 436.1 |

TABLE 1-continued

| Example | IUPAC NAME | CHEMICAL STRUCTURE | Salt | MS |
|---|---|---|---|---|
| 171 | 1-((2-fluoropyridin-4-yl)methyl)-2-(methoxymethyl)-6-(4-methoxypyrrolo[1,2-b]pyridazin-5-yl)-1H-imidazo[4,5-b]pyridine | 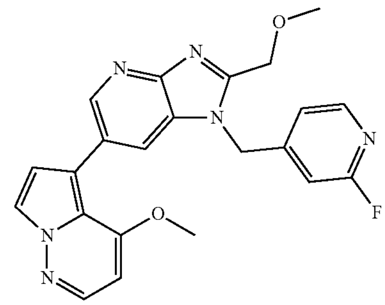 [SMILES: COCc1nc2ncc(-c3ccn4nccc(OC)c34)cc2n1Cc1ccnc(F)c1] | | 417.1 |
| 172 | 2-cyclopropyl-1-((2-fluoropyridin-4-yl)methyl)-6-(4-methoxypyrrolo[1,2-b]pyridazin-5-yl)-1H-imidazo[4,5-b]pyridine | 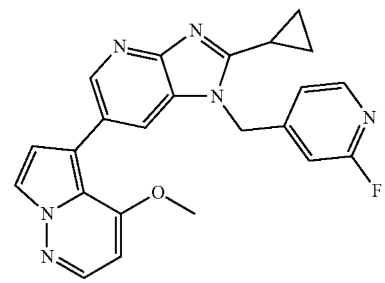 [SMILES: COc1ccnn2ccc(-c3cnc4nc(C5CC5)n(Cc5ccnc(F)c5)c4c3)c12] | | 413.1 |
| 173 | 2-(azetidin-1-yl)-1-((2-fluoropyridin-4-yl)methyl)-6-(4-methoxypyrrolo[1,2-b]pyridazin-5-yl)-1H-imidazo[4,5-b]pyridine | 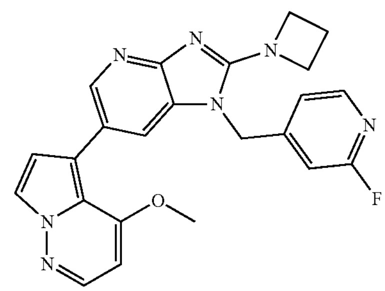 [SMILES: COc1ccnn2ccc(-c3cnc4nc(N5CCC5)n(Cc5ccnc(F)c5)c4c3)c12] | | 430.2 |
| 174 | 1-(3,5-difluorobenzyl)-2-methyl-6-(pyrrolo[1,2-b]pyridazin-5-yl)-1H-imidazo[4,5-b]pyridine | 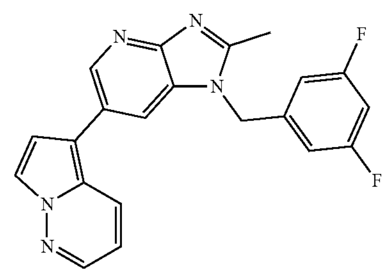 [SMILES: Cc1nc2ncc(-c3ccn4ncccc34)cc2n1Cc1cc(F)cc(F)c1] | | 376.1 |
| 175 | 1-(3-fluorobenzyl)-6-(4-methoxypyrrolo[2,1-f][1,2,4]triazin-5-yl)-2-methyl-1H-imidazo[4,5-b]pyridine | 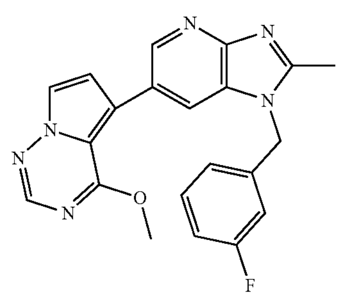 [SMILES: COc1ncnn2ccc(-c3cnc4nc(C)n(Cc5cccc(F)c5)c4c3)c12] | | 389.2 |

TABLE 1-continued

| Example | IUPAC NAME | CHEMICAL STRUCTURE | Salt | MS |
|---------|------------|--------------------|------|-----|
| 176 | (1-(3,5-difluorobenzyl)-6-(4-methoxypyrrolo[2,1-f][1,2,4]triazin-5-yl)-1H-imidazo[4,5-b]pyridin-2-yl)methanol | 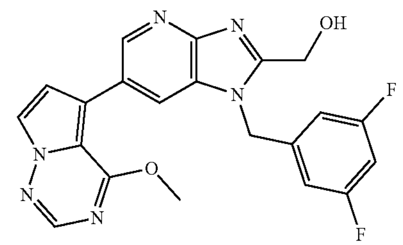 [SMILES: COc1ncnn2ccc(-c3cnc4nc(CO)n(Cc5cc(F)cc(F)c5)c4c3)c12] | | 423.1 |
| 177 | 1-(3,5-difluorobenzyl)-2-methyl-6-(pyrrolo[2,1-f][1,2,4]triazin-5-yl)-1H-imidazo[4,5-b]pyridine | 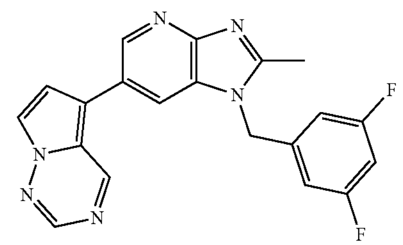 [SMILES: Cc1nc2ncc(-c3ccn4ncncc34)cc2n1Cc1cc(F)cc(F)c1] | | 377.2 |
| 178 | 1-((2-fluoropyridin-4-yl)methyl)-6-(4-methoxypyrrolo[2,1-f][1,2,4]triazin-5-yl)-2-methyl-1H-imidazo[4,5-b]pyridine | 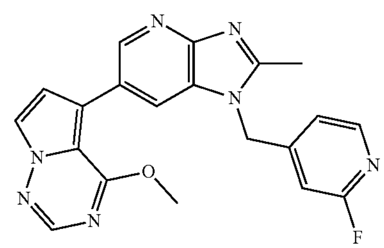 [SMILES: COc1ncnn2ccc(-c3cnc4nc(C)n(Cc5ccnc(F)c5)c4c3)c12] | | 390.2 |
| 179 | 6-(4-methoxypyrrolo[2,1-f][1,2,4]triazin-5-yl)-2-methyl-1-((1-methyl-1H-pyrazol-5-yl)methyl)-1H-imidazo[4,5-b]pyridine | 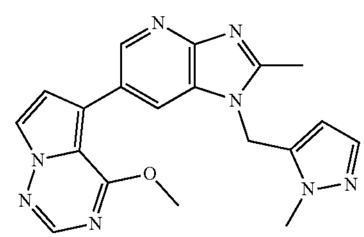 [SMILES: COc1ncnn2ccc(-c3cnc4nc(C)n(Cc5ccnn5C)c4c3)c12] | | 375.2 |
| 180 | 1-((2-fluoropyridin-4-yl)methyl)-2-(methoxymethyl)-6-(4-methoxypyrrolo[2,1-f][1,2,4]triazin-5-yl)-1H-imidazo[4,5-b]pyridine | 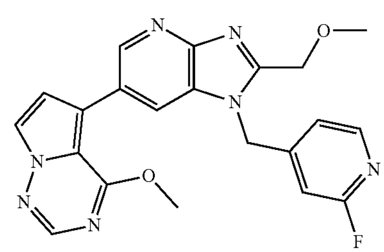 [SMILES: COCc1nc2ncc(-c3ccn4ncnc(OC)c34)cc2n1Cc1ccnc(F)c1] | | 420.2 |
| 181 | 1-(1-(3,5-difluorobenzyl)-6-(4-methoxypyrrolo[2,1-f][1,2,4]triazin-5-yl)-1H-imidazo[4,5-b]pyridin-2-yl)ethanol | 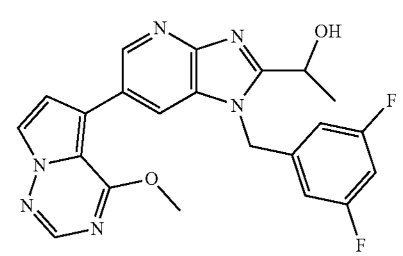 [SMILES: COc1ncnn2ccc(-c3cnc4nc(C(C)O)n(Cc5cc(F)cc(F)c5)c4c3)c12] | | 437.2 |

TABLE 1-continued

| Example | IUPAC NAME | CHEMICAL STRUCTURE | Salt | MS |
|---|---|---|---|---|
| 182 | 2-(azetidin-1-yl)-1-((2-fluoropyridin-4-yl)methyl)-6-(4-methoxypyrrolo[2,1-f][1,2,4]triazin-5-yl)-1H-imidazo[4,5-b]pyridine | 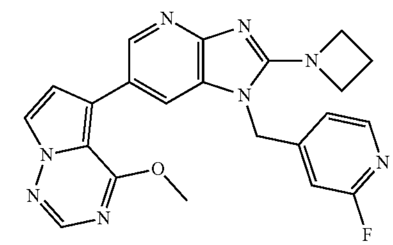 [SMILES: COc1ncnn2ccc(-c3cnc4nc(N5CCC5)n(Cc5ccnc(F)c5)c4c3)c12] | | 431.2 |
| 183 | 6-(4-methoxypyrrolo[2,1-f][1,2,4]triazin-5-yl)-2-methyl-1-((2-(trifluoromethyl)pyridin-4-yl)methyl)-1H-imidazo[4,5-b]pyridine | 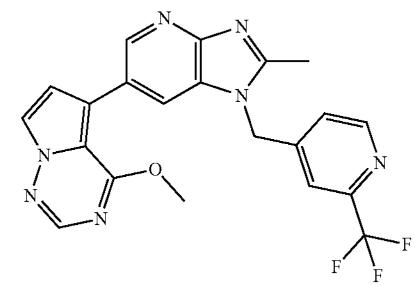 [SMILES: COc1ncnn2ccc(-c3cnc4nc(C)n(Cc5ccnc(C(F)(F)F)c5)c4c3)c12] | | 440.1 |
| 184 | 1-((2-methoxypyridin-4-yl)methyl)-6-(4-methoxypyrrolo[2,1-f][1,2,4]triazin-5-yl)-2-methyl-1H-imidazo[4,5-b]pyridine | 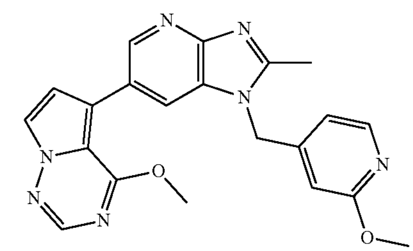 [SMILES: COc1cc(Cn2c(C)nc3ncc(-c4ccn5ncnc(OC)c45)cc32)ccn1] | | 402.1 |
| 185 | 1-((2-chloropyridin-4-yl)methyl)-6-(4-methoxypyrrolo[2,1-f][1,2,4]triazin-5-yl)-2-methyl-1H-imidazo[4,5-b]pyridine | 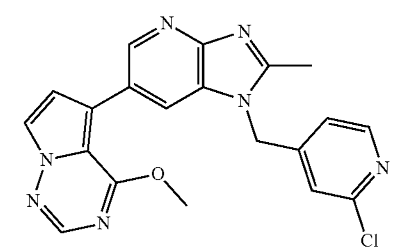 [SMILES: COc1ncnn2ccc(-c3cnc4nc(C)n(Cc5ccnc(Cl)c5)c4c3)c12] | | 406.1 |
| 186 | 6-(4-methoxypyrrolo[2,1-f][1,2,4]triazin-5-yl)-2-methyl-1-((3-methyl-1,2,4-oxadiazol-5-yl)methyl)-1H-imidazo[4,5-b]pyridine | 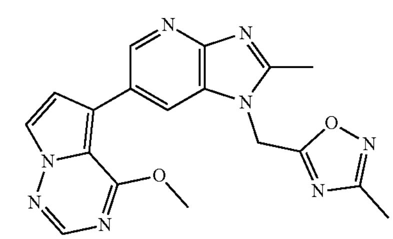 [SMILES: COc1ncnn2ccc(-c3cnc4nc(C)n(Cc5nc(C)no5)c4c3)c12] | | 377.2 |
| 187 | 2-cyclopropyl-1-((2-fluoropyridin-4-yl)methyl)-6-(4-methoxypyrrolo[2,1-f][1,2,4]triazin-5-yl)-1H-imidazo[4,5-b]pyridine | 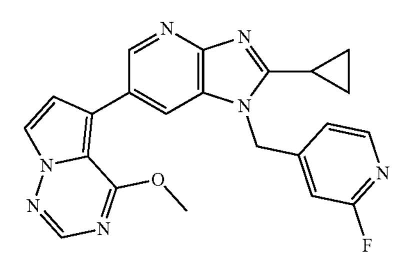 [SMILES: COc1ncnn2ccc(-c3cnc4nc(C5CC5)n(Cc5ccnc(F)c5)c4c3)c12] | | 416.1 |

TABLE 1-continued

| Example | IUPAC NAME | CHEMICAL STRUCTURE | Salt | MS |
|---|---|---|---|---|
| 188 | 2-(3,3-difluorocyclobutyl)-1-((2-fluoropyridin-4-yl)methyl)-6-(4-methoxypyrrolo[2,1-f][1,2,4]triazin-5-yl)-1H-imidazo[4,5-b]pyridine | 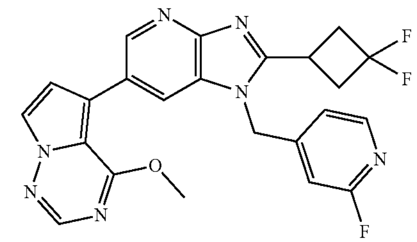 [SMILES: COc1ncnn2ccc(-c3cnc4nc(C5CC(F)(F)C5)n(Cc5ccnc(F)c5)c4c3)c12] | | 466.2 |
| 189 | 1-(1-(3,5-difluorobenzyl)-6-(4-methoxypyrrolo[2,1-f][1,2,4]triazin-5-yl)-1H-imidazo[4,5-b]pyridin-2-yl)ethanol | 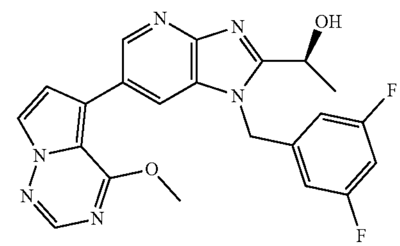 [SMILES: COc1ncnn2ccc(-c3cnc4nc([C@H](C)O)n(Cc5cc(F)cc(F)c5)c4c3)c12] | | 437.1 |
| 190 | 1-(1-(3,5-difluorobenzyl)-6-(4-methoxypyrrolo[2,1-f][1,2,4]triazin-5-yl)-1H-imidazo[4,5-b]pyridin-2-yl)ethanol | 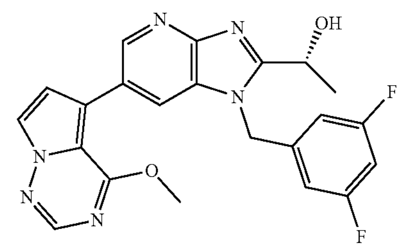 [SMILES: COc1ncnn2ccc(-c3cnc4nc([C@@H](C)O)n(Cc5cc(F)cc(F)c5)c4c3)c12] | | 437.1 |
| 191 | 6-(4-methoxypyrrolo[2,1-f][1,2,4]triazin-5-yl)-2-methyl-1-(1,3-thiazol-2-ylmethyl)-1H-imidazo[4,5-b]pyridine | 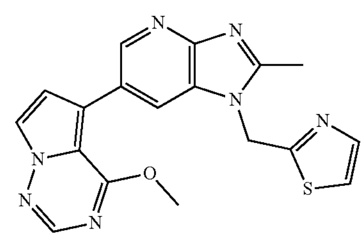 [SMILES: COc1ncnn2ccc(-c3cnc4nc(C)n(Cc5nccs5)c4c3)c12] | | 378.2 |
| 192 | 3-(1-(3,5-difluorobenzyl)-6-(4-methoxypyrrolo[2,1-f][1,2,4]triazin-5-yl)-1H-imidazo[4,5-b]pyridin-2-yl)propanenitrile | 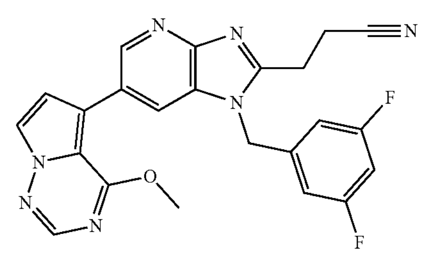 [SMILES: COc1ncnn2ccc(-c3cnc4nc(CCC#N)n(Cc5cc(F)cc(F)c5)c4c3)c12] | | 446.1 |
| 193 | 6-(4-methoxypyrrolo[2,1-f][1,2,4]triazin-5-yl)-2-methyl-1-((5-methyl-1,3,4-oxadiazol-2-yl)methyl)-1H-imidazo[4,5-b]pyridine | 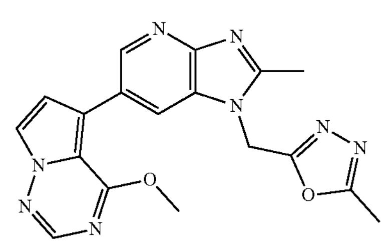 [SMILES: COc1ncnn2ccc(-c3cnc4nc(C)n(Cc5nnc(C)o5)c4c3)c12] | | 377.2 |

TABLE 1-continued

| Example | IUPAC NAME | CHEMICAL STRUCTURE | Salt | MS |
|---|---|---|---|---|
| 194 | 1-((6-fluoropyridin-2-yl)methyl)-6-(4-methoxypyrrolo[2,1-f][1,2,4]triazin-5-yl)-2-methyl-1H-imidazo[4,5-b]pyridine | 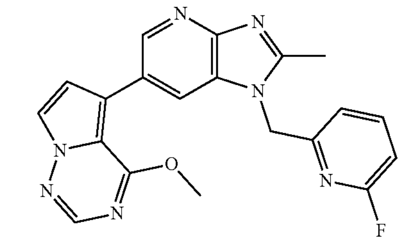 [SMILES: COc1ncnn2ccc(-c3cnc4nc(C)n(Cc5cccc(F)n5)c4c3)c12] | | 390.1 |
| 195 | 1-((6-chloropyridin-2-yl)methyl)-6-(4-methoxypyrrolo[2,1-f][1,2,4]triazin-5-yl)-2-methyl-1H-imidazo[4,5-b]pyridine | 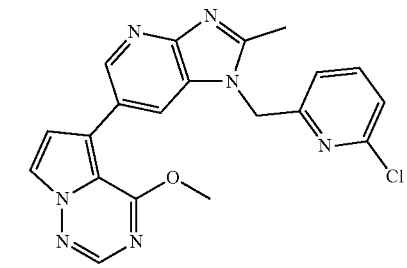 [SMILES: COc1ncnn2ccc(-c3cnc4nc(C)n(Cc5cccc(Cl)n5)c4c3)c12] | | 406.1 |
| 196 | 1-(1-(3,5-difluorobenzyl)-6-(4-methoxypyrrolo[2,1-f][1,2,4]triazin-5-yl)-1H-imidazo[4,5-b]pyridin-2-yl)azetidin-3-ol | 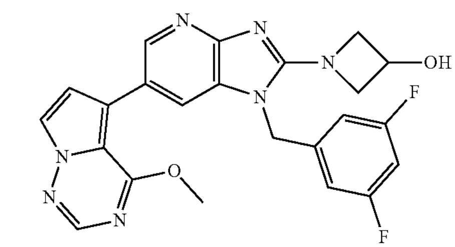 [SMILES: COc1ncnn2ccc(-c3cnc4nc(N5CC(O)C5)n(Cc5cc(F)cc(F)c5)c4c3)c12] | | 464.2 |
| 197 | 2-ethoxy-1-((2-fluoropyridin-4-yl)methyl)-6-(4-methoxypyrrolo[2,1-f][1,2,4]triazin-5-yl)-1H-imidazo[4,5-b]pyridine | 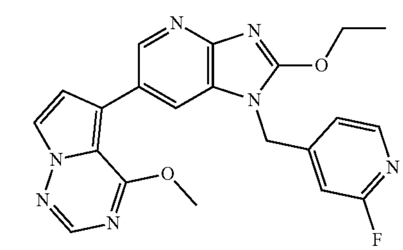 [SMILES: CCOc1nc2ncc(-c3ccn4ncnc(OC)c34)cc2n1Cc1ccnc(F)c1] | | 420.2 |
| 198 | (1-(3,5-difluorobenzyl)-6-(4-ethoxypyrrolo[2,1-f][1,2,4]triazin-5-yl)-1H-imidazo[4,5-b]pyridin-2-yl)methanol | 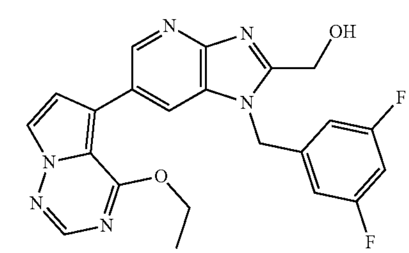 [SMILES: CCOc1ncnn2ccc(-c3cnc4nc(CO)n(Cc5cc(F)cc(F)c5)c4c3)c12] | | 437.1 |
| 199 | 6-(4-methoxypyrrolo[2,1-f][1,2,4]triazin-5-yl)-2-methyl-1-((2-methyl-1,3-oxazol-4-yl)methyl)-1H-imidazo[4,5-b]pyridine | 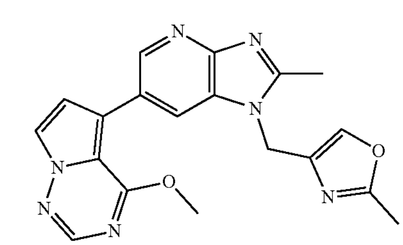 [SMILES: COc1ncnn2ccc(-c3cnc4nc(C)n(Cc5coc(C)n5)c4c3)c12] | | 376.2 |

TABLE 1-continued

| Example | IUPAC NAME | CHEMICAL STRUCTURE | Salt | MS |
|---|---|---|---|---|
| 200 | 6-(4-methoxypyrrolo[2,1-f][1,2,4]triazin-5-yl)-2-methyl-1-((2-methylpyridin-4-yl)methyl)-1H-imidazo[4,5-b]pyridine | 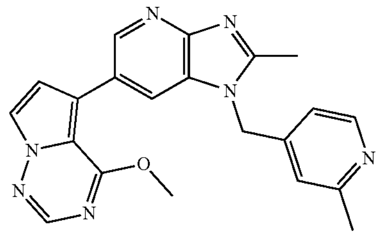 [SMILES: COc1ncnn2ccc(-c3cnc4nc(C)n(Cc5ccnc(C)c5)c4c3)c12] | | 386.1 |
| 201 | 1-((2-chloro-6-methylpyridin-4-yl)methyl)-6-(4-methoxypyrrolo[2,1-f][1,2,4]triazin-5-yl)-2-methyl-1H-imidazo[4,5-b]pyridine | 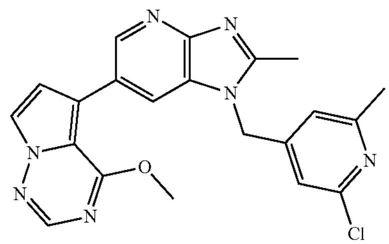 [SMILES: COc1ncnn2ccc(-c3cnc4nc(C)n(Cc5cc(C)nc(Cl)c5)c4c3)c12] | | 420.1 |
| 202 | (1-(3-fluorobenzyl)-6-(4-methoxypyrrolo[2,1-f][1,2,4]triazin-5-yl)-1H-imidazo[4,5-b]pyridin-2-yl)methanol | 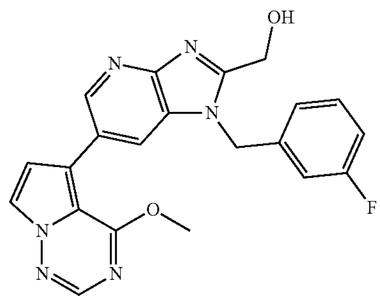 [SMILES: COc1ncnn2ccc(-c3cnc4nc(CO)n(Cc5cccc(F)c5)c4c3)c12] | | 405.1 |
| 203 | 6-(4-methoxypyrrolo[2,1-f][1,2,4]triazin-5-yl)-2-methyl-1-((1-methyl-1H-pyrazol-3-yl)methyl)-1H-imidazo[4,5-b]pyridine | 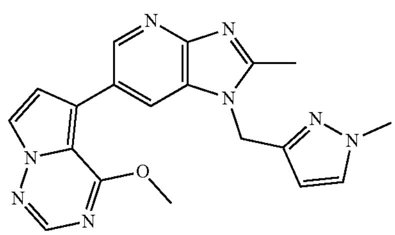 [SMILES: COc1ncnn2ccc(-c3cnc4nc(C)n(Cc5ccn(C)n5)c4c3)c12] | | 375.2 |
| 204 | 6-(4-methoxypyrrolo[2,1-f][1,2,4]triazin-5-yl)-2-methyl-1-((2-methyl-1,3-thiazol-4-yl)methyl)-1H-imidazo[4,5-b]pyridine | 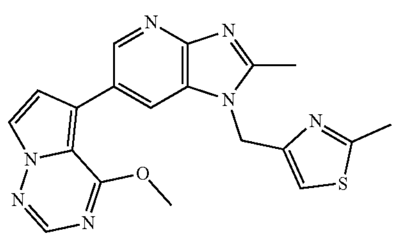 [SMILES: COc1ncnn2ccc(-c3cnc4nc(C)n(Cc5csc(C)n5)c4c3)c12] | | 392.1 |
| 205 | 6-(4-methoxypyrrolo[2,1-f][1,2,4]triazin-5-yl)-2-methyl-1-(1,3-oxazol-2-ylmethyl)-1H-imidazo[4,5-b]pyridine | 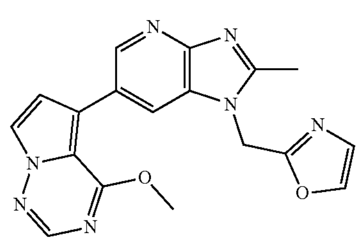 [SMILES: COc1ncnn2ccc(-c3cnc4nc(C)n(Cc5ncco5)c4c3)c12] | | 362.2 |

TABLE 1-continued

| Example | IUPAC NAME | CHEMICAL STRUCTURE | Salt | MS |
|---|---|---|---|---|
| 206 | 6-(4-methoxypyrrolo[2,1-f][1,2,4]triazin-5-yl)-2-methyl-1-((1-methyl-1H-1,2,3-triazol-4-yl)methyl)-1H-imidazo[4,5-b]pyridine | 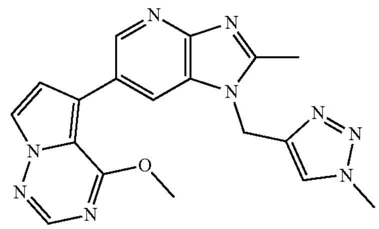 [SMILES: COc1ncnn2ccc(-c3cnc4nc(C)n(Cc5cn(C)nn5)c4c3)c12] | | 376.2 |
| 207 | 6-(4-methoxypyrrolo[2,1-f][1,2,4]triazin-5-yl)-2-methyl-1-((2-methyl-1,3-oxazol-5-yl)methyl)-1H-imidazo[4,5-b]pyridine | 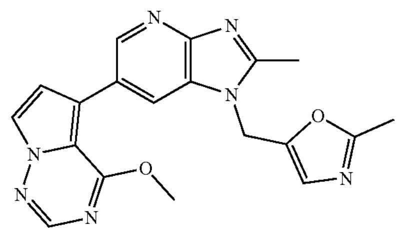 [SMILES: COc1ncnn2ccc(-c3cnc4nc(C)n(Cc5cnc(C)o5)c4c3)c12] | | 376.2 |
| 208 | 6-(4-methoxypyrrolo[2,1-f][1,2,4]triazin-5-yl)-2-methyl-1-(pyrazin-2-ylmethyl)-1H-imidazo[4,5-b]pyridine | 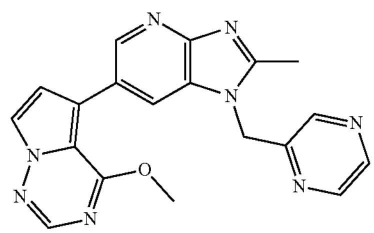 [SMILES: COc1ncnn2ccc(-c3cnc4nc(C)n(Cc5cnccn5)c4c3)c12] | | 373.2 |
| 209 | 6-(4-methoxypyrrolo[2,1-f][1,2,4]triazin-5-yl)-2-methyl-1-(pyrimidin-2-ylmethyl)-1H-imidazo[4,5-b]pyridine | 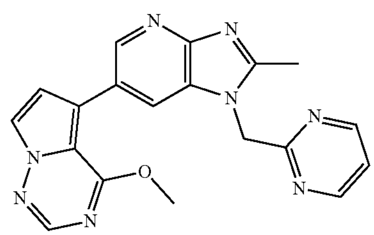 [SMILES: COc1ncnn2ccc(-c3cnc4nc(C)n(Cc5ncccn5)c4c3)c12] | | 373.2 |
| 210 | 6-(4-methoxypyrrolo[2,1-f][1,2,4]triazin-5-yl)-2-methyl-1-(pyridin-4-ylmethyl)-1H-imidazo[4,5-b]pyridine | 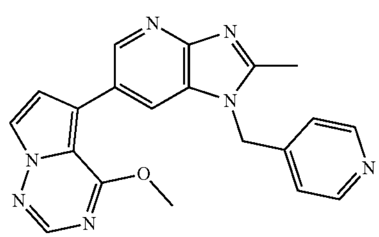 [SMILES: COc1ncnn2ccc(-c3cnc4nc(C)n(Cc5ccncc5)c4c3)c12] | | 372.2 |
| 211 | 6-(4-methoxypyrrolo[2,1-f][1,2,4]triazin-5-yl)-2-methyl-1-(pyridin-3-ylmethyl)-1H-imidazo[4,5-b]pyridine | 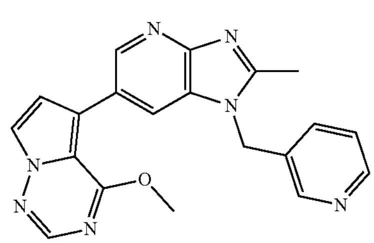 [SMILES: COc1ncnn2ccc(-c3cnc4nc(C)n(Cc5cccnc5)c4c3)c12] | | 372.2 |

TABLE 1-continued

| Example | IUPAC NAME | CHEMICAL STRUCTURE | Salt | MS |
|---|---|---|---|---|
| 212 | 6-(4-methoxypyrrolo[2,1-f][1,2,4]triazin-5-yl)-2-methyl-1-((5-methyl-1,2-oxazol-3-yl)methyl)-1H-imidazo[4,5-b]pyridine | 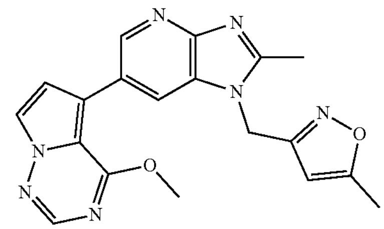 [SMILES: COc1ncnn2ccc(-c3cnc4nc(C)n(Cc5cc(C)on5)c4c3)c12] | | 376.2 |
| 213 | 6-(4-methoxypyrrolo[2,1-f][1,2,4]triazin-5-yl)-2-methyl-1-((2-methyl-1,3-thiazol-5-yl)methyl)-1H-imidazo[4,5-b]pyridine | 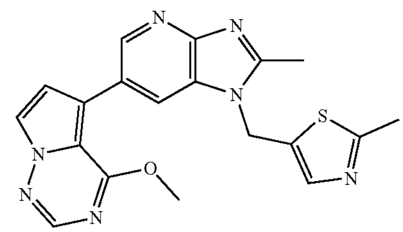 [SMILES: COc1ncnn2ccc(-c3cnc4nc(C)n(Cc5cnc(C)s5)c4c3)c12] | | 392.1 |
| 214 | 6-(4-methoxypyrrolo[2,1-f][1,2,4]triazin-5-yl)-2-methyl-1-((5-methyl-1,2,4-oxadiazol-3-yl)methyl)-1H-imidazo[4,5-b]pyridine | 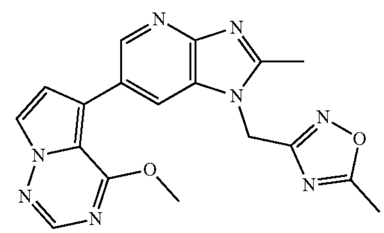 [SMILES: COc1ncnn2ccc(-c3cnc4nc(C)n(Cc5noc(C)n5)c4c3)c12] | | 377.2 |
| 215 | 6-(4-methoxypyrrolo[2,1-f][1,2,4]triazin-5-yl)-2-methyl-1-((3-methyl-1,2-oxazol-5-yl)methyl)-1H-imidazo[4,5-b]pyridine | 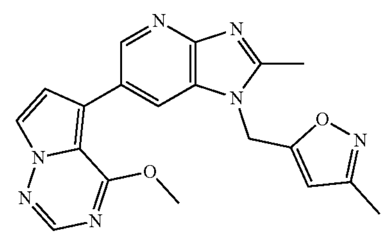 [SMILES: COc1ncnn2ccc(-c3cnc4nc(C)n(Cc5cc(C)no5)c4c3)c12] | | 376.2 |
| 216 | 1-((3-cyclopropyl-1,2,4-oxadiazol-5-yl)methyl)-6-(4-methoxypyrrolo[2,1-f][1,2,4]triazin-5-yl)-2-methyl-1H-imidazo[4,5-b]pyridine | 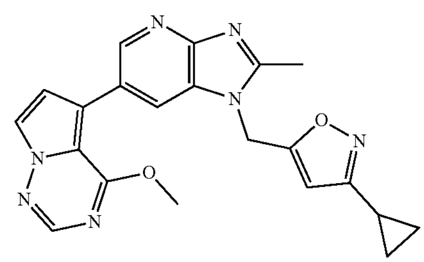 [SMILES: COc1ncnn2ccc(-c3cnc4nc(C)n(Cc5cc(C6CC6)no5)c4c3)c12] | | 401.1 |
| 217 | 1-((3-(difluoromethyl)-1,2,4-oxadiazol-5-yl)methyl)-6-(4-methoxypyrrolo[2,1-f][1,2,4]triazin-5-yl)-2-methyl-1H-imidazo[4,5-b]pyridine | 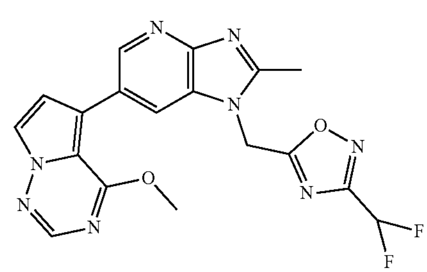 [SMILES: COc1ncnn2ccc(-c3cnc4nc(C)n(Cc5nc(C(F)F)no5)c4c3)c12] | | 411.1 |

TABLE 1-continued

| Example | IUPAC NAME | CHEMICAL STRUCTURE | Salt | MS |
|---|---|---|---|---|
| 218 | 1-((1,3-dimethyl-1H-pyrazol-5-yl)methyl)-6-(4-methoxypyrrolo[2,1-f][1,2,4]triazin-5-yl)-2-methyl-1H-imidazo[4,5-b]pyridine | 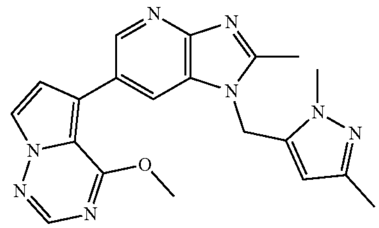 | | 389.2 |
| 219 | 1-((2-fluoropyridin-3-yl)methyl)-6-(4-methoxypyrrolo[2,1-f][1,2,4]triazin-5-yl)-2-methyl-1H-imidazo[4,5-b]pyridine | 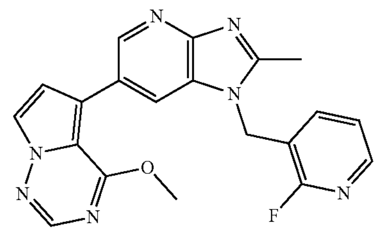 [SMILES: COc1ncnn2ccc(-c3cnc4nc(C)n(Cc5cccnc5F)c4c3)c12] | | 390.2 |
| 220 | 6-(4-methoxypyrrolo[2,1-f][1,2,4]triazin-5-yl)-2-methyl-1-((5-methyl-1,3,4-thiadiazol-2-yl)methyl)-1H-imidazo[4,5-b]pyridine | 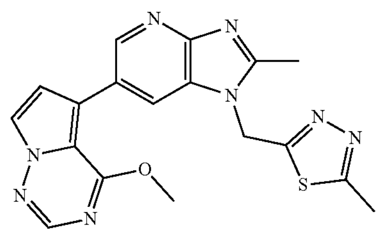 | | 393.2 |
| 221 | 1-((4-chloropyridin-2-yl)methyl)-6-(4-methoxypyrrolo[2,1-f][1,2,4]triazin-5-yl)-2-methyl-1H-imidazo[4,5-b]pyridine | 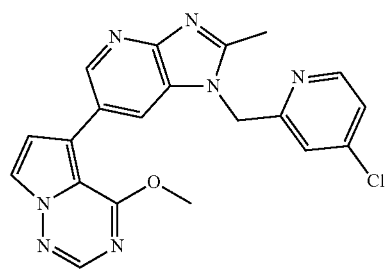 [SMILES: COc1ncnn2ccc(-c3cnc4nc(C)n(Cc5cc(Cl)ccn5)c4c3)c12] | | 406.1 |
| 222 | 6-(4-methoxypyrrolo[2,1-f][1,2,4]triazin-5-yl)-2-methyl-1-((3-methyl-1,2-thiazol-5-yl)methyl)-1H-imidazo[4,5-b]pyridine | 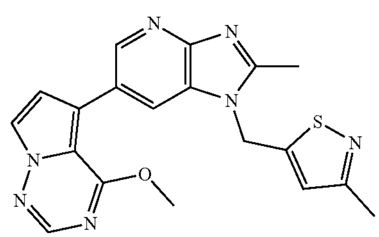 | | 392.1 |
| 223 | 2-(1-(3,5-difluorobenzyl)-6-(4-methoxypyrrolo[2,1-f][1,2,4]triazin-5-yl)-1H-imidazo[4,5-b]pyridin-2-yl)ethanol | 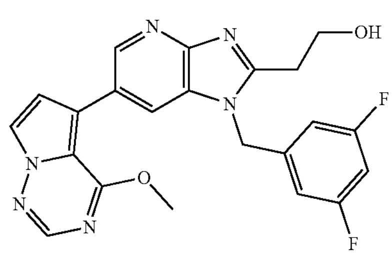 [SMILES: COc1ncnn2ccc(-c3cnc4nc(CCO)n(Cc5cc(F)cc(F)c5)c4c3)c12] | | 437.2 |

TABLE 1-continued

| Example | IUPAC NAME | CHEMICAL STRUCTURE | Salt | MS |
|---|---|---|---|---|
| 224 | 1-((3,5-dimethyl-1,2-oxazol-4-yl)methyl)-6-(4-methoxypyrrolo[2,1-f][1,2,4]triazin-5-yl)-2-methyl-1H-imidazo[4,5-b]pyridine | 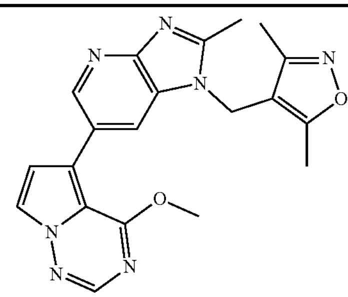 | | 390.2 |
| 225 | 6-(4-methoxypyrrolo[2,1-f][1,2,4]triazin-5-yl)-2-methyl-1-((4-methyl-1,3-thiazol-2-yl)methyl)-1H-imidazo[4,5-b]pyridine | 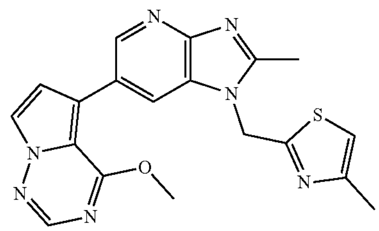 | | 391.9 |
| 226 | 1-((3-ethyl-1,2,4-oxadiazol-5-yl)methyl)-6-(4-methoxypyrrolo[2,1-f][1,2,4]triazin-5-yl)-2-methyl-1H-imidazo[4,5-b]pyridine | 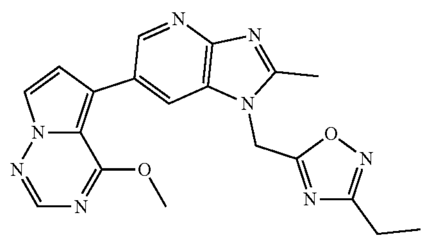 [SMILES: CCc1noc(Cn2c(C)nc3ncc(-c4ccn5ncnc(OC)c45)cc32)n1] | | 389.0 |
| 227 | 1-((5-fluoropyridin-3-yl)methyl)-6-(4-methoxypyrrolo[2,1-f][1,2,4]triazin-5-yl)-2-methyl-1H-imidazo[4,5-b]pyridine | 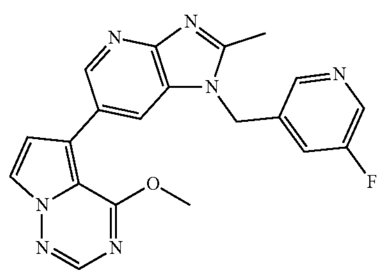 [SMILES: COc1ncnn2ccc(-c3cnc4nc(C)n(Cc5cncc(F)c5)c4c3)c12] | | 390.2 |
| 228 | (1-(3,4-difluorobenzyl)-6-(4-methoxypyrrolo[2,1-f][1,2,4]triazin-5-yl)-1H-imidazo[4,5-b]pyridin-2-yl)methanol | 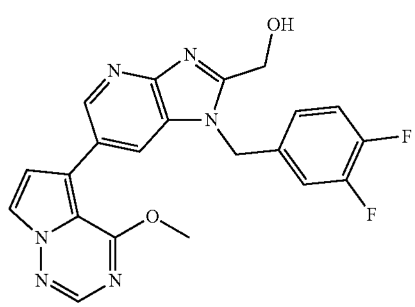 [SMILES: COc1ncnn2ccc(-c3cnc4nc(CO)n(Cc5ccc(F)c(F)c5)c4c3)c12] | | 423.1 |
| 229 | 6-(4-methoxypyrrolo[2,1-f][1,2,4]triazin-5-yl)-2-methyl-1-((3-methyl-1,2,4-thiadiazol-5-yl)methyl)-1H-imidazo[4,5-b]pyridine | 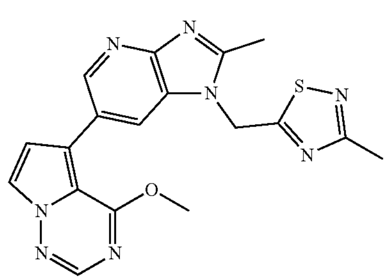 [SMILES: COc1ncnn2ccc(-c3cnc4nc(C)n(Cc5nc(C)ns5)c4c3)c12] | | 393.2 |

TABLE 1-continued

| Example | IUPAC NAME | CHEMICAL STRUCTURE | Salt | MS |
|---------|------------|---------------------|------|-----|
| 230 | 6-(4-methoxypyrrolo[2,1-f][1,2,4]triazin-5-yl)-2-methyl-1-((1-methyl-1H-pyrazol-4-yl)methyl)-1H-imidazo[4,5-b]pyridine | 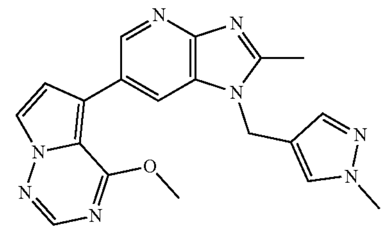 | | 375.2 |
| 231 | 6-(4-methoxypyrrolo[2,1-f][1,2,4]triazin-5-yl)-2-methyl-1-((1-methyl-1H-1,2,4-triazol-3-yl)methyl)-1H-imidazo[4,5-b]pyridine | 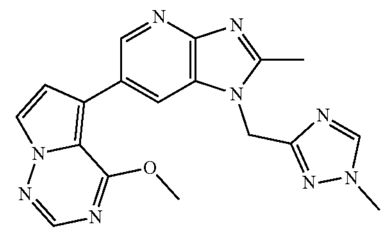 [SMILES: COc1ncnn2ccc(-c3cnc4nc(C)n(Cc5ncn(C)n5)c4c3)c12] | | 376.2 |
| 232 | 6-(4-methoxypyrrolo[2,1-f][1,2,4]triazin-5-yl)-2-methyl-1-((5-methyl-1,3-thiazol-2-yl)methyl)-1H-imidazo[4,5-b]pyridine | 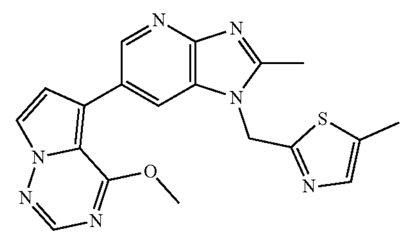 | | 392.1 |
| 233 | 3-((6-(4-methoxypyrrolo[2,1-f][1,2,4]triazin-5-yl)-2-methyl-1H-imidazo[4,5-b]pyridin-1-yl)methyl)-4-methyl-1,2,4-oxadiazol-5(4H)-one | 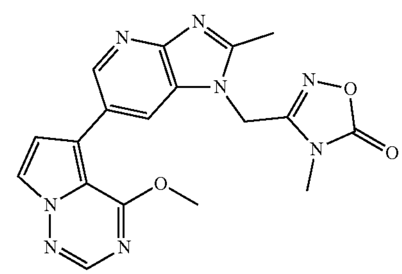 [SMILES: COc1ncnn2ccc(-c3cnc4nc(C)n(Cc5noc(=O)n5C)c4c3)c12] | | 393.2 |
| 234 | 6-(4-methoxypyrrolo[2,1-f][1,2,4]triazin-5-yl)-2-methyl-1-((3-(trifluoromethyl)-1,2,4-oxadiazol-5-yl)methyl)-1H-imidazo[4,5-b]pyridine | 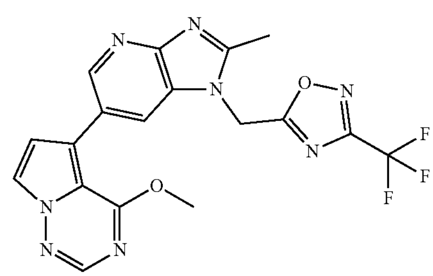 [SMILES: COc1ncnn2ccc(-c3cnc4nc(C)n(Cc5nc(C(F)(F)F)no5)c4c3)c12] | | 429.0 |
| 235 | 6-(4-methoxypyrrolo[2,1-f][1,2,4]triazin-5-yl)-2-methyl-1-((2-methylpyrimidin-4-yl)methyl)-1H-imidazo[4,5-b]pyridine | 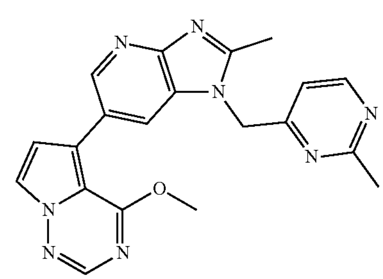 [SMILES: COc1ncnn2ccc(-c3cnc4nc(C)n(Cc5ccnc(C)n5)c4c3)c12] | | 387.2 |

TABLE 1-continued

| Example | IUPAC NAME | CHEMICAL STRUCTURE | Salt | MS |
|---|---|---|---|---|
| 236 | 1-(2-furylmethyl)-6-(4-methoxypyrrolo[2,1-f][1,2,4]triazin-5-yl)-2-methyl-1H-imidazo[4,5-b]pyridine | 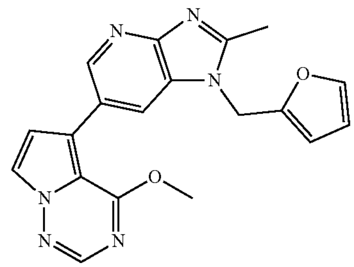 [SMILES: COc1ncnn2ccc(-c3cnc4nc(C)n(Cc5ccco5)c4c3)c12] | | 361.2 |
| 237 | 6-(4-methoxypyrrolo[2,1-f][1,2,4]triazin-5-yl)-2-methyl-1-(pyridin-2-ylmethyl)-1H-imidazo[4,5-b]pyridine | 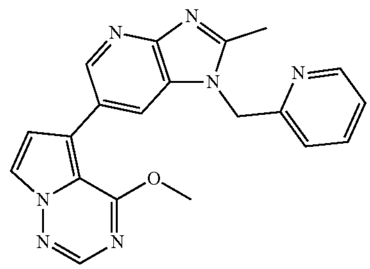 [SMILES: COc1ncnn2ccc(-c3cnc4nc(C)n(Cc5ccccn5)c4c3)c12] | | 372.2 |
| 238 | 1-((1,5-dimethyl-1H-pyrazol-3-yl)methyl)-6-(4-methoxypyrrolo[2,1-f][1,2,4]triazin-5-yl)-2-methyl-1H-imidazo[4,5-b]pyridine | 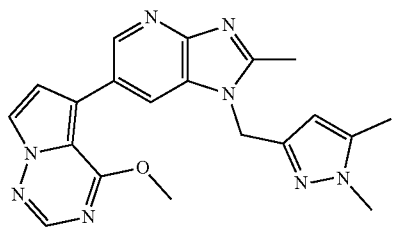 [SMILES: COc1ncnn2ccc(-c3cnc4nc(C)n(Cc5cc(C)n(C)n5)c4c3)c12] | | 389.2 |
| 239 | 2-(methoxymethyl)-6-(4-methoxypyrrolo[2,1-f][1,2,4]triazin-5-yl)-1-((3-methyl-1,2,4-oxadiazol-5-yl)methyl)-1H-imidazo[4,5-b]pyridine | 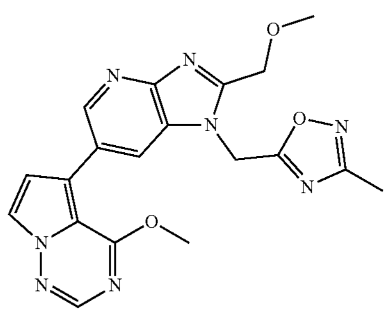 [SMILES: COCc1nc2ncc(-c3ccn4ncnc(OC)c34)cc2n1Cc1nc(C)no1] | | 405.0 |
| 240 | 1-((3-methoxy-1-methyl-1H-pyrazol-5-yl)methyl)-6-(4-methoxypyrrolo[2,1-f][1,2,4]triazin-5-yl)-2-methyl-1H-imidazo[4,5-b]pyridine | 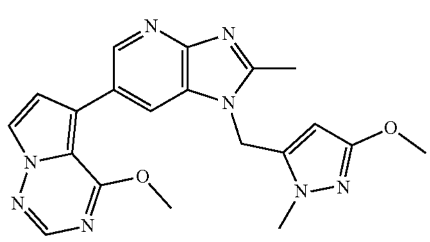 [SMILES: COc1cc(Cn2c(C)nc3ncc(-c4ccn5ncnc(OC)c45)cc32)n(C)n1] | | 405.2 |

TABLE 1-continued

| Example | IUPAC NAME | CHEMICAL STRUCTURE | Salt | MS |
|---|---|---|---|---|
| 241 | 2,2,2-trifluoro-1-(1-((2-fluoropyridin-4-yl)methyl)-6-(4-methoxypyrrolo[2,1-f][1,2,4]triazin-5-yl)-1H-imidazo[4,5-b]pyridin-2-yl)ethanol | 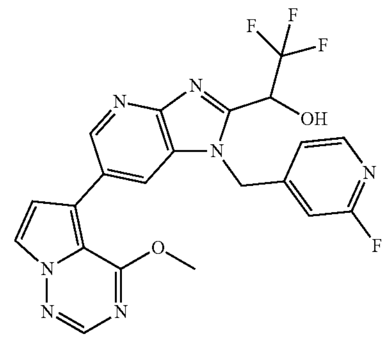 [SMILES: COc1ncnn2ccc(-c3cnc4nc(C(O)C(F)(F)F)n(Cc5ccnc(F)c5)c4c3)c12] | | 474.1 |
| 242 | 1-((5-(difluoromethyl)-1,3,4-oxadiazol-2-yl)methyl)-6-(4-methoxypyrrolo[2,1-f][1,2,4]triazin-5-yl)-2-methyl-1H-imidazo[4,5-b]pyridine | 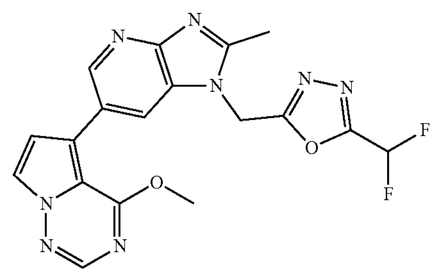 [SMILES: COc1ncnn2ccc(-c3cnc4nc(C)n(Cc5nnc(C(F)F)o5)c4c3)c12] | | 413.2 |
| 243 | 1-((5-(1,1-difluoroethyl)-1,2,4-oxadiazol-3-yl)methyl)-6-(4-methoxypyrrolo[2,1-f][1,2,4]triazin-5-yl)-2-methyl-1H-imidazo[4,5-b]pyridine | 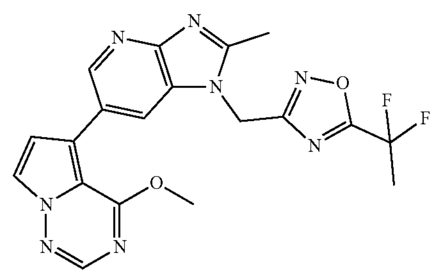 [SMILES: COc1ncnn2ccc(-c3cnc4nc(C)n(Cc5noc(C(C)(F)F)n5)c4c3)c12] | | 425.0 |
| 244 | 1-((4,6-dimethylpyrimidin)-2-yl)methyl)-6-(4-methoxypyrrolo[2,1-f][1,2,4]triazin-5-yl)-2-methyl-1H-imidazo[4,5-b]pyridine | 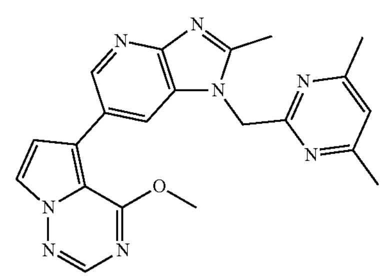 [SMILES: COc1ncnn2ccc(-c3cnc4nc(C)n(Cc5nc(C)cc(C)n5)c4c3)c12] | | 401.2 |
| 245 | 1-((1-(difluoromethyl)-1H-pyrazol-3-yl)methyl)-6-(4-methoxypyrrolo[2,1-f][1,2,4]triazin-5-yl)-2-methyl-1H-imidazo[4,5-b]pyridine | 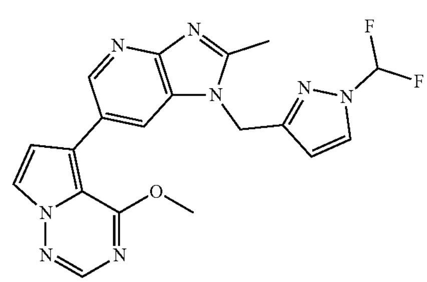 [SMILES: COc1ncnn2ccc(-c3cnc4nc(C)n(Cc5ccn(C(F)F)n5)c4c3)c12] | | 411.2 |

| Example | IUPAC NAME | CHEMICAL STRUCTURE | Salt | MS |
|---|---|---|---|---|
| 246 | 6-(4-methoxypyrrolo[2,1-f][1,2,4]triazin-5-yl)-2-methyl-1-((1-methyl-3-(trifluoromethyl)-1H-pyrazol-5-yl)methyl)-1H-imidazo[4,5-b]pyridine | 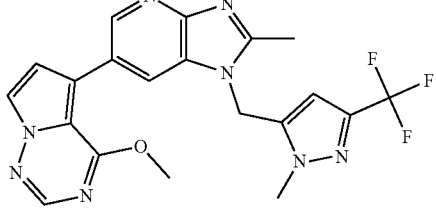 | | 443.2 |
| 247 | 1-((1-(difluoromethyl)-1H-pyrazol-5-yl)methyl)-6-(4-methoxypyrrolo[2,1-f][1,2,4]triazin-5-yl)-2-methyl-1H-imidazo[4,5-b]pyridine | 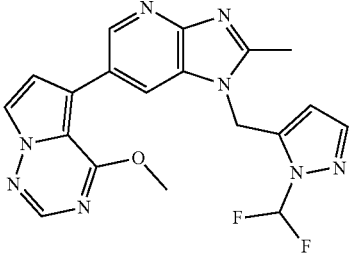 [SMILES: COc1ncnn2ccc(-c3cnc4nc(C)n(Cc5ccnn5C(F)F)c4c3)c12] | | 411.2 |
| 248 | 1-((6-chloropyrazin-2-yl)methyl)-6-(4-methoxypyrrolo[2,1-f][1,2,4]triazin-5-yl)-2-methyl-1H-imidazo[4,5-b]pyridine | 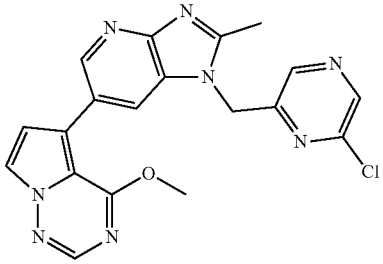 [SMILES: COc1ncnn2ccc(-c3cnc4nc(C)n(Cc5cncc(Cl)n5)c4c3)c12] | | 405.0 |
| 249 | 1-((2-methoxypyridin-3-yl)methyl)-6-(4-methoxypyrrolo[2,1-f][1,2,4]triazin-5-yl)-2-methyl-1H-imidazo[4,5-b]pyridine | 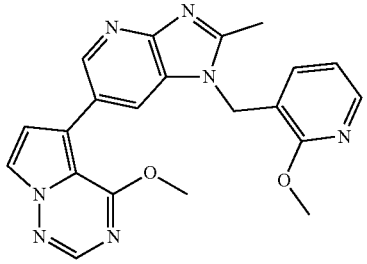 [SMILES: COc1ncccc1Cn1c(C)nc2ncc(-c3ccn4ncnc(OC)c34)cc21] | | 402.2 |
| 250 | 6-(4-methoxypyrrolo[2,1-f][1,2,4]triazin-5-yl)-2-methyl-1-((5-(trifluoromethyl)-1,3,4-oxadiazol-2-yl)methyl)-1H-imidazo[4,5-b]pyridine | 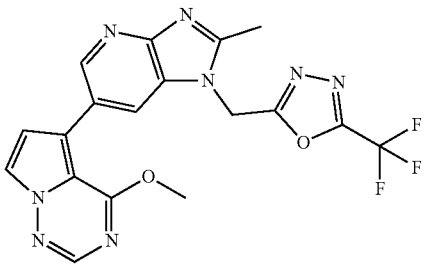 [SMILES: COc1ncnn2ccc(-c3cnc4nc(C)n(Cc5nnc(C(F)(F)F)o5)c4c3)c12] | | 431.1 |
| 251 | 2-(3-((6-(4-methoxypyrrolo[2,1-f][1,2,4]triazin-5-yl)-2-methyl-1H-imidazo[4,5-b]pyridin-1-yl)methyl)-1,2,4-oxadiazol-5-yl)propan-2-ol | 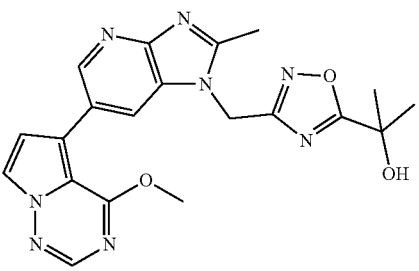 [SMILES: COc1ncnn2ccc(-c3cnc4nc(C)n(Cc5noc(C(C)(C)O)n5)c4c3)c12] | | 421.2 |

TABLE 1-continued

| Example | IUPAC NAME | CHEMICAL STRUCTURE | Salt | MS |
|---------|------------|---------------------|------|-----|
| 252 | 1-((5-ethyl-1,3,4-oxadiazol-2-yl)methyl)-6-(4-methoxypyrrolo[2,1-f][1,2,4]triazin-5-yl)-2-methyl-1H-imidazo[4,5-b]pyridine | 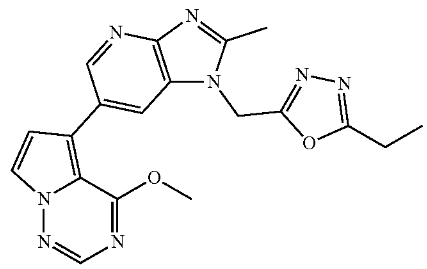 [SMILES: CCc1nnc(Cn2c(C)nc3ncc(-c4ccn5ncnc(OC)c45)cc32)o1] | | 391.2 |
| 253 | 1-((5-cyclopropyl-1,3,4-oxadiazol-2-yl)methyl)-6-(4-methoxypyrrolo[2,1-f][1,2,4]triazin-5-yl)-2-methyl-1H-imidazo[4,5-b]pyridine | 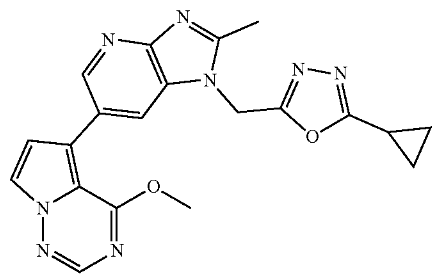 [SMILES: COc1ncnn2ccc(-c3cnc4nc(C)n(Cc5nnc(C6CC6)o5)c4c3)c12] | | 403.2 |
| 254 | 1-((5-(methoxymethyl)-1,3,4-oxadiazol-2-yl)methyl)-6-(4-methoxypyrrolo[2,1-f][1,2,4]triazin-5-yl)-2-methyl-1H-imidazo[4,5-b]pyridine | 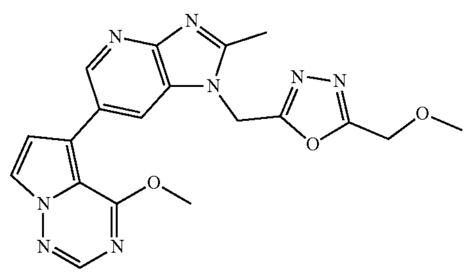 [SMILES: COCc1nnc(Cn2c(C)nc3ncc(-c4ccn5ncnc(OC)c45)cc32)o1] | | 407.2 |
| 255 | (1-((2-chloro-6-methylpyridin-4-yl)methyl)-6-(4-methoxypyrrolo[2,1-f][1,2,4]triazin-5-yl)-1H-imidazo[4,5-b]pyridin-2-yl)methanol | 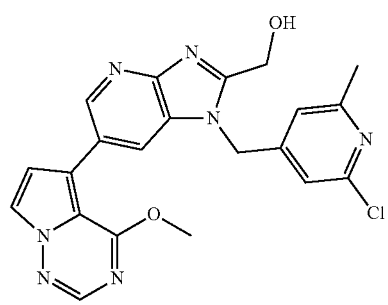 [SMILES: COc1ncnn2ccc(-c3cnc4nc(CO)n(Cc5cc(C)nc(Cl)c5)c4c3)c12] | | 433.9 |
| 256 | (1-(4-fluorobenzyl)-6-(4-methoxypyrrolo[2,1-f][1,2,4]triazin-5-yl)-1H-imidazo[4,5-b]pyridin-2-yl)methanol | 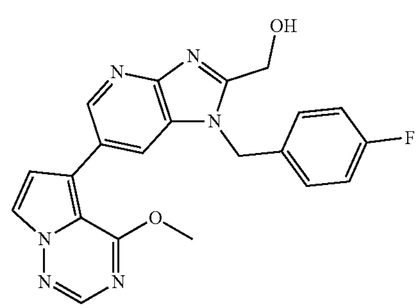 [SMILES: COc1ncnn2ccc(-c3cnc4nc(CO)n(Cc5ccc(F)cc5)c4c3)c12] | | 405.1 |

TABLE 1-continued

| Example | IUPAC NAME | CHEMICAL STRUCTURE | Salt | MS |
|---|---|---|---|---|
| 257 | (1-(4-chlorobenzyl)-6-(4-methoxypyrrolo[2,1-f][1,2,4]triazin-5-yl)-1H-imidazo[4,5-b]pyridin-2-yl)methanol | 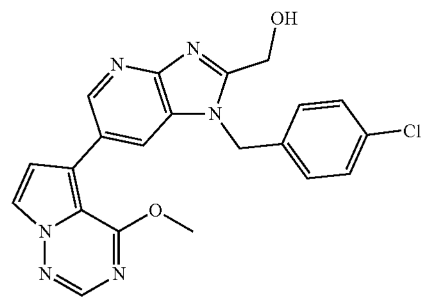 [SMILES: COc1ncnn2ccc(-c3cnc4nc(CO)n(Cc5ccc(Cl)cc5)c4c3)c12] | | 421.2 |
| 258 | 1-((1,4-dimethyl-1H-pyrazol-5-yl)methyl)-6-(4-methoxypyrrolo[2,1-f][1,2,4]triazin-5-yl)-2-methyl-1H-imidazo[4,5-b]pyridine | 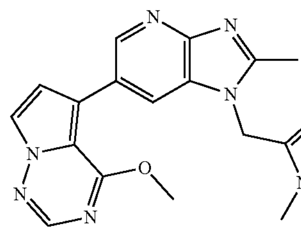 | | 389.3 |
| 259 | 1-((1-(difluoromethyl)-1H-pyrazol-4-yl)methyl)-6-(4-methoxypyrrolo[2,1-f][1,2,4]triazin-5-yl)-2-methyl-1H-imidazo[4,5-b]pyridine | 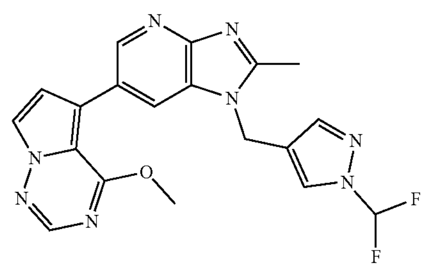 [SMILES: COc1ncnn2ccc(-c3cnc4nc(C)n(Cc5cnn(C(F)F)c5)c4c3)c12] | | 411.2 |
| 260 | 1-((2,5-dimethyl-1,3-oxazol-4-yl)methyl)-6-(4-methoxypyrrolo[2,1-f][1,2,4]triazin-5-yl)-2-methyl-1H-imidazo[4,5-b]pyridine | 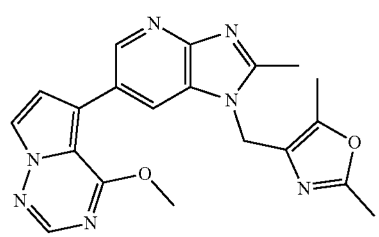 [SMILES: COc1ncnn2ccc(-c3cnc4nc(C)n(Cc5nc(C)oc5C)c4c3)c12] | | 390.2 |
| 261 | 1-((2,4-dimethyl-1,3-oxazol-5-yl)methyl)-6-(4-methoxypyrrolo[2,1-f][1,2,4]triazin-5-yl)-2-methyl-1H-imidazo[4,5-b]pyridine | 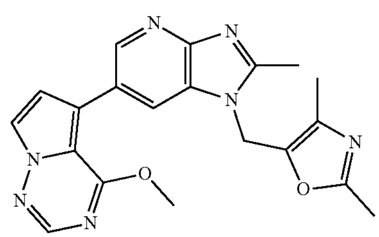 [SMILES: COc1ncnn2ccc(-c3cnc4nc(C)n(Cc5oc(C)nc5C)c4c3)c12] | | 390.2 |
| 262 | 1-((1,4-dimethyl-1H-pyrazol-3-yl)methyl)-6-(4-methoxypyrrolo[2,1-f][1,2,4]triazin-5-yl)-2-methyl-1H-imidazo[4,5-b]pyridine | 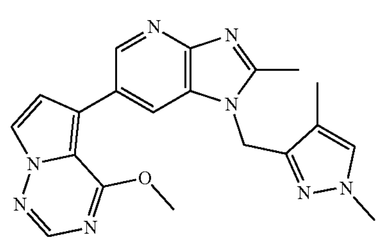 [SMILES: COc1ncnn2ccc(-c3cnc4nc(C)n(Cc5nn(C)cc5C)c4c3)c12] | | 389.2 |

| Example | IUPAC NAME | CHEMICAL STRUCTURE | Salt | MS |
|---|---|---|---|---|
| 263 | 6-(4-methoxypyrrolo[2,1-f][1,2,4]triazin-5-yl)-2-methyl-1-((4-methylpyrimidin-2-yl)methyl)-1H-imidazo[4,5-b]pyridine | 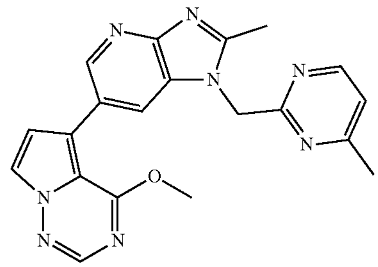 [SMILES: COc1ncnn2ccc(-c3cnc4nc(C)n(Cc5nccc(C)n5)c4c3)c12] | | 387.2 |
| 264 | 6-(4-methoxypyrrolo[2,1-f][1,2,4]triazin-5-yl)-2-methyl-1-((4-(trifluoromethyl)pyrimidin-2-yl)methyl)-1H-imidazo[4,5-b]pyridine | 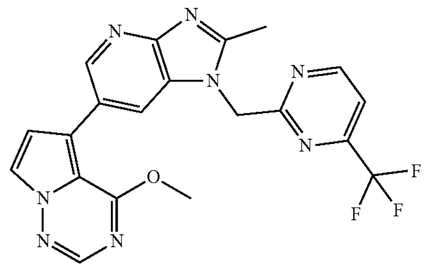 [SMILES: COc1ncnn2ccc(-c3cnc4nc(C)n(Cc5nccc(C(F)(F)F)n5)c4c3)c12] | | 441.1 |
| 265 | 1-((5-isobutyl-1,3,4-oxadiazol-2-yl)methyl)-6-(4-methoxypyrrolo[2,1-f][1,2,4]triazin-5-yl)-2-methyl-1H-imidazo[4,5-b]pyridine | 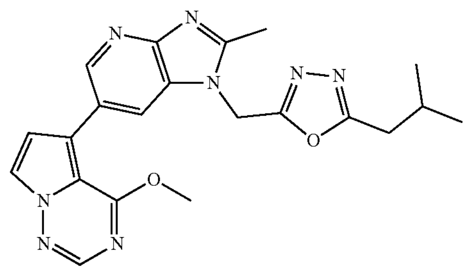 [SMILES: COc1ncnn2ccc(-c3cnc4nc(C)n(Cc5nnc(CC(C)C)o5)c4c3)c12] | | 419.2 |
| 266 | 6-(4-methoxypyrrolo[2,1-f][1,2,4]triazin-5-yl)-2-methyl-1-((4-methyl)-6-(trifluoromethyl)pyrimidin-2-yl)methyl)-1H-imidazo[4,5-b]pyridine | 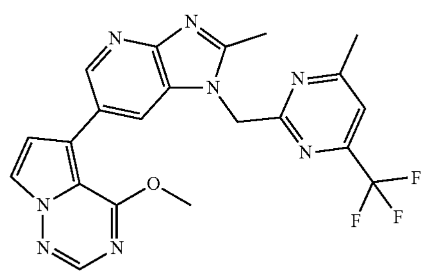 [SMILES: COc1ncnn2ccc(-c3cnc4nc(C)n(Cc5nc(C)cc(C(F)(F)F)n5)c4c3)c12] | | 455.2 |
| 267 | 1-((5-isopropyl-1,3,4-oxadiazol-2-yl)methyl)-6-(4-methoxypyrrolo[2,1-f][1,2,4]triazin-5-yl)-2-methyl-1H-imidazo[4,5-b]pyridine | 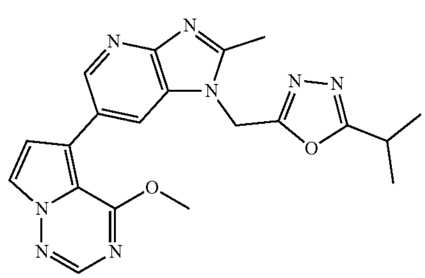 [SMILES: COc1ncnn2ccc(-c3cnc4nc(C)n(Cc5nnc(C(C)C)o5)c4c3)c12] | | 405.2 |

TABLE 1-continued

| Example | IUPAC NAME | CHEMICAL STRUCTURE | Salt | MS |
|---|---|---|---|---|
| 268 | 1-((5-cyclobutyl-1,3,4-oxadiazol-2-yl)methyl)-6-(4-methoxypyrrolo[2,1-f][1,2,4]triazin-5-yl)-2-methyl-1H-imidazo[4,5-b]pyridine | 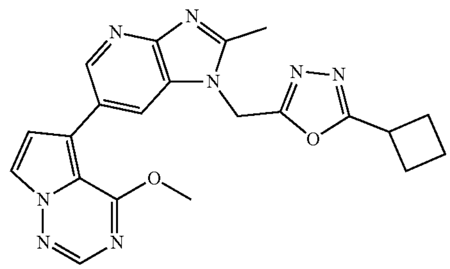 [SMILES: COc1ncnn2ccc(-c3cnc4nc(C)n(Cc5nnc(C6CCC6)o5)c4c3)c12] | | 417.2 |
| 269 | 1-((5-(3,3-difluorocyclobutyl)-1,3,4-oxadiazol-2-yl)methyl)-6-(4-methoxypyrrolo[2,1-f][1,2,4]triazin-5-yl)-2-methyl-1H-imidazo[4,5-b]pyridine | 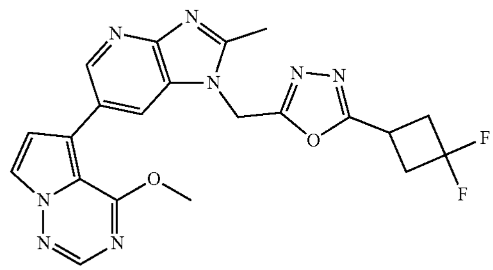 [SMILES: COc1ncnn2ccc(-c3cnc4nc(C)n(Cc5nnc(C6CC(F)(F)C6)o5)c4c3)c12] | | 453.2 |
| 270 | 6-(4-methoxypyrrolo[2,1-f][1,2,4]triazin-5-yl)-2-methyl-1-((5-(1-methylcyclopropyl)-1,3,4-oxadiazol-2-yl)methyl)-1H-imidazo[4,5-b]pyridine | 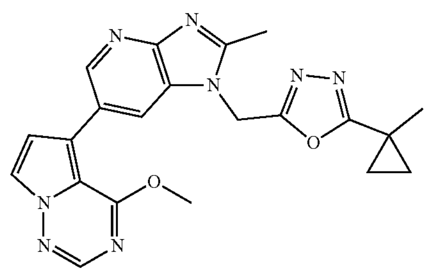 [SMILES: COc1ncnn2ccc(-c3cnc4nc(C)n(Cc5nnc(C6(C)CC6)o5)c4c3)c12] | | 417.2 |
| 271 | 1-((5-(1,1-difluoropropyl)-1,3,4-oxadiazol-2-yl)methyl)-6-(4-methoxypyrrolo[2,1-f][1,2,4]triazin-5-yl)-2-methyl-1H-imidazo[4,5-b]pyridine | 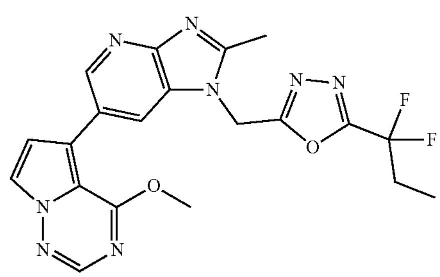 [SMILES: CCC(F)(F)c1nnc(Cn2c(C)nc3ncc(-c4ccn5ncnc(OC)c45)cc32)o1] | | 441.2 |
| 272 | 6-(4-methoxypyrrolo[2,1-f][1,2,4]triazin-5-yl)-2-methyl-1-((5-(1,1,2,2-tetrafluoroethyl)-1,3,4-oxadiazol-2-yl)methyl)-1H-imidazo[4,5-b]pyridine | 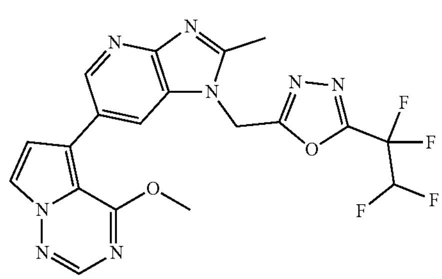 [SMILES: COc1ncnn2ccc(-c3cnc4nc(C)n(Cc5nnc(C(F)(F)C(F)F)o5)c4c3)c12] | | 461.0 |

TABLE 1-continued

| Example | IUPAC NAME | CHEMICAL STRUCTURE | Salt | MS |
|---|---|---|---|---|
| 273 | 6-(4-methoxypyrrolo[2,1-f][1,2,4]triazin-5-yl)-1,2-dimethyl-1H-imidazo[4,5-b]pyridine | 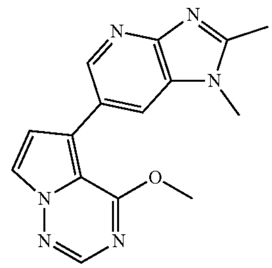 [SMILES: COc1ncnn2ccc(-c3cnc4nc(C)n(C)c4c3)c12] | | 295.1 |
| 274 | 1-((5-(1,1-difluoroethyl)-1,3,4-oxadiazol-2-yl)methyl)-6-(4-methoxypyrrolo[2,1-f][1,2,4]triazin-5-yl)-2-methyl-1H-imidazo[4,5-b]pyridine | 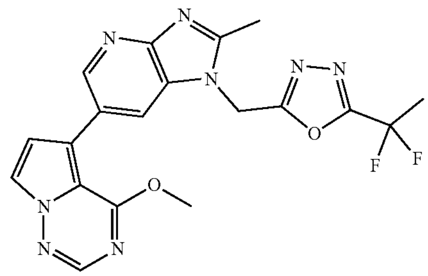 [SMILES: COc1ncnn2ccc(-c3cnc4nc(C)n(Cc5nnc(C(C)(F)F)o5)c4c3)c12] | | 427.1 |
| 275 | 6-(4-methoxypyrrolo[2,1-f][1,2,4]triazin-5-yl)-2-methyl-1-((5-(3-methyloxetan-3-yl)-1,3,4-oxadiazol-2-yl)methyl)-1H-imidazo[4,5-b]pyridine | 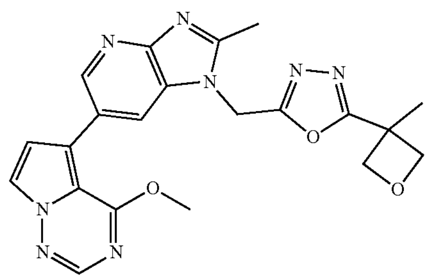 [SMILES: COc1ncnn2ccc(-c3cnc4nc(C)n(Cc5nnc(C6(C)COC6)o5)c4c3)c12] | | 433.2 |
| 276 | 1-((5-(2,2-difluorocyclopropyl)-1,3,4-oxadiazol-2-yl)methyl)-6-(4-methoxypyrrolo[2,1-f][1,2,4]triazin-5-yl)-2-methyl-1H-imidazo[4,5-b]pyridine | 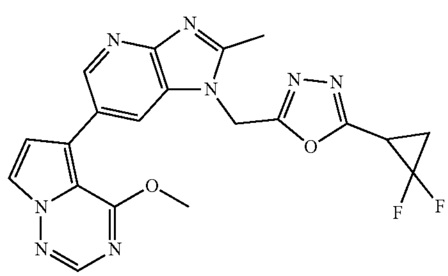 [SMILES: COc1ncnn2ccc(-c3cnc4nc(C)n(Cc5nnc(C6CC6(F)F)o5)c4c3)c12] | | 439.2 |
| 277 | 1-((5-(2-fluoropropan-2-yl)-1,3,4-oxadiazol-2-yl)methyl)-6-(4-methoxypyrrolo[2,1-f][1,2,4]triazin-5-yl)-2-methyl-1H-imidazo[4,5-b]pyridine | 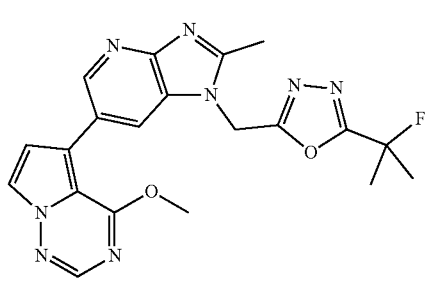 [SMILES: COc1ncnn2ccc(-c3cnc4nc(C)n(Cc5nnc(C(C)(C)F)o5)c4c3)c12] | | 423.2 |

TABLE 1-continued

| Example | IUPAC NAME | CHEMICAL STRUCTURE | Salt | MS |
|---|---|---|---|---|
| 278 | 1-((6-methoxypyrazin-2-yl)methyl)-6-(4-methoxypyrrolo[2,1-f][1,2,4]triazin-5-yl)-2-methyl-1H-imidazo[4,5-b]pyridine | 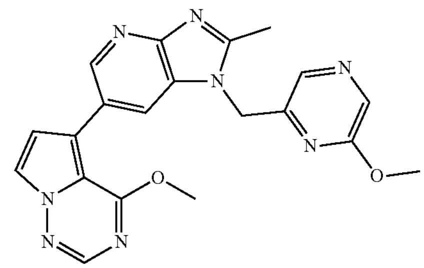 [SMILES: COc1cncc(Cn2c(C)nc3ncc(-c4ccn5ncnc(OC)c45)cc32)n1] | | 403.2 |
| 279 | 1-((5-(1-fluoroethyl)-1,3,4-oxadiazol-2-yl)methyl)-6-(4-methoxypyrrolo[2,1-f][1,2,4]triazin-5-yl)-2-methyl-1H-imidazo[4,5-b]pyridine | 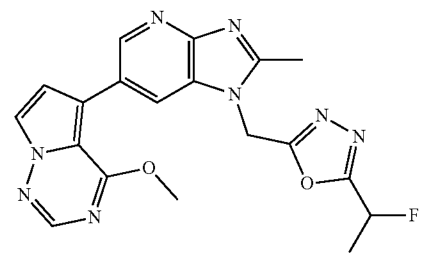 [SMILES: COc1ncnn2ccc(-c3cnc4nc(C)n(Cc5nnc(C(C)F)o5)c4c3)c12] | | 409.2 |
| 280 | 6-(4-methoxypyrrolo[2,1-f][1,2,4]triazin-5-yl)-2-methyl-1-(1,2,3-thiadiazol-4-ylmethyl)-1H-imidazo[4,5-b]pyridine | 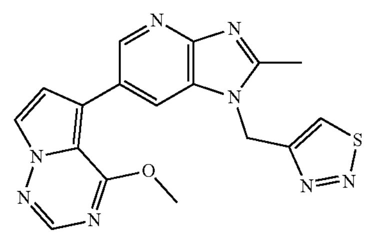 [SMILES: COc1ncnn2ccc(-c3cnc4nc(C)n(Cc5csnn5)c4c3)c12] | | 379.2 |
| 281 | 6-(4-methoxypyrrolo[2,1-f][1,2,4]triazin-5-yl)-2-methyl-1-((5-(2,2,2-trifluoroethyl)-1,3,4-oxadiazol-2-yl)methyl)-1H-imidazo[4,5-b]pyridine | 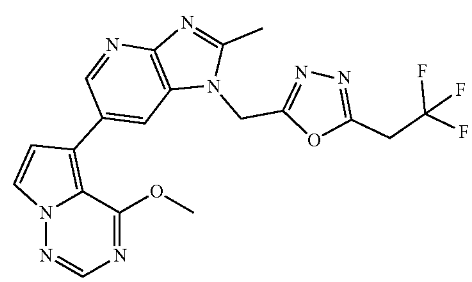 [SMILES: COc1ncnn2ccc(-c3cnc4nc(C)n(Cc5nnc(CC(F)(F)F)o5)c4c3)c12] | | 445.2 |
| 282 | 6-(4-methoxypyrrolo[2,1-f][1,2,4]triazin-5-yl)-2-methyl-1-(1,2,3-thiadiazol-5-ylmethyl)-1H-imidazo[4,5-b]pyridine | 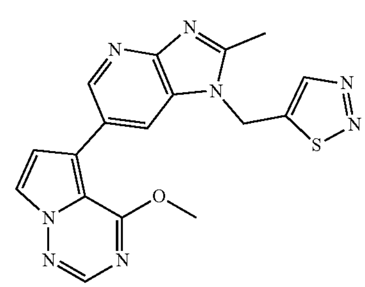 [SMILES: COc1ncnn2ccc(-c3cnc4nc(C)n(Cc5cnns5)c4c3)c12] | | 379.2 |
| 283 | 1-((5-(1-fluorocyclopropyl)-1,3,4-oxadiazol-2-yl)methyl)-6-(4-methoxypyrrolo[2,1-f][1,2,4]triazin-5-yl)-2-methyl-1H-imidazo[4,5-b]pyridine | 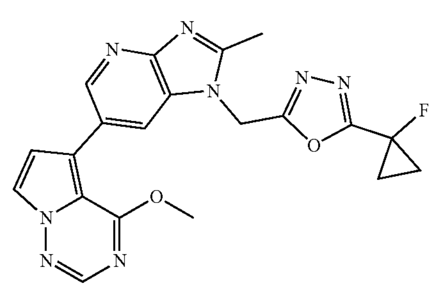 [SMILES: COc1ncnn2ccc(-c3cnc4nc(C)n(Cc5nnc(C6(F)CC6)o5)c4c3)c12] | | 421.2 |

TABLE 1-continued

| Example | IUPAC NAME | CHEMICAL STRUCTURE | Salt | MS |
|---|---|---|---|---|
| 284 | 1-((5-(1-fluorocyclobutyl)-1,3,4-oxadiazol-2-yl)methyl)-6-(4-methoxypyrrolo[2,1-f][1,2,4]triazin-5-yl)-2-methyl-1H-imidazo[4,5-b]pyridine | 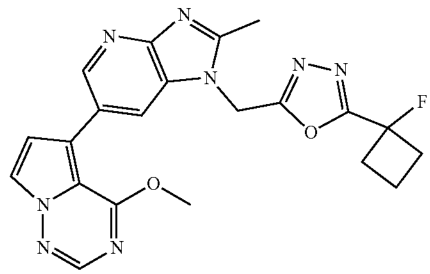 [SMILES: COc1ncnn2ccc(-c3cnc4nc(C)n(Cc5nnc(C6(F)CCC6)o5)c4c3)c12] | | 435.2 |
| 285 | 6-(4-methoxypyrrolo[2,1-f][1,2,4]triazin-5-yl)-2-methyl-1-((4-methyl-1,2,3-thiadiazol-5-yl)methyl)-1H-imidazo[4,5-b]pyridine | 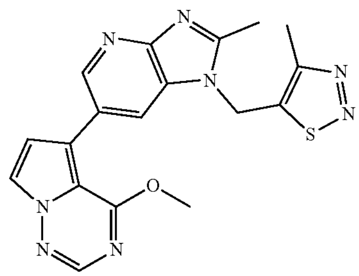 [SMILES: COc1ncnn2ccc(-c3cnc4nc(C)n(Cc5snnc5C)c4c3)c12] | | 393.2 |
| 286 | 1-((5-((1R)-1-fluoroethyl)-1,3,4-oxadiazol-2-yl)methyl)-6-(4-methoxypyrrolo[2,1-f][1,2,4]triazin-5-yl)-2-methyl-1H-imidazo[4,5-b]pyridine | 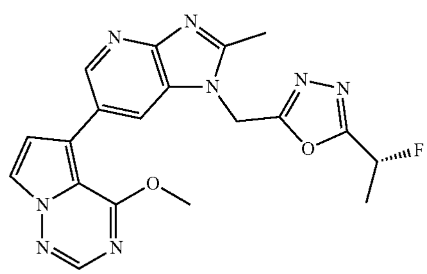 [SMILES: COc1ncnn2ccc(-c3cnc4nc(C)n(Cc5nnc([C@@H](C)F)o5)c4c3)c12] | | 409.3 |
| 287 | 1-((5-((1S)-1-fluoroethyl)-1,3,4-oxadiazol-2-yl)methyl)-6-(4-methoxypyrrolo[2,1-f][1,2,4]triazin-5-yl)-2-methyl-1H-imidazo[4,5-b]pyridine | 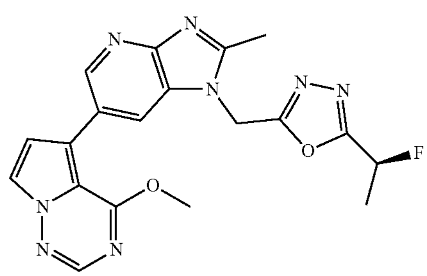 [SMILES: COc1ncnn2ccc(-c3cnc4nc(C)n(Cc5nnc([C@H](C)F)o5)c4c3)c12] | | 409.3 |
| 288 | 1-((5-(difluoromethyl)-1,3,4-oxadiazol-2-yl)methyl)-6-(4-methoxypyrrolo[1,2-b]pyridazin-5-yl)-2-methyl-1H-imidazo[4,5-b]pyridine | 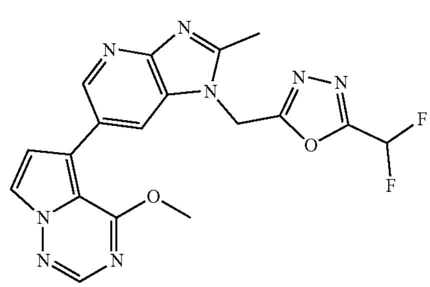 [SMILES: COc1ncnn2ccc(-c3cnc4nc(C)n(Cc5nnc(C(F)F)o5)c4c3)c12] | | 410.0 |

TABLE 1-continued

| Example | IUPAC NAME | CHEMICAL STRUCTURE | Salt | MS |
|---|---|---|---|---|
| 289 | 1-((5-(difluoromethyl)-1,3,4-thiadiazol-2-yl)methyl)-6-(4-methoxypyrrolo[2,1-f][1,2,4]triazin-5-yl)-2-methyl-1H-imidazo[4,5-b]pyridine | 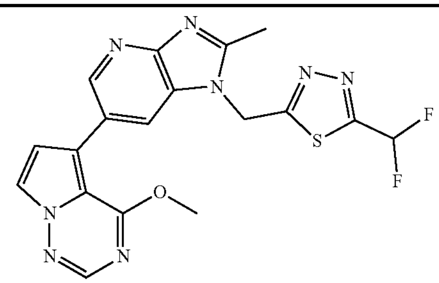 | | 429.2 |
| 290 | 6-(4-methoxypyrrolo[2,1-f][1,2,4]triazin-5-yl)-2-methyl-1-((6-methylpyrazin-2-yl)methyl-1H-imidazo[4,5-b]pyridine | 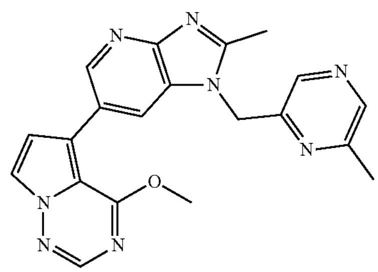 [SMILES: COc1ncnn2ccc(-c3cnc4nc(C)n(Cc5cncc(C)n5)c4c3)c12] | | 387.3 |

Preparation Example 1

A medicament containing the present invention compound as an active ingredient can be produced in accordance with, for example, the following formulation.

| Equation 1 1. capsule | |
|---|---|
| (1) compound obtained in Example 1 | 40 mg |
| (2) lactose | 70 mg |
| (3) microcrystalline cellulose | 9 mg |
| (4) magnesium stearate | 1 mg |
| one capsule | 120 mg |

Components (1), (2) and (3), and one-half of component (4) are mixed, and then granulated. The remainder of component (4) is added thereto, and the whole of the mixture is encapsulated in a gelatin capsule.

| Equation 2 2. tablet | |
|---|---|
| (1) compound obtained in Example 1 | 40 mg |
| (2) lactose | 58 mg |
| (3) corn starch | 18 mg |
| (4) microcrystalline cellulose | 3.5 mg |
| (5) magnesium stearate | 0.5 mg |
| one tablet | 120 mg |

Components (1), (2) and (3), two-thirds of component (4), and one-half of component (5) are mixed, and then granulated. The remainders of components (4) and (5) are added to the resulting granule, and the mixture is press-molded into a tablet.

Preparation Example 2

50 mg of the compound obtained in each of examples is dissolved in 50 mL of injection distilled water in Japanese Pharmacopoeia, and injection distilled water in Japanese Pharmacopoeia Japanese is added so that the volume of the solution is 100 mL. The solution is filtered under sterile conditions, and 1 mL of the solution is then taken, filled into an injection vial under sterile conditions, freeze-dried, and hermetically sealed.

Test Example 1 (Test Method: Measurement of CLK2 Inhibitory Activity)

A test compound dissolved in DMSO was added to a reaction solution (50 mM HEPES (pH: 7.5), 10 mM $MgCl_2$, 1 mM EGTA, 2 mM DTT, 0.01% Tween 20, 0.01% BSA) containing a CLK2 enzyme (Thermo Fisher Scientific) and an ULight-labeled MBP peptide (PerkinElmer), and the mixture was then reacted at room temperature for 10 minutes. An ATP solution was added to a final concentration of 1 mM to initiate an enzyme reaction, and the reaction was carried out at room temperature for 60 minutes. A europium-labeled anti-phosphorylated MBP antibody (PerkinElmer) and a LANCE Detection buffer (PerkinElmer) containing EDTA with a final concentration of 20 mM were added to stop the reaction, the mixture was left standing for 60 minutes, and the time-resolved fluorescence value (excitation 320 nm, and emission 615 nm and 665 nm) was measured by Envision (PerkinElmer). The inhibition ratio (%) of CLK2 by the test compound was calculated in accordance with the following expression.

Inhibition ratio (%)=(1−(count of test compound−blank)÷(control−blank))×100

The count of the CLK2 enzyme reaction solution without addition of the compound was described as a control, and the count without addition of the compound and addition of the CLK2 enzyme was described as a blank. The concentration at which the inhibition ratio was 50% was defined as an $IC_{50}$ value.

The test results are shown in Table 2.

TABLE 2

| Example No. | CLK2 activity inhibition ratio at compound concentration of 1 μM (ATP 1 mM) |
|---|---|
| 7 | 100% |
| 102 | 100% |
| 105 | 100% |
| 110 | 100% |
| 160 | 100% |
| 161 | 100% |
| 175 | 100% |
| 176 | 100% |
| 186 | 99% |
| 193 | 100% |
| 214 | 99% |
| 215 | 100% |
| 229 | 100% |
| 242 | 100% |
| 274 | 100% |
| 277 | 100% |
| 283 | 100% |
| 286 | 100% |

These results showed that the present invention compound had CLK2 inhibitory activity.

Test Example 2 (Measurement of Growth Inhibitory Activity Using HCT116 Cells)

HCT 116 cells (ATCC) were seeded in a 384-well plate at a density of 6×10² cells/well, and cultured overnight in a cell culture medium McCoy's 5A (Thermo Fisher Scientific) containing 10% FBS (fetal bovine serum) and 1% penicillin/streptomycin. The dissolved test compound was added in the cell medium, and the cell medium was left standing in a $CO_2$ incubator (37° C.) for 3 days. A Cell Titer-Glo solution (Promega Corporation) was added, the mixture was stirred at room temperature for 10 minutes, and the emission value was measured by Envision (PerkinElmer). The inhibition ratio (%) of HCT116 cell growth by the test compound was calculated in accordance with the following expression.

Inhibition ratio (%)=(1−(count of test compound−blank)÷(control−blank))×100

The count of the HCT116 cell suspension without addition of the compound was described as a control, and the count without addition of the compound and addition of HCT116 cells was described as a blank. The concentration at which the inhibition ratio was 50% was defined as an $IC_{50}$ value.

The test results are shown in Table 3.

TABLE 3

| Example No. | Cell growth inhibition ratio at compound concentration of 1 μM |
|---|---|
| 7 | 92% |
| 102 | 95% |
| 105 | 96% |
| 110 | 92% |
| 160 | 98% |
| 161 | 97% |
| 175 | 91% |
| 176 | 85% |
| 186 | 96% |
| 193 | 98% |
| 214 | 96% |
| 215 | 95% |
| 229 | 97% |
| 242 | 94% |
| 274 | 93% |
| 277 | 95% |
| 283 | 96% |
| 286 | 95% |

These results showed that the present invention compound inhibited growth of colon adenocarcinoma cells.

In Vitro CLK2 Phosphorylation Inhibitory Action and p53 Activation Action in Human Colon Adenocarcinoma Cells HCT 116

1000 μl (8,0000 cells/well) of a cell suspension of human colon adenocarcinoma cells HCT116 (purchased from ATCC) was seeded in a 12-well plate, and cultured at 37° C. for 2 days in a 5% $CO_2$ gas incubator. The test compound solution was added to a final concentration of 300 nM, and the mixture was cultured for 16 hours. The plate was washed with PBS, a protein extract (10% glycerol, 1% sodium dodecyl sulfate, 62.5 mM Tris-HCl (pH: 7.5)) was then added to dissolve the cells, and the solution was treated at 95° C. for 5 minutes. Thereafter, the amount of protein was determined using BCA Protein Assay Kit (Thermo Fisher Scientific).

The amount of the protein in each sample was adjusted, SDS-PAGE was then performed, and the protein was transferred to a PVDF membrane using an iBlot (registered trademark) gel transfer system (Invitrogen). Blocking was performed using StartingBlock T20 (PBS) Blocking Buffer (Thermo Fisher Scientific), and the sample was reacted at 4° C. overnight with anti-phosphorylation CLK2 (Ser98), an anti-MDM4 antibody (Bethyl Laboratories, Inc., A300-287A), an anti-p53 antibody (Santa Cruz, Inc., sc-126) and anti-p21 antibody (Santa Cruz, Inc., sc-6246) each diluted 1000 times with Can Get Signal Immunoreaction Enhancer Solution 1 (TOYOBO CO., LTD.). The membrane was washed with Tris-buffered saline (Bio-Rad Laboratories, Inc.) containing 0.05% of Tween 20 (Bio-Rad Laboratories, Inc.), and the sample was then reacted at room temperature for 1 hour with a HRP-labeled rabbit IgG polyclonal antibody (NA 9340 from GE Healthcare) diluted 5000 times with Can Get Signal Immunoreaction Enhancer Solution 2 (TOYOBO CO., LTD.). The membrane was washed in the same procedure as described above, a phosphorylated CLK2 protein, a MDM4 protein, a p53 protein and a p21 protein each labeled with an antibody were then made chemiluminescent using ImmunoStar ZETA (Wako Pure Chemical Industries, Ltd.), and luminescence was detected with LAS-3000 Image Analyzer (Fujifilm Corporation). The luminescence intensity was determined using Multi Gauge Ver. 3.1 (Fujifilm Corporation), and quantified.

The CLK2 phosphorylation inhibitory activity of the test compound is calculated as a phosphorylated CLK2 residual ratio (%) in accordance with the following expression, and shown in Table 4.

Residual ratio (%)=(phosphorylated CLK2 signal of test compound÷phosphorylated CLK2 signal of control group)×100

TABLE 4

| Test compound (Example No.) | Concentration (nM) | Residual ratio (%) |
|---|---|---|
| 286 | 300 | 71.4 |

The MDM4 inhibitory activity of the test compound is calculated as a residual ratio (%) in accordance with the following expression, and shown in the table.

Residual ratio (%)=(MDM4 signal of test compound÷MDM4 signal of control group)×100

TABLE 5

| Test compound (Example No.) | Concentration (nM) | Residual ratio (%) |
|---|---|---|
| 286 | 300 | 43.6 |

The p53 induction activity of the test compound is calculated as an increase ratio (%) in accordance with the following expression, and shown in Table 5.

Increase ratio (%)=(p53 signal of test compound÷p53 signal of control group))×100

TABLE 6

| Test compound (Example No.) | Concentration (nM) | Increase ratio (%) |
|---|---|---|
| 286 | 300 | 620.7 |

The p21 induction activity of the test compound is calculated as an increase ratio (%) in accordance with the following expression, and shown in Table 6.

Increase ratio (%)=(p21 signal of test compound÷p21 signal of control group))×100

TABLE 7

| Test compound (Example No.) | Concentration (nM) | Increase ratio (%) |
|---|---|---|
| 286 | 300 | 556.4 |

These results showed that the present invention compound inhibited phosphorylation of CLK2, decreased the amount of the MDM4 protein, and increased the amounts of the p53 and p21 proteins in colon adenocarcinoma cells.

In Vitro MDM4 Alternative Splicing Ratio in Human Colon Adenocarcinoma Cell HCT 116

1000 μl (20,0000 cells/well) of a cell suspension of human colon adenocarcinoma cells HCT116 (purchased from ATCC) was seeded in a 12-well plate, and cultured at 37° C. for 1 day in a 5% $CO_2$ gas incubator. The test compound solution was added to a final concentration of 300 nM, and the mixture was cultured for 6 hours. The plate was washed with PBS, the cells were then dissolved using RNeasy Mini Kit (QIAGEN), and RNA was extracted. Using cDNA after reverse transcription reaction, the number of copies of the MDM4 transcription product containing exon 6 (MDM4 FL) and the MDM4 transcription product in which exon 6 was skipped (MDM4 S) was measured by quantitative PCR. Primers with the following sequences were used for the measurement.

Primers with the following sequences were used for the measurement.

MDM4 FL (Hs 00967241_m1, Thermo Fisher Scientific)

MDM4 S
(Forward primer, GACCCAAGCCCTCTCTATGATATG;
Reverse primer, TCTGTAGTTCTTTTTCTGGAAGTGGAA;
probe, TACTACAGCAAAGTGCAGAGG, Thermo Fisher Scientific)

The following oligos were used for preparing a calibration curve.

MDM4 FL Oligo
(CCCTCTCTATGATATGCTAAGAAAGAATCTTGTCACTTTAGCCACTGC
TACTACAGATGCTGCTCAGACTCTCGCTCTCGCACAGGATCACAGTATG
GA, Thermo Fisher Scientific);

MDM4 S Oligo
(TGAAAGACCCAAGCCCTCTCTATGATATGCTAAGAAAGAATCTTGTCA
CTTTAGCCACTGCTACTACAGCAAAGTGCAGAGGAAAGTTCCACTTCCA
GAAAAAGAACTACAGAAGACG, Thermo Fisher Scientific)

A change in MDM4 alternative splicing ratio (PSI) is calculated in accordance with the following expression, and changes caused by the test compound are shown in Table 8.

PSI=(number of copies of MDM4 FL÷(number of copies of MDM4 FL+number of copies of MDM4 S))×100

TABLE 8

| Test compound (Example No.) | PSI |
|---|---|
| Control (DMSO) | 75.75 |
| 286 | 45.81 |

These results showed that the present invention compound increased the ratio of transcription product (MDM4 S) in which exon 6 of MDM4 was skipped in colon adenocarcinoma cells.

In Vitro MYC-Induced Human Malignant Melanoma Cell SK-MEL-28 Growth Inhibitory Action Human MYC cDNA was inserted downstream of the TRE of a lentiviral vector (modified pTRIPZ: GE Healthcare) having a tetracycline responsive sequence (TRE) in the promoter region. The produced virus was infected with human malignant melanoma cells SK-MEL-28 (purchased from ATCC) to establish SK-MEL-28 cells (SK-MEL-28-MYC) inducing expression of MYC in the presence of doxycycline (Takara Bio Inc.) which is a tetracycline derivative. SK-MEL-28 cells (SK-MEL-28—Control) having an empty vector with only modified pTRIPZ were also established. 20 μL/well of 2.5 μg/mL doxycycline-containing medium was added to a 96-well plate, and 80 μl/well (1,000 cells/well) of a cell suspension was added, and cultured at 37° C. for 2 days in a 5% $CO_2$ gas incubator. Thereafter, 100 μl of a 250 nM test compound solution was added (final concentration: 125 nM), and the mixture was further cultured for 3 days. 50 μl/well of a CellTiter-Glo™ Luminescent Cell Viability Assay reagent (Promega Corporation) was added to a 96-well plate, the amount of luminescence was measured by a luminometer, and the amount of remaining ATP was determined as a cell amount. The inhibition ratio (%) of cell growth by the test compound was calculated in accordance with the following expression.

Inhibition ratio (%)=(1-(amount of luminescence of test compound)÷(amount of luminescence of control group))×100

The inhibition ratios of the test compounds are shown in Table 9.

TABLE 9

| Cell | Inhibition ratio (%) by compound (125 nM) of Example 286 | |
|---|---|---|
| | Doxycycline (−) | Doxycycline (+) |
| SK-MEL-28-Control | 34.4 | 35.7 |
| SK-MEL-28-MYC | 24.7 | 69.3 |

These results showed that the present invention compound had a stronger growth inhibitory action on a cancer cell line in which MYC was induced than on a cancer cell line in which MYC was not induced.

Antitumor Action on Tumor-Bearing Model Derived from Patient with Acute Myeloid Leukemia Having SF3B1 Gene Mutation A tumor derived from a myelogenous leukemia patient having a mutation in the SF3B1 gene was subcutaneously transplanted into mice to establish a clinical tumor model capable of undergoing in vivo passage. A fragment of the tumor was subcutaneously transplanted into a six-week-old NOG female mice (CLEA Japan, Inc.) with a trocar, the tumor diameter of the developed tumor was measured 52 days after the transplantation, and the tumor volume was calculated in accordance with the following expression.

Tumor volume=long diameter×short diameter×short diameter×(½)

Individuals with a tumor developed to a tumor volume of about 200 mm³ were selected, and six mice per group were used for the experiment. A 0.5% methylcellulose solution (Wako Pure Chemical Industries, Ltd.) suspension of the test compound was orally administered at a dose of 50 mg/kg (10 mL/kg) twice a day on 2 days per week for 2 weeks. The tumor volume was chronologically measured on the day before the start of administration and every 3 to 4 days, the tumor diameter was finally measured on the day after completion of administration for 14 days, and the tumor volume was calculated.

The tumor growth in the test compound administration group with respect to the control administration group was calculated as a T/C value in accordance with the following expression.

T/C=(tumor volume after completion of administration in test compound administration group−tumor volume on day before start of administration in test compound administration group)/ (tumor volume after completion of administration in control administration group−tumor volume before start of administration in control administration group))×100

The T/C values of the test compound are shown in Table 10.

TABLE 10

| Test compound (Example No.) | Dose (mg/kg) | T/C (%) |
|---|---|---|
| 286 | 50 | −30.4 |

These results showed that the present invention compound had an antitumor action in a tumor model derived from an acute myeloid leukemia patient having a mutation in the SF3B1 gene.

The present application is based on JP-A-2016-091717 filed in Japan, the disclosure of which is incorporated herein in its entirety.

INDUSTRIAL APPLICABILITY

The present invention compound has a CLK inhibitory action. Therefore, the present invention compound can be used as a CLK inhibitor, and is useful as a prophylactic or therapeutic agent for CLK-related diseases including cancer.

The invention claimed is:

1. A method for treating at least one cancer selected from the group consisting of colon cancer, melanoma and acute myeloid leukemia in a mammal, the method comprising administering to the mammal an effective amount of a compound represented by the formula (I), or a salt or hydrate thereof,

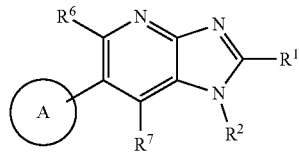

(I)

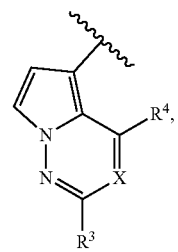

(1)

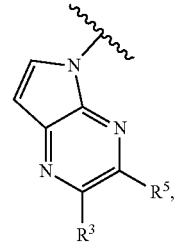

(2)

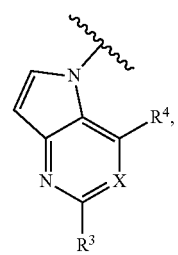

(3)

wherein:

$R^1$ represents a substituent or a hydrogen atom;

$R^2$ represents an optionally substituted hydrocarbon group or an optionally substituted heterocyclic group;

$R^6$ and $R^7$ each independently represent a hydrogen atom, a halogen atom or an optionally substituted hydrocarbon group; and ring A represents a bicyclic aromatic heterocycle selected from the following formulas (1), (2), (3), (4) and (5):

-continued

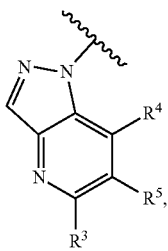

(4)

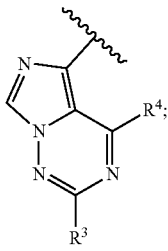

(5)

wherein Xs each independently represent N or C(R$^5$); and

R$^3$, R$^4$ and R$^5$ each independently represent a hydrogen atom or a substituent.

2. The method according to claim 1, wherein the compound represented by the formula (I), or a salt or hydrate thereof is 6-(4-methoxypyrrolo[2,1-f][1,2,4]triazin-5-yl)-2-methyl-1-(3-methyl-1,2,4-thiadiazol-5-yl)methyl)-1H-imidazo[4,5-b]pyridine.

3. The method according to claim 1, wherein the compound represented by the formula (I), or a salt or hydrate thereof is 1-((5-(difluoromethyl)-1,3,4-oxadiazol-2-yl)methyl)-6-(4-methoxypyrrolo[2,1-f][1,2,4]triazin-5-yl)-2-methyl-1H-imidazo[4,5-b]pyridine.

4. The method according to claim 1, wherein the compound represented by the formula (I), or a salt or hydrate thereof is 1-((5-(1,1-difluoroethyl)-1,3,4-oxadiazol-2-yl)methyl)-6-(4-methoxypyrrolo[2,1-f][1,2,4]triazin-5-yl)-2-methyl-1H-imidazo[4,5-b]pyridine.

5. The method according to claim 1, wherein the compound represented by the formula (I), or a salt or hydrate thereof is 1-((5-(1R)-1-fluoroethyl)-1,3,4-oxadiazol-2-yl)methyl)-6-(4-methoxypyrrolo[2,1-f][1,2,4]triazin-5-yl)-2-methyl-1H-imidazo[4,5-b]pyridine.

* * * * *

SEQUENCE LISTING

<160> NUMBER OF SEQ ID NOS: 5

<210> SEQ ID NO 1
<211> LENGTH: 24
<212> TYPE: DNA
<213> ORGANISM: Artificial Sequence
<220> FEATURE:
<223> OTHER INFORMATION: Synthetic

<400> SEQUENCE: 1
gacccaagcc ctctctatga tatg          24

<210> SEQ ID NO 2
<211> LENGTH: 27
<212> TYPE: DNA
<213> ORGANISM: Artificial Sequence
<220> FEATURE:
<223> OTHER INFORMATION: Synthetic

<400> SEQUENCE: 2
tctgtagttc tttttctgga agtggaa          27

<210> SEQ ID NO 3
<211> LENGTH: 21
<212> TYPE: DNA
<213> ORGANISM: Artificial Sequence
<220> FEATURE:
<223> OTHER INFORMATION: Synthetic

```
<400> SEQUENCE: 3
tactacagca aagtgcagag g                                     21

<210> SEQ ID NO 4
<211> LENGTH: 99
<212> TYPE: DNA
<213> ORGANISM: Artificial Sequence
<220> FEATURE:
<223> OTHER INFORMATION: Synthetic

<400> SEQUENCE: 4
ccctctctat gatatgctaa gaaagaatct tgtcacttta gccactgcta ctacagatgc    60
tgctcagact ctcgctctcg cacaggatca cagtatgga                          99

<210> SEQ ID NO 5
<211> LENGTH: 118
<212> TYPE: DNA
<213> ORGANISM: Artificial Sequence
<220> FEATURE:
<223> OTHER INFORMATION: Synthetic

<400> SEQUENCE: 5
tgaaagaccc aagccctctc tatgatatgc taagaaagaa tcttgtcact ttagccactg    60
ctactacagc aaagtgcaga ggaaagttcc acttccagaa aaagaactac agaagacg    118
```